(12) United States Patent
Belouski et al.

(10) Patent No.: US 9,221,915 B2
(45) Date of Patent: Dec. 29, 2015

(54) HUMAN MONOCLONAL ANTIBODIES TO ACTIVIN RECEPTOR-LIKE KINASE-1

(75) Inventors: Shelley Sims Belouski, Camarillo, CA (US); Sirid-Aimée Kellerman, Menlo Park, CA (US); Michael Aidan North, Rancho Santa Fe, CA (US); Karin Kristina Amundson, San Diego, CA (US); Vahe Bedian, Framingham, MA (US); Dana Dan Hu-Lowe, Encinitas, CA (US); Xin Jiang, San Diego, CA (US); Shannon Marie Karlicek, San Diego, CA (US); James Arthur Thomson, San Diego, CA (US); Jianying Wang, San Diego, CA (US); Grant Raymond Wickman, San Diego, CA (US); Jingchuan Zhang, Boulder, CO (US)

(73) Assignees: Pfizer Inc., New York, NY (US); Amgen Fremont Inc., Fremont, CA (US)

( * ) Notice: Subject to any disclaimer, the term of this patent is extended or adjusted under 35 U.S.C. 154(b) by 976 days.

(21) Appl. No.: 13/282,065

(22) Filed: Oct. 26, 2011

(65) Prior Publication Data
US 2012/0052074 A1 Mar. 1, 2012

Related U.S. Application Data

(62) Division of application No. 12/402,854, filed on Mar. 12, 2009, now Pat. No. 8,080,646, which is a division of application No. 11/517,530, filed on Sep. 6, 2006, now Pat. No. 7,537,762.

(60) Provisional application No. 60/715,292, filed on Sep. 7, 2005.

(51) Int. Cl.
*C07K 16/40* (2006.01)
*C07K 16/28* (2006.01)
*A61K 39/00* (2006.01)

(52) U.S. Cl.
CPC ............. *C07K 16/40* (2013.01); *C07K 16/2863* (2013.01); *A61K 2039/505* (2013.01); *C07K 2317/21* (2013.01); *C07K 2317/33* (2013.01); *C07K 2317/55* (2013.01); *C07K 2317/56* (2013.01); *C07K 2317/565* (2013.01); *C07K 2317/76* (2013.01); *C07K 2317/77* (2013.01); *C07K 2317/92* (2013.01)

(58) Field of Classification Search
CPC .............. C07K 16/2863; C07K 16/40; C07K 2317/56; C07K 2317/565; C07K 2317/76
USPC .......................................... 424/142.1, 143.1
See application file for complete search history.

(56) References Cited

U.S. PATENT DOCUMENTS

| 4,399,216 A | 8/1983 | Axel et al. |
| 4,510,245 A | 4/1985 | Cousens et al. |
| 4,634,665 A | 1/1987 | Axel et al. |
| 4,740,461 A | 4/1988 | Kaufman |
| 4,912,040 A | 3/1990 | Kaufman et al. |
| 4,959,455 A | 9/1990 | Clark et al. |
| 4,968,615 A | 11/1990 | Koszinowski et al. |
| 5,151,510 A | 9/1992 | Stec et al. |
| 5,168,062 A | 12/1992 | Stinski |
| 5,179,017 A | 1/1993 | Axel et al. |
| 5,223,409 A | 6/1993 | Ladner et al. |
| 5,466,823 A | 11/1995 | Talley et al. |
| 5,521,207 A | 5/1996 | Graneto |
| 5,545,806 A | 8/1996 | Lonberg et al. |
| 5,545,807 A | 8/1996 | Surani et al. |
| 5,569,825 A | 10/1996 | Lonberg et al. |
| 5,587,458 A | 12/1996 | King et al. |
| 5,591,669 A | 1/1997 | Krimpenfort et al. |
| 5,608,082 A | 3/1997 | Varney et al. |
| 5,612,205 A | 3/1997 | Kay et al. |
| 5,625,126 A | 4/1997 | Lonberg et al. |
| 5,633,425 A | 5/1997 | Lonberg et al. |
| 5,643,763 A | 7/1997 | Dunn et al. |

(Continued)

FOREIGN PATENT DOCUMENTS

| EP | 0216846 | 4/1987 |
| EP | 0256055 | 2/1988 |

(Continued)

OTHER PUBLICATIONS

Voskoglou-Nomikos (Clin. Can. Res. 9:4227-4239 (2003)).*
Dennis (Nature 442:739-741 (2006)).*
Cespdes et al. (Clin. Transl. Oncol. 8(5):318-329 (2006)).*
Talmadge et al. (Am. J. Pathol 170(3):793-804 (2007)).*
Fujimori et al. (J. Nuc. Med. 31:1191-1198 (1990)).*
Beckman et al. (Can. 109:170-179 (2007)).*
Thurber et al. (Adv. Drug Deliv. Rev. 60:1421-1434 (2008)).*
Rudnick et al. (Can. Biotherp. & Radiopharm. 24: 155-162 (2009)).*
Hu-Lowe et al. (Can Res 71:1362 (Feb. 15, 2011; on-line Jan. 6, 2011).*
Goumans et al., "Balancing the activation state of the endothelium via two distinct TGF-β type I receptors," The EMBO Journal, 21(7):1743-1753 (2002).

(Continued)

*Primary Examiner* — Lynn Bristol
(74) *Attorney, Agent, or Firm* — Ropes & Gray LLP; Z. Ying Li; Brian M. Gummow

(57) ABSTRACT

The present invention relates to antibodies including human antibodies and antigen-binding portions thereof that bind to the extracellular domain (ECD) of activin receptor-like, kinase-1 (ALK-1) and that function to abrogate the ALK-1/TGF-beta-1/Smad1 signaling pathway. The invention also relates to heavy and light chain immunoglobulins derived from human anti-ALK-1 antibodies and nucleic acid molecules encoding such immunoglobulins. The present invention also relates to methods of making human anti-ALK-1 antibodies, compositions comprising these antibodies and methods of using the antibodies and compositions. The invention also relates to transgenic animals or plants comprising nucleic acid molecules of the present invention.

26 Claims, 15 Drawing Sheets

(56) References Cited

U.S. PATENT DOCUMENTS

| | | | |
|---|---|---|---|
| 5,661,016 A | 8/1997 | Lonberg et al. |
| 5,663,272 A | 9/1997 | Slack et al. |
| 5,679,666 A | 10/1997 | Clark |
| 5,721,367 A | 2/1998 | Kay et al. |
| 5,741,957 A | 4/1998 | Deboer et al. |
| 5,750,172 A | 5/1998 | Meade et al. |
| 5,756,687 A | 5/1998 | Denman et al. |
| 5,770,429 A | 6/1998 | Lonberg et al. |
| 5,770,592 A | 6/1998 | Clark |
| 5,789,215 A | 8/1998 | Berns et al. |
| 5,789,650 A | 8/1998 | Lonberg et al. |
| 5,792,783 A | 8/1998 | Tang et al. |
| 5,814,318 A | 9/1998 | Lonberg et al. |
| 5,827,690 A | 10/1998 | Meade et al. |
| 5,834,504 A | 11/1998 | Tang et al. |
| 5,877,305 A | 3/1999 | Huston et al. |
| 5,883,113 A | 3/1999 | Tang et al. |
| 5,886,020 A | 3/1999 | Tang et al. |
| 5,916,771 A | 6/1999 | Hori et al. |
| 5,932,598 A | 8/1999 | Talley et al. |
| 5,939,598 A | 8/1999 | Kucherlapati et al. |
| 5,959,177 A | 9/1999 | Hein et al. |
| 5,968,752 A | 10/1999 | Ichijo et al. |
| 5,985,615 A | 11/1999 | Jakobovits et al. |
| 5,994,619 A | 11/1999 | Stice et al. |
| 5,998,209 A | 12/1999 | Jakobovits et al. |
| 6,034,256 A | 3/2000 | Carter et al. |
| 6,046,037 A | 4/2000 | Hiatt et al. |
| 6,071,935 A | 6/2000 | Lyssikatos |
| 6,075,181 A | 6/2000 | Kucherlapati et al. |
| 6,080,769 A | 6/2000 | Lyssikatos et al. |
| 6,091,001 A | 7/2000 | Jakobovits et al. |
| 6,114,598 A | 9/2000 | Kucherlapati et al. |
| 6,130,364 A | 10/2000 | Jakobovits et al. |
| 6,150,377 A | 11/2000 | Lyssikatos et al. |
| 6,150,584 A | 11/2000 | Kucherlapati et al. |
| 6,162,963 A | 12/2000 | Kucherlapati et al. |
| 6,180,651 B1 | 1/2001 | Nicolai et al. |
| 6,194,438 B1 | 2/2001 | Yang et al. |
| 6,207,814 B1 | 3/2001 | Miyazono et al. |
| 6,258,824 B1 | 7/2001 | Yang |
| 6,271,365 B1 | 8/2001 | Miyazono et al. |
| 6,284,764 B1 | 9/2001 | Kath et al. |
| 6,316,217 B1 | 11/2001 | Miyazone et al. |
| 6,331,621 B1 | 12/2001 | Miyazono et al. |
| 6,417,429 B1 | 7/2002 | Hein et al. |
| 6,465,449 B1 | 10/2002 | Kath et al. |
| 6,495,564 B1 | 12/2002 | Lyssikatos et al. |
| 6,517,529 B1 | 2/2003 | Quinn |
| 6,534,524 B1 | 3/2003 | Kania et al. |
| 6,584,504 B1 | 6/2003 | Choe |
| 6,586,447 B1 | 7/2003 | Lyssikatos et al. |
| 6,596,735 B1 | 7/2003 | Yang |
| 6,653,308 B2 | 11/2003 | Guan et al. |
| 6,692,925 B1 | 2/2004 | Miyazono et al. |
| 6,982,319 B2 | 1/2006 | Miyazono et al. |
| 2003/0152514 A1 | 8/2003 | Gudas |
| 2005/0048607 A1 | 3/2005 | Miyazono et al. |
| 2005/0054019 A1 | 3/2005 | Michaud et al. |
| 2007/0203329 A1 | 8/2007 | Miyazono et al. |

FOREIGN PATENT DOCUMENTS

| | | |
|---|---|---|
| EP | 0323997 | 7/1989 |
| EP | 0338841 | 10/1989 |
| EP | 0677104 | 3/2003 |
| WO | WO-9110741 | 7/1991 |
| WO | WO-9117271 | 11/1991 |
| WO | WO-9101047 | 1/1992 |
| WO | WO-9209690 | 6/1992 |
| WO | WO-9215679 | 9/1992 |
| WO | WO-9301288 | 1/1993 |
| WO | WO-9402602 | 2/1994 |
| WO | WO-9411502 | 5/1994 |
| WO | WO-9507982 | 3/1995 |
| WO | WO-9519970 | 7/1995 |
| WO | WO-9521613 | 8/1995 |
| WO | WO-9633735 | 10/1996 |
| WO | WO-9634096 | 10/1996 |
| WO | WO-9713760 | 4/1997 |
| WO | WO-9722596 | 6/1997 |
| WO | WO-9732856 | 9/1997 |
| WO | WO-9802434 | 1/1998 |
| WO | WO-9802437 | 1/1998 |
| WO | WO-9802438 | 1/1998 |
| WO | WO-9803484 | 1/1998 |
| WO | WO-9816654 | 4/1998 |
| WO | WO-9824893 | 6/1998 |
| WO | WO-9850356 | 11/1998 |
| WO | WO-9850433 | 11/1998 |
| WO | WO-9852976 | 11/1998 |
| WO | WO-9854093 | 12/1998 |
| WO | WO-9910349 | 3/1999 |
| WO | WO-9911605 | 3/1999 |
| WO | WO-9916755 | 4/1999 |
| WO | WO-9924440 | 5/1999 |
| WO | WO-9935132 | 7/1999 |
| WO | WO-9935146 | 7/1999 |
| WO | WO-9945031 | 9/1999 |
| WO | WO-9946386 | 9/1999 |
| WO | WO-9953049 | 10/1999 |
| WO | WO-9961422 | 12/1999 |
| WO | WO-9962890 | 12/1999 |
| WO | WO-0034317 | 6/2000 |
| WO | WO-0140217 | 6/2001 |
| WO | WO-0198277 | 12/2001 |
| WO | WO-0224719 | 3/2002 |
| WO | WO-02053596 | 7/2002 |
| WO | WO-03040170 | 5/2003 |
| WO | WO-2004020431 | 3/2004 |
| WO | WO-2006096269 | 9/2006 |

OTHER PUBLICATIONS

Lux, A., et al., Definition, *Homo sapiens* activin A receptor type II-like 1 (ACVRL1), mRNA, Database DDBJ/EMBL/GenBank [online], Accession No. NM_000020, Jul. 19, 2005, [retrieved on Mar. 5, 2012], URL http://www.ncbi.nlm.nih.gov/nuccore/4557242?sat=34&satkey=13274975.

Seki et al., "Arterial Endothelium-Specific Activin Receptor-Like Kinase 1 Expression Suggests Its Role in Arterialization and Vascular Remodeling," Circulation Research, 93:682-689 (2003).

Goumans et al., "Activin receptor-like kinase (ALK)1 is an antagonistic mediator of lateral TGFβ/ALK5 signaling," Molecular Cell, 12(4):817-828 (2003).

Wong et al., "Endoglin expression on human microvascular endothelial cells association with betaglycan and formation of higher order complexes with TGF-β signalling receptors," European Journal of Biochemistry, 267(17):5550-5560 (2000).

Abdalla, S., et al., "Analysis of ALK-1 and endoglin in newborns from families with hereditary hemorrhagic telangiectasia type 2," Human Mol. Gen., 9:1227-1237 (2000).

Abdalla, S., et al., "Visceral manifestations in hereditary haemorrhagic telangiectasia type 2," J. Med. Genet., 40:494-502 (2003).

Adamis, A., et al., "Angiogenesis and ophthalmic disease," Angiogenesis, 3:9-14 (1999).

Alexander, J., et al., "Tumor-Specific Expression and Alternate Splicing of Messenger Ribonucleic Acid Encoding Activin/Transforming Growth Factor-β Receptors in Human Pituitary Adenomas," Journal of Clinical Endocrinology and Metabolism, 81:783-790 (1996).

Altschul, et al., "Basic Local Alignment Search Tool," J. Mol Biol, 215:403-410 (1990).

Altschul, et al., "Gapped Blast and PSI-Blast: a new generation of protein database search programs," Nucleic Acids Res., 25: 3389-3402 (1997).

Anandarajah, A. and Ritchlin, C., "Pathogenensis of psoriatic arthritis," Curr. Opin. Rheumatol., 16:338-343 (2004).

ATCC Seach Output for PTA-6808 (p. 1).

Attisano, L., et al., "Identification of Human Activin and TGFβ Type I Receptors That Form Heteromeric Kinase Complexes with Type II Receptors," Cell, 75:671-680 (1993).

(56) References Cited

OTHER PUBLICATIONS

Babcook, J., et al., "A novel strategy for generating monoclonal antibodies from single, isolated lymphocytes producing antibodies of defined specificities," Proceedings of the National Academy of Sciences of the USA, 93:7843-7844 (1996).
Bainbridge, J., et al., "Gene therapy for ocular angiogenesis," Clinical Science, 104:561-575 (2003).
Bassing, C.H., et al., "A Transforming Growth Factor β Type I Receptor That Signals to Activate Gene Expression," Science, 263:87-89 (1994).
Bergers et al., "Tumorigenesis and the Angiogenic Switch," Nature Reviews, 3:401-410 (2003).
Bird, R., et al., "Single-Chain Antigen-Binding Proteins," Science, 242:423-426 (1988).
Blanco, F., et al, "Interaction and functional interplay between endoglin and ALK-1, two components of the endothelial transforming growth factor-β receptor complex," Journal of Cellular Physiology, (2003).
Bonnet, C. and Walsh, D., "Osteoarthritis, angiogenesis and inflammation," Rheumatology, 44:7-16 (2005).
Brorson et al., "Mutational analysis of avidity and fine specificity of anti-levan antibodies," Journal of Immunology, 163(12):6694-6701 (1999).
Brummell et al., "Probing the combining site of an anti-carbohydrate antibody by saturation-mutagenesis: role of the heavy-chain CDR3 residues," Biochemistry, 32:1180-1187 (1993).
Burkes et al., "In vitro scanning saturation mutagenesis of an antibody binding pocket," PNAS, 94:412-417 (1997).
Carmeliet, et al., "Angiogenesis in Health and Disease," Nature Medicine, 9:653-660 (2003).
Casset et al., "A peptide mimetic of an anti-CD4 monoclonal antibody by rational design," Biochemical and Biophysical Research Communications, 307:198-205 (2003).
Chen et al., "Selection and analysis of an optimized anti-VEGF antibody: crystal structure of an affinity-matured Fab in complex with antigen," Journal of Molecular Biology, 293:865-881 (1999).
Clavel, G., et al., "Recent data on the role for angiogenesis in rheumatoid arthritis," Joint Bone Spine, 70:321-326 (2003).
Coleman, "Effects of amino acid sequence changes on antibody-antigen interactions," Research in Immunology, 145:33-36 (1994).
Creamer, D., et al., "Angiogenesis in psoriasis," Angiogenesis, 5:231-236 (2002).
de Iongh, R., et al., "BMP and activin receptor expression in lens development," Molecular Vision, 10:566-576 (2004).
Dickson, M.C., et al., "Defective haematopoiesis and vasculogenesis in transforming growth factor β1 knockout mice," Development, 121:1845-1854 (1995).
Fernandez et al., "Blood outgrowth endothelial cells from Hereditary Haemorrhagic Telangiectasia patients reveal abnormalities compatible with vascular lesions," Cardiovascular Research, 68:235-248 (2005).
Franzén, P., et al., "Cloning of a TGFβ Type I Receptor That Forms a Heteromeric Complex with the TGFβ Type II Receptor," Cell, 75:681-692 (1993).
Gajdusek, C.M., et al., "Basic Fibroblast Growth Factor and Transforming Growth Factor Beta-1: Synergistic Mediators of Angiogenesis In Vitro," Journal of Cellular Physiology, 157:133-144 (1993).
Gonnet et al., "Exhaustive Matching of the Entire Protein Sequence Database," Science, 256:1443-1445 (1992).
Green, L., et al., "Antigen-specific human monoclonal antibodies from mice engineered with human Ig heavy and light chain YACs," Nature Genetics, 7:13-21 (1994).
Griffiths, A., et al., "Isolation of high affinity human antibodies directly from large synthetic repertoires," EMBO J., 13:3245-3260 (1994).
Hanahan, D., et al., "Patterns and Emerging Mechanisms of the Angiogenic Switch during Tumorigenesis," Cell, 86:353-364 (1996).
Heldin, C., et al, "TGF-β signalling from cell membrane to nucleus through SMAD proteins," Nature, 390:465-471 (1997).

Holliger, P., et al., "Diabodies: Small bivalent and bispecific antibody fragments," Proceedings of the National Academy of Sciences of the USA, 90:6444-6448 (1993).
Holm et al., "Functional mapping and single chain construction of the anti-cytokeratin 8 monoclonal antibody TS1," Molecular Immunology, 44:1075-1084 (2007).
Huston, J., et al., "Protein engineering of antibody binding sites: Recovery of specific activity in an anti-digoxin single-chain Fv analogue produced in *Escherichia coli*," Proceedings of the National Academy of Sciences of the USA, 85:5879-5883 (1988).
Jang et al., "The structural basis for DNA binding by an anti-DNA autoantibody," Molecular Immunology, 35(18):1207-1217 (1998).
Johnson, D., et al., "Mutations in the activin receptor-like kinase 1 gene in hereditary haemorrhagic telangiectasia type 2," Nature Genetics, 13:189-195 (1996).
Kipriyanov, S., et al., "Recombinant Single-Chain Fv Fragments Carrying C-Terminal Cysteine Residues: Production of Bivalent and Biotinylated Miniantibodies," Molecular Immunology, 31(14):1047-1058 (1994).
Kipriyanov, S., et al., "Single-chain antibody streptavidin fusions: Tetrameric bifunctional scFv-complexes with biotin binding activity and enhanced affinity to antigen," Human Antibodies and Hybridomas, 6:93-101 (1995).
Klaus, D., et al., "Novel Missense and Frameshift Mutations in the Activin Receptor-Like Kinase-1 Gene in Hereditary Hemorrhagic Telangiectasia," Human Mutation, vol. 12(2), 137-142 (1998).
Kobayashi et al., "Tryptophan H33 plays an important role in pyrimidine (6-4) pyrimidone photoproduct binding by a high-affinity antibody," Protein Engineering, 12(10):879-884 (1999).
Kretzschmar, M. and Massagué, J., "SMADs: mediators and regulators of TGF-β signaling," Current Opinion in Genetics & Development, 8:103-111 (1998).
Kumar et al., "Molecular cloning and expression of the Fabs of human autoantibodies in *Escherichia coli*. Determination of the heavy or light chain contribution to the anti-DNA/-cardiolipin activity of the Fab," Journal of Biological Chemistry. 275:35129-35136 (2000).
Lamouille et al., "Activin receptor—like kinase 1 is implicated in the maturation phase of angiogenesis," Blood, 100(13):4495-4501 (2002).
Lebrin, F., et al., "Endoglin promotes endothelial cell proliferation and TGF-β/ALK1 signal transduction," The EMBO Journal, 23:4018-4028 (2004).
Lechleider, R., et al, "Serine Phosphorylation, Chromosomal Localization, and Transforming Growth Factor-β Signal Transduction by Human bsp-1," The Journal of Biological Chemistry, 271:17617-17620 (1996).
Li, D.Y., et al., "Defective Angiogenesis in Mice Lacking Endoglin," Science, 284:1534-1537 (1999).
Lux, A., et al., "Assignment of Transforming Growth Factor β1 and β3 and a Third New Ligand to the Type I Receptor ALK-1," J. Biol. Chem., 274:9984-9992 (1999).
MacCallum et al., "Antibody-antigen interactions: contact analysis and binding site topography," Journal of Molecular Biology, 262(5):732-745 (1996).
Macias-Silva, M., et al., "Specific Activation of Smad1 Signaling Pathways by the BMP7 Type I Receptor, ALK2," The Journal of Biol. Chem., 273:25628-25636 (1998).
Massagué, J., "TGF-β Signal Transduction," Annu. Rev. Biochem., 67:753-791 (1998).
Massagué, J., "TGFβ Signaling in Growth Control, Cancer, and Heritable Disorders," Cell, 103:295-309 (2000).
McAllister, K., et al., "Endoglin, a TGF-β binding protein of endothelial cells, is the gene for hereditary haemorrhagic telangiectasia type 1," Nature Genetics, 8:345-351 (1994).
Miyazono et al.. "Id: A Target of BMP Signaling," Science's STKE, 2002 (151):PE40 (2002).
Molema, G., et al., "Tumor Vasculature Targeted Therapies," Biochemical Pharmacology, 55:1939-1945 (1998).
Ng, E. and Adamis, P., "Targeting angiogenesis, the underlying disorder in neovascular age-related macular degeneration," Can. J. Ophthalmol., 40:352-368 (2005).

(56) References Cited

OTHER PUBLICATIONS

Oh, S.P., et al., "Activin receptor-like kinase 1 modulates transforming growth factor-β1 signaling in the regulation of angiogenesis," PNAS, 97:2626-2631 (2000).
Oshima, M., et al., "TGF-β Receptor Type II Deficiency Results in Defects of Yolk Sac Hematopoiesis and Vasculogenesis," Developmental Biology, 179: 297-302 (1996).
Panchenko, M., et al, "Type I receptor serine-threonine kinase preferential expressed in pulmonary blood vessels," 1996 the American Physiological Society, L547-L558 (1996).
Pascalis et al., "Grafting of "abbreviated" complementarity-determining regions containing specificity-determining residues essential for ligand contact to engineer a less immunogenic humanized monoclonal antibody," The Journal of Immunology, 169:3076-3084 (2002).
Paul, William E., Fundamental Immunology, 242, M.D. Ed. 1993.
Pearson, et al., "Using the FASTA Program to Search Protein and DNA Sequence Databases,", Methods Mol. Biol., 24:307-331 (1994).
Penheiter, S., et al., "Internalization-Dependent and -Independent Requirements for Transforming Growth Factor β Receptor Signaling via the Smad Pathway," Molecular and Cellular Biology, 22:4750-4759 (2002).
Pepper, M., "Transforming Growth Factor-beta: Vasculogenesis, Angiogenesis, and Vessel Wall Integrity," Cytokine & Growth Factor Reviews, 8:21-43 (1997).
Pepper, M., et al., "Biphasic Effect of Transforming Growth Factor-β1 or in Vitro Angiogenesis," Experimental Cell Research, 204:356-363 (1993).
Poljak, R., "Production and structure of diabodies," Structure, 2(12):1121-1123 (1994).
R&D Systems: "Monoclonal anti-human ALK-1 Antibody," (downloaded from www.mdsystems.com/pdf/mab370.pdf) May 20, 2007.
R&D Systems: "New products from R&D Systems, Mar. 2002," (downloaded from www.rndsystems.com/DAM_public/5322.pdf) May 30, 2007.
Risau, W., "Mechanisms of angiogenesis," Nature, 386:671-674 (1997).
Rydén, M., et al., "A Novel Type I Receptor Serine-Threonine Kinase Predominantly Expressed in the Adult Central Nervous System," The Journal of Biological Chemistry, 48:30603-30609 (1996).
Sadick, H., et al., "Patients with hereditary hemorrhagic telangiectasia have increased plasma levels of vascular endothelial grown factor and transforming grown factor-β1 as well as high ALK1 tissue expression," Haematolgica, 90:818-828 (2005).
Sankar, S., et al., "Modulation of Transforming Growth Factor β Receptor Levels on Microvascular Endothelial Cells during In Vitro Angiogenesis," J. Clin. Invest., 97:1436-1446 (1996).
Satoh, T., et al, "Lack of circulating autoantibodies to bone morphogenetic protein receptor-II or activin receptor-like kinase 1 in mixed connective tissue disease patients with pulmonary arterial hypertension," Rheumatology, 44:192-196 (2004).
Smith-Gill et al., "Contributions of immunoglobulin heavy and light chains to antibody specificity for lysozyme and two haptens," Journal of Immunology, 139(12):4135-4144 (1987).
Song et al., "Light chain of natural antibody plays a dominant role in protein antigen binding," Biochemical and Biophysical Research Communications, 268(2)390-394 (2000).
Tahtis, K. et al., "Expression and Targeting of Human Fibroblast Activation Protein in a Human Skin/Severe Combined Immunodeficient Mouse Breast Cancer Xenograft Model," Molecular Cancer Therapeutics, 2:729-737 (2003).
ten Dijke, P., et al., "Activin receptor-like kinases: a novel subclass of cell-surface receptors with predicted serine/threonine kinase activity," Oncogene, 8:2879-2887 (1993).
ten Dijke, P., et al., "Characterization of type I receptors for transforming growth factor-beta and activin," Science, 264:101-104 (1994).
Thornton, et al., "Prediction of progress at last," Nature, 354:105-106 (1991).
Trembath, R., et al, "Clinical and Molecular Genetic Features of Pulmonary Hypertension in Patients With Hereditary Hemorrhagic Telangiectasia," N. Engl. J. Med., 345:325-334 (2001).
Urness, L., et al., "Arteriovenous malformations in mice lacking activin receptor-like kinase-1," Nature Genetics, 26:328-331 (2000).
Vajdoos, et al., "Comprehensive functional maps of the antigen-binding site of an anti-ErbB2 antibody obtained with shotgun scanning mutagenesis," Journal of Molecular Biology, 320(2):415-428 (2002).
Volpert, O., et al., "Id1 regulates angiogenesis through transcriptional repression of thrombospondin-1," Cancer Cell, 2:473-483 (2002).
Ward, E., et al., "Binding activities of a repertoire of single immunoglobulin variable domains secreted from *Escherichia coli*," Nature, 341:544-546 (1989).
Witmer, A., et al., "Vascular endothelial growth factors and angiogenesis in eye disease," Progress in Retinal and Eye Research, 22:1-29 (2003).
Wu et al, "Humanization of a murine monoclonal antibody by simultaneous optimization of framework and CDR residues," Journal of Molecular Biology, 294:151-162 (1999).
Yan, H-C., et al., "Human/Severe Combined Immunodeficient Mouse Chimeras, An Experimental in Vivo Model System to Study the Regulation of Human Endothelial Cell-Leukocyte Adhesion Molecules," J. Clinical Investigation, 91:986-996 (1993).
Yingling, J., et al, "Mammalian dwarfins are phosphorylated in response to transforming growth factor β and are implicated in control of cell growth," PNAS, 93:8940-8944 (1996).
Brown et al., "Tolerance of single, but not multiple, amino acid replacements in antibody VH CDR 2: a means of minimizing B cell wastage from somatic hypermutation?," Journal of Immunology, 155(9):3285-3291 (1996).
Davies et al., "Affinity improvement of single antibody VH domains: residues in all three hypervariable regions affect antigen binding," Immunotechnology, 2(3):169-179 (1996).
Giusti et al., "Somatic diversification of S107 from an antiphosphocholine to an anti-DNA autoantibody is due to a single base change in its heavy chain variable region," Proc. Nat. Acad. Sci. USA, 84(9):2926-2930 (1987).
Holt et al., "Domain antibodies: proteins for therapy," Trends in Biotechnology, 21(11):484-490 (2003).
Krieg et al., "Functional analysis of B and T lymphocyte attenuator engagement on CD4+ and CD8+ T cells," Journal of Immunology, 175(10):6420-6427 (2005).
Kussie et al., "A single engineered amino acid substitution changes antibody fine specificity," Journal of Immunology, 152(1):146-152 (1994).
Liu et al., "Fine mapping of the antigen-antibody interaction of scFv215, a recombinant antibody inhibiting RNA polymerase II from *Drosophila melanogaster*," Journal of Molecular Recognition, 12(2):103-111 (1999).
Maynard et al., "Antibody engineering," Annual Review of Biomedical Engineering, 2:339-376 (2000).
Pini et al., "Design and use of a phage display library. Human antibodies with subnanomolar affinity against a marker of angiogenesis eluted from a two-dimensional gel," Journal of Biological Chemistry, 273(34):21769-21776 (1998).
Rudikoff et al., "Single amino acid substitution altering antigen-binding specificity," Proc. Nat. Acad. Sci. USA, 79(6):1979-1983 (1982).
Schildbach et al., "Contribution of a single heavy chain residue to specificity of an anti-digoxin monoclonal antibody," Protein Science, 3(5):737-749 (1994).
Schildbach et al., "Heavy chain position 50 is a determinant of affinity and specificity for the anti-digoxin antibody 26-10," Journal of Biological Chemistry, 268(29):21739-21747 (1993).
Xiang et al., "Study of B72.3 combining sites by molecular modeling and site-directed mutagenesis," Protein Engineering, 13(5):339-344 (2000).

* cited by examiner

FIG. 2

```
human  MTLGSPRKGLLMLLMALVTQGDPVKPSRGPLVTCTCESPHCKGPTCRGAWCTVVLVREEG  60
Cyno   MTLGSPRRGLLMLLMALVTQGDPVKPSRGPLVTCTCESPHCRGPTCQGAWCTVVLVREEG  60
       ****:*******************************::********* human  RHPQEHRGCGNLHRELCRGRPTEFVNHYCCDSHLCNHNVSLVLEATQPPSEQPGTDGQLA  120
Cyno   RHPQEHRGCGNLHRELCRGRPTEFVNHYCCDSHLCNRNVSLVLEATQTPSEQPGTDSQLA  120
       *********************************:******.***:* human  LILGPVLALLALVALGVLGLWHVRRRQEKQRGLHSELGESSLILKASEQGDTMLGDLLDS  180
Cyno   LILGPVLALLALVALGVVGLWHVRRRQEKQRGLHSELGESSLILKASEQGDSMLGDLLDS  180
       ***************:*****************************:***** human  DCTTGSGSGLPFLVQRTVARQVALVECVGKGRYGEVWRGLWHGESVAVKIFSSRDEQSWF  240
Cyno   DCTTGSGSGLPFLVQRTVARQVALVECVGKGRYGEVWRGLWHGESVAVKIFSSRDEQSWF  240
       ************************************************************ human  RETEIYNTVLLRHDNILGFIASDMTSRNSSTQLWLITHYHEHGSLYDFLQRQTLEPHLAL  300
Cyno   RETEIYNTVLLRHDNILGFIASDMTSRNSSTQLWLITHYHEHGSLYDFLQRQTLEPHLAL  300
       ************************************************************ human  RLAVSAACGLAHLHVEIFGTQGKPAIAHRDFKSRNVLVKSNLQCCIADLGLAVMHSQGSD  360
Cyno   RLAVSAACGLAHLHVEIFGTQGKPAIAHRDFKSRNVLVKSNLQCCIADLGLAVMHSQGSD  360
       ************************************************************ human  YLDIGNNPRVGTKRYMAPEVLDEQIRTDCFESYKWTDIWAFGLVLWEIARRTIVNGIVED  420
Cyno   YLDIGNNPRVGTKRYMAPEVLDEQIRTDCFESYKWTDIWAFGLVLWEIARRTIVNGIVED  420
       ************************************************************ human  YRPPFYDVVPNDPSFEDMKKVVCVDQQTPTIPNRLAADPVLSGLAQMMRECWYPNPSARL  480
Cyno   YRPPFYDVVPNDPSFEDMKKVVCVDQQTPTIPNRLAADPVLSGLAQMMRECWYPNPSARL  480
       ************************************************************ human  TALRIKKTLQKISNSPEKPKVIQ 503    (SEQ. ID NO.:130)
Cyno   TALRIKKTLQKISNSPEKPKVIQ 503    (SEQ. ID NO.:93)
       ***********************
```

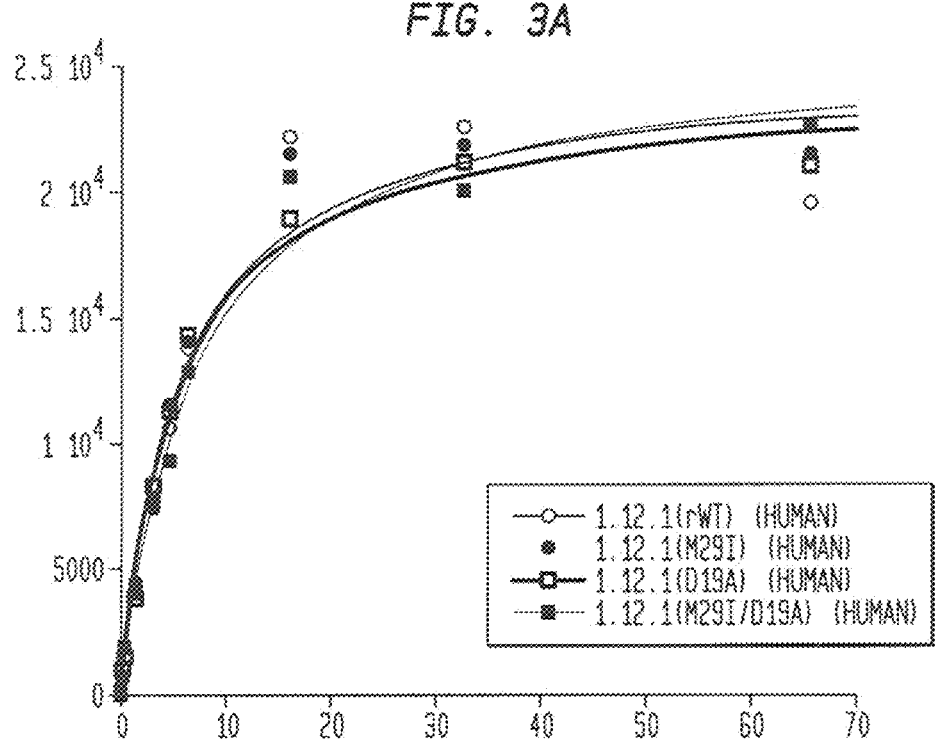
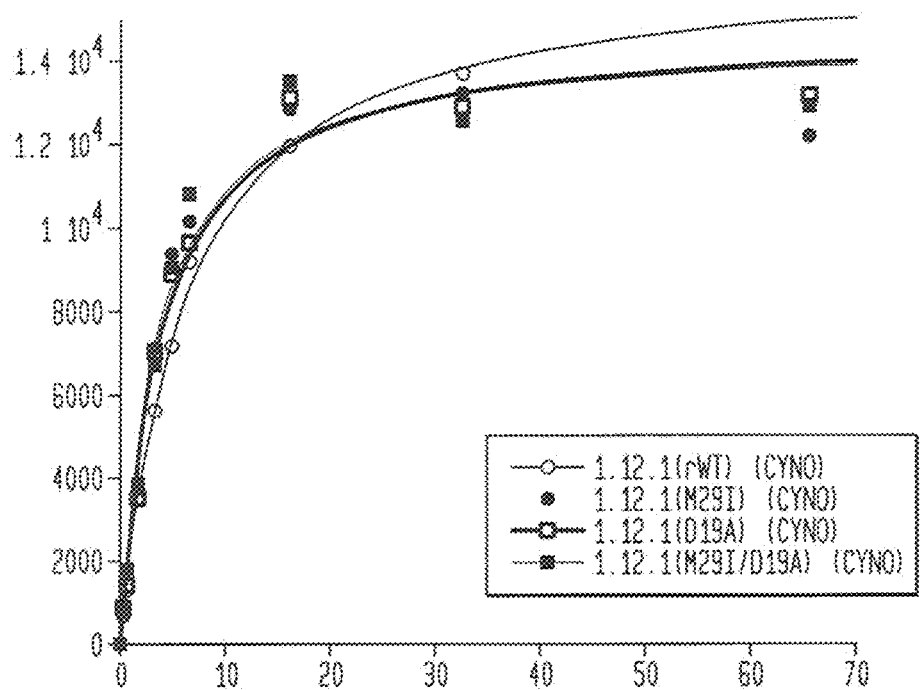

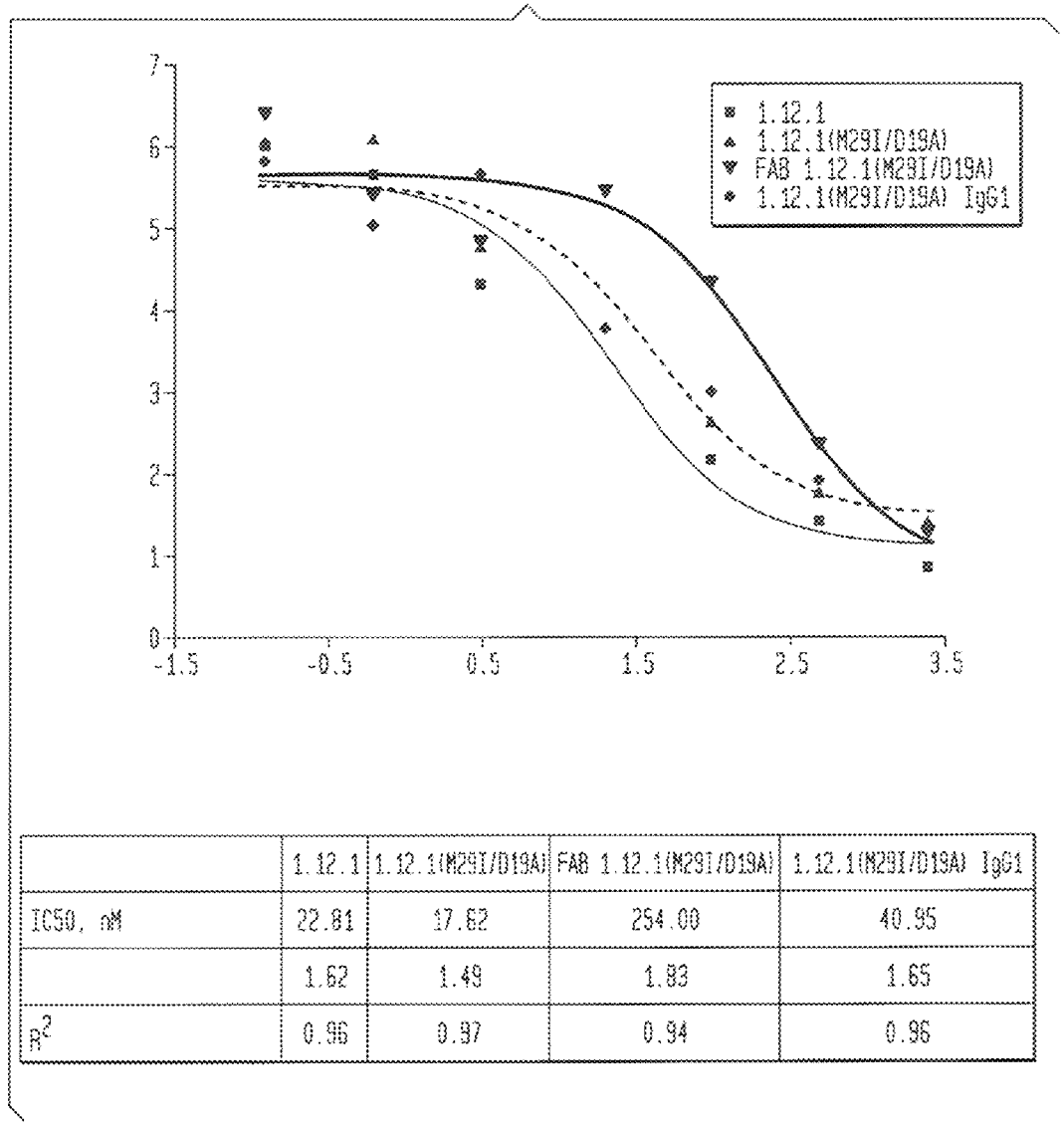

FIG. 7A

```
Expressed:      1  QVQLQESGPGLVKPSQTLSLTCTVSGGS SSG YYW WIRQHPGKGLEWIGYIYYSGSTY  60
(SEQ ID NO:104)
Germline:       1  QVQLQESGPGLVKPSQTLSLTCTVSGGSISSGGYYWSWIRQHPGKGLEWIGYIYYSGSTY  60
(SEQ ID NO:131)

Expressed:     61  YNPSLKSRVTISVDTSKNQFSLKLSSVTAADTAVYYCAR - VAG-FDYWGQGTLVTVSS  118
Germline:      61  YNPSLKSRVTISVDTSKNQFSLKLSSVTAADTAVYYCARGLAVAGYFDYWGQGTLVTVSS  120

Expressed:      1  EIVLTQSPGTLSLSPGER TLSCRASQSVSSSYLAWYQQKPGQAPRLLIYG SSRATGIP  60
(SEQ ID NO:127)
Germline:       1  EIVLTQSPGTLSLSPGERATLSCRASQSVSSSYLAWYQQKPGQAPRLLIYGASSRATGIP  60
(SEQ ID NO:132)

Expressed:     61  DRFSGSGSGTDFTLTISRLEPEDFAVYYCQQYGSSPITFGQGTRLEIK  108
Germline:      61  DRFSGSGSGTDFTLTISRLEPEDFAVYYCQQYGSSPITFGQGTRLEIK  108
```

FIG. 7B

```
            10              20              30
   ----------+---------------+---------------+--
 1 EIVLTQSPGTLSLSPGER  TLSCRASQSVS  1.12.1 VL (SEQ ID 127)
 1 EIVLTQSPGTLSLSPGERATLSCRASQSVS   1.14.1 VL (SEQ ID 20)
 1 EIVLTQSPGTLSLSPGERATLSCRASQSVS   1.162.1 VL (SEQ ID 20)
 1 EIVLTQSPGTLSLSPGERATLSCRASQSVS   1.31.1 VL (SEQ ID 135)
 1 ESVLTQSPGTLSLSPGERATLSCRASQSVS   4.62.1 VL (SEQ ID 69)
 1 EIVLTQSPGTLSLSPGERATLSCRASQSVS   4.72.1 VL (SEQ ID 69)
 1 EIVLTQSPGTLSLSPGERATLSCRASQSVS   Germline (A27) (SEQ ID NO:133)

40              50              60
   ----------+---------------+---------------+--
31 SSYLAWYQQKPGQAPRLLIYG  SSRATGIP  1.12.1 VL
31 S YLAW  QQKPGQAPRLLIYG  SSRA  G P  1.14.1 VL
31 SSYLAWYQQKPGQAPRLLIYGASSRATGIP  1.162.1 VL
31 SSYLAWYQQKPGQAPRLLIYGASSRATGIP  1.31.1 VL
31 SSYLAWYQQKPGQAPRLLIYG  SSRATGIP  4.62.1 VL
31 SSYLAWYQ KPGQAPRLLIYG  SSRATGIP  4.72.1 VL
31 SSYLAWYQQKPGQAPRLLIYGASSRATGIP  Germline (A27)

70              80              90
   ----------+---------------+---------------+--
61 DRFSGSGSGTDFTLTISRLEPEDFAVYYCQ  1.12.1 VL
61 DRFSGSGSGTDFTLTISRLEPEDFAVYYCQ  1.14.1 VL
61 DRFSGSGSGTDFTLTI RL  PEDFAVYYCQ  1.162.1 VL
61 DRFSGSGSGTDFTLTISRLEPEDFAVYYCQ  1.31.1 VL
61 DRFSGSGSGTDFTLTISRLEPEDFAVYYCQ  4.62.1 VL
61 DRFSGSGSGTDFTLTISRLEPEDFAVYYCQ  4.72.1 VL
61 DRFSGSGSGTDFTLTISRLEPEDFAVYYCQ  Germline (A27)

100
   ----------+--------
91 QYGSSPITFGQGTRLEIK   1.12.1 VL
91 QYGSSPITFGQGTRLEIK   1.14.1 VL
91   YGSSPITFGQGTRLEIK  1.162.1 VL
91    GSSPITFGQGTRLEIK  1.31.1 VL
91 QYGSSPITFGQGTRLEIK   4.62.1 VL
91 QYGSS  ITFGQGTRLEIK  4.72.1 VL
91 QYGSSP               Germline (A27)
```

FIG. 7C

```
                    10                  20                  30
     ----+---------+---------+---------+---------+---------+--
   1 Q V Q L Q E S G P G L V K P S Q T L S L T C T V S G G S M S  1.12.1 VH (SEQ ID 104)
   1 Q V Q L Q E S G P G L V K P S Q T L S L T C T V S G G S I S  1.151.1 VH (SEQ ID 22)
   1 Q V Q L Q E S G P G L V K P S Q T L S L I C T V S G G S I S  1.162.1 VH (SEQ ID 26)
   1 Q M Q L Q E S G P G L V K P S Q T L S L T C T V S G G S I S  1.8.1 VH (SEQ ID 34)
   1 Q V Q L Q E S G P G L V K P S Q T L S L T C T V S G G S I S  4.24.1 VH (SEQ ID 46)
   1 Q V Q L Q E S G P G L V K P S Q T L S L T C T V S G G S I S  4.38.1 VH (SEQ ID 50)
   1 Q V Q L Q E S G P G L V K P S Q T L S L T C T V S G G S I S  4.58.1 VH (SEQ ID 54)
   1 Q V Q L Q E S G P G L V K P S Q T L S L T C T V S G G S I S  4.62.1 VH (SEQ ID 58)
   1 Q V Q L Q E S G P G L V K P S Q T L S L T C T V S G G S I S  4.68.1 VH (SEQ ID 62)
   1 Q V Q L Q E S G P G L V K P S Q T L S L T C T V S G G S I S  4.72.1 VH (SEQ ID 66)
   1 Q V Q L Q E S G P G L V K P S Q T L S L T C T V S G G S I S  5.13.1 VH (SEQ ID 70)
   1 Q V Q L Q E S G P G L V K P S Q T L S L T C T V S G G S I S  5.34.1 VH (SEQ ID 74)
   1 Q V Q L Q E S G P G L V K P S Q T L S L T C T V S G G S I S  4-31 Germline (SEQ ID NO:134)

40                  50                  60
     ----+---------+---------+---------+---------+---------+--
  31 S G E Y Y W N W I R Q H P G K G L E W I G Y I Y Y S G S T Y  1.12.1 VH
  31 S G G H Y W S W I R Q H P G K G L E W I G Y I Y Y S G S T Y  1.151.1 VH
  31 S G E Y Y W S W I R Q H P G K G L E W I G Y I Y Y S G S T Y  1.162.1 VH
  31 S G G H Y W S W I R Q H P G K G L E W I G Y I Y Y S G S A Y  1.8.1 VH
  31 S N Q Y Y W N W I R Q H P G K G L E W I G Y I Y Y S G S T Y  4.24.1 VH
  31 S G D Y Y W S W I R Q H P G K G L E W I G Y I Y Y S G S T Y  4.38.1 VH
  31 S G D Y Y W N W I R Q H P G K G L E W I G Y I Y Y S G S T Y  4.58.1 VH
  31 S G D Y Y W N W I R Q H P G K G L E W I G Y I Y Y S G S T Y  4.62.1 VH
  31 S G D Y Y W N W I R Q H P G K G L E W I G Y I Y Y S G S T Y  4.68.1 VH
  31 S G E Y Y W S W I R Q H P G K G L E W I G Y I F Y S G S T Y  4.72.1 VH
  31 S G D Y Y W N W I R Q H P G K G L E W I G Y I Y Y S G S T Y  5.13.1 VH
  31 S G D Y Y W N W I R Q H P G K G L E W I G Y I Y Y S G S T Y  5.34.1 VH
  31 S G G Y Y W S W I R Q H P G K G L E W I G Y I Y Y S G S T Y  4-31 Germline
```

FIG. 7D

```
              70             80             90
    ----------+--------------+--------------+-
 61 Y N P S L K S R V T I S V D T S K N Q F S L K L S S V T A A    1.12.1 VH
 61 Y N P S L K S R V T I S V D T S K N Q F S L K L S S V T A A    1.151.1 VH
 61 Y N P S L K S R L T I S V D T S K N Q F S L K L S S V T A A    1.162.1 VH
 61 Y N P S L K S R V T I S V D T S K N Q F S L K L S S V T A A    1.8.1 VH
 61 Y N P S L K S R V T I S V D T S K N Q F S L K L S S V T A A    4.24.1 VH
 61 Y N P S L K S R V T I S I D T S K N Q F S L K L S S V T A A    4.38.1 VH
 61 Y N P S L K S R V T I S V A T S K N Q F S L K L S S V T A A    4.58.1 VH
 61 Y N P S L K S R V T I S V D T S K N Q F S L K L S S V T A A    4.62.1 VH
 61 Y N P S L K S R V T I S V D T S K N Q F S L K L S S V T A A    4.68.1 VH
 61 Y N P S L K S R V T I S L D T S K N Q F S L K L S S V T A A    4.72.1 VH
 61 Y N P S L K S R V T I S V D T S K N Q F S L K L S S V T A A    5.13.1 VH
 61 Y N S S L K S R V T I S V D T S K N Q F S L K L S S V T A A    5.34.1 VH
 61 Y N P S L K S R V T I S V D T S K N Q F S L K L S S V T A A    4-31 Germline 91 D T A V Y Y C A R    1.12.1 VH
 91 D T A V Y Y C A R    1.151.1 VH
 91 D T A V Y Y C A R    1.162.1 VH
 91 D T A V Y Y C A R    1.8.1 VH
 91 D T A V Y Y C A R    4.24.1 VH
 91 D T A V Y Y C A R    4.38.1 VH
 91 D T A V Y Y C A R    4.58.1 VH
 91 D T A V Y Y C A R    4.62.1 VH
 91 D T A V Y Y C A R    4.68.1 VH
 91 D T A V Y Y C A R    4.72.1 VH
 91 D T A V Y Y C A R    5.13.1 VH
 91 D T A V Y Y C A R    5.34.1 VH
 91 D T A V Y Y C A R    4-31 Germline
```

HUMAN MONOCLONAL ANTIBODIES TO ACTIVIN RECEPTOR-LIKE KINASE-1

This application is a divisional application under 35 U.S.C. §121 of U.S. application Ser. No. 12/402,854, filed Mar. 12, 2009 and issued as U.S. Pat. No. 8,080,646 on Dec. 20, 2011, which is a divisional application of U.S. application Ser. No. 11/517,530, filed Sep. 6, 2006 and issued as U.S. Pat. No. 7,537,762 on May 26, 2009, which claims priority under 35 U.S.C. §119(e) from U.S. provisional application 60/715,292, filed Sep. 7, 2005. The disclosures of all of the aforementioned priority applications are incorporated herein by reference in their entirety.

The instant application contains a Sequence Listing that has been submitted in ASCII format via EFS-Web and is hereby incorporated by reference in its entirety. Said ASCII file, created on Oct. 26, 2011, is named sequencelisting.TXT and is 114,229 bytes in size.

FIELD OF THE INVENTION

The present invention relates to human monoclonal antibodies and antigen-binding portions thereof that bind to the extracellular domain (ECD) of activin receptor-like kinase-1 (ALK-1). The invention also relates to nucleic acid molecules encoding such antibodies and antigen-binding portions, methods of making human anti-ALK-1 antibodies and antigen-binding portions, compositions comprising these antibodies and antigen-binding portions and methods of using the antibodies, antigen-binding portions, and compositions.

BACKGROUND OF THE INVENTION

ALK-1 is a type I cell surface receptor for transforming growth factor beta receptor type 1 (TGF-beta-1). Human ALK-1 is a 503 amino acid polypeptide, which includes a signal sequence (amino acids: 1-21), a N-terminal extracellular TGF-beta-1 ligand binding domain or ECD (amino acids: 22-118), a single transmembrane domain (amino acids: 119-141) a regulatory glycine/serine rich (GS) domain (amino acids: 142-202) and a C-terminal a serine-threonine kinase domain (202-492). The amino acid sequence of human ALK-1 disclosed in Attisano et al, *Cell*, 1993, vol. 75, pp. 671-680 includes Ser at position 172 (Genbank record L17075), while U.S. Pat. No. 6,316,217 claims the amino acid sequence of human ALK-1 with Thr at position 172 (Genbank record NM_000020), ACVRL1 gene encoding a full-length human ALK-1 disclosed in Attisano et al. is commercially available from Invitrogen Inc., Clone ID IOH21048. Although ALK-1 shares 60-80% overall homology with other type I receptors (ALK-2 through ALK-7). ECD of ALK-1 is remarkably divergent from ECDs of other ALK family members. For example, in human, only ECD of ALK-2 is significantly related ECD of ALK-1 (sharing approximately 25% amino acid identity), U.S. Pat. No. 6,316,217; ten Dijke et al. *Oncogene*, 1993, vol. 8, pp. 2879-2887; Attisano et al. *Cell*, 1993, vol. 75, pp. 671-680.

In general, TGF-beta superfamily ligands exert their biological activities via binding to heteromeric receptor complexes of two types (I and II) of serine/threonine kinases. Type II receptors are constitutively active kinases that phosphorylate type I receptor upon ligand binding. In turn, activated type I kinases phosphorylate downstream signaling molecules including the various Smads, which translocate to the nucleus and lead to a transcriptional response. Heldin et al. *Nature*, 1997, vol. 390, pp. 465-471. In the case of ALK-1, we have shown that Smad1 is specifically phosphorylated and translocates to the nucleus where it directly regulates the expression of the Smad1 responsive genes Id1 and EphB2.

ALK-1 is expressed highly and selectively in endothelial cells and other highly vascularized tissues such as placenta or brain. We have shown by AFFYMETRIX® profiling and real-time RT-PCR that the expression of ALK-1 in endothelial cells highly exceeds the expression of its co-receptors activin type II and endoglin, its ligand TGF-beta-1 ALK-5. Mutations in ALK-1 are associated with heredity hemorrhagic telangiectasia (HHT), suggesting a critical role for ALK-1 in the control of blood vessel development or repair. Abdalla et al. *J. Med. Genet.*, 2003, vol. 40, pp. 494-502; Sadick et al. *Hematologica/The Hematology J.*, 2005, vol. 90, 818-828. Furthermore, two independent studies of ALK-1 knockout mice provide the key in vivo evidence for ALK-1 function during angiogenesis. Oh et al. *Proc Natl Acad Sci USA*, 2000, vol. 97, pp. 2626-2631; Urness et al. *Nature Genetics*, 2000, vol. 26, pp. 328-331.

Angiogenesis is the physiological process involving the formation of new blood vessels from pre-existing vessels and/or circulating endothelial stem cells. This is a normal process in growth and development, as well as in wound healing. However, this is also a fundamental step in the transition of tumors from a dormant state to a malignant state. Hanahan and Folkman, "Patterns and Emerging Mechanisms of the Angiogenic Switch During Tumorigenesis," *Cell*, 86(3):353-364, 1996; Carmeliet, "Angiogenesis in Health and Disease," *Nature Medicine*, 9(6):653-660, 2003; Bergers and Benjamin, "Tumorigenesis and the Angiogenic Switch," *Nature Reviews*, 3:401-410, 2003. In diseases like cancer, the body loses the ability to maintain balanced angiogenesis. New blood vessels feed diseased tissues, destroy normal tissues, and in the case of some cancers, the new vessels can allow tumor cells to escape into the circulation and lodge in other organs (tumor metastases). Angiogenesis inhibitors, including monoclonal antibodies (mAbs), are a very promising class of drugs targeted against this abnormal process to block or slow tumor growth.

In addition to a role in solid tumor growth and metastasis, other notable conditions with an angiogenic component are, for example, arthritis, psoriasis, neovascular age-related macular degeneration and diabetic retinopathy. Bonnet et al. "Osteoarthritis, Angiogenesis and Inflammation," *Rheumatology*, 2005, vol. 44, pp. 7-16; Creamer et al. "Angiogenesis in psoriasis," *Angiogenesis*, 2002, vol. 5, pp. 231-236; Clavel et al. "Recent data on the role for angiogenesis in rheumatoid arthritis," *Joint Bone Spine*, 2003, vol. 70, pp. 321-326; Anandarajah et al. "Pathogenesis of psoriatic arthritis," *Curr. Opin. Rheumatol.*, 2004, vol. 16, pp. 338-343; Ng et al. "Targeting angiogenesis, the underlying disorder in neovascular age-related macular degeneration," *Can. J. Ophthalmol.*, 2005, vol. 40, pp. 352-368; Witmer et al. "Vascular endothelial growth factors and angiogenesis in eye disease," *Progress in Retinal & Eye Research*, 2003, vol. 22, pp. 1-29; Adamis et al. "Angiogenesis and ophthalmic disease," *Angiogenesis*, 1999, vol. 3, pp. 9-14.

Anti-angiogenic therapies are expected to be chronic in nature. Accordingly, targets with highly selective endothelial function, such as ALK-1, are preferred to reduce attrition resulting from side effects. Furthermore, given the remarkable divergence of the ALK-1 ECD from ECDs of other ALK family members, mAb raised against the human ALK-1 ECD are expected to selectively target ALK-1. Based on these considerations, a monoclonal antibody against the ALK-1 extracellular domain that may inhibit dimerization with the type receptor and therefore block Smad1 phosphorylation and the downstream transcriptional response is highly desirable.

R&D Systems, Inc. makes and sells a monoclonal anti-human ALK-1 antibody (Cat. # MAB370) produced from a hybridoma resulting from the fusion of mouse myeloma with B cells obtained from a mouse immunized with purified NS0-derived recombinant human ALK-1 extracellular domain. We have shown that this antibody neither neutralizes the interaction between ALK-1 and TGF-beta-1 nor abrogates Smad1 phosphorylation. Rabbit antisera have been generated against a synthetic peptide corresponding to a part of the intracellular juxtamembrane region of ALK-1 (amino acid residues 145-166), coupled to key-hole limpet haemocyanin (KLH) (U.S. Pat. No. 6,692,925) and against the entire ALK-1 extracellular domain except for the leading sequence (Lux et al., *J. Biol. Chem.*, 1999, vol. 274, pp. 9984-9992). Abdalla et al (*Human Mol. Gen.*, 2000, vol. 9, pp. 1227-1237) report generation of a polyclonal antibody to ALK-1 using a recombinant vaccinia virus construct. R&D Systems, Inc. makes and sells a polyclonal anti-human ALK-1 antibody (Cat. # AF370) produced in goats immunized with purified, NS0-derived, recombinant human ALK-1 extracellular domain.

To date, no fully human monoclonal antibodies to the ECD of ALK-1 have been reported, and no-one has demonstrated the efficacy of any monoclonal antibody to the ECD of ALK-1 in abrogating the ALK-1/TGF-beta-1/Smad1 signaling pathway.

SUMMARY OF THE INVENTION

The invention pertains to isolated neutralizing anti-ALK-1 monoclonal antibodies or antigen-binding portions thereof that bind to primate ALK-1, preferably the ECD of primate ALK-1, more preferably the ECD of human ALK-1. In a preferred embodiment, the neutralizing antibodies are fully human monoclonal antibodies or antigen-binding portions thereof.

In another aspect, the present invention is an anti-ALK-1 antibody or antigen-binding portion thereof which antibody or antigen-binding portion thereof abrogates the ALK-1/TGF-beta-1/Smad1 signaling pathway. In a preferred embodiment, the antibodies are fully human monoclonal antibodies or antigen-binding portions thereof.

In another aspect, the present invention is an anti-ALK-1 antibody or antigen-binding portion thereof which antibody or antigen-binding portion thereof is an antagonist of TGF-beta-1-stimulated angiogenesis. In a preferred embodiment, the antibodies are fully human monoclonal antibodies or antigen-binding portions thereof.

In another aspect, the present invention is a fully-human anti-ALK-1 antibody or antigen-binding portion thereof which antibody or antigen-binding portion thereof is an antagonist of TGF-beta-1-stimulated tumor angiogenesis.

In another aspect, the present invention is a well-tolerated, injectable, fully-human anti-ALK-1 antibody or antigen-binding portion thereof which antibody or antigen-binding portion thereof is an antagonist of TGF-beta-1-stimulated angiogenesis.

In another aspect, the present invention is an anti-ALK-1 antibody or antigen-binding portion thereof which antibody or antigen-binding portion thereof inhibits up-regulation of a specific downstream target gene of ALK-1, Id1. In a preferred embodiment, the antibodies are fully human monoclonal antibodies or antigen-binding portions thereof.

In another aspect, the present invention is an anti-ALK-1 monoclonal antibody or antigen-binding portion thereof wherein the antibody or antigen-binding portion thereof is described in terms of at least one of several functional properties as described below.

For example, in one embodiment the antibody or antigen-binding portion thereof binds to the extracellular domain of primate ALK-1 with an avidity value of 1 µM or less as measured by surface plasmon resonance. In a further embodiment, the antibody or portion binds to the extracellular domain of primate ALK-1 with an avidity value of less than 100 nM, less than 5 nM, less than 1 nM, less than 500 pM, less than 100 pM, less than 50 pM, less than 20 pM, less than 10 pM, or less than 1 pM, as measured by surface plasmon resonance. In certain embodiments, the avidity value is from 0.1 pM to 1 µM. In other embodiments, the avidity value is from 1 pM to 100 nM. In other embodiments, the avidity value is from 1 pM to 5 nM. In other embodiments, the avidity value is from 1 pM to 500 pM. In other embodiments, the avidity value is from 1 pM to 100 pM. In other embodiments, the avidity is from 1 pM to 10 pM.

In another embodiment, the antibody or antigen-binding portion thereof binds to the extracellular domain of human ALK-1 with an avidity value of 100 nM or less as measured by surface plasmon resonance. In a further embodiment, the antibody or portion binds to the extracellular domain of human ALK-1 with an avidity value of less than 10 nM, less than 5 nM, less than 1 nM, less than 500 pM, less than 100 pM, less than 50 pM, less than 20 pM, less than 10 pM, or less than 1 pM, as measured by surface plasmon resonance. In certain embodiments, the avidity value is from 1 pM to 100 nM. In other embodiments, the avidity value is from 1 pM to 5 nM. In other embodiments, the avidity value is from 1 pM to 500 pM. In other embodiments, the avidity value is from 1 pM to 100 pM. In other embodiments, the avidity is from 10 pM to 10 pM.

In another embodiment, the antibody or portion thereof has an off rate ($k_{off}$) for human ALK-1 of $5 \times 10^{-3}$ s$^{-1}$ or smaller as measured by surface plasmon resonance. For example, in certain embodiments the antibody or portion has a $k_{off}$ for human ALK-1 of less than $10^{-3}$ s$^{-1}$, less than $5 \times 10^{-4}$ s$^{-1}$, less than $10^{-4}$ s$^{-1}$, less than $5 \times 10^{-5}$ s$^{-1}$, less than $10^{-5}$ s$^{-1}$, or less than $5 \times 10^{-6}$ s$^{-1}$. In other embodiments, the $k_{off}$ is from $10^{-6}$ s$^{-1}$ to $10^{-4}$ s$^{-1}$. In other embodiments, the $k_{off}$ is from $10^{-6}$ s$^{-1}$ to $5 \times 10^{-5}$ s$^{-1}$.

In another embodiment, the antibody or portion thereof binds to primate ALK-1 with a $K_D$ of 1000 nM or less. In a further embodiment, the antibody or portion binds to human ALK-1 with a $K_D$ of less than 500 nM, less than 100 nM, less than 50 nM, less than 20 nM, less than 10 nM, or less than 1 nM, as measured by surface plasmon resonance. In certain embodiments, the $K_D$ is from 1 µM to 100 nM. In other embodiments, the $K_D$ is from 100 nM to 10 nM. In other embodiments, $K_D$ is from 50 nM to 0.1 nM. Such $K_D$ values can be measured by any technique known those of skill in the art, such as by ELISAs, RIAs, flow cytometry, or surface plasmon resonance, such as BIACORE®.

In another embodiment, the antibody or portion thereof has a greater binding affinity for primate ALK-1 ($K_D(P)$) than for rodent ALK-1 ($K_D(R)$). In one embodiment, the antibodies or antigen-binding portions thereof of the present invention have a $K_D(R)/K_D(P)$ that is greater than or equal to 1.5. In a further embodiment the antibodies or antigen-binding portions thereof of the present invention have a $K_D(R)/K_D(P)$ that is greater than or equal 2, greater than or equal to 3, greater than or equal to 5, greater than or equal to 10, greater than or equal to 20, greater than or equal to 50, greater than or equal to 100, greater than or equal to 200, greater than or equal to 500, or greater than or equal to 1000. Such $K_D$ values for both primate ALK-1 and for rodent ALK-1 can be measured by any technique known to those of skill in the art, such as by flow cytometry, ELISA, RIA, or surface plasmon resonance, such as BIACORE®.

In another embodiment, the anti-ALK-1 antibody or portion thereof has an $IC_{50}$ of 500 nM or less as measured by their ability to inhibit up-regulation of a specific downstream target gene of ALK-1, Id1. In a further embodiment, said $IC_{50}$ is less than 300 nM, less than 200 nM, less than 150 nM, less than 100 nM, less than 50 nM, less than 20 nM, less than 10 nM, or less than 1 nM. In certain embodiments, the $IC_{50}$ is from 1 nM to 500 nM. In other embodiments, the $IC_{50}$ is from 5 nM to 250 nM. In other embodiments, the $IC_{50}$ is from 10 nM to 100 nM.

In another embodiment, the anti-ALK-1 antibody or portion thereof has an $IC_{50}$ of 250 nM or less as measured by their ability to inhibit Smad1 phosphorylation determined by Western Blotting using ODYSSEY® Infrared Imaging System. In a further embodiment, said $IC_{50}$ is less than 200 nM, less than 150 nM, less than 100 nM, less than 50 nM, less than 20 nM, less than 10 nM, or less than 1 nM. In certain embodiments, the $IC_{50}$ is from 1 nM to 250 nM. In other embodiments, the $IC_{50}$ is from 5 nM to 200 nM. In other embodiments, the $IC_{50}$ is from 10 nM to 100 nM.

In another embodiment, the anti-ALK-1 antibody or portion thereof inhibits human vessel angiogenesis in a SCID mouse engrafted with human foreskin tissue, in which human melanoma M24met tumor cells are intradermally implanted as determined by IHC analysis of human CD-31 signal assay by at least 40% as compared to a control sample. In a further embodiment, the anti-ALK-1 antibody or portion thereof inhibits human vessel angiogenesis in a SCID mouse engrafted with human foreskin tissue, in which human melanoma M24met tumor cells are intradermally implanted by at least 30%, at least 40%, at least 50%, or at least 60% as compared to a control sample.

In another embodiment, the anti-ALK-1 antibody or portion thereof has an $EC_{50}$ of 500 nM or less as measured by their ability to inhibit human vessel angiogenesis in a SCID mouse engrafted with human foreskin tissue, in which human melanoma M24met tumor cells are intradermally implanted. In a further embodiment, said $EC_{50}$ is less than 400 nM, less than 300 nM, less than 200 nM, less than 150 nM, less than 100 nM, less than 50 nM, less than 25 nM, or less than 5 nM. In certain embodiments, the $EC_{50}$ is from 5 nM to 500 nM. In other embodiments, the $IC_{50}$ is from 25 nM to 300 nM. In other embodiments, the $IC_{50}$ is from 50 nM to 150 nM.

In another embodiment, the anti-ALK-1 antibody or portion thereof inhibits human vessel angiogenesis in a SCID mouse engrafted with human foreskin tissue, in which a mixture of collagen plus human macrovascular endothelial cells is intradermally implanted as determined by IHC analysis of human CD-31 signal assay by at least 25% as compared to a control sample. In a further embodiment, the anti-ALK-1 antibody or portion thereof inhibits human vessel angiogenesis in a SCID mouse engrafted with human foreskin tissue, in which collagen is intradermally implanted by at least 50% as compared to a control sample. In a further embodiment, the anti-ALK-1 antibody or portion thereof inhibits by at least 75%, by at least 80%, by at least 85%, by at least 90% or at least 95% as compared to control.

In another embodiment, the anti-ALK-1 antibody or portion thereof competes for binding to ALK-1 with an antibody selected from the group consisting of 1.11.1; 1.12.1; 1.12.1 (rWT), 1.12.1(M29I/D19A); 1.12.1(M29I); 1.12.1(D19A); 1.13.1; 1.14.1; 1.151.1; 1.162.1; 1.183.1; 1.27.1; 1.29.1; 1.31.1; 1.8.1; 1.9.1; 4.10.1; 4.24.1; 4.38.1; 4.58.1; 4.62.1; 4.68.1; 4.72.1; 5.13.1; 5.34.1; 5.53.1; 5.56.1; 5.57.1; and 5.59.1.

In another embodiment, the anti-ALK-1 antibody or portion thereof cross-competes for binding to ALK-1 with an antibody selected from the group consisting of 1.11.1; 1.12.1; 1.12.1(rWT); 1.12.1(M29I/D19A); 1.12.1(M29I); 1.12.1 (D19A); 1.13.1; 1.14.1; 1.151.1; 1.162.1; 1.183.1; 1.27.1; 1.29.1; 1.31.1; 1.8.1; 1.9.1; 4.10.1; 4.24.1; 4.38.1; 4.58.1; 4.62.1; 4.68.1; 4.72.1; 5.13.1; 5.34.1; 5.53.1; 5.56.1; 5.57.1; and 5.59.1.

In another embodiment, the anti-ALK-1 antibody or portion thereof binds to the same epitope of ALK-1 as an antibody selected from the group consisting of 1.11.1; 1.12.1; 1.12.1(rWT), 1.12.1(M29I/D19A); 1.12.1(M29I), 1.12.1 (D19A); 1.13.1; 1.14.1; 1.151.1; 1.162.1; 1.183.1; 1.27.1; 1.29.1; 1.31.1; 1.8.1; 1.9.1; 4.10.1; 4.24.1; 4.38.1; 4.58.1; 4.62.1; 4.68.1; 4.72.1; 5.13.1; 5.34.1; 5.53.1; 5.56.1; 5.57.1; and 5.59.1.

In another embodiment, the anti-ALK-1 antibody or portion thereof binds to ALK-1 with substantially the same $K_D$ as an antibody selected from the group consisting of 1.11.1; 1.12.1; 1.12.1(rWT); 1.12.1(M29I/D19A); 1.12.1(M29I); 1.12.1(D19A); 1.13.1; 1.14.1; 1.151.1; 1.162.1; 1.183.1; 1.27.1; 1.29.1; 1.31.1; 1.8.1; 1.9.1; 4.10.1; 4.24.1; 4.38.1; 4.58.1; 4.62.1; 4.68.1; 4.72.1; 5.13.1; 5.34.1; 5.53.1; 5.56.1; 5.57.1; and 5.59.1.

In another embodiment, the anti-ALK-1 antibody or portion thereof binds ALK-1 with substantially the same $k_{off}$ as an antibody selected from the group consisting of 1.11.1; 1.12.1; 1.12.1(rWT); 1.12.1(M29I/D19A); 1.12.1(M29I); 1.12.1 (D19A); 1.13.1; 1.14.1; 1.151.1; 1.162.1; 1.183.1; 1.27.1; 1.29.1; 1.31.1; 1.8.1; 1.9.1; 4.10.1; 4.24.1; 4.38.1; 4.58.1; 4.62.1; 4.68.1; 4.72.1; 513.1; 5.34.1; 5.53.1; 5.56.1; 5.57.1; and 5.59.1.

A further aspect of the present invention is an antibody or antigen-binding portion thereof with at least one of the functional properties described previously, and comprises a $V_H$ domain that is at least 90% identical in amino acid sequence to any one of SEQ ID NOs: 6; 10; 14; 18; 22; 26; 30; 34; 38; 42; 46; 50; 54; 58; 62; 66; 70; 74; 78; 82; 86; 90; or 104. In one embodiment, said $V_H$ domain is at least 91%, at least 93%, at least 95%, at least 97%, at least 99%, or 100% identical in amino acid sequence to any one of SEQ ID NOs: 6; 10; 14; 18; 22; 26; 30; 34; 38; 42; 46; 50; 54; 58; 62; 66; 70; 74; 78; 82; 86; 90; or 104.

In a further embodiment, the antibody or portion thereof has at least one of the functional properties described previously, and comprises a $V_H$ domain that is any of SEQ ID NOs: 6; 10; 14; 18; 22; 26; 30; 34; 38; 42; 46; 50; 54; 58; 62; 66; 70; 74; 78; 82; 86; 90; or 104, or differs from any one of SEQ ID NOs: 6; 10; 14; 18; 22; 26; 30; 34; 38; 42; 46; 50; 54; 58; 62; 66; 70; 74; 78; 82; 86; 90; or 104 by having at least one conservative amino acid substitution. For example, the $V_H$ domain can differ by 1, 2, 3, 4, 5, 6, 7, 8, 9, 10, 11, 12, 13, 14 or 15 conservative amino acid substitutions from any one of SEQ ID NOs: 6; 10; 14; 18; 22; 26; 30; 34; 38; 42; 46; 50; 54; 58; 62; 66; 70; 74; 78; 82; 86; 90; or 104 in a further embodiment, any of these conservative amino acid substitutions can occur in the CDR1, CDR2, and/or CDR3 regions.

A further aspect of the present invention is an antibody or antigen-binding portion thereof with at least one of the functional properties described previously, and comprises a $V_L$ domain that is at least 90% identical in amino acid sequence to any one of SEQ ID NOs: 8; 12; 16; 20; 24; 28; 32; 36; 40; 44; 48; 52; 56; 60; 64; 68; 72; 76; 80; 84; 88; 92; or 127. In one embodiment, said $V_L$ domain is at least 91%, at least 93%, at least 95%, at least 97%, at least 99%, or 100% identical in amino acid sequence to any one of SEQ ID NOs: 8; 12; 16; 20; 24; 28; 32; 36; 40; 44; 48; 52; 56; 60; 64; 68; 72; 76; 80; 84; 88; 92; or 127.

In a further embodiment, the antibody or portion thereof has at least one of the functional properties described previously, and comprises a $V_L$ domain that is any one of SEQ ID NOs: 8; 12; 16; 20; 24; 28; 32; 36; 40; 44; 48; 52; 56; 60; 64; 68; 72; 76; 80; 84; 88; 92; or 127, or differs from any one of SEQ ID Nos: 8; 12; 16; 20; 24; 28; 32; 36; 40; 44; 48; 52; 56; 60; 64; 68; 72; 76; 80; 84; 88; 92; or 127 by having at least one conservative amino acid substitution. For example, the $V_L$ domain can differ by 1, 2, 3, 4, 5, 6, 7, 8, 9, 10, 11, 12, 13, 14 or 15 conservative amino acid substitutions from any one of SEQ ID NOs: 8; 12; 16; 20; 24; 28; 32; 36; 40; 44; 48; 52; 56; 60; 64; 68; 72; 76; 80; 84; 88; 92; or 127. In a further embodiment, any of these conservative amino acid substitutions can occur in the CDR1, CDR2, and/or CDR3 regions.

Another aspect of the present invention is an antibody or antigen-binding portion thereof with at least one of the functional properties described previously wherein the $V_L$ and $V_H$ domains are each at least 90% identical in amino acid sequence to the $V_L$ and $V_H$ domains, respectively, of any one of monoclonal antibodies 1.11.1; 1.12.1; 1.12.1(rWT); 1.12.1 (M29I/D19A); 1.12.1(M29I); 1.12.1(D19A); 1.13.1; 1.14.1; 1.151.1; 1.162.1; 1.183.1; 1.27.1; 1.29.1; 1.31.1; 1.8.1; 1.9.1; 4.10.1; 4.24.1; 4.38.1; 4.58.1; 4.62.1; 4.68.1; 4.72.1; 5.13.1; 5.34.1; 5.53.1; 5.56.1; 5.57.1; and 5.59.1. For example, the $V_L$ and $V_H$ domains are each at least 91%, 93%, 95%, 97%, 99% or 100% identical in amino acid sequences to the $V_L$ and $V_H$ domains, respectively, of any one of monoclonal antibodies 1.11.1; 1.12.1; 1.12.1(rWT); 1.12.1(M29I/D19A); 1.12.1 (M29I); 1.12.1(D19A); 1.13.1; 1.14.1; 1.151.1; 1.162.1; 1.183.1; 1.27.1; 1.29.1; 1.31.1; 1.8.1; 1.9.1; 4.10.1; 4.24.1; 4.38.1; 4.58.1; 4.62.1; 4.68.1; 4.72.1; 5.13.1; 5.34.1; 5.53.1; 5.56.1; 5.57.1; and 5.59.1.

In another aspect of the present invention is a monoclonal antibody or antigen-binding portion thereof that is selected from the group consisting of: a) an antibody or portion thereof that comprises a $V_H$ domain as set forth in SEQ ID NO: 6, and a $V_L$ domain as set forth in SEQ ID NO: 8; b) an antibody or portion thereof that comprises a $V_H$ domain as set forth in SEQ ID NO: 10, and a $V_L$ domain as set forth in SEQ ID NO: 12; c) an antibody or portion thereof that comprises a $V_H$ domain as set forth in SEQ ID NO: 14 and a domain as set forth in SEQ ID NO: 16; d) an antibody or portion thereof that comprises a domain as set forth in SEQ ID NO: 18, and a $V_L$ domain as set forth in SEQ ID NO: 20; e) an antibody or portion thereof that comprises a $V_H$ domain as set forth in SEQ ID NO: 22 and a $V_L$ domain as set forth in SEQ ID NO: 24; f) an antibody or portion thereof that comprises a $V_H$ domain as set forth in SEQ ID NO: 26 and a $V_L$ domain as set forth in SEQ ID NO: 28; g) an antibody or portion thereof that comprises a $V_H$ domain as set forth in SEQ ID NO: 30 and a $V_L$ domain as set forth in SEQ ID NO: 32; h) an antibody or portion thereof that comprises a $V_H$ domain as set forth in SEQ ID NO: 34 and a $V_L$ domain as set forth in SEQ ID NO: 36; i) an antibody or portion thereof that comprises a $V_H$ domain as set forth in SEQ ID NO: 38 and a $V_L$ domain as set forth in SEQ ID NO: 40; j) an antibody or portion thereof that comprises a $V_H$ domain as set forth in SEQ ID NO: 42 and a $V_L$ domain as set forth in SEQ ID NO: 44; k) an antibody or portion thereof that comprises a $V_H$ domain as set forth in SEQ ID NO: 46 and a $V_L$ domain as set forth in SEQ ID NO: 48; l) an antibody or portion thereof that comprises a $V_H$ domain as set forth in SEQ ID NO: 50 and a $V_L$ domain as set forth in SEQ ID NO: 52; m) an antibody or portion thereof that comprises a $V_H$ domain as set forth in SEQ ID NO: 54 and a $V_L$ domain as set forth in SEQ ID NO: 56; n) an antibody or portion thereof that comprises a $V_H$ domain as set forth in SEQ ID NO: 58 and a $V_L$ domain as set forth in SEQ ID NO: 60; o) an antibody or portion thereof that comprises a $V_H$ domain as set forth in SEQ ID NO: 62 and a $V_L$ domain as set forth in SEQ ID NO: 64; p) an antibody or portion thereof that comprises a $V_H$ domain as set forth in SEQ ID NO: 66 and a $V_L$ domain as set forth in SEQ ID NO: 68; q) an antibody or antigen-binding portion thereof that comprises a domain as set forth in SEQ ID NO: 70 and a $V_L$ domain as set forth in SEQ ID NO: 72; r) an antibody or portion thereof that comprises a $V_H$ domain as set forth in SEQ ID NO: 74 and a $V_L$ domain as set forth in SEQ ID NO: 76; s) an antibody or portion thereof that comprises a $V_H$ domain as set forth in SEQ ID NO: 78 and a $V_L$ domain as set forth in SEQ ID NO: 80; t) an antibody or portion thereof that comprises a $V_H$ domain as set forth in SEQ ID NO: 82 and a $V_L$ domain as set forth in SEQ ID NO: 84; u) an antibody or portion thereof that comprises a $V_H$ domain as set forth in SEQ ID NO: 86 and a $V_L$ domain as set forth in SEQ ID NO: 88; v) an antibody or portion thereof that comprises a $V_H$ domain as set forth in SEQ ID NO: 90 and a $V_L$ domain as set forth in SEQ ID NO: 92; w) an antibody or portion thereof that comprises a $V_H$ domain as set forth in SEQ ID NO: 104 and a $V_L$ domain as set forth in SEQ ID NO: 127; x) an antibody or portion thereof that comprises a $V_H$ domain as set forth in SEQ ID NO: 6 and a $V_L$ domain as set forth in SEQ ID NO: 127; and y) an antibody or portion thereof that comprises a $V_H$ domain as set forth in SEQ ID NO: 104 and a $V_L$ domain as set forth in SEQ ID NO: 8.

In a further embodiment, for any of the antibodies or portions thereof as described above in groups a) to v) the $V_H$ and/or $V_L$ domains can differ from the specific SEQ ID NOs recited therein by at least one conservative amino acid substitution. For example, the $V_H$ and/or $V_L$ domains can differ from the recited SEQ ID NO by 1, 2, 3, 4, 5, 6, 7, 8, 9, 10, 11, 12, 13, 14 or 15 conservative amino acid substitutions. In a further embodiment, any of these conservative amino acid substitutions can occur in the CDR1, CDR2, and/or CDR3 regions.

In another embodiment, the present invention provides a monoclonal antibody or antigen-binding portion thereof with at least one of the functional properties described previously, wherein the $V_H$ domain is independently selected from any one of SEQ ID NOs: 6; 10; 14; 18; 22; 26; 30; 34; 38; 42; 46; 50; 54; 58; 62; 66; 70; 74; 78; 82; 86; 90; or 104, or a sequence that differs from any one of SEQ ID NOs: 6; 10; 14; 18; 22; 26; 30; 34; 38; 42; 46; 50; 54; 58; 62; 66; 70; 74; 78; 82; 86; 90; or 104, by at least one conservative amino acid substitution, and the $V_L$ domain is independently selected from any one of SEQ ID NOs: 8; 12; 16; 20; 24; 28; 32; 36; 40; 44; 48; 52; 56; 60; 64; 68; 72; 76; 80; 84; 88; 92; or 127, or a sequence that differs from any one of SEQ ID NOs: 8; 12; 16; 20; 24; 28; 32; 36; 40; 44; 48; 52; 56; 60; 64; 68; 72; 76; 80; 84; 88; 92; or 127, by at least one conservative amino acid substitution. For example, the $V_H$ and $V_L$ domains can each differ from SEQ ID NOs: 6; 10; 14; 18; 22; 26; 30; 34; 38; 42; 46; 50; 54; 58; 62; 66; 70; 74; 78; 82; 86; 90; or 104, and 8; 12; 16; 20; 24; 28; 32; 36; 40; 44; 48; 52; 56; 60; 64; 68; 72; 76; 80; 84; 88; 92; or 127, respectively, by 1, 2, 3, 4, 5, 6, 7, 8, 9, 10, 11, 12, 13, 14 or 15 conservative amino acid substitutions.

In a further embodiment, the present invention provides a monoclonal antibody or antigen-binding portion thereof with at least one of the functional properties described previously, wherein said antibody or portion comprises $V_H$ CDR1, CDR2 and CDR3 sequences independently selected from the heavy chain CDR1, CDR2, or CDR3 sequences, respectively, found in any one of SEQ ID NOs: 6; 10; 14; 18; 22; 26; 30; 34; 38; 42; 46; 50; 54; 58; 62; 66; 70; 74; 78; 82; 86; 90; or 104, or a sequence that differs from any one of SEQ ID NOs: 6; 10; 14; 18; 22; 26; 30; 34; 38; 42; 46; 50; 54; 58; 62; 66; 70; 74; 78; 82; 86; 90; or 104, by at least one conservative amino acid substitution. For example, the $V_H$ CDR1, CDR2 and CDR3 can differ from the CDR1, CDR2 and CDR3, respectively, of any SEQ ID NOs: 6; 10; 14; 18; 22; 26; 30; 34; 38; 42; 46; 50; 54; 58; 62; 66; 70; 74; 78; 82; 86; 90; or 104, by 1, 2, 3, 4, 5, 6, 7, 8, 9, 10, 11, 12, 13, 14 or 5 conservative amino acid substitutions.

In a further embodiment, the present invention provides a monoclonal antibody or antigen-binding portion thereof with at least one of the functional properties described previously, wherein said antibody or portion comprises $V_L$ CDR1, CDR2 and CDR3 sequences independently selected from the light chain CDR1, CDR2, or CDR3 sequences, respectively, found in any one of SEQ ID NOs: 8; 12; 16; 20; 24; 28; 32; 36; 40; 44; 48; 52; 56; 60; 64; 68; 72; 76; 80; 84; 88; 92; or 127, or a sequence that differs from any one of SEQ ID NOs: 8; 12; 16; 20; 24; 28; 32; 36; 40; 44; 48; 52; 56; 60; 64; 68; 72; 76; 80; 84; 88; 92; or 127, by at least one conservative amino acid substitution. For example, the $V_L$ CDR1, CDR2 and CDR3 can differ from the CDR1, CDR2 and CDR3, respectively, of any of SEQ ID NOs: 8; 12; 16; 20; 24; 28; 32; 36; 40; 44; 48; 52; 56; 60; 64; 68; 72; 76; 80; 84; 88; 92; or 127 by 1, 2, 3, 4, 5, 6, 7, 8, 9, 10, 11, 12, 13, 14 or 15 conservative amino acid substitutions.

The present invention further provides a monoclonal antibody or antigen-binding portion thereof with at least one of the functional properties described previously, wherein said antibody or antigen-binding portion comprises the $V_H$ and $V_L$ CDR1, the $V_H$ and $V_L$ CDR2, and the $V_H$ and $V_L$ CDR3 as found in any one of monoclonal antibodies 1.11.1; 1.12.1; 1.12.1(rWT); 1.12.1(M29I/D19A); 1.12.1(M29I); 1.12.1 (D19A); 1.13.1; 1.14.1; 1.151.1; 1.162.1; 1.183.1; 1.27.1; 1.29.1; 1.31.1; 1.8.1; 1.9.1; 4.10.1; 4.24.1; 4.38.1; 4.58.1; 4.62.1; 4.68.1; 4.72.1; 5.13.1; 5.34.1; 5.53.1; 5.56.1; 5.57.1; and 5.59.1.

The present invention further provides a monoclonal antibody or antigen-binding portion thereof with at least one of the functional properties described previously, wherein said antibody or antigen-binding portion comprises a heavy chain that utilizes a human $V_H$4-31, $V_H$3-11, $V_H$3-15; $V_H$3-33, $V_H$4-61 or $V_H$4-59 gene. In some embodiments, the heavy chain utilizes a human $V_H$3-33 gene, a human D 6-19 gene and a human $J_H$3B gene; a human $V_H$4-31 gene, a human D 6-19 gene and a human $J_H$4B gene; a human $V_H$4-61 gene, a human D 6-19 gene and a human $J_H$4B gene; a human $V_H$4-31 gene, a human D 3-3 gene and a human $J_H$3B gene; a human $V_H$4-31 gene and a human $J_H$3B gene; a human $V_H$4-59 gene, a human D 6-19 gene and a human $J_H$4B gene; a human $V_H$3-11 gene, a human D 3-22 gene and a human $J_H$6B gene; a human $V_H$3-15 gene, a human D 3-22 gene and a human $J_H$4B gene; a human $V_H$4-31 gene, a human D 5-12 gene and a human $J_H$6B gene; a human $V_H$4-31 gene, a human D 4-23 gene and a human $J_H$4B gene; a human $V_H$4-31 gene, a human D 2-2 gene and a human $J_H$5B gene; a human $V_H$4-31 gene and a human $J_H$6B gene; human $V_H$3-15 gene, a human D 1-1 gene and a human $J_H$4B gene; a human $V_H$3-11 gene, a human D 6-19 gene and a human $J_H$6B gene; a human $V_H$3-11 gene, a human D 3-10 gene and a human $J_H$6B gene; or a human $V_H$3-11 gene, a human D 6-6 gene and a human $J_H$6B gene.

The present invention further provides a monoclonal antibody or antigen-binding portion thereof with at least one of the functional properties described previously, wherein said antibody or antigen-binding portion comprises a light chain that utilizes a human $V_K$A27, $V_K$A2, $V_K$A1, $V_K$A3, $V_K$B3, $V_K$B2, $V_K$L1 or $V_K$L2 gene. In some embodiments, the light chain utilizes a human $V_K$L1 gene and a human $J_K$4 gene; a human $V_K$A27 gene and a human $J_K$5 gene or a human $J_K$4 gene; a human $V_K$B3 gene and a human $J_K$1 gene; a human $V_K$L2 gene and a human $J_K$3 gene; a human $V_K$A2 gene and a human $J_K$1 gene; a human $V_K$A3 gene and a human $J_K$4 gene; a human $V_K$A1 gene and a human $J_K$1 gene; a human $V_K$B2 gene and a human $J_K$4 gene; or a human $V_K$A2 gene and a human $J_K$1 gene.

The present invention further provides a monoclonal antibody or antigen-binding portion thereof with at least one of the functional properties described previously, wherein said antibody or antigen-binding portion comprises one or more of a heavy chain and/or light chain FR1, FR2, FR3 or FR4 amino acid sequence as found in any one of monoclonal antibodies 1.11.1; 1.12.1; 1.12.1(rWT); 1.12.1(M29I/D19A); 1.12.1 (M29I); 1.12.1(D19A); 1.13.1; 1.14.1; 1.151.1; 1.162.1; 1.183.1; 1.27.1; 1.29.1; 1.31.1; 1.8.1; 1.9.1; 4.10.1; 4.24.1; 4.38.1; 4.58.1; 4.62.1; 4.68.1; 4.72.1; 5.13.1; 5.34.1; 5.53.1; 5.56.1; 5.57.1; and 5.59.1.

The present invention further provides a monoclonal antibody comprising the amino acid sequences set forth in: a) SEQ ID NO: 2 and SEQ ID NO: 4; b) SEQ ID NO: 2 and SEQ ID NO: 102; c) SEQ ID NO: 100 and SEQ ID NO: 4; and d) SEQ ID NO: 100 and SEQ ID NO: 102.

In a further embodiment of the present invention is any of the antibodies described previously that is an IgG, an IgM, an IgE, an IgA, or an IgD molecule, or is derived therefrom. For example, the antibody can be an $IgG_1$ or $IgG_2$.

Another embodiment provides any of the antibodies or antigen-binding portions described above which is an Fab fragment, an F(ab')$_2$ fragment, an $F_V$ fragment, a single chain Fv fragment, a single chain $V_H$ fragment, a single chain $V_L$ fragment, a humanized antibody, a chimeric antibody or a bispecific antibody.

In a further embodiment is a derivatized antibody or antigen-binding portion comprising any of the antibodies or portions thereof as described previously and at least one additional molecular entity. For example, the at least one additional molecular entity can be a another antibody (e.g., a bispecific antibody or a diabody), a detection agent, a label, a cytotoxic agent, a pharmaceutical agent, and/or a protein or peptide that can mediate association of the antibody or antibody portion with another molecule (such as a streptavidin core region or a polyhistidine tag). For example, useful detection agents with which an antibody or antigen-binding portion of the invention may be derivatized include fluorescent compounds, including fluorescein, fluorescein isothiocyanate, rhodamine, 5-dimethylamine-1-napthalenesulfonyl chloride, phycaerythrin, lanthanide phosphors, and the like. An antibody can also be labeled with enzymes that are useful for detection, such as horseradish peroxidase, β-galactosidase, luciferase, alkaline phosphatase, glucose oxidase, and the like. In a further embodiment the antibodies or portions thereof of the present invention can also be labeled with biotin, or with a predetermined polypeptide epitope recognized by a secondary reporter (e.g., leucine zipper pair sequences, binding sites for secondary antibodies, metal binding domains, epitope tags). In a still further embodiment of the present invention, any of the antibodies or portions thereof can also be derivatized with a chemical group such as polyethylene glycol (PEG), a methyl or ethyl group, or a carbohydrate group.

In some embodiments, the anti-ALK-1 antibodies or antigen binding portions disclosed herein are attached to a solid support.

In some embodiments, the C-terminal lysine of the heavy chain of any of the anti-ALK-1 antibodies of the invention is cleaved. In various embodiments of the invention, the heavy and light chains of the anti-ALK-1 antibodies may optionally include a signal sequence.

The present invention also provides a pharmaceutical composition comprising any of the antibodies or antigen-binding portions thereof as described above and a pharmaceutically acceptable carrier.

In another embodiment, the invention relates to an isolated nucleic acid molecule comprising a nucleotide sequence that encodes any of the antibodies or antigen binding portions thereof as described herein. In one particular embodiment, an isolated nucleic acid molecule comprises the nucleotide sequence set forth in SEQ ID NO: 1, which sequence encodes a heavy chain. In another particular embodiment, an isolated nucleic acid molecule comprises the nucleotide sequence set forth in SEQ ID NO: 3, which sequence encodes a light chain.

In another particular embodiment an isolated nucleic acid molecule comprises a polynucleotide comprising an open reading frame of the cDNA sequence of a clone deposited under an ATCC accession number PTA-6864. In another particular embodiment an isolated nucleic acid molecule comprises a polynucleotide comprising an open reading frame of the cDNA sequence of a clone deposited under an ATCC accession number PTA-6865.

In another particular embodiment, an isolated nucleic acid molecule comprises the nucleotide sequence set forth in SEQ ID NO: 95 or 128, each of which sequences encodes a heavy chain. In another particular embodiment, an isolated nucleic acid molecule comprises the nucleotide sequence set forth in SEQ ID NO: 101, which sequence encodes a light chain.

The invention further relates to a vector comprising any of the nucleic acid molecules described herein, wherein the vector optionally comprises an expression control sequence operably linked to the nucleic acid molecule.

Another embodiment provides a host cell comprising any of the vectors described herein or comprising any of the nucleic acid molecules described herein. The present invention also provides an isolated cell line that produces any of the antibodies or antigen-binding portions as described herein or that produces the heavy chain or light chain of any of said antibodies or said antigen-binding portions.

In another embodiment, the present invention relates to a method for producing an anti-ALK-1 antibody or antigen-binding portion thereof, comprising culturing any of the host cells or cell lines described herein under suitable conditions and recovering said antibody or antigen-binding portion.

The present invention also relates to a non-human transgenic animal or transgenic plant comprising any of the nucleic acids described herein, wherein the non-human transgenic animal or transgenic plant expresses said nucleic acid.

The present invention further provides a method for isolating an antibody or antigen-binding portion thereof that binds to ALK-1, comprising the step of isolating the antibody from the non-human transgenic animal or transgenic plant as described herein.

In another embodiment, the invention relates to a hybridoma deposited under an ATCC accession number of PTA-6808.

The present invention also provides a method for determining if a substance inhibits up-regulation of a specific downstream target gene of ALK-1, Id1, the method comprising contacting a first sample of cells that express Id1 with the substance and determining if Id1 expression is inhibited, wherein a reduced level of Id1 expression in the first sample of cells contacted with the substance as compared to a control sample of cells is indicative of said substance inhibiting Id1 expression. The present invention further provides the method, wherein the substance is an antibody that binds to the extracellular domain of ALK-1.

The present invention also provides a method for treating abnormal cell growth in a mammal in need thereof, comprising the step of administering to said mammal any of the antibodies or antigen-binding portions thereof, or any of the pharmaceutical compositions, as described herein. The present invention further provides a method for treating abnormal cell growth in a mammal in need thereof with an antibody or antigen-binding portion thereof that binds to ALK-1 comprising the steps of administering to said mammal an effective amount of any of the nucleic acid molecules described herein under suitable conditions that allow expression of said nucleic acid molecules. In another embodiment, the method of treating abnormal cell growth further comprises administering an amount of one or more substances selected from anti-tumor agents, anti-angiogenesis agents, signal transduction inhibitors, and antiproliferative agents, which amounts are together effective in treating said abnormal cell growth. In particular embodiments, said abnormal cell growth is cancerous.

The present invention also provides an isolated Cynomolgus monkey ALK-1 protein having an amino acid sequence of SEQ ID NO: 93. The present invention further provides an isolated nucleic acid molecule encoding a protein having an amino acid sequence of SEQ ID NO: 93. The present invention further provides an isolated nucleic acid molecule of SEQ ID NO: 94.

BRIEF DESCRIPTION OF THE DRAWINGS

FIG. 2 shows sequence alignment of human and Cyno ALK-1 proteins.

FIG. 3 shows $K_D$ determination of the recombinant 1.12.1 antibody binding to cell surface ALK-1. (a) Human. (b) Cyno.

1.12.1(rWT) refers to the mAb 1.12.1 variant that was expressed recombinant mAb.

1.12.1(M29I/D19A) refers to the mAb 1.12.1 variant that was expressed recombinant mAb containing two specific amino acid mutations (methionine at position 29 in the heavy chain replaced with isoleucine and aspartic acid at position 19 in the light chain replaced with alanine).

1.12.1 (M29I) refers to the mAb 1.12.1 variant that was expressed recombinant mAb containing a specific single amino acid mutation where the methionine at position 29 in the heavy chain was replaced with isoleucine.

1.12.1(D19A) refers to the mAb 1.12.1 variant that was expressed recombinant mAb containing a specific single amino acid mutation where the aspartic acid at position 19 in the light chain was replaced with alanine.

Figure 1:
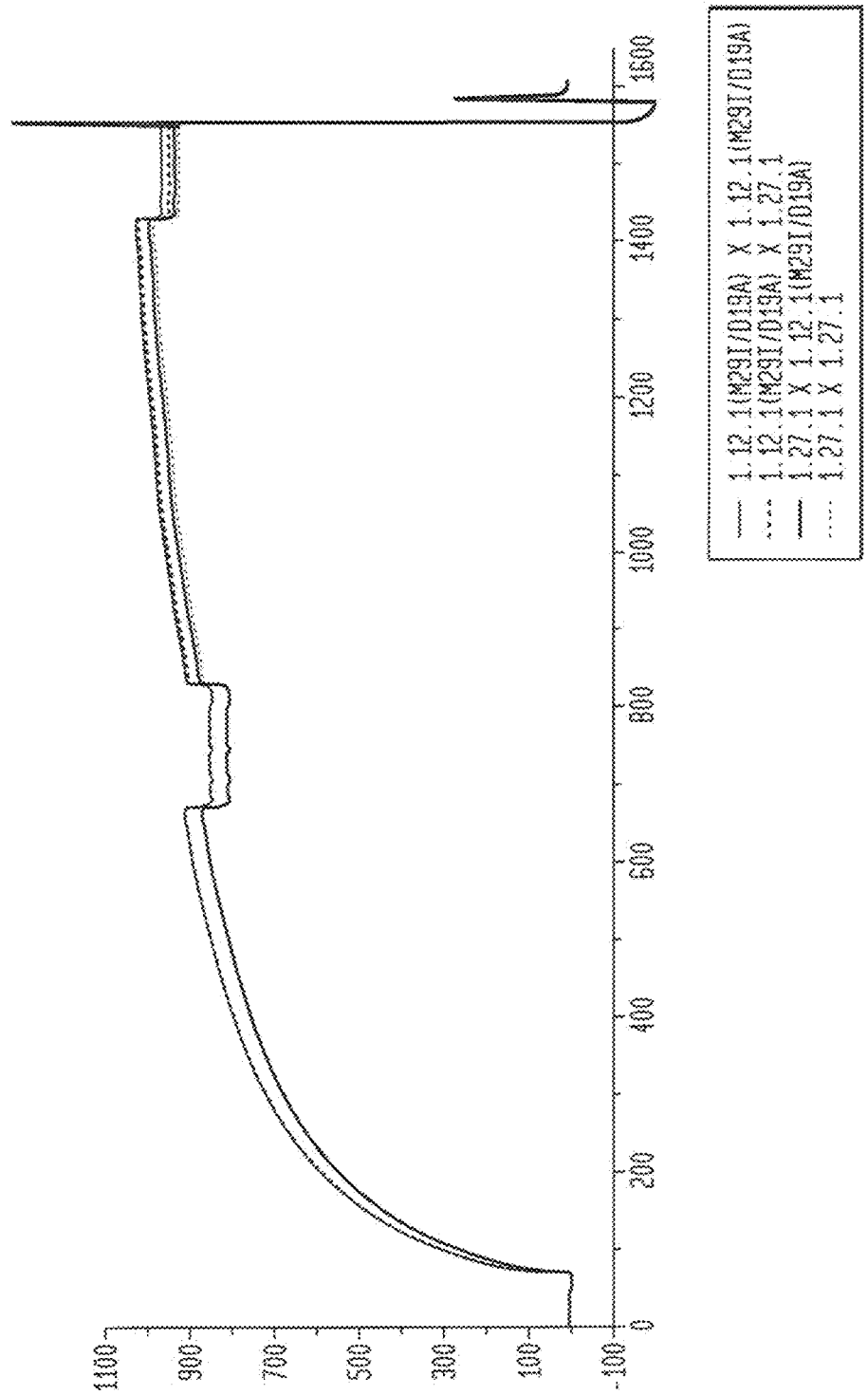
FIG. 1 shows an example of epitope binding data. The 1.12.1(M29I/D19A) antibody was injected for 10 minutes followed by a second 10 minute injection of the 1.12.1(M29I/D19A) antibody. This defines the maximum response for a 20 minute injection of that antibody. The 20 minute injection maximum response was similarly determined for the 1.27.1 antibody. The 1.12.1(M29I/D19A) antibody was injected for 10 minutes followed by a 10 minute injection of the 1.27.1 antibody. If the total response falls between the defined maximum responses then the two antibodies must bind to the same epitope. If the total response exceeds the highest maximum response then the antibodies must bind to different epitopes. The experiment was repeated with the order of injections reversed as described in Example 9.
Figure 4:
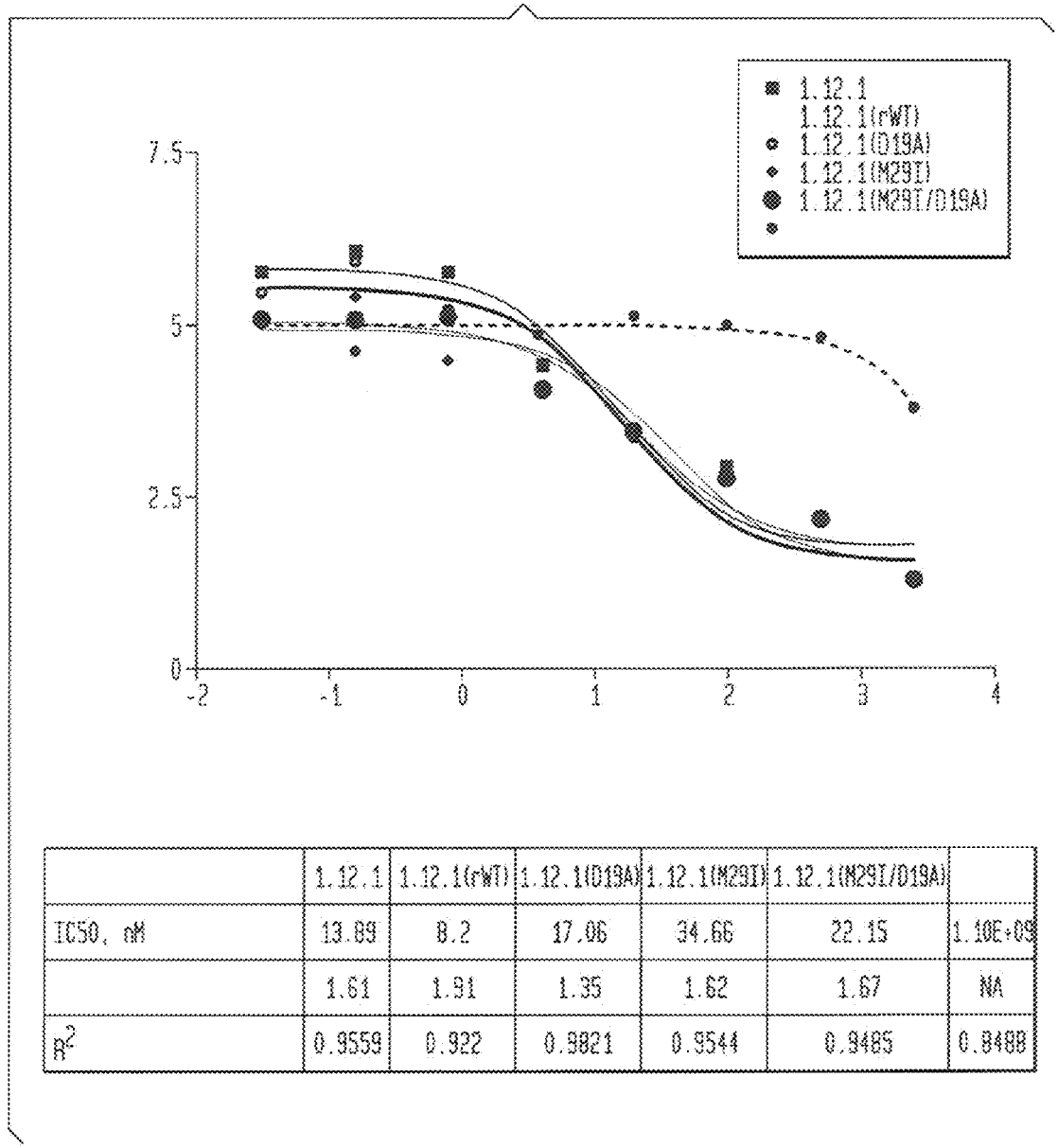

FIG. 4 shows examples of ID1 titrations using ID1 TAQ-MAN® Assay for the 1.12.1 antibody variants.

1.12.1 refers to the mAb 1.12.1 variant that was isolated from the hybridoma.

1.12.1(rWT) refers to the mAb 1.12.1 variant that was expressed recombinant mAb.

1.12.1(M29I/D19A) refers to the mAb 1.12.1 variant that was expressed recombinant mAb containing two specific amino acid mutations (methionine at position 29 in the heavy chain replaced with isoleucine and aspartic acid at position 19 in the light chain replaced with alanine).

1.12.1(M29I) refers to the mAb 1.12.1 variant that was expressed recombinant mAb containing a specific single amino acid mutation where the methionine at position 29 in the heavy chain was replaced with isoleucine.

1.12.1(D19A) refers to the mAb 1.12.1 variant that was expressed recombinant mAb containing a specific single amino acid mutation where the aspartic acid at position 19 in the light chain was replaced with alanine.

FIG. 5 shows examples of ID1 titrations using ID1 TAQ-MAN® Assay for the 1.12.1 antibody sequence variants and the Fab derivative.

1.12.1 refers to the mAb 1.12.1 variant that was isolated from the hybridoma.

1.12.1(rWT) refers to the mAb 1.12.1 variant that was expressed recombinant mAb.

1.12.1(M29I) refers to the mAb 1.12.1 variant that was expressed recombinant mAb containing a specific single amino acid mutation where the methionine at position 29 in the heavy chain was replaced with isoleucine.

1.12.1(D19A) refers to the mAb 1.12.1 variant that was expressed recombinant mAb containing a specific single amino acid mutation where the aspartic acid at position 19 in the light chain was replaced with alanine.

1.12.1(M29I/D19A) refers to the mAb 1.12.1 variant that was expressed recombinant mAb containing two specific amino acid mutations (methionine at position 29 in the heavy chain replaced with isoleucine and aspartic acid at position 19 in the light chain replaced with alanine).

Fab 1.12.1(M29I/D19A) refers to the Fab fragment of mAb 1.12.1(M29I/D19A) prepared by digesting 1.12.1(M29I/D19A) IgG1 using papain.

Figure 6A:
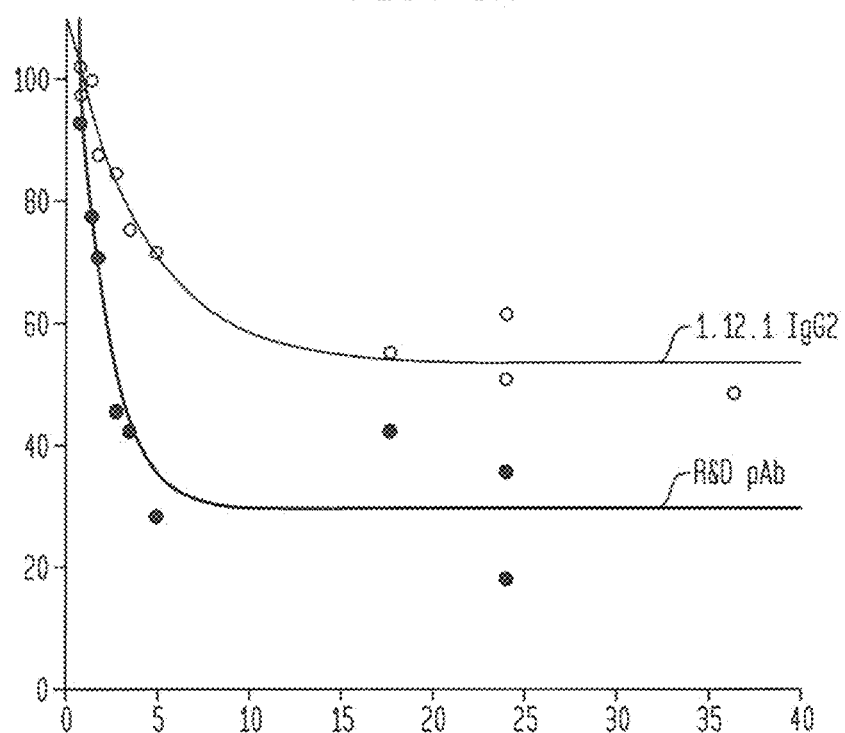
Figure 6B:
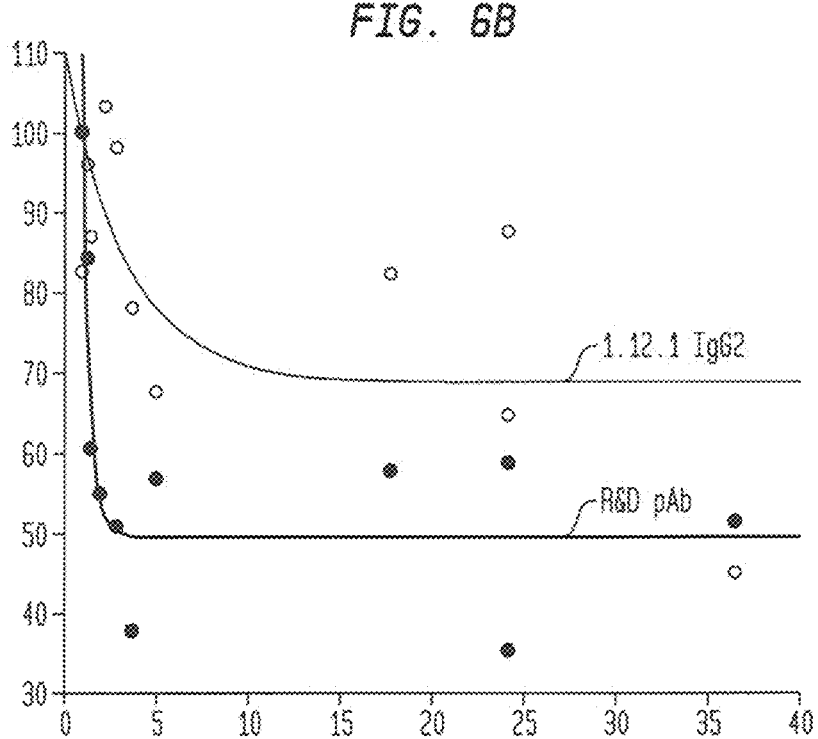

FIG. 6 shows ALK-1 internalization. (a) Monitor neutralizing antibody remaining on cell surface. (b) Monitor remaining cell surface receptor ALK-1.

FIG. 7A shows alignment of variable domain sequences for anti-ALK-1 antibodies of the invention, to germline sequences. Mutations compared to germline are in bold. CDR sequences are underlined. FIG. 7B shows alignment of the predicted amino acid sequences of light chain variable domains for anti-ALK-1 antibodies 1.12.1, 1.14.1, 1.162.1, 1.31.1, 4.62.1 and 4.72.1 to the human germline A27 Vκ sequence. FIGS. 7C and 7D show alignment of the predicted amino acid sequences of heavy light chain variable domains for anti-ALK-1 antibodies 1.12.1, 1.151.1, 1.162.1, 1.8.1, 4.24.1, 4.38.1, 4.58.1, 4.62.1, 4.68.1, 4.72.1, 5.13.1 and 5.34.1 to the human germline 4-31 $V_H$ sequence.

Figure 8:
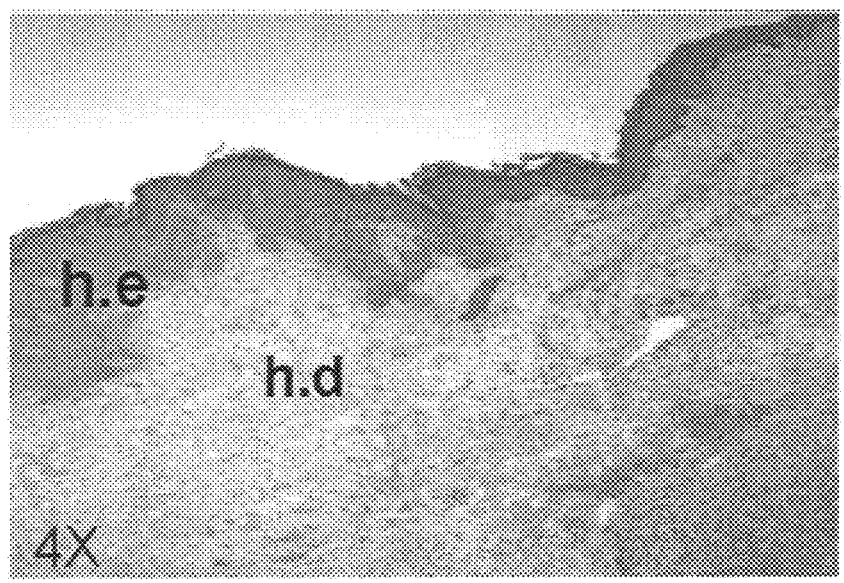

FIG. 8 shows an example of the histological (H & E Staining) analysis of a section of the engrafted human skin post surgery.

Figure 9A:
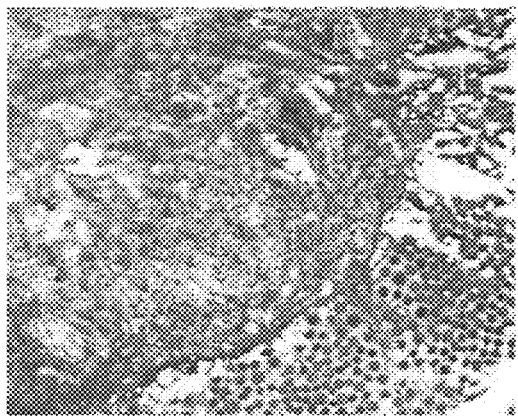
Figure 9B:
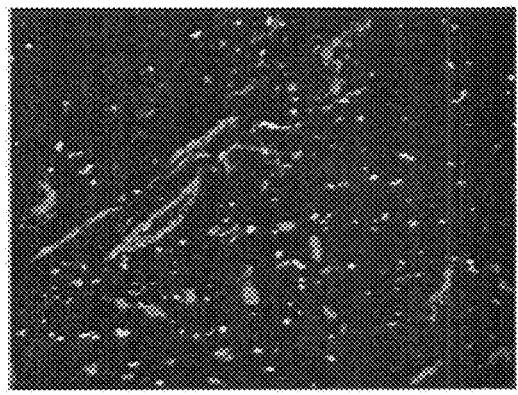

FIG. 9 (A) shows the trichrome staining of collagen in a human skin chimera mouse.

FIG. 9 (B) shows detecting human vessels in the collagen gel implanted in a human foreskin chimera mouse. Tex-red: human vessels. FITC: mouse vessels. Yellow: co-staining.

Figure 10:
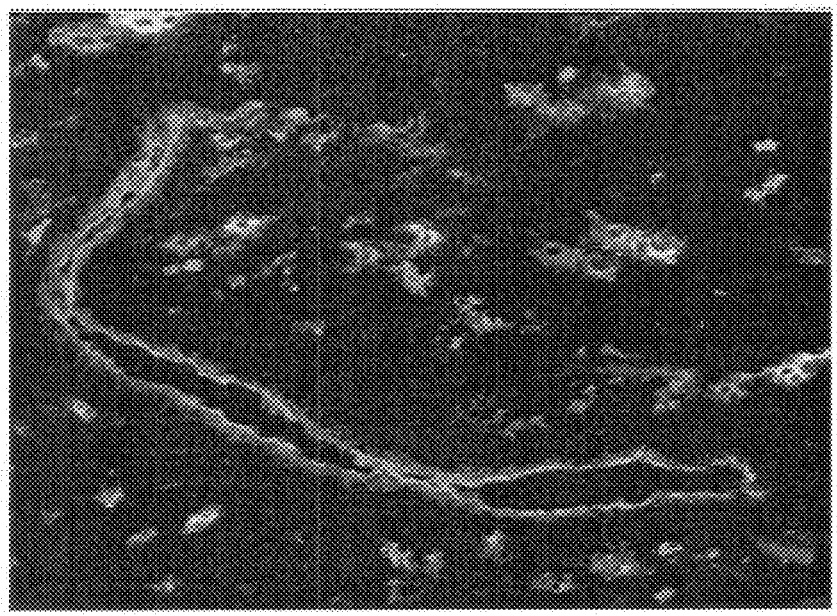

FIG. 10 shows an immunofluorescent image of human (red) and mouse (green) vessels of the M24met tumor in the human foreskin SCID chimera mouse.

Figure 11:
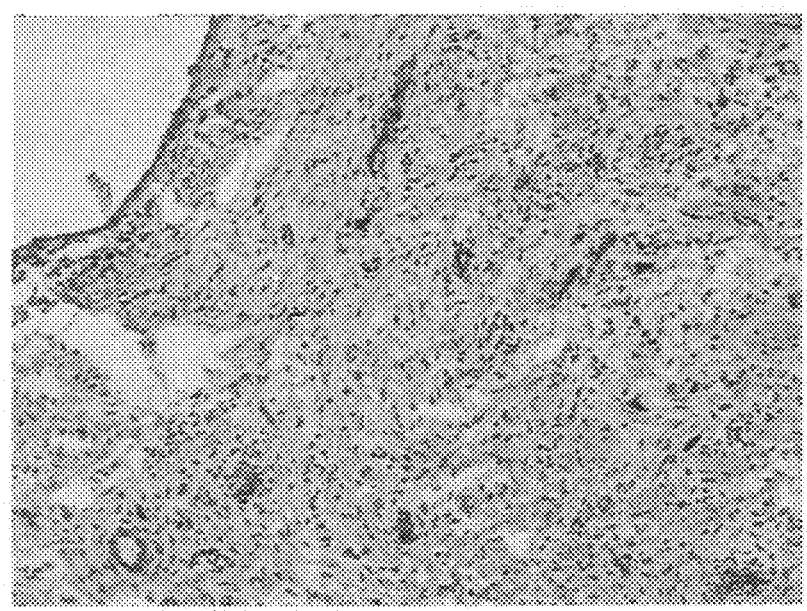

FIG. 11 shows the IHC image of human vessels (brown) of the M24met tumor in the human foreskin SCID chimera mouse.

Figure 12:
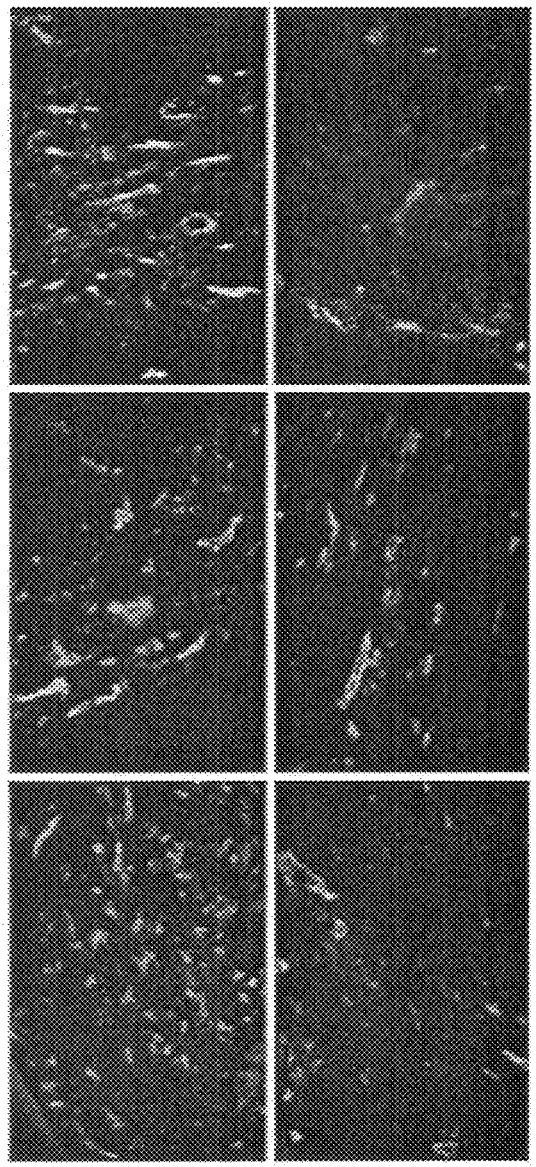

FIG. 12 shows the representative immunofluorescent images of human (red) and mouse (green) vessels of the control and the 1.12.1(M29I/D19A) antibody treated (10 mg/kg) M24met tumors in the human foreskin SCID chimera mouse.

Figure 13:
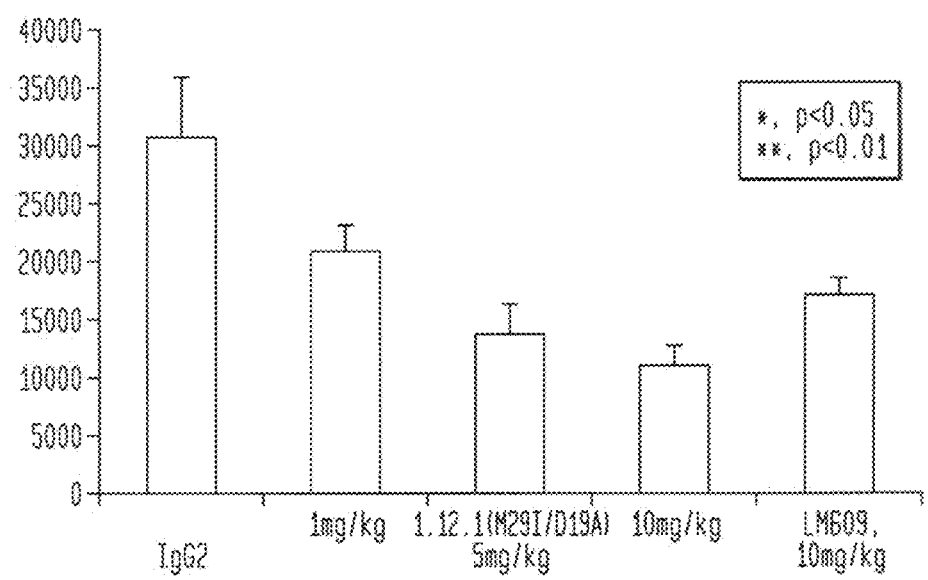

FIG. 13 shows dose-dependent inhibition of human tumor vessel growth by the 1.12.1(M29I/D19A) antibody in the human foreskin SCID chimera mouse model.

Figure 14:
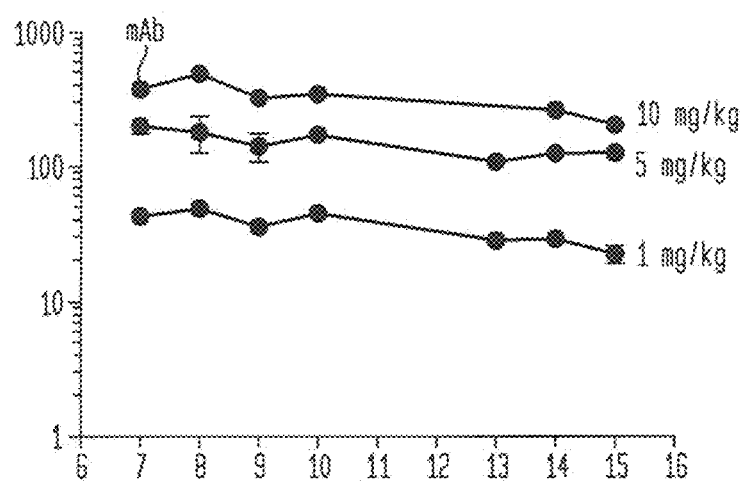

FIG. 14 shows the SCID mouse plasma concentration of the 1.12.1(M29I/D19A) antibody.

Figure 15:
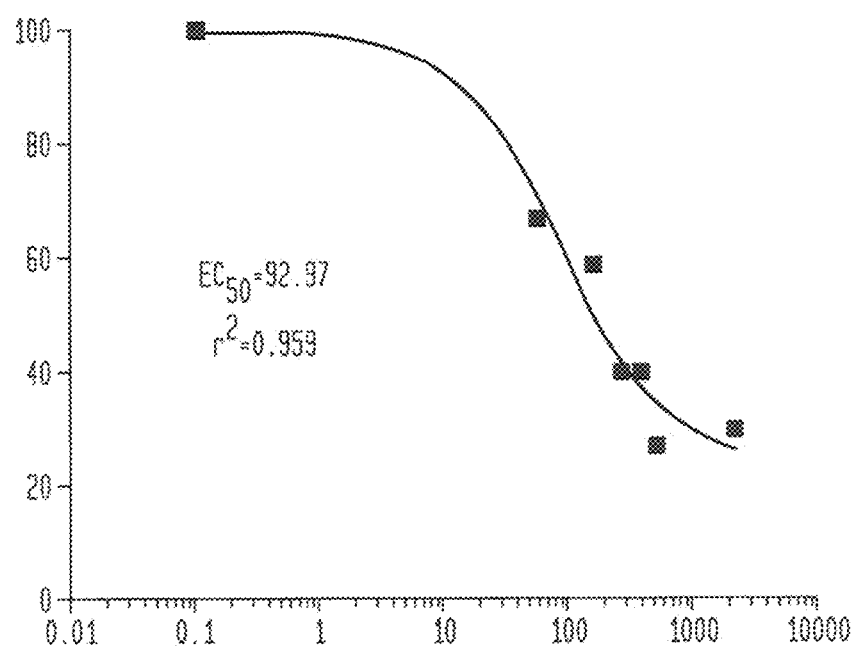

FIG. 15 shows the estimated $EC_{50}$ for the 1.12.1(M29I/D19A) antibody in the M24met foreskin SCID-chimera model. The control value at 100% was given an artificial serum concentration of 0.1 nM for graphing purposes. This does not alter the apparent $EC_{50}$.

DETAILED DESCRIPTION OF THE INVENTION

Definitions and General Techniques

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclature used in connection with, and techniques of, cell and tissue culture, molecular biology, immunology, microbiology, genetics and protein and nucleic acid chemistry and hybridization described herein are those well known and commonly used in the art.

The methods and techniques of the present invention are generally performed according to conventional methods well known in the art and as described in various general and more specific references that are cited and discussed throughout the present specification unless otherwise indicated. See, e.g., Sambrook J. & Russell D. *Molecular Cloning: A Laboratory Manual*, 3rd ed., Cold Spring Harbor Laboratory Press, Cold Spring Harbor, N.Y. (2000); Ausubel et al., *Short Protocols in Molecular Biology: A Compendium of Methods from Current Protocols in Molecular Biology*, Wiley, John & Sons, Inc. (2002); Harlow and Lane *Using Antibodies: A Laboratory Manual*, Cold Spring Harbor Laboratory Press, Cold Spring Harbor, N.Y. (1998); and Caligan et al., *Short Protocols in Protein Science*, Wiley, John & Sons, Inc. (2003), incorporated herein by reference. Enzymatic reactions and purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those well known and commonly used in the art.

The following terms, unless otherwise indicated, shall be understood to have the following meanings:

As used herein, the term "ALK-1" refers to mammalian activin receptor-like kinase-1. The term ALK-1 is intended to include recombinant ALK-1 and recombinant chimeric forms of ALK-1, which can be prepared by standard recombinant expression methods.

As used herein, the acronym "mAb" refers to a monoclonal antibody.

As used herein, an antibody that is referred to by number is a monoclonal antibody (mAb) that is obtained from the hybridoma of the same number. For example, monoclonal antibody 1.12.1 is obtained from hybridoma 1.12.1.

1.12.1 refers to the mAb 1.12.1 variant that was isolated from the hybridoma.

1.12.1(rWT) refers to the mAb 1.12.1 variant that was expressed recombinant mAb.

1.12.1 (M29I/D19A) refers to the mAb 1.12.1 variant that was expressed recombinant mAb containing two specific amino acid mutations (methionine at position 29 in the heavy chain replaced with isoleucine and aspartic acid at position 19 in the light chain replaced with alanine).

1.12.1(M29I) refers to the mAb 1.12.1 variant that was expressed recombinant mAb containing a specific single amino acid mutation where the methionine at position 29 in the heavy chain was replaced with isoleucine.

1.12.1(D19A) refers to the mAb 1.12.1 variant that was expressed recombinant mAb containing a specific single amino acid mutation where the aspartic acid at position 19 in the light chain was replaced with alanine.

As used herein, "abnormal cell growth", unless otherwise indicated, refers to cell growth that is independent of normal regulatory mechanisms (e.g., loss of contact inhibition).

As used herein, the term "adjacent" is used to refer to nucleotide sequences which are directly attached to one another, having no intervening nucleotides. By way of example, the pentanucleotide 5'-AAAAA-3' is adjacent to the trinucleotide 5'-TTT-3' when the two are connected thus: 5'-AAAAATTT-3' or 5'-TTTAAAAA-3', but not when the two are connected thus: 5'-AAAAACTTT-3'.

The term "agent" is used herein to denote a chemical compound, a mixture of chemical compounds, a biological macromolecule, or an extract made from biological materials.

As used herein, to "alleviate" a disease, disorder or condition means reducing the severity of the symptoms of the disease, disorder, or condition. This includes, but is not limited to, affecting the size, growth and/or mass of a tumor, the extent or progression of metastasis, and the like, in a patient compared with these same parameters in the patient prior to or in the absence of the method of treatment.

As used herein, the acronym "Id1" refers to a specific downstream target gene of ALK-1, the Id1 gene, which is important for angiogenesis. The Id1 gene has been reported to control the angiogenesis pathway in certain cancers by turning off the production of a protein, thrombospondin-1 (TSP-1), a naturally occurring angiogenesis suppressor. For example, it has been reported that the Id1 gene, which is highly expressed in melanoma, breast, head and neck, brain, cervical, prostate, pancreatic and testicular cancers, results in decreased expression of TSP-1 and increased tumor blood vessel formation. Volpert, Olga V. et al, "Id1 regulates angiogenesis through transcriptional repression of thrombospondin-1" Cancer Cell, December 2002, Vol. 2, pp. 473-483.

As used herein, the term "Smad" refers to Smad domain proteins found in a range of species from nematodes to humans. These highly conserved proteins contain an N-terminal MH1 domain that contacts DNA, and is separated by a short linker region from the C-terminal MH2 domain, the latter showing a striking similarity to forkhead-associated (FHA) domains. FHA and Smad (MH2) domains share a common structure consisting of a sandwich of eleven beta strands in two sheets with Greek key topology. Smad proteins mediate signalling by the TGF-beta/activin/BMP-2/4 cytokines from receptor Ser/Thr protein kinases at the cell surface to the nucleus. Smad proteins fall into three functional classes: the receptor-regulated Smads (R-Smads), including Smad1, -2, -3, -5, and -8, each of which is involved in a ligand-specific signalling pathway; the comediator Smads (co-Smads), including Smad4, which interact with R-Smads to participate in signalling; and the inhibitory Smads (I-Smads), including Smad-6 and -7, which block the activation of R-Smarts and Co-Smads, thereby negatively regulating signalling pathways.

As used herein, the term "TGF-beta" refers to the transforming growth factors-beta, which constitutes a family of multi-functional cytokines (TGF-beta 1-5) that regulate cell growth and differentiation. Transforming growth factor (TGF) is one of many characterized growth factors that exist in nature. It plays crucial roles in "SCID" mice with severe combined immunodeficiency. Many cells synthesize TGF-beta, and essentially all have specific receptors for this peptide. TGF-beta regulates the actions of many other peptide growth factors and determines a positive or negative direction of their effects. TGF-beta is a tumor suppressing cytokine with growth inhibitory effects in epithelial cells. TGF-β may also act as a tumor promoter by eliciting an epithelial-to-mesenchymal transition. TGF-β inactivates several proteins involved in cell cycle progression and thereby exerts its growth-inhibitory effects on epithelial cells by causing them to arrest in the G1 phase of the cell cycle. The protein functions as a disulphide-linked homodimer. Its sequence is characterised by the presence of several C-terminal cysteine residues, which form interlocking disulphide links arranged in a knot-like topology. A similar "cystine-knot" arrangement has been noted in the structures of some enzyme inhibitors and neurotoxins that bind to voltage-gated $Ca^{2+}$ channels, although the precise topology differs. TGF-beta genes are expressed differentially, suggesting that the various TGF-beta species may have distinct physiological roles in vivo.

As used herein, the term "TGF-beta 1" refers to transforming growth factor beta receptor type 1, which is a peptide of 112 amino acid residues derived by proteolytic cleavage from the C-terminal of a precursor protein. Examination of TGF-beta 1 mRNA levels in adult murine tissues indicates that expression is predominant in spleen, lung and placenta. TGF-beta 1 is believed to play important roles in pathologic processes.

As used herein, the term "SCID" refers to nice with severe combined immunodeficiency.

As used her in, the term "HUVEC" refers to human umbilical vein endothelial cells.

As used herein, "amino acids" are represented by the full name thereof, by the three letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |

-continued

| Full Name | Three-Letter Code | One-Letter Code |
|---|---|---|
| Leucine | Leu | L |
| Isoleucine | Ile | I |
| Methionine | Met | M |
| Proline | Pro | P |
| Phenylalanine | Phe | F |
| Tryptophan | Trp | W |

As used herein, the twenty conventional amino acids and their abbreviations follow conventional usage. See *Immunology—A Synthesis* (2nd Edition, E. S. Golub and D. R. Gren, Eds., Sinauer Associates, Sunderland, Mass. (1991)), which is incorporated herein by reference.

A "conservative amino acid substitution" is one in which an amino acid residue is substituted by another amino acid residue having a side chain R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson, *Methods Mol. Biol.* 243:307-31 (1994).

Examples of groups of amino acids that have side chains with similar chemical properties include 1) aliphatic side chains: glycine, alanine, valine, leucine, and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartic acid and glutamic acid; and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine.

Alternatively, a conservative replacement is any change having a positive value in the PAM250 log-likelihood matrix disclosed in Gonnet et al., *Science* 256:1443-45 (1992), herein incorporated by reference. A "moderately conservative" replacement is any change having a nonnegative value in the PAM250 log-likelihood matrix.

In certain embodiments, amino acid substitutions to an anti-ALK-1 antibody or antigen-binding portion thereof are those which: (1) reduce susceptibility to proteolysis, (2) reduce susceptibility to oxidation, (3) alter binding affinity for forming protein complexes, and (4) confer or modify other physicochemical or functional properties of such analogs, but still retain specific binding to ALK-1. Analogs can include various substitutions to the normally-occurring peptide sequence. For example, single or multiple amino acid substitutions, preferably conservative amino acid substitutions, may be made in the normally-occurring sequence, for example in the portion of the polypeptide outside the domain(s) forming intermolecular contacts. Amino acid substitutions can also be made in the domain(s) that form intermolecular contacts that can improve the activity of the polypeptide. A conservative amino acid substitution should not substantially change the structural characteristics of the parent sequence; e.g., a replacement amino acid should not alter the anti-parallel β-sheet that makes up the immunoglobulin binding domain that occurs in the parent sequence, or disrupt other types of secondary structure that characterizes the parent sequence. In general, glycine and proline would not be used in an anti-parallel β-sheet. Examples of art-recognized polypeptide secondary and tertiary structures are described in *Proteins, Structures and Molecular Principles* (Creighton, Ed., W. H, Freeman and Company, New York (1984)); *Introduction to Protein Structure* (C. Branden and J. Tooze, eds., Garland Publishing, New York, N.Y. (1991)); and Thornton et al., *Nature* 354:105 (1991), incorporated herein by reference.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG contains programs such as "Gap" and "BEST-FIT®" which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson, *Methods Enzymol.* 183:63-98 (1990); Pearson, *Methods Mol. Biol.* 132:185-219 (2000)). Another preferred algorithm when comparing a sequence of the invention to a database containing a large number of sequences from different organisms is the computer program BLAST, especially blastp or tblastn, using default parameters. See, e.g., Altschul et al., *J. Mol. Biol.* 215:403-410 (1990); Altschul et al., *Nucleic Acids Res.* 25:3389-402 (1997); herein incorporated by reference.

The length of polypeptide sequences compared for homology will generally be at least about 16 amino acid residues, usually at least about 20 residues, more usually at least about 24 residues, typically at least about 28 residues, and preferably more than about 35 residues. When searching a database containing sequences from a large number of different organisms, it is preferable to compare amino acid sequences. The term "analog" as used herein refers to polypeptides which are comprised of a segment of at least 25 amino acids that has substantial identity to a portion of a deduced naturally-occurring amino acid sequence and which has at least one of the properties of the naturally-occurring polypeoptide. Typically, polypeptide analogs comprise a conservative amino acid substitution (or addition or deletion) with respect to the naturally-occurring sequence. Analogs typically are at least 20 amino acids long, preferably at least 50 amino acids long or longer, and can often be as long as a full-length naturally-occurring polypeptide.

Peptide analogs are commonly used in the pharmaceutical industry as non-peptide drugs with properties analogous to those of the template peptide. These types of non-peptide compound are termed "peptide mimetics" or "peptidomimetics". Fauchere, *J. Adv. Drug Res.* 15:29 (1986); Veber and Freidinger *TINS* p. 392 (1985); and Evans et al. *J. Med. Chem.* 30:1229 (1987), which are incorporated herein by reference. Such compounds are often developed with the aid of computerized molecular modeling.

Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from the group consisting of: —CH$_2$NH—, —CH$_2$S—, —CH$_2$—CH$_2$—, —CH═CH— (cis and trans), —COCH$_2$—, —CH(OH)CH$_2$—, and CH$_2$SO$_3$, by methods well known in the art. Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch *Ann. Rev. Biochem.* 61:387 (1992), incorporated herein by reference); for example, by adding internal cysteine residues capable of forming intramolecular disulfide bridges which cyclize the peptide.

An intact "antibody" or "immunoglobulin" (Ig) comprises at least two heavy (H) chains (about 50-70 kDa) and two light (L) chains (about 25 kDa) inter-connected by disulfide bonds. There are only two types of light chain; λ and κ. In humans they are similar, but only one type is present in each antibody. Heavy chains are classified as mu, delta, gamma, alpha, or epsilon, and define the antibody's isotype as IgM, IgD, IgG, IgA, and IgE, respectively. See generally, *Fundamental Immunology* Ch. 7 (Paul, W., ed., 2nd ed. Raven Press, N.Y. (1989)) (incorporated by reference in its entirety for all purposes). In a preferred embodiment, the antibody is an IgG and is an IgG1, IgG2, IgG3 or IgG4 subtype. In a more preferred embodiment, the anti-ALK-1 antibody is subclass IgG2.

Each heavy chain is comprised of a heavy chain variable domain (V$_H$) and a heavy chain constant region (C$_H$). The heavy chain constant region is comprised of three domains, CH1, CH2 and CH3. Each light chain is comprised of a light chain variable domain (V$_L$) and a light chain constant region. The light chain constant region is comprised of one domain, C$_L$. Within light and heavy chains, the variable and constant regions are joined by a "J" region of about 12 or more amino acids, with the heavy chain also including a "D" region of about 3 or more amino acids. The V$_H$ and V$_L$ regions can be further subdivided into regions of hypervariability, termed "complementarity determining regions" (CDR), interspersed with regions that are more conserved, termed "framework regions" (FR). Each V$_H$ and V$_L$ is composed of three CDRs and four FRs, arranged from amino-terminus to carboxyl-terminus in the following order: FR1, CDR1, FR2, CDR2, FR3, CDR3, FR4. The assignment of amino acids to each domain is in accordance with the definitions of Kabat, *Sequences of Proteins of Immunological Interest* (National Institutes of Health, Bethesda, Md. (1987 and 1991)), or Chothia & Lesk, *J. Mol. Biol.* 196:901-917 (1987); Chothia et al., *Nature* 342:878-883 (1989).

The variable domains of each heavy/light chain pair (V$_H$ and V$_L$) form the antibody binding site that interacts with an antigen. Thus, an intact IgG antibody, for example, has two binding sites. Except in bifunctional or bispecific antibodies, the two binding sites are the same. The constant regions of the antibodies may mediate the binding of the immunoglobulin to host tissues or factors, including various cells of the immune system (e.g., effector cells) and the first component (Clq) of the classical complement system.

Antibodies must have enough antigen-binding diversity to recognize every possible pathogen (many V regions) while maintaining the biological effectiveness of their C regions (few C regions). Ig genes are randomly spliced together from gene segments that allow many V regions to be used with a few C regions. Gene segments encoding Ig H, kappa and lambda chains are found on three different chromosomes. During B cell development, recombinase enzymes remove introns and some exons from the DNA and splice segments into functional Ig genes.

Ig gene segments in mammals are arranged in groups of "variable" (V), "diversity" (D), "joining" (J), and "constant" (C) exons. V kappa (Vκ) segments each encode the first two CDR and three FR of the kappa chain V region, plus a few residues of CDR3. J kappa (Jκ) segments each encode the remainder of CDR3 and the fourth FR. C kappa (Cκ) encodes the complete C region of the kappa light chain. DNA encoding human kappa chain includes approximately 40 functional V kappa (Vκ) segments, five J kappa (Jκ) segments, and one C kappa (Cκ) gene segment, as well as some gene segments which contain stop codons ("pseudogenes"). Human lambda (λ) chain DNA contains approximately 30 functional V lambda (Vλ) segments and four functional sets of J lambda (Jλ) and C lambda (Cλ) segments. A particular J lambda (Jλ) always pairs with its corresponding C lambda (Cλ), unlike J kappa (Jκ) which all pair with the same C kappa (Cκ). DNA for human H chain includes approximately 50 functional V$_H$ segments, 30 D$_H$ segments, and six J$_H$ segments. The first two CDR and three FR of the heavy chain variable domain are encoded by V$_H$. CDR3 is encoded by a few nucleotides of V$_H$, all of D$_H$, and part of J$_H$, while FR4 is encoded by the remainder of the J$_H$ gene segment. There are also individual gene segments in the DNA for each heavy chain domain and membrane region of each isotype, arranged in the order in which they are expressed by B cells.

The term "polypeptide" encompasses native or artificial proteins, protein fragments and polypeptide analogs of a protein sequence. A polypeptide may be monomeric or polymeric.

The term "isolated protein", "isolated polypeptide" or "isolated antibody" is a protein, polypeptide or antibody that by virtue of its origin or source of derivation (1) is not associated with naturally associated components that accompany it in its native state, (2) is free of other proteins from the same species, (3) is expressed by a cell from a different species, or (4) does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

Examples of isolated antibodies include, but not limited to, an anti-ALK-1 antibody that has been affinity purified using ALK-1, and an anti-ALK-1 antibody that has been synthesized by a cell line in vitro.

A protein or polypeptide is "substantially pure," "substantially homogeneous," or "substantially purified" when at least about 60 to 75% of a sample exhibits a single species of polypeptide. The polypeptide or protein may be monomeric or multimeric. A substantially pure polypeptide or protein can typically comprise about 50%, 60%, 70%, 80% or 90% w/w of a protein sample, more usually about 95%, and preferably can be over 99% pure. Protein purity or homogeneity may be indicated by a number of means well known in the art, such as polyacrylamide gel electrophoresis of a protein sample, followed by visualizing a single polypeptide band upon staining the gel with a stain well known in the art. For certain purposes, higher resolution may be provided by using HPLC or other means well known in the art of purification.

The term "polypeptide fragment" as used herein refers to a polypeptide that has an amino-terminal and/or carboxy-terminal deletion, but where the remaining amino acid sequence is identical to the corresponding positions in the naturally-occurring sequence. In some embodiments, fragments are at least 5, 6, 8 or 10 amino acids long. In other embodiments, the fragments are at least 14, at least 20, at least 50, or at least 70, 80, 90, 100, 150 or 200 amino acids long.

The term "analog" or "polypeptide analog" as used herein refers to a polypeptide that comprises a segment that has substantial identity to some reference amino acid sequence and has substantially the same function or activity as the reference amino acid sequence. Typically, polypeptide analogs comprise a conservative amino acid substitution (or insertion or deletion) with respect to the reference sequence. Analogs can be at least 20 or 25 amino acids long, or can be at least 50, 60, 70, 80, 90, 100, 150 or 200 amino acids long or longer, and can often be as long as the full-length polypeptide. Some embodiments of the invention include polypeptide fragments or polypeptide analog antibodies with 1, 2, 3, 4, 5, 6, 7, 8, 9, 10, 11, 12, 13, 14, 15, 16 or 17 substitutions from the germline amino acid sequence. Fragments or analogs of antibodies or immunoglobulin molecules can be readily prepared by those of ordinary skill in the art following the teachings of this specification.

The term "antigen-binding portion" of an antibody (or simply "antibody portion"), as used herein, refers to one or more fragments of an antibody that retain the ability to specifically bind to an antigen (e, g. ALK-1 or ECD ALK-1). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_H1$ domains; (ii) a F(ab')$_2$ fragment, a bivalent fragment comprising two Fab fragments linked by a disulfide bridge at the hinge region; (iii) a Fd fragment consisting of the $V_H$ and $C_H1$ domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv)); see e.g., Bird et al. *Science* 242:423-426 (1988) and Huston et al. *Proc. Natl. Acad. Sci. USA* 85:5879-5883 (1988)). Such single chain antibodies are also intended to be encompassed within the term "antigen-binding portion" of an antibody. Other forms of single chain antibodies, such as diabodies are also encompassed. Diabodies are bivalent, bispecific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see e.g., Holliger et al. *Proc. Natl. Acad. Sci. USA* 90:6444-6448 (1993); Poljak et al. *Structure* 2:1121-1123 (1994)).

Still further, an antibody or antigen-binding portion thereof may be part of larger immunoadhesion molecules, formed by covalent or noncovalent association of the antibody or antibody portion with one or more other proteins or peptides. Examples of such immunoadhesion molecules include use of the streptavidin core region to make a tetrameric scFv molecule (Kipriyanov et al. *Human Antibodies and Hybridomas* 6:93-101 (1995)) and use of a cysteine residue, a marker peptide and a C-terminal polyhistidine tag to make bivalent and biotinylated scFv molecules (Kipriyanov et al. *Mol. Immunol,* 31:1047-1058 (1994)). Other examples include where one or more CDRs from an antibody are incorporated into a molecule either covalently or noncovalently to make it an immunoadhesin that specifically binds to an antigen of interest, such as ALK-1 or ECD of ALK-1. In such embodiments, the CDR(s) may be incorporated as part of a larger polypeptide chain, may be covalently linked to another polypeptide chain, or may be incorporated noncovalently.

Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

As used herein, the term "human antibody" means any antibody in which the variable and constant domain sequences are human sequences. The term encompasses antibodies with sequences derived from human genes, but which have been changed, e.g. to decrease possible immunogenicity, increase affinity, eliminate cysteines that might cause undesirable folding, etc. The term also encompasses such antibodies produced recombinantly in non-human cells, which might impart glycosylation not typical of human cells. These antibodies may be prepared in a variety of ways, as described below.

As used herein, the term "neutralizing antibody," "an inhibitory antibody" or antagonist antibody means an antibody that inhibits the ALK-1/TGF-beta-1/Smad1 signaling pathway. In a preferred embodiment, the antibody inhibits the ALK-1/TGF-beta-1/Smad1 signaling pathway by at least about 20%, preferably 40%, more preferably 60%, even more preferably 80%, or even more preferably 85%. Neutralizing or inhibiting potential of human anti-ALK-1 antibodies may be determined, for example, by their ability to inhibit up-regulation of a specific downstream target gene of ALK-1, Id1, as presented in Example 12; to inhibit Smad1 phosphorylation determined by Western Blotting using ODYSSEY® Infrared Imaging System from LI-COR Biosciences as presented in Example 13.

The term "chimeric antibody" as used herein means an antibody that comprises regions from two or more different antibodies. For example, one or more of the CDRs of a chimeric antibody can be derived from a human anti-ALK-1 antibody. In another example, all of the CDRs can be derived from human anti-ALK-1 antibodies. In another example, the CDRs from more than one human anti-ALK-1 antibody can be combined in a chimeric antibody. For instance, a chimeric antibody may comprise a CDR1 from the light chain of a first human anti-ALK-1 antibody, a CDR2 from the light chain of a second human anti-ALK-1 antibody and a CDR3 from the light chain of a third human anti-ALK-1 antibody, and CDRs from the heavy chain may be derived from one or more other anti-ALK-1 antibodies. Further, the framework regions may be derived from one of the anti-ALK-1 antibodies from which one or more of the CDRs are taken or from one or more different human antibodies. Moreover, as discussed previously herein, chimeric antibody includes an antibody comprising a portion derived from the germline sequences of more than one species.

In some embodiments, a chimeric antibody of the invention is a humanized anti-ALK-1 antibody. A humanized anti-ALK-1 antibody of the invention comprises the amino acid sequence of one or more framework regions and/or the amino acid sequence from at least a portion of the constant region of one or more human anti-ALK-1 antibodies of the invention and further comprises sequences derived from a non-human anti-ALK-1 antibody, for example CDR sequences.

As used herein, the term "ELISA" refers to an enzyme-linked immunosorbent assay. This assay is well known to those of skill in the art. Examples of this assay can be found in Vaughan, T. J. et al., *Nature Biotech,* 14:309-314 (1996), as well as in Example 2 of the present application.

The term "surface plasmon resonance", as used herein, refers to an optical phenomenon that allows for the analysis of real-time biospecific interactions by detection of alterations in protein concentrations within a biosensor matrix, for example using the BIACORE® system (Pharmacia Biosensor AB, Uppsala, Sweden and Piscataway, N.J.). For further descriptions, see Jonsson et al., *Ann. Biol. Clin.* 51:19-26 (1993); Jonsson et al., *Biotechniques* 11:620-627 (1991); Jonsson et al., *J. Mol. Recognit.* 8:125-131 (1995); and Johnsson et al., *Anal. Biochem.* 198:268-277 (1991).

The term "affinity" refers to a measure of the attraction between an antigen and an antibody. The intrinsic attractiveness of the antibody for the antigen is typically expressed as the binding affinity equilibrium constant ($K_D$) of a particular antibody-antigen interaction. An antibody is said to specifically bind an antigen when the $K_D$ is ≤1 mM, preferably ≤100 nM. A $K_D$ binding affinity constant can be measured by surface plasmon resonance, for example using the BIACORE® system as discussed in Examples 7 and 8.

The term "$k_{off}$" refers to the dissociation rate constant of a particular antibody-antigen interaction. A $k_{off}$ dissociation rate constant can be measured by surface plasmon resonance, for example using the BIAcore system as discussed in Examples 7 and 8.

The term "avidity" refers to the functional combining strength of an antibody with its antigen which is based on both affinity and valences of the antibody. As used herein, this term describes the increased affinity that occurs as result of multiple antigen binding sites on an immunoglobulin.

As used herein, the term "molecular selectivity" refers to the binding affinity of an antibody for a specific antigen being greater than for other antigens. For example, the antibodies of the present invention can be selective for ALK-1 over ALK-2 through ALK-7, meaning that the binding affinity of the antibody for ALK-1 is at least 2-fold greater, for example 4-fold, or 10-fold, or 50-fold, or 100-fold or more, than for ALK-2 through ALK-7. Such binding affinities can be measured using standard techniques known to those of skill in the art.

The term "epitope" includes any protein determinant capable of specific binding to an immunoglobulin or T-cell receptor or otherwise interacting with a molecule. Epitopic determinants generally consist of chemically active surface groupings of molecules such as amino acids or carbohydrate or sugar side chains and generally have specific three dimensional structural characteristics, as well as specific charge characteristics. An epitope may be "linear" or "conformational." In a linear epitope, all of the points of interaction between the protein and the interacting molecule (such as an antibody) occur linearally along the primary amino acid sequence of the protein. In a conformational epitope, the points of interaction occur across amino acid residues on the protein that are separated from one another. Once a desired epitope on an antigen is determined, it is possible to generate antibodies to that epitope, e.g., using the techniques described in the present invention. Alternatively, during the discovery process, the generation and characterization of antibodies may elucidate information about desirable epitopes. From this information, it is then possible to competitively screen antibodies for binding to the same epitope. An approach to achieve this is to conduct cross-competition studies to find antibodies that competitively bind with one another, i.e. the antibodies compete for binding to the antigen. A high throughput process for "binning" antibodies based upon their cross-competition is described in International Patent Application No. WO 03/48731.

As used herein, the term "binning" refers to a method to group antibodies based on their antigen binding characteristics. The assignment of bins is somewhat arbitrary, depending on how different are the observed binding patterns for all the antibodies tested. Therefore, bins do not always correlate with epitopes determined by other means and should not be used to define epitopes.

The term "compete", as used herein with regard to an antibody, means that a first antibody, or an antigen-binding portion thereof, competes for binding to the antigen with a second antibody, or an antigen-binding portion thereof, where binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Both competing and cross-competing antibodies are encompassed by the present invention. Regardless of the mechanism by which such competition or cross-competition occurs (e.g., steric hindrance, conformational change, or binding to a common epitope, or portion thereof, and the like), the skilled artisan would appreciate, based upon the teachings provided herein, that such competing and/or cross-competing antibodies are encompassed and can be useful for the methods disclosed herein.

The term "polynucleotide" as referred to herein means a polymeric form of nucleotides of at least 10 bases in length, either ribonucleotides or deoxynucleotides or a modified form of either type of nucleotide. The term includes single and double stranded forms.

The term "isolated polynucleotide" as used herein means a polynucleotide of genomic, cDNA, or synthetic origin or some combination thereof, which by virtue of its origin the "isolated polynucleotide" (1) is not associated with all or a portion of polynucleotides with which the "isolated polynucleotide" is found in nature, (2) is operably linked to a polynucleotide to which it is not linked in nature, or (3) does not occur in nature as part of a larger sequence.

The term "naturally occurring nucleotides" as used herein includes deoxyribonucleotides and ribonucleotides. The term "modified nucleotides" as used herein includes nucleotides with modified or substituted sugar groups and the like. The term "oligonucleotide linkages" referred to herein includes oligonucleotides linkages such as phosphorothioate, phosphorodithioate, phosphoroselenoate, phosphorodiselenoate, phosphoroanilothioate, phoshoraniladate, phosphoroamidate, and the like. See e.g., LaPlanche et al., *Nucl. Acids Res.* 14:9081 (1986); Stec et al., *J. Am. Chem. Soc.* 106:6077 (1984); Stein et al., *Nucl. Acids Res.* 16:3209 (1988); Zon et al., *Anti-Cancer Drug Design* 6:539 (1991); Zan et al., *Oligonucleotides and Analogues: A Practical Approach*, pp. 87-108 (F. Eckstein, Ed., Oxford University Press, Oxford England (1991)); U.S. Pat. No. 5,151,510; Uhlmann and Peyman, *Chemical Reviews* 90:543 (1990), the disclosures of which are hereby incorporated by reference. An oligonucleotide can include a label for detection, if desired.

"Operably linked" sequences include both expression control sequences that are contiguous with the gene of interest and expression control sequences that act in trans or at a distance to control the gene of interest.

The term "expression control sequence" as used herein means polynucleotide sequences that are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences.

The term "vector", as used herein, means a nucleic acid molecule capable of transporting another nucleic acid to which it has been linked. In some embodiments, the vector is a plasmid, i.e., a circular double stranded piece of DNA into which additional DNA segments may be ligated. In some embodiments, the vector is a viral vector, wherein additional DNA segments may be ligated into the viral genome. In some embodiments, the vectors are capable of autonomous replication in a host cell into which they are introduced (e.g., bacterial vectors having a bacterial origin of replication and episomal mammalian vectors). In other embodiments, the vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors").

The term "recombinant host cell" (or simply "host cell"), as used herein, means a cell into which a recombinant expression vector has been introduced. It should be understood that "recombinant host cell" and "host cell" mean not only the particular subject cell but also the progeny of such a cell. Because certain modifications may occur in succeeding generations due to either mutation or environmental influences, such progeny may not, in fact, be identical to the parent cell, but are still included within the scope of the term "host cell" as used herein.

As used herein, the term "germline" refers to the nucleotide sequences and amino acid sequences of the antibody genes and gene segments as they are passed from parents to offspring via the germ cells. This germline sequence is distinguished from the nucleotide sequences encoding antibodies in mature B cells which have been altered by recombination and hypermutation events during the course of B cell maturation. An antibody that "utilizes" a particular germline has a nucleotide or amino acid sequence that most closely aligns with that germline nucleotide sequence or with the amino acid sequence that it specifies. Such antibodies frequently are mutated compared with the germline sequence.

The term "percent sequence identity" in the context of nucleic acid sequences means the residues in two sequences that are the same when aligned for maximum correspondence. The length of sequence identity comparison may be over a stretch of at least about nine nucleotides, usually at least about 18 nucleotides, more usually at least about 24 nucleotides, typically at least about 28 nucleotides, more typically at least about 32 nucleotides, and preferably at least about 36, 48 or more nucleotides. There are a number of different algorithms known in the art which can be used to measure nucleotide sequence identity. For instance, polynucleotide sequences can be compared using FASTA, Gap or BESTFIT®, which are programs in Wisconsin Package Version 10.0, Genetics Computer Group (GCG), Madison, Wis. FASTA, which includes, e.g., the programs FASTA2 and FASTA3, provides alignments and percent sequence identity of the regions of the best overlap between the query and search sequences (Pearson, Methods Enzymol. 183:63-98 (1990); Pearson, Methods Mol. Biol. 132:185-219 (2000); Pearson, Methods Enzymol. 266:227-258 (1996); Pearson, J. Mol. Biol. 276:71-84 (1998); incorporated herein by reference). Unless otherwise specified, default parameters for a particular program or algorithm are used. For instance, percent sequence identity between nucleic acid sequences can be determined using FASTA with its default parameters (a word size of 6 and the NOPAM factor for the scoring matrix) or using Gap with its default parameters as provided in GCG Version 6.1, incorporated herein by reference.

A reference to a nucleotide sequence encompasses its complement unless otherwise specified. Thus, a reference to a nucleic acid having a particular sequence should be understood to encompass its complementary strand, with its complementary sequence.

The term "substantial similarity" or "substantial sequence similarity," when referring to a nucleic acid or fragment thereof, means that when optimally aligned with appropriate nucleotide insertions or deletions with another nucleic acid (or its complementary strand), there is nucleotide sequence identity in at least about 85%, preferably at least about 90%, and more preferably at least about 95%, 96%, 97%, 98% or 99% of the nucleotide bases, as measured by any well-known algorithm of sequence identity, such as FASTA, BLAST or Gap, as discussed above.

The term "percent sequence identity" in the context of amino acid sequences means the residues in two sequences that are the same when aligned for maximum correspondence. The length of sequence identity comparison may be over a stretch of at least about five amino acids, usually at least about 20 amino acids, more usually at least about 30 amino acids, typically at least about 50 amino acids, more typically at least about 100 amino acids, and even more typically about 150, 200 or more amino acids. There are a number of different algorithms known in the art that can be used to measure amino acid sequence identity. For instance, amino acid sequences can be compared using FASTA, Gap or BESTFIT®, which are programs in Wisconsin Package Version 10.0, Genetics Computer Group (GCG), Madison, Wis.

As applied to polypeptides, the term "substantial identity" or "substantial similarity" means that two amino acid sequences, when optimally aligned, such as by the programs GAP or BESTFIT® using default gap weights as supplied with the programs, share at least 70%, 75% or 80% sequence identity, preferably at least 90% or 95% sequence identity, and more preferably at least 97%, 98% or 99% sequence identity. In certain embodiments, residue positions that are not identical differ by conservative amino acid substitutions.

The term "signal sequence," also called signal peptide, leader peptide, refers to a segment of about 15 to 30 amino acids at the N terminus of a protein that enables the protein to be secreted (pass through a cell membrane). The signal sequence is removed as the protein is secreted.

As used herein, the terms "label" or "labeled" refers to incorporation of another molecule in the antibody. In one embodiment, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). In another embodiment, the label or marker can be therapeutic, e.g., a drug conjugate or toxin. Various methods of labeling polypeptides and glycoproteins are known in the art and may be used. Examples of labels for polypeptides include, but are not limited to, the following: radioisotopes or radionuclides (e.g., $^3$H, $^{14}$C, $^{15}$N, $^{35}$S, $^{90}$Y, $^{99}$Tc, $^{111}$In, $^{125}$I, $^{131}$I), fluorescent labels (e.g., FITC, rhodamine, lanthanide phosphors), enzymatic labels (e.g., horseradish peroxidase, β-galactosidase, luciferase, alkaline phosphatase), chemiluminescent markers, biotinyl groups, predetermined polypeptide epitopes recognized by a secondary reporter (e.g., leucine zipper pair sequences, binding sites for secondary antibodies, metal binding domains, epitope tags), magnetic agents, such as gadolinium chelates, toxins such as pertussis toxin, TAXOL® (paclitaxel), cytochalasin B, gramicidin D, ethidium bromide, emetine, mitomycin, etoposide, tenoposide, vincristine, vinblastine, colchicine, doxorubicin, daunorubicin, dihydroxy anthracin drone, mitoxantrone, mithramycin, actinomycin D, 1-dehydrotestosterone, glucocorticoids, procaine, tetracaine, lidocaine, propranolol, and puromycin and analogs or homologs thereof. In some embodiments, labels are attached by spacer arms of various lengths to reduce potential steric hindrance.

The term "primate" refers to a mammal of the order primates, which includes the anthropoids and prosimians, characterized by refined development of the hands and feet, a shortened snout, and a large brain. The mammalian order Primates includes humans, apes, monkeys, and prosimians, or lower primates.

"Therapeutically effective amount" refers to that amount of the therapeutic agent being administered which will relieve to some extent one or more of the symptoms of the disorder being treated. In reference to the treatment of cancer, a therapeutically effective amount refers to that amount which has at least one of the following effects: reducing the size of the tumor; inhibiting (that is, slowing to some extent, preferably stopping) tumor metastasis; inhibiting to some extent (that is, slowing to some extent, preferably stopping) tumor growth, and relieving to some extent (or, preferably, eliminating) one or more symptoms associated with the cancer.

"Treat", "treating" and "treatment" refer to a method of alleviating or abrogating a biological disorder and/or its attendant symptoms. With regard to cancer, these terms simply mean that the life expectancy of an individual affected with a cancer will be increased or that one or more of the symptoms of the disease will be reduced.

"Contacting" refers to bringing an antibody or antigen binding portion thereof of the present invention and a target ALK-1, or epitiope thereof, together in such a manner that the antibody can affect the biological activity of the ALK-1. Such "contacting" can be accomplished "in vitro," i.e., in a test tube, a petri dish, or the like. In a test tube, contacting may involve only an antibody or antigen binding portion thereof and ALK-1 or epitope thereof or it may involve whole cells. Cells may also be maintained or grown in cell culture dishes and contacted with antibodies or antigen binding portions thereof in that environment. In this context, the ability of a particular antibody or antigen binding portion thereof to affect a ALK-1-related disorder, i.e., the $IC_{50}$ of the antibody, can be determined before use of the antibody in vivo with more complex living organisms is attempted. For cells outside the organism, multiple methods exist, and are well-known to those skilled in the art, to contact ALK-1 with the antibodies or antigen-binding portions thereof.

The acronym "FACS" refers to Fluorescence Activated Cell Sorting. The acronym FACS and flow cytometry are used interchangeably. Fluorescent labeling allows investigation of cell structure and function. Immunofluorescence, the most widely used application, involves the staining of cells with antibodies conjugated to fluorescent dyes such as fluorescein and phycoerythrin. This method is often used to label molecules on the cell surface, but antibodies can be directed at targets in cytoplasm. In direct immunofluorescence an antibody to a molecule is directly conjugated to a fluorescent dye, and cells are stained in one step. In indirect immunofluorescence the primary antibody is not labeled, and a second fluorescently conjugated antibody is added which is specific for the first antibody.

Anti-ALK-1 Antibodies

This invention pertains to isolated neutralizing anti-ALK-1 monoclonal antibodies or antigen-binding portions thereof that bind to primate ALK-1, preferably the ECD of primate ALK-1, more preferably the ECD of human ALK-1. In a preferred embodiment, the invention pertains to isolated neutralizing antibodies that are fully human monoclonal antibodies or antigen-binding portions thereof. Preferably, the human antibodies are recombinant human anti-ALK-1 antibodies that have greater affinity for ALK-1 than for ALK-2 through ALK-7. In some embodiments, human anti-ALK-1 antibodies are produced by immunizing a non-human transgenic animal, e.g., a rodent, whose genome comprises human immunoglobulin genes so that the transgenic animal produces human antibodies. Various aspects of the invention relate to such antibodies and antigen-binding portions, and pharmaceutical compositions thereof, as well as nucleic acids, recombinant expression vectors and host cells for making such antibodies and antigen-binding portions. Methods of using the antibodies and antigen-binding portions of the present invention to abrogate the ALK-1/TGF-beta-1/Smad1 signaling pathway or to detect ALK-1, either in vitro or in vivo, are also encompassed by the invention.

An anti-ALK-1 antibody of the invention can comprise a human kappa or a human lambda light chain or an amino acid sequence derived therefrom. In some embodiments comprising a kappa light chain, the light chain variable domain ($V_L$) utilizes a human A27, A2, A1, A3, B3, B2, L1 or L2 $V_K$ gene. In some embodiments, the light chain utilizes a human $V_K$ L1 gene and a human $J_K$ 4 gene; a human $V_K$ A27 gene and a human $J_K$ 5 gene or a human $J_K$ 4 gene; a human $V_K$ B3 gene and a human $J_K$ 1 gene; a human $V_K$ L2 gene and a human $J_K$ 3 gene; a human $V_K$ A2 gene and a human $J_K$ 1 gene; a human $V_K$ A3 gene and a human $J_K$ 4 gene; a human $V_K$ A1 gene and a human $J_K$ 1 gene; a human $V_K$ B2 gene and a human $J_K$ 4 gene; or a human $V_K$ A2 gene and a human $J_K$ 1 gene.

In some embodiments, the $V_L$ of the anti-ALK-1 antibody comprises one or more amino acid substitutions, deletions or insertions (additions) relative to the germline $V_K$ amino acid sequence. In some embodiments, the $V_L$ of the anti-ALK-1 antibody comprises 1, 2, 3, 4, 5, 6, 7, 8, 9, 10, 11, 12, 13, 14 or 15 amino acid substitutions relative to the germline $V_K$ amino acid sequence. In some embodiments, one or more of the substitutions from germline is in the CDR regions of the light chain. In some embodiments, the $V_K$ amino acid substitutions relative to germline are at one or more of the same positions as the substitutions relative to germline found in any one or more of the $V_L$ of the antibodies provided herein as shown, for example, at FIG. 7. In some embodiments, the amino acid changes are at one or more of the same positions, but involve a different substitution than in the reference antibody.

In some embodiments, amino acid substitutions relative to germline occur at one or more of the same positions as substitutions from germline in any of the $V_L$ of antibodies 1.11.1; 1.12.1; 1.12.1(rWT); 1.13.1; 1.14.1; 1.151.1; 1.162.1; 1.183.1; 1.27.1; 1.29.1; 1.31.1; 1.8.1; 1.9.1; 4.10.1; 4.24.1; 4.38.1; 4.58.1; 4.62.1; 4.68.1; 4.72.1; 5.13.1; 5.34.1; 5.53.1; 5.56.1; 5.57.1; and 5.59.1, but the substitutions may represent conservative amino acid substitutions at such position(s) relative to the amino acid in the reference antibody. For example, if a particular position in one of these antibodies is changed relative to germline and is glutamate, one may substitute aspartate at that position. Similarly, if an amino acid substitution compared to germline in an exemplified antibody is serine, one may conservatively substitute threonine for serine at that position. Conservative amino acid substitutions are discussed supra.

In some embodiments, the anti-ALK-1 antibody comprises a light chain amino acid sequence of SEQ ID NO: 4. In other embodiments, the light chain comprises the light chain amino acid sequence of antibody 1.11.1; 1.12.1; 1.12.1(rWT); 1.12.1(M29I/D19A); 1.12.1(M29I); 1.12.1(D19A); 1.13.1; 1.14.1; 1.151.1; 1.162.1; 1.183.1; 1.27.1; 1.29.1; 1.31.1; 1.8.1; 1.9.1; 4.10.1; 4.24.1; 4.38.1; 4.58.1; 4.62.1; 4.68.1; 4.72.1; 5.13.1; 5.34.1; 5.53.1; 5.56.1; 5.57.1; or 5.59.1.

In some embodiments, the light chain of the human anti-ALK-1 antibody comprises the $V_L$ amino acid sequence of antibody 1.12.1 (SEQ ID NO: 8); 1.11.1 (SEQ ID NO: 12); 1.13.1 (SEQ ID NO: 16); 1.14.1 (SEQ ID NO: 20); 1.151.1 (SEQ ID NO: 24); 1.162.1 (SEQ ID NO: 28); 1.183.1 (SEQ ID NO: 32); 1.8.1 (SEQ ID NO: 36); 1.9.1 (SEQ ID NO: 40); 4.10.1 (SEQ ID NO: 44); 4.24.1 (SEQ ID NO: 48); 4.38.1 (SEQ ID NO: 52); 4.58.1 (SEQ ID NO: 56); 4.62.1 (SEQ ID NO: 60); 4.68.1 (SEQ ID NO: 64); 4.72.1 (SEQ ID NO: 68); 5.13.1 (SEQ ID NO: 72); 5.34.1 (SEQ ID NO: 76); 5.53.1 (SEQ ID NO: 80); 5.56.1 (SEQ ID NO: 84); 5.57.1 (SEQ ID NO: 88); or 5.59.1 (SEQ ID NO: 92); or said amino acid sequence having up to 1, 2, 3, 4, 5, 6, 7, 8, 9, 10, 11, 12, 13, 14 or 15 conservative amino acid substitutions and/or a total of up to 3 non-conservative amino acid substitutions. In other embodiments the light chain of the human anti-ALK-1 antibody comprises the $V_L$ amino acid sequence of antibody 1.27.1; 1.29.1 or 1.31.1. In some embodiments, the light chain comprises the amino acid sequence from the beginning of the CDR1 to the end of the CDR3 of any one of the foregoing antibodies.

In some embodiments, the light chain may comprise the amino acid sequences of CDR1, CDR2 and CDR3 regions independently selected from the light chain CDR1, CDR2 and CDR3 regions, respectively, of two or more monoclonal antibodies selected from 1.11.1; 1.12.1; 1.12.1(rWT); 1.12.1 (M29I/D19A); 1.12.1(M29I); 1.12.1(D19A); 1.13.1; 1.14.1; 1.151.1; 1.162.1; 1.183.1; 1.27.1; 1.29.1; 1.31.1; 1.8.1; 1.9.1; 4.10.1; 4.24.1; 4.38.1; 4.58.1; 4.62.1; 4.68.1; 4.72.1; 5.13.1; 5.34.1; 5.53.1; 5.56.1; 5.57.1; or 5.59.1, or said CDR regions each having less than 3 or less than 2 conservative amino acid substitutions and/or a total of three or fewer non-conservative amino acid substitutions.

In certain embodiments, the light chain of the anti-ALK-1 antibody comprises the amino acid sequences of the light chain CDR1, CDR2 and CDR3 regions of an antibody selected from 1.11.1; 1.12.1; 1.12.1(rWT); 1.12.1(M29I/D19A); 1.12.1(M29I); 1.12.1(D19A); 1.13.1; 1.14.1; 1.151.1; 1.162.1; 1.183.1; 1.27.1; 1.29.1; 1.31.1; 1.8.1; 1.9.1; 4.10.1; 4.24.1; 4.38.1; 4.58.1; 4.62.1; 4.68.1; 4.72.1; 5.13.1; 5.34.1; 5.53.1; 5.56.1; 5.57.1; or 5.59.1, or said CDR regions each having less than 3 or less than 2 conservative amino acid substitutions and/or a total of three or fewer non-conservative amino acid substitutions.

With regard to the heavy chain, in some embodiments, the variable domain ($V_H$) utilizes a human $V_H$ 4-31, $V_H$ 3-11, $V_H$ 3-15, $V_H$ 3-33, $V_H$ 4-61 or $V_H$ 4-59 gene. In some embodiments, the $V_H$ sequence of the anti-ALK-1 antibody contains one or more amino acid substitutions, deletions or insertions (additions), collectively "mutations", relative to the germline $V_H$ amino acid sequence. In some embodiments, the variable domain of the heavy chain comprises 1, 2, 3, 4, 5, 6, 7, 8, 9, 10 or 11 mutations from the germline $V_H$ amino acid sequence. In some embodiments, the mutation(s) are non-conservative substitutions compared to the germline amino acid sequence. In some embodiments, the mutations are in the CDR regions of the heavy chain. In some embodiments, the heavy chain utilizes a human $V_H$ 3-33 gene, a human D 6-19 gene and a human $J_H$ 3B gene; a human $V_H$ 4-31 gene, a human D 6-19 gene and a human $J_H$ 4B gene; a human $V_H$ 4-61 gene, a human D 6-19 gene and a human $J_H$ 4B gene; a human $V_H$ 4-31 gene, a human D 3-3 gene and a human $J_H$ 3B gene; a human $V_H$ 4-31 gene and a human $J_H$ 3B gene; a human $V_H$ 4-59 gene, a human D 6-19 gene and a human $J_H$ 4B gene; a human $V_H$ 3-11 gene, a human D 3-22 gene and a human $J_H$ 6B gene; a human $V_H$ 3-15 gene, a human D 3-22 gene and a human $J_H$ 4B gene; a human $V_H$ 4-31 gene, a human D 5-12 gene and a human $J_H$ 6B gene; a human $V_H$ 4-31 gene, a human D 4-23 gene and a human $J_H$ 4B gene; a human $V_H$ 4-31 gene, a human D 2-2 gene and a human $J_H$ 5B gene; a human $V_H$ 4-31 gene and a human $J_H$ 6B gene; human $V_H$ 3-15 gene, a human D 1-1 gene and a human $J_H$ 4B gene; a human $V_H$ 3-11 gene, a human D 6-19 gene and a human $J_H$ 6B gene; a human $V_H$ 3-11 gene, a human D 3-10 gene and a human $J_H$ 6B gene; or a human $V_H$ 3-11 gene, a human D 6-6 gene and a human $J_H$ 6B gene.

In some embodiments, amino acid substitutions are at one or more of the same positions as the substitutions from germline in any one or more of the $V_H$ of antibodies 1.11.1; 1.12.1; 1.12.1(rWT); 1.12.1(M29I/D19A); 1.12.1(M29I); 1.12.1(D19A); 1.13.1; 1.14.1; 1.151.1; 1.162.1; 1.183.1; 1.27.1; 1.29.1; 1.31.1; 1.8.1; 1.9.1; 4.10.1; 4.24.1; 4.38.1; 4.58.1; 4.62.1; 4.68.1; 4.72.1; 5.13.1; 5.34.1; 5.53.1; 5.56.1; 5.57.1; or 5.59.1. In other embodiments, the amino acid changes are at one or more of the same positions but involve a different substitution than in the reference antibody.

In some embodiments, the heavy chain comprises an amino acid sequence of SEQ ID NO: 2, in other embodiments, the heavy chain comprises the heavy chain amino acid sequence of antibody 1.11.1; 1.12.1; 1.12.1(rWT); 1.12.1 (M29I/D19A); 1.12.1(M29I); 1.12.1(D19A); 1.13.1; 1.14.1; 1.151.1; 1.162.1; 1.183.1; 1.27.1; 1.29.1; 1.31.1; 1.8.1; 1.9.1; 4.10.1; 4.24.1; 4.38.1; 4.58.1; 4.62.1; 4.68.1; 4.72.1; 5.13.1; 5.34.1; 5.53.1; 5.56.1; 5.57.1; or 5.59.1. In some embodiments, the heavy chain comprises the $V_H$ amino acid sequence of antibody 1.12.1 (SEQ ID NOS: 6); 1.11.1 (SEQ ID NO: 10); 1.13.1 (SEQ ID NO: 14); 1.14.1 (SEQ ID NO: 18); 1.151.1 (SEQ ID NO: 22); 1.162.1 (SEQ ID NO: 26); 1.183.1 (SEQ ID NO: 30); 1.8.1 (SEQ ID NO: 34); 1.9.1 (SEQ ID NO: 38); 4.10.1 (SEQ ID NO: 42); 4.24.1 (SEQ ID NO: 46); 4.38.1 (SEQ ID NO: 50); 4.58.1 (SEQ ID NO: 54); 4.62.1 (SEQ ID NO: 58); 4.68.1 (SEQ ID NO: 62); 4.72.1 (SEQ ID NO: 66); 5.13.1 (SEQ ID NO: 70); 5.34.1 (SEQ ID NO: 74); 5.53.1 (SEQ ID NO: 78); 5.56.1 (SEQ ID NO: 82); 5.57.1 (SEQ ID NO: 86); or 5.59.1 (SEQ ID NO: 90); or said V$_H$ amino acid sequence having up to 1, 2, 3, 4, 6, 8, 9, 10 or 11 conservative amino acid substitutions and/or a total of up to 3 non-conservative amino acid substitutions. In other embodiments, the heavy chain comprises the V$_H$ amino acid sequence of antibody 1.27.1; 1.29.1 or 1.31.1. In some embodiments, the heavy chain comprises the amino acid sequence from the beginning of the CDR1 to the end of the CDR3 of any one of the foregoing antibodies.

In some embodiments, the heavy chain comprises the heavy chain CDR1. CDR2 and CDR3 regions of antibody 1.11.1; 1.12.1; 1.12.1(rWT); 1.12.1(M29I/D19A); 1.12.1 (M29I); 1.12.1(D19A); 1.13.1; 1.14.1; 1.151.1; 1.162.1; 1.183.1; 1.27.1; 1.29.1; 1.31.1; 1.8.1; 1.9.1; 4.10.1; 4.24.1; 4.38.1; 4.58.1; 4.62.1; 4.68.1; 4.72.1; 5.13.1; 5.34.1; 5.53.1; 5.56.1; 5.57.1; or 5.59.1, or said CDR regions each having less than 8, less than 6, less than 4, or less than 3 conservative amino acid substitutions and/or a total of three or fewer non-conservative amino acid substitutions.

In some embodiments, the heavy chain CDR regions are independently selected from the CDR regions of two or more antibodies selected from antibodies 1.11.1; 1.12.1; 1.12.1 (rWT); 1.12.1(M29I/D19A); 1.12.1(M29I); 1.12.1(D19A); 1.13.1; 1.14.1; 1.151.1; 1.162.1; 1.183.1; 1.27.1; 1.29.1; 1.31.1; 1.8.1; 1.9.1; 4.10.1; 4.24.1; 4.38.1; 4.58.1; 4.62.1; 4.68.1; 4.72.1; 5.13.1; 5.34.1; 5.53.1; 5.56.1; 5.57.1; or 5.59.1. In another embodiment, the antibody comprises a light chain as disclosed above and a heavy chain as disclosed above. In a further embodiment, the light chain CDRs and the heavy chain CDRs are from the same antibody.

In various embodiments, the anti-ALK-1 antibodies have the full-length heavy chain and full length light chain amino acid sequence(s), the V$_H$ and V$_L$ amino acid sequences, the heavy chain CDR1, CDR2 and CDR3 and light chain CDR1, CDR2 and CDR3 amino acid sequences or the heavy chain amino acid sequence from the beginning of the CDR1 to the end of the CDR3 and the light chain amino acid sequence from the beginning of the CDR1 to the end of the CDR3 of an anti-ALK-1 antibody provided herein.

One type of amino acid substitution that may be made is to change one or more cysteines in the antibody, which may be chemically reactive, to another residue, such as, without limitation, alanine or serine. In one embodiment, there is a substitution of a non-canonical cysteine. The substitution can be made in a CDR or framework region of a variable domain or in the constant domain of an antibody. In some embodiments, the cysteine is canonical.

Another type of amino acid substitution that may be made is to remove potential proteolytic sites in the antibody. Such sites may occur in a CDR or framework region of a variable domain or in the constant domain of an antibody. Substitution of cysteine residues and removal of proteolytic sites may decrease the risk of heterogeneity in the antibody product and thus increase its homogeneity. Another type of amino acid substitution is to eliminate asparagine-glycine pairs, which form potential deamidation sites, by altering one or both of the residues.

In some embodiments, the C-terminal lysine of the heavy chain of the anti ALK-1 antibody of the invention is cleaved. In various embodiments of the invention, the heavy and light chains of the anti-ALK-1 antibodies may optionally include a signal sequence.

In one aspect, the invention provides twenty five inhibitory human anti-ALK-1 monoclonal antibodies and the hybridoma cell lines that produce them. In certain embodiments, antibodies of the present invention are IgGs designated as: 1.11.1; 1.12.1; 1.12.1(rWT); 1.12.1(M29I/D19A); 1.12.1 (M29I); 1.12.1(D19A); 1.13.1; 1.14.1; 1.151.1; 1.162.1; 1.183.1; 1.27.1; 1.29.1; 1.31.1; 1.8.1; 1.9.1; 4.10.1; 4.24.1; 4.38.1; 4.58.1; 4.62.1; 4.68.1; 4.72.1; 5.13.1; 5.34.1; 5.53.1; 5.56.1; 5.57.1; and 5.59.1. In preferred embodiments, the human anti-ALK-1 antibody is antibody 1.12.1, 1.12.1 (M29I/D19A), 1.12.1(M29I), 1.12.1(D19A), 1.27.1, 1.14.1, 1.162.1, 1.31.1, 4.62.1 or 4.72.1.

Antibodies recognize surface-exposed epitopes on antigens as regions of linear (primary) sequence or structural (secondary) sequence. BIAcore was used in order to define the functional epitope landscape and determine the epitope exclusivity of the anti-ALK-1 antibodies exemplified by this invention.

Table 1 lists the sequence identifiers (SEQ ID NO) of the nucleic acids encoding the full-length heavy and light chains of 1.12.1 antibody variants and variable domain-containing portions of anti-ALK-1 antibodies of the invention, and the corresponding deduced amino acid sequences.

TABLE 1

SEQUENCE IDENTIFIERS (SEQ ID NO)

| Antibody | FULL LENGTH | | | | V DOMAIN CONTAINING PORTION | | | |
|---|---|---|---|---|---|---|---|---|
| | Heavy | | Light | | Heavy | | Light | |
| | DNA | PROTEIN | DNA | PROTEIN | DNA | PROTEIN | DNA | PROTEIN |
| 1.11.1 | | | | | 9 | 10 | 11 | 12 |
| 1.12.1(M29I/D19A) | 1 | 2 | 3 | 4 | 5 | 6 | 7 | 8 |
| 1.12.1 | 95 | 100 | 101 | 102 | 103 | 104 | 126 | 127 |
| 1.12.1(rWT) | 128 | 100 | 101 | 102 | 129 | 104 | 126 | 127 |
| 1.13.1 | | | | | 13 | 14 | 15 | 16 |
| 1.14.1 | | | | | 17 | 18 | 19 | 20 |
| 1.151.1 | | | | | 21 | 22 | 23 | 24 |
| 1.162.1 | | | | | 25 | 26 | 27 | 28 |
| 1.183.1 | | | | | 29 | 30 | 31 | 32 |
| 1.8.1 | | | | | 33 | 34 | 35 | 36 |
| 1.9.1 | | | | | 37 | 38 | 39 | 40 |
| 4.10.1 | | | | | 41 | 42 | 43 | 44 |
| 4.24.1 | | | | | 45 | 46 | 47 | 48 |
| 4.38.1 | | | | | 49 | 50 | 51 | 52 |
| 4.58.1 | | | | | 53 | 54 | 55 | 56 |
| 4.62.1 | | | | | 57 | 58 | 59 | 60 |
| 4.68.1 | | | | | 61 | 62 | 63 | 64 |
| 4.72.1 | | | | | 65 | 66 | 67 | 68 |
| 5.13.1 | | | | | 69 | 70 | 71 | 72 |
| 5.34.1 | | | | | 73 | 74 | 75 | 76 |
| 5.53.1 | | | | | 77 | 78 | 79 | 80 |
| 5.56.1 | | | | | 81 | 82 | 83 | 84 |
| 5.57.1 | | | | | 85 | 86 | 87 | 88 |
| 5.59.1 | | | | | 89 | 90 | 91 | 92 |

1.12.1(M29I/D19A) refers to the anti-ALK-1 antibody containing a specific single amino acid mutation in the heavy chain where the methionine at position 29 was replaced with isoleucine and a specific single amino acid mutation in the light chain where the aspartic acid at position 19 was replaced with alanine as described in Example 4.

1.12.1 refers to the mAb 1.12.1 variant that was isolated from the hybridoma.

1.12.1(rWT) refers to the mAb 1.12.1 variant that was expressed as a recombinant mAb described in Example 3.

The invention further provides heavy and/or light chain variants of certain of the above-listed human anti-ALK-1 antibodies, comprising one or more amino acid modifications. To designate the variants, the first letter is the one letter symbol for the amino acid of the naturally-occurring antibody chain, the number refers to the position of the amino acid (wherein position one is the N-terminal amino acid of the FR1), and the second letter is the one letter symbol for the variant amino acid.

In still further embodiments, the invention includes antibodies comprising variable domain amino acid sequences with more than 80%, more than 85%, more than 90%, more than 95%, more than 96%, more than 97%, more than 98% or more than 99% sequence identity to a variable domain amino acid sequence of any of the above-listed human anti-ALK-1 antibodies.

Class and Subclass of Anti-ALK-1 Antibodies

The class and subclass of anti-ALK-1 antibodies may be determined by any method known in the art. In general, the class and subclass of an antibody may be determined using antibodies that are specific for a particular class and subclass of antibody. Such antibodies are available commercially. The class and subclass can be determined by ELISA, Western Blot as well as other techniques. Alternatively, the class and subclass may be determined by sequencing all or a portion of the constant domains of the heavy and/or light chains of the antibodies, comparing their amino acid sequences to the known amino acid sequences of various class and subclasses of immunoglobulins, and determining the class and subclass of the antibodies.

The class of an anti-ALK-1 antibody obtained as described above may be switched with another. In one aspect of the invention, a nucleic acid molecule encoding $V_L$ or $V_H$ is isolated using methods well-known in the art such that it does not include nucleic acid sequences encoding $C_L$ or $C_H$, "Antibody Engineering" (Kontermann & Dubel, Eds., Springer-Verlag, Berlin (2001)). The nucleic acid molecules encoding $V_L$ or $V_H$ are then operatively linked to a nucleic acid sequence encoding a $C_L$ or $C_H$, respectively, from a different class of immunoglobulin molecule. This may be achieved using a vector or nucleic acid molecule that comprises a $C_L$ or $C_H$ chain, as described above. For example, an anti-ALK-1 antibody that was originally IgM may be class switched to an IgG. Further, the class switching may be used to convert one IgG subclass to another, e.g., from IgG1 to IgG2. A preferred method for producing an antibody of the invention comprising a desired isotypes comprises the steps of isolating a nucleic acid molecule encoding the heavy chain of an anti-ALK-1 antibody and a nucleic acid molecule encoding the light chain of an anti-ALK-1 antibody, obtaining the variable domain of the heavy chain, ligating the variable domain of the heavy chain with the constant domain of a heavy chain of the desired isotype, expressing the light chain and the ligated heavy chain in a cell, and collecting the anti-ALK-1 antibody with the desired isotype.

In some embodiments, the anti-ALK-1 antibody is a monoclonal antibody. The anti-ALK-1 antibody can be an IgG, an IgM, an IgE, an IgA, or an IgD molecule. In a preferred embodiment, the anti-ALK-1 antibody is an IgG and is an IgG1, IgG2, IgG3, IgG4 subclass. In another preferred embodiment, the antibody is subclass IgG2.

Identification of ALK-1 Epitopes
Recognized by Anti-ALK-1 Antibodies

The invention provides a human anti-ALK-1 monoclonal antibody that binds to ALK-1 and competes or cross-competes with and/or binds the same epitope as: (a) an antibody selected from 1.11.1; 1.12.1; 1.12.1(rWT); 1.12.1(M29I/D19A); 1.12.1(M29I); 1.12.1(D19A); 1.13.1; 1.14.1; 1.151.1; 1.162.1; 1.183.1; 1.27.1; 1.29.1; 1.31.1; 1.8.1; 1.9.1; 4.10.1; 4.24.1; 4.38.1; 4.58.1; 4.62.1; 4.68.1; 4.72.1; 5.13.1; 5.34.1; 5.53.1; 5.56.1; 5.57.1; and 5.59.1; (b) an antibody that comprises a heavy chain variable domain having the amino acid sequence of the $V_H$ domain in any one of SEQ ID NOS: 6; 10; 14; 18; 22; 26; 30; 34; 38; 42; 46; 50; 54; 58; 62; 66; 70; 74; 78; 82; 86; 90 or 104, (c) an antibody that comprises a light chain variable domain having the amino acid sequence of the $V_L$ domain in any one of SEQ ID NOS: and 8; 12; 16; 20; 24; 28; 32; 36; 40; 44; 48; 52; 56; 60; 64; 68; 72; 76; 80; 84; 88; 92 or 127, (d) an antibody that comprises both a heavy chain variable domain as defined in (b) and light chain variable domain as defined in (c).

One can determine whether an antibody binds to the same epitope or cross competes for binding with an anti-ALK-1 antibody by using methods known in the art. In one embodiment, one allows the anti-ALK-1 antibody of the invention to bind to ALK-1 under saturating conditions and then measures the ability of the test antibody to bind to ALK-1. If the test antibody is able to bind to ALK-1 at the same time as the reference anti-ALK-1 antibody, then the test antibody binds to a different epitope than the reference anti-ALK-1 antibody. However, if the test antibody is not able to bind to ALK-1 at the same time, then the test antibody binds to the same epitope, an overlapping epitope, or an epitope that is in close proximity to the epitope bound by the anti-ALK-1 antibody of the invention. This experiment can be performed using ELISA, RIA, BIACORE®, or flow cytometry. To test whether an anti-ALK-1 antibody cross-competes with another anti-ALK-1 antibody, one may use the competition method described above in two directions, i.e. determining if the known antibody blocks the test antibody and vice versa. In a preferred embodiment, the experiment is performed using BIACORE®.

Binding Affinity of Anti-ALK-1 Antibodies to ALK-1

The binding affinity ($K_D$) and dissociation rate ($k_{off}$) of an anti-ALK-1 antibody or antigen-binding portion thereof to ALK-1 can be determined by methods known in the art. The binding affinity can be measured by ELISAs, RIAs, flow cytometry, or surface plasmon resonance, such as BIACORE®. The dissociation rate can be measured by surface plasmon resonance. Preferably, the binding affinity and dissociation rate is measured by surface plasmon resonance. More preferably, the binding affinity and dissociation rate are measured using BIACORE®. One can determine whether an antibody has substantially the same $K_D$ as an anti-ALK-1 antibody by using methods known in the art. Such methods of determining $K_D$ and $k_{off}$ can be used during the initial screening stage, as well as during subsequent optimization stages.

Inhibition of ALK-1 Activity by Anti-ALK-1 Antibody

Anti-ALK-1 monoclonal antibodies that inhibit ALK-1 binding can be identified using a number of assays. For example, neutralizing anti-ALK-1 antibodies can be identified by their inhibition of up-regulation of a specific downstream target gene of ALK-1, Id1, as described in Example 12. Preferred anti-ALK-1 antibodies have an $IC_{50}$ of no more than 500 nM, 300 nM, 200 nM, 150 nM, 100 nM, 50 nM, 20 nM, 10 nM, or 1 nM.

One also can determine the ability of an anti-ALK-1 antibody to inhibit Smad1 phosphorylation determined by Western Blotting using ODYSSEY® Infrared Imaging System, as described in Example 13. In various embodiments, the anti-ALK-1 antibody has an $IC_{50}$ in this assay of no more than 250 nM, 200 nM, 150 nM, 100 nM, 50 nM, 20 nM, 10 nM, or 1 nM.

Inhibition of Angiogenesis by Anti-ALK-1 Antibody

In another embodiment, the anti-ALK-1 antibody or portion thereof inhibits human vessel angiogenesis as demonstrated in a SCID mouse engrafted with human foreskin tissue, in which human melanoma M24met tumor cells are intradermally implanted as determined by IHC analysis of human CD-31 signal assay by a factor of at least 40% as compared to a control sample as described in Example 17 and shown in Table 13.

In another embodiment, the anti-ALK-1 antibody or portion thereof inhibits human vessel angiogenesis as demonstrated in a SCID mouse engrafted with human foreskin tissue, in which collagen is intradermally implanted as determined by IHC analysis of human CD-31 signal assay by a factor of at least 50% as compared to a control sample as described in Example 16 and shown in Table 12.

Species and Molecular Selectivity

In another aspect of the invention, the anti-ALK-1 antibodies demonstrate both species and molecular selectivity. Following the teachings of the specification, one may determine the species or molecular selectivity for the anti-ALK-1 antibody using methods well known in the art. For instance, one may determine the species selectivity using Western blot, surface plasmon resonance, e.g., BIACORE®, ELISA, immunoprecipitation or RIA.

In some embodiments, the anti-ALK-1 antibody binds to primate ALK-1 with a $K_D$ that is at least two times smaller than its $K_D$ for rodent ALK-1. In a further embodiment, the $K_D$ for primate ALK-1 is at least 3-fold, at least 10-fold, at least 50-fold, at least 100-fold, at least 200-fold, at least 500-fold, or at least 1000-fold smaller than its $K_D$ for rodent ALK-1 as measured by flow cytometry.

In other embodiments, the anti-ALK-1 antibody has a selectivity for ALK-1 over ALK-2 through ALK-7. In some embodiments, the anti-ALK-1 antibody does not exhibit any appreciable specific binding to any other protein other than ALK-1. Preferably, the anti-ALK-1 antibody binds to the ECD of human ALK-1.

Methods of Producing Antibodies and
Antibody Producing Cell Lines
Alk-1 Immunogen In some embodiments, the ALK-1 immunogen or antigen is isolated and/or purified ALK-1. In some embodiments, the ALK-1 immunogen is human ALK-1. In preferred embodiments, the ALK-1 immunogen is the ECD of human ALK-1. Human ALK-1, or antigenic portions thereof, can be prepared according to methods well known to those in the art, or can be purchased from commercial vendors. The human ALK-1 amino acid and nucleotide sequences are known (see e.g. Genbank record Accession No. L17075). ACVRL1 gene encoding a full-length ALK-1 is commercially available from Invitrogen Inc., Clone ID IOH21048. For example, R&D Systems, Inc. sells the recombinant human ALK-1/Fc chimera (Catalog Number 370-AL) prepared by expression of a DNA sequence encoding the ECD amino acid residues 1-118 of ALK-1, which DNA sequence was fused to a DNA sequence encoding the $F_c$ region of human IgG via a DNA sequence encoding a polypeptide linker in a mouse myeloma cell line. The recombinant mature human ALK-1/Fc chimera is a disulfide-linked homodimeric protein having Asp 22 at the amino-terminus. In addition, Example 1 describes preparation of ALK-1 ECD His-Tag protein which has been used for generation of hybridomas producing an anti-ALK-1 antibody according to the present invention.

In other embodiments, the ALK-1 antigen is a cell that expresses or overexpresses ALK-1. In other embodiments, the ALK-1 antigen is a recombinant protein expressed from yeast, insect cells, bacteria such as *E. coli*, or other resources by recombinant technology.

Immunization

In some embodiments, human antibodies are produced by immunizing a non-human, transgenic animal comprising within its genome some or all of human immunoglobulin heavy chain and light chain loci with a ALK-1 antigen. In a preferred embodiment, the non-human animal is a XENOMOUSE® animal. (Abgenix, Inc., Fremont, Calif.).

XENOMOUSE® mice are engineered mouse strains that comprise large fragments of human immunoglobulin heavy chain and light chain loci and are deficient in mouse antibody production. See, e.g., Green et al., Nature Genetics 7:13-21 (1994) and U.S. Pat. Nos. 5,916,771, 5,939,598, 5,985,615, 5,998,209, 6,075,181, 6,091,001, 6,114,598, 6,130,364, 6,162,963 and 6,150,584. See also WO 91/10741, WO 94/02602, WO 96/34096, WO 96/33735, WO 98/16654, WO 98/24893, WO 98/50433, WO 99/45031, WO 99/53049, WO 00/09560, and WO 00/037504.

In another aspect, the invention provides a method for making anti-ALK-1 antibodies from non-human, non-mouse animals by immunizing non-human transgenic animals that comprise human immunoglobulin loci with an ALK-1 antigen. One can produce such animals using the methods described in the above-cited documents. The methods disclosed in these documents can be modified as described in U.S. Pat. No. 5,994,619, which is hereby incorporated by reference. U.S. Pat. No. 5,994,619 describes methods for producing novel cultured inner cell mass (CICM) cells and cell lines, derived from pigs and cows, and transgenic CICM cells into which heterologous DNA has been inserted. CICM transgenic cells can be used to produce cloned transgenic embryos, fetuses, and offspring. The '619 patent also describes methods of producing transgenic animals that are capable of transmitting the heterologous DNA to their progeny. In preferred embodiments of the current invention, the non-human animals are mammals, particularly rats, sheep, pigs, goats, cattle, horses or chickens.

XENOMOUSE® mice produce an adult-like human repertoire of fully human antibodies and generate antigen-specific human antibodies. In some embodiments, the XENOMOUSE® mice contain approximately 80% of the human antibody V gene repertoire through introduction of megabase sized, germline configuration fragments of the human heavy chain loci and kappa light chain loci in yeast artificial chromosome (YAC). In other embodiments, XENOMOUSE® mice further contain approximately all of the human lambda light chain locus. See Mendez et al., *Nature Genetics* 15:146-156 (1997), Green and Jakobovits, *J. Exp. Med.* 188:483-495 (1998), and WO 98/24893, the disclosures of which are hereby incorporated by reference.

In some embodiments, the non-human animal comprising human immunoglobulin genes are animals that have a human immunoglobulin "minilocus". In the minilocus approach, an exogenous Ig locus is mimicked through the inclusion of individual genes from the Ig locus. Thus, one or more $V_H$ genes, one or more $D_H$ genes, one or more $J_H$ genes, a mu constant domain, and a second constant domain (preferably a gamma constant domain) are formed into a construct for insertion into an animal. This approach is described, inter alia, in U.S. Pat. Nos. 5,545,807, 5,545,806, 5,569,825, 5,625,126, 5,633,425, 5,661,016, 5,770,429, 5,789,650, 5,814,318, 5,591,669, 5,612,205, 5,721,367, 5,789,215, and 5,643,763, hereby incorporated by reference.

In another aspect, the invention provides a method for making humanized anti-ALK-1 antibodies. In some embodiments, non-human animals are immunized with a ALK-1 antigen as described below under conditions that permit antibody production. Antibody-producing cells are isolated from the animals, and nucleic acids encoding the heavy and light chains of an anti-ALK-1 antibody of interest are isolated from the isolated antibody-producing cells or from an immortalized cell line produced from such cells. These nucleic acids are subsequently engineered using techniques known to those of skill in the art and as described further below to reduce the amount of non-human sequence, i.e., to humanize the antibody to reduce the immune response in humans.

Immunization of animals can be by any method known in the art. See, e.g., Harlow and Lane, *Antibodies: A Laboratory Manual*, New York: Cold Spring Harbor Press, 1990. Methods for immunizing non-human animals such as mice, rats, sheep, goats, pigs, cattle and horses are well known in the art. See, e.g., Harlow and Lane, supra, and U.S. Pat. No. 5,994, 619. In a preferred embodiment, the ALK-1 antigen is administered with an adjuvant to stimulate the immune response. Exemplary adjuvants include complete or incomplete Freund's adjuvant, RIBI (muramyl dipeptides) or ISCOM (immunostimulating complexes). Such adjuvants may protect the polypeptide from rapid dispersal by sequestering it in a local deposit, or they may contain substances that stimulate the host to secrete factors that are chemotactic for macrophages and other components of the immune system. Preferably, if a polypeptide is being administered, the immunization schedule will involve two or more administrations of the polypeptide, spread out over several weeks. Example 2 exemplifies a method for producing anti-ALK-1 monoclonal antibodies in XENOMOUSE® mice.

Production of Antibodies and Antibody-Producing Cell Lines

After immunization of an animal with a ALK-1 antigen, antibodies and/or antibody-producing cells can be obtained from the animal. In some embodiments, anti-ALK-1 antibody-containing serum is obtained from the animal by bleeding or sacrificing the animal. The serum may be used as it is obtained from the animal, an immunoglobulin fraction may be obtained from the serum, or the anti-ALK-1 antibodies may be purified from the serum.

In some embodiments, antibody-producing cell lines are prepared from cells isolated from the immunized animal. After immunization, the animal is sacrificed and lymph node and/or splenic B cells are immortalized by any means known in the art. Methods of immortalizing cells include, but are not limited to, transfecting them with oncogenes, infecting them with an oncogenic virus and cultivating them under conditions that select for immortalized cells, subjecting them to carcinogenic or mutating compounds, fusing them with an immortalized cell, e.g., a myeloma cell, and inactivating a tumor suppressor gene. See, e.g., Harlow and Lane, supra. If fusion with myeloma cells is used, the myeloma cells preferably do not secrete immunoglobulin polypeptides (a non-secretory cell line). Immortalized cells are screened using ALK-1, or a portion thereof. In a preferred embodiment, the initial screening is performed using an enzyme-linked immunoassay (ELISA) or a radioimmunoassay. An example of ELISA screening is provided in WO 00/37504, incorporated herein by reference.

Anti-ALK-1 antibody-producing cells, e.g., hybridomas, are selected, cloned and further screened for desirable characteristics, including robust growth, high antibody production and desirable antibody characteristics, as discussed further below. Hybridomas can be expanded in vivo in syngeneic animals, in animals that lack an immune system, e.g., nude mice, or in cell culture in vitro. Methods of selecting, cloning and expanding hybridomas are well known to those of ordinary skill in the art.

In a preferred embodiment, the immunized animal is a non-human animal that expresses human immunoglobulin genes and the splenic B cells are fused to a myeloma cell line from the same species as the non-human animal. In a more preferred embodiment, the immunized animal is a XENOMOUSE® mouse and the myeloma cell line is a non-secretory mouse myeloma. In an even more preferred embodiment, the myeloma cell line is P3-X63-Ag8.653 (American Type Culture Collection). See, e.g., Example 2.

Thus, in one embodiment, the invention provides methods for producing a cell line that produces a human monoclonal antibody or a fragment thereof directed to ALK-1 comprising (a) immunizing a non-human transgenic animal described herein with ALK-1, a portion of ALK-1 or a cell or tissue expressing ALK-1; (b) allowing the transgenic animal to mount an immune response to ALK-1; (c) isolating antibody-producing cells from transgenic animal; (d) immortalizing the antibody-producing cells; (e) creating individual monoclonal populations of the immortalized antibody-producing cells; and (f) screening the immortalized antibody-producing cells to identify an antibody directed to ALK-1.

In another aspect, the invention provides a cell line that produces a human anti-ALK-1 antibody. In some embodiments the cell line is a hybridoma cell line. In some embodiments, the hybridomas are mouse hybridomas, as described above. In other embodiments, the hybridomas are produced in a non-human, non-mouse species such as rats, sheep, pigs, goats, cattle or horses. In another embodiment, the hybridomas are human hybridomas.

In another embodiment, a transgenic animal is immunized with an ALK-1 antigen, primary cells, e.g., spleen or peripheral blood B cells, are isolated from an immunized transgenic animal and individual cells producing antibodies specific for the desired antigen are identified. Polyadenylated mRNA from each individual cell is isolated and reverse transcription polymerase chain reaction (RT-PCR) is performed using sense primers that anneal to variable domain sequences, e.g., degenerate primers that recognize most or all of the FR1 regions of human heavy and light chain variable domain genes and anti-sense primers that anneal to constant or joining region sequences. cDNAs of the heavy and light chain variable domains are then cloned and expressed in any suitable host cell, e.g., a myeloma cell, as chimeric antibodies with respective immunoglobulin constant regions, such as the heavy chain and κ or λ constant domains. See Babcook, J. S. et al., *Proc. Natl. Acad. Sci. USA* 93:7843-48, 1996, incorporated herein by reference. Anti ALK-1 antibodies may then be identified and isolated as described herein.

In another embodiment, phage display techniques can be used to provide libraries containing a repertoire of antibodies with varying affinities for ALK-1. For production of such repertoires, it is unnecessary to immortalize the B cells from the immunized animal. Rather, the primary B cells can be used directly as a source of DNA. The mixture of cDNAs obtained from B cell, e.g., derived from spleens, is used to prepare an expression library, for example, a phage display library transfected into *E. coli*. The resulting cells are tested for immunoreactivity ALK-1. Techniques for the identification of high affinity human antibodies from such libraries are described by Griffiths et al., *EMBO J.*, 13:3245-3260 (1994); Nissim et al., ibid, pp. 692-698 and by Griffiths et al., ibid, 12:725-734, which are incorporated by reference. Ultimately, clones from the library are identified that produce binding affinities of a desired magnitude for the antigen and the DNA encoding the product responsible for such binding is recovered and manipulated for standard recombinant expression. Phage display libraries may also be constructed using previously manipulated nucleotide sequences and screened in a similar fashion. In general, the cDNAs encoding heavy and light chains are independently supplied or linked to form Fv analogs for production in the phage library.

The phage library is then screened for the antibodies with the highest affinities for ALK-1 and the genetic material recovered from the appropriate clone. Further rounds of screening can increase affinity of the original antibody isolated.

Nucleic Acids, Vectors, Host Cells, and
Recombinant Methods of Making Antibodies
Nucleic Acids The present invention also encompasses nucleic acid molecules encoding anti-ALK-1 antibodies or an antigen-binding fragments thereof. In some embodiments, different nucleic acid molecules encode a heavy chain and a light chain of an anti-ALK-1 immunoglobulin. In other embodiments, the same nucleic acid molecule encodes a heavy chain and a light chain of an anti-ALK-1 immunoglobulin.

In some embodiments, the nucleic acid molecule encoding the variable domain of the light chain ($V_L$) utilizes a human A27, A2, A1, A3, B3, B2, L1 or L2 $V_K$ gene, and a human Jκ5, Jκ1, Jκ3 or Jκ4 gene. In some embodiments the nucleic acid molecule utilizes a human A27 Vκ gene and a human Jκ5 gene. In other embodiments, the nucleic acid molecule utilizes a human A2 gene and a human Jκ1 gene. In some embodiments, the nucleic acid molecule encoding the light chain encodes an amino acid sequence comprising 1, 2, 3, 4, 5, 6, 7, 8, 9, 10, 11, 12, 13, 14 or 15 substitutions from the germline amino acid sequence(s). In some embodiments, the nucleic acid molecule comprises a nucleotide sequence that encodes a $V_L$ amino acid sequence comprising 1, 2, 3, 4, 5, 6, 7, 8, 9, 10, 11, 12, 13, 14 or 15 conservative amino acid substitutions and/or 1, 2, or 3 non-conservative substitutions compared to germline $V_K$ and $J_K$ sequences. Substitutions may be in the CDR regions, the framework regions, or in the constant domain.

In some embodiments, the nucleic acid molecule encodes a $V_L$ amino acid sequence comprising one or more mutations compared to the germline sequence that are identical to the mutations from germline found in the $V_L$ of any one of antibodies 1.11.1; 1.12.1; 1.12.1(rWT); 1.12.1(M29I/D19A); 1.12.1(M29I); 1.12.1(D19A); 1.13.1; 1.14.1; 1.151.1; 1.162.1; 1.183.1; 1.27.1; 1.29.1; 1.31.1; 1.8.1; 1.9.1; 4.10.1; 4.24.1; 4.38.1; 4.58.1; 4.62.1; 4.68.1; 4.72.1; 5.13.1; 5.34.1; 5.53.1; 5.56.1; 5.57.1; or 5.59.1.

In some embodiments, the nucleic acid molecule encodes at least three amino acid substitutions compared to the germline sequence that are identical to the mutations from germline found in the of any one of antibodies 1.11.1; 1.12.1; 1.12.1(rWT); 1.12.1(M29I/D19A); 1.12.1(M29I); 1.12.1 (D19A); 1.13.1; 1.14.1; 1.151.1; 1.162.1; 1.183.1; 1.27.1; 1.29.1; 1.31.1; 1.8.1; 1.9.1; 4.10.1; 4.24.1; 4.38.1; 4.58.1; 4.62.1; 4.68.1; 4.72.1; 5.13.1; 5.34.1; 5.53.1; 5.56.1; 5.57.1; or 5.59.1.

In some embodiments, the nucleic acid molecule comprises a nucleotide sequence selected from the group consisting of SEQ ID NOs: 7, 11, 15, 19, 23, 27, 31, 35, 39, 43, 47, 51, 55, 59, 63, 67, 71, 75, 79, 83, 87, 91 or 126, which encodes the $V_L$ amino acid sequence of monoclonal antibody 1.12.1 (M29I/D19A), 1.11.1, 1.13.1; 1.14.1; 1.151.1; 1.162.1; 1.183.1; 1.27.1; 1.29.1; 1.31.1; 1.8.1; 1.9.1; 4.10.1; 4.24.1; 4.38.1; 4.58.1; 4.62.1; 4.68.1; 4.72.1; 5.13.1; 5.34.1; 5.53.1; 5.56.1; 5.57.1; 5.59.1 or 1.12.1.

In some embodiments, the nucleic acid molecule comprises a nucleotide sequence that encodes the amino acid sequence of one of SEQ ID NOs: 8; 12; 16; 20; 24; 28; 32; 36; 40; 44; 48; 52; 56; 60; 64; 68; 72; 76; 80; 84; 88; 92 or 127. In some embodiments, the nucleic acid molecule comprises the nucleotide sequence of SEQ ID NO: 3 or a portion thereof. In some embodiments, the nucleic acid encodes the amino acid sequence of the light chain of one, two or all three CDRs of said antibody. In some embodiments, said portion encodes a contiguous region from CDR1-CDR3 of the light chain of an anti-ALK-1 antibody.

In some embodiments, the nucleic acid molecule encodes a $V_L$ amino acid sequence that is at least 70%, 75%, 80%, 85%, 90%, 95%, 97%, 98% or 99% identical to the $V_L$ amino acid sequence of any one of antibodies 1.11.1; 1.12.1; 1.12.1(rWT); 1.12.1(M29I/D19A); 1.12.1(M29I); 1.12.1 (D19A); 1.13.1; 1.14.1; 1.151.1; 1.162.1; 1.183.1; 1.27.1; 1.29.1; 1.31.1; 1.8.1; 1.9.1; 4.10.1; 4.24.1; 4.38.1; 4.58.1; 4.62.1; 4.68.1; 4.72.1; 5.13.1; 5.34.1; 5.53.1; 5.56.1; 5.57.1; or 5.59.1, or to the amino acid sequence of the $V_L$ region of SEQ ID NO: 4. Nucleic acid molecules of the invention include nucleic acids that hybridize under highly stringent conditions, such as those described above, or that are at least 70%, 75%, 80%, 85%, 90%, 95%, 97%, 98% or 99% identical to a nucleic acid encoding the amino acid sequence the $V_L$ region of SEQ ID NOs: 8; 12; 16; 20; 24; 28; 32; 36; 40; 44; 48; 52; 56; 60; 64; 68; 72; 76; 80; 84; 88; 92 or 126 or to a nucleic acid comprising the $V_L$ region nucleotide sequence of SEQ ID NO: 4.

In other preferred embodiments, the nucleic acid molecule encodes the variable domain of a heavy chain ($V_H$) that utilizes a human $V_H$4-31, $V_H$3-11, $V_H$3-15, $V_H$3-33, $V_H$4-61 or $V_H$4-59 gene sequence or a sequence derived therefrom. In some embodiments, the nucleic acid molecule utilizes a human $V_H$ 4-31 gene, a DH6-19 gene and a human JH4B gene.

In some embodiments, the nucleic acid molecule encodes an amino acid sequence comprising 1, 2, 3, 4, 5, 6, 7, 8, 9, 10 or 11 mutations compared to the germline amino acid sequence of the human V, D or J genes. In some embodiments, said mutations are in the $V_H$ region. In some embodiments, said mutations are in the CDR regions.

In some embodiments, the nucleic acid molecule encodes a $V_H$ sequence comprising one or more amino acid mutations compared to the germline $V_H$ sequence that are identical to amino acid mutations found in the $V_H$ of any one of monoclonal antibody 1.11.1; 1.12.1; 1.12.1(rWT); 1.12.1(M29I/D19A); 1.12.1(M29I); 1.12.1(D19A); 1.13.1; 1.14.1; 1.151.1; 1.162.1; 1.183.1; 1.27.1; 1.29.1; 1.31.1; 1.8.1; 1.9.1; 4.10.1; 4.24.1; 4.38.1; 4.58.1; 4.62.1; 4.68.1; 4.72.1; 5.13.1; 5.34.1; 5.53.1; 5.56.1; 5.57.1; or 5.59.1. In some embodiments, the nucleic acid encodes at least three amino acid mutations compared to the germline sequences that are identical to at least three amino acid mutations found in one of the above-listed monoclonal antibodies.

In some embodiments, the nucleic acid molecule comprises a nucleotide sequence selected from the group consisting of SEQ ID NOs: 5, 13, 17, 21, 25, 29, 33, 37, 41, 45, 49, 53, 57, 61, 65, 69, 73, 77, 81, 85, 89, or 103, which encodes the $V_H$ amino acid sequence of monoclonal antibody 1.12.1 (M29I/D19A), 1.11.1, 1.13.1; 1.14.1; 1.151.1; 1.162.1; 1.183.1; 1.27.1; 1.29.1; 1.31.1; 1.8.1; 1.9.1; 4.10.1; 4.24.1; 4.38.1; 4.58.1; 4.62.1; 4.68.1; 4.72.1; 5.13.1; 5.34.1; 5.53.1; 5.56.1; 5.57.1; 5.59.1 or 1.12.1.

In some embodiments, the nucleic acid molecule comprises a nucleotide sequence that encodes the amino acid sequence of one of SEQ ID NOs: SEQ ID NOs: 2; 6; 10; 14; 18; 22; 26; 30; 34; 38; 42; 46; 50; 54; 58; 62; 66; 70; 74; 78; 82; 86; 90 or 104. In various preferred embodiments, the nucleic acid molecule comprises at least a portion of the nucleotide sequence of SEQ ID NOS: 1 or 95. In some embodiments, said portion encodes the $V_H$ region, a CDR3 region, all three CDR regions, or a contiguous region including CDR1-CDR3.

In some embodiments, the nucleic acid molecule encodes a $V_H$ amino acid sequence that is at least 70%, 75%, 80%, 85%, 90%, 95%, 97%, 98% or 99% identical to the $V_H$ amino acid sequence in any one of SEQ ID NOS: SEQ ID NOs: 2; 6; 10; 14; 18; 22; 26; 30; 34; 38; 42; 46; 50; 54; 58; 62; 66; 70; 74; 78; 82; 86; 90 or 104. Nucleic acid molecules of the invention include nucleic acids that hybridize under highly stringent conditions, such as those described above, or that are at least 70%, 75%, 80%, 85%, 90%, 95%, 97%, 98% or 99% identical to a nucleic acid encoding the amino acid sequence of SEQ ID NOs: 2; 6; 10; 14; 18; 22; 26; 30; 34; 38; 42; 46; 50; 54; 58; 62; 66; 70; 74; 78; 82; 86; 90, 100 or 104, or to a $V_H$ region thereof, or to a nucleic acid comprising the nucleotide sequence of SEQ ID NOs: 1, 5, 9, 13, 17, 21, 25, 29, 33, 37, 41, 45, 49, 53, 57, 61, 65, 69, 73, 77, 81, 85, 89, 95, 103, 128, or 129, or the nucleotide sequence that encodes a $V_H$ region thereof.

In another embodiment, the nucleic acid encodes a full-length heavy chain of an antibody selected from the group consisting of 1.11.1; 1.12.1; 1.12.1(rWT); 1.12.1(M29I/D19A); 1.12.1(M29I); 1.12.1(D19A); 1.13.1; 1.14.1; 1.151.1; 1.162.1; 1.183.1; 1.27.1; 1.29.1; 1.31.1; 1.8.1; 1.9.1; 4.10.1; 4.24.1; 4.38.1; 4.58.1; 4.62.1; 4.68.1; 4.72.1; 5.13.1; 5.34.1; 5.53.1; 5.56.1; 5.57.1; and 5.59.1, or a heavy chain comprising the amino acid sequence of SEQ ID NO: 2. Further, the nucleic acid may comprise the nucleotide sequence of SEQ ID NOs: 1 or 95.

A nucleic acid molecule encoding the heavy or light chain of an anti-ALK-1 antibody or portions thereof can be isolated from any source that produces such antibody. In various embodiments, the nucleic acid molecules are isolated from a B cell that expresses an anti-ALK-1 antibody isolated from an animal immunized with ALK-1 or from an immortalized cell derived from such a B cell. Methods of isolating nucleic acids encoding an antibody are well-known in the art. See, e.g., Sambrook J. & Russell D. *Molecular Cloning: A Laboratory Manual,* 3rd ed., Cold Spring Harbor Laboratory Press, Cold Spring Harbor, N.Y. (2000). mRNA may be isolated and used to produce cDNA for use in the polymerase chain reaction (PCR) cDNA cloning of antibody genes. In a preferred embodiment, the nucleic acid molecule is isolated from a hybridoma that has as one of its fusion partners a cell from a non-human transgenic animal, said cell producing a human immunoglobulin. In an even more preferred embodiment, the cell producing human immunoglobulin is isolated from a XENOMOUSE® animal. In another embodiment, the cell producing the human immunoglobulin is isolated from a non-human, non-mouse transgenic animal, as described above. In another embodiment, the nucleic acid is isolated from a non-human, non-transgenic animal. The nucleic acid molecules isolated from a non-human, non-transgenic animal may be used, e.g., for humanized antibodies that comprise one or more amino acid sequences from a human anti-ALK-1 antibody of the present invention.

In some embodiments, a nucleic acid encoding a heavy chain of an anti-ALK-1 antibody of the invention can comprise a nucleotide sequence encoding a $V_H$ domain of the invention joined in-frame to a nucleotide sequence encoding a heavy chain constant domain from any source. Similarly, a nucleic acid molecule encoding a light chain of an anti-ALK-1 antibody of the invention can comprise a nucleotide sequence encoding a $V_L$ domain of the invention joined in-frame to a nucleotide sequence encoding a light chain constant domain from any source.

In a further aspect of the invention, nucleic acid molecules encoding the variable domain of the heavy ($V_H$) and/or light ($V_L$) chains are "converted" to full-length antibody genes. In one embodiment, nucleic acid molecules encoding the $V_H$ or $V_L$ domains are converted to full-length antibody genes by insertion into an expression vector already encoding heavy chain constant ($C_H$) or light chain constant ($C_L$) domains, respectively, such that the $V_H$ segment is operatively linked to the $C_H$ segment(s) within the vector, and/or the $V_L$ segment is operatively linked to the $C_L$ segment within the vector. In another embodiment, nucleic acid molecules encoding the $V_H$ and/or $V_L$ domains are converted into full-length antibody genes by linking, e.g., ligating, a nucleic acid molecule encoding a $V_H$ and/or $V_L$ domains to a nucleic acid molecule encoding a $C_H$ and/or $C_L$ domain using standard molecular biological techniques. Nucleic acid sequences of human heavy and light chain immunoglobulin constant domain genes are known in the ad. See, e.g., Kabat et al., *Sequences of Proteins of Immunological Interest,* 5th Ed., NIH Publ. No. 91-3242, 1991. Nucleic acid molecules encoding the full-length heavy and/or light chains may then be expressed from a cell into which they have been introduced and the anti-ALK-1 antibody isolated.

The nucleic acid molecules may be used to recombinantly express large quantities of anti-ALK-1 antibodies. The nucleic acid molecules also may be used to produce chimeric antibodies, bispecific antibodies, single chain antibodies, immunoadhesins, diabodies, mutated antibodies and antibody derivatives, as described further below. If the nucleic acid molecules are derived from a non-human, non-transgenic animal, the nucleic acid molecules may be used for antibody humanization, also as described below.

In another embodiment, a nucleic acid molecule of the invention is used as a probe or PCR primer for a specific antibody sequence. For instance, the nucleic acid can be used as a probe in diagnostic methods or as a PCR primer to amplify regions of DNA that could be used, inter alia, to isolate additional nucleic acid molecules encoding variable domains of anti-ALK-1 antibodies. In some embodiments, the nucleic acid molecules are oligonucleotides. In some embodiments, the oligonucleotides are from highly variable domains of the heavy and light chains of the antibody of interest. In some embodiments, the oligonucleotides encode all or a part of one or more of the CDRs of antibodies 1.11.1; 1.12.1; 1.12.1(rWT); 1.12.1(M29I/D19A); 1.12.1(M29I); 1.12.1(D19A); 1.13.1; 1.14.1; 1.151.1; 1.162.1; 1.183.1; 1.27.1; 1.29.1; 1.31.1; 1.8.1; 1.9.1; 4.10.1; 4.24.1; 4.38.1; 4.58.1; 4.82.1; 4.68.1; 4.72.1; 5.13.1; 5.34.1; 5.53.1; 5.56.1; 5.57.1; or 5.59.1 or variants thereof as described herein.

Vectors

The invention provides vectors comprising nucleic acid molecules that encode the heavy chain of an anti-ALK-1 antibody of the invention or an antigen-binding portion thereof. The invention also provides vectors comprising nucleic acid molecules that encode the light chain of such antibodies or antigen-binding portion thereof. The invention further provides vectors comprising nucleic acid molecules encoding fusion proteins, modified antibodies, antibody fragments, and probes thereof.

In some embodiments, the anti-ALK-1 antibodies of the invention or antigen-binding portions are expressed by inserting DNAs encoding partial or full-length light and heavy chains, obtained as described above, into expression vectors such that the genes are operatively linked to necessary expression control sequences such as transcriptional and translational control sequences. Expression vectors include plasmids, retroviruses, adenoviruses, adeno-associated viruses (AAV), plant viruses such as cauliflower mosaic virus, tobacco mosaic virus, cosmids, YACs, EBV derived episomes, and the like. The antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vectors. In a preferred embodiment, both genes are inserted into the same expression vector. The antibody genes are inserted into the expression vector by standard methods (e.g., ligation of complementary restriction sites on the antibody gene fragment and vector, or blunt end ligation if no restriction sites are present).

A convenient vector is one that encodes a functionally complete human $C_H$ or $C_L$ immunoglobulin sequence, with appropriate restriction sites engineered so that any $V_H$ or $V_L$ sequence can easily be inserted and expressed, as described above. In such vectors, splicing usually occurs between the splice donor site in the inserted J region and the splice acceptor site preceding the human C domain, and also at the splice regions that occur within the human $C_H$ exons. Polyadenylation and transcription termination occur at native chromosomal sites downstream of the coding regions. The recombinant expression vector also can encode a signal peptide that facilitates secretion of the antibody chain from a host cell. The antibody chain gene may be cloned into the vector such that the signal peptide is linked in-frame to the amino terminus of the immunoglobulin chain. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from retroviral LTRs, cytomegalovirus (CMV) (such as the CMV promoter/enhancer), Simian Virus 40 (SV40) (such as the SV40 promoter/enhancer), adenovirus, (e.g., the adenovirus major late promoter (AdMLP)), polyoma and strong mammalian promoters such as native immunoglobulin and actin promoters. For further description of viral regulatory elements, and sequences thereof, see e.g., U.S. Pat. No. 5,168,062, U.S. Pat. No. 4,510,245 and U.S. Pat. No. 4,968,615. Methods for expressing antibodies in plants, including a description of promoters and vectors, as well as transformation of plants is known in the art. See, e.g., U.S. Pat. No. 6,517,529, incorporated herein by reference. Methods of expressing polypeptides in bacterial cells or fungal cells, e.g., yeast cells, are also well known in the art.

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017, incorporated herein by reference). For example, typically the selectable marker gene confers resistance to drugs, such as G418, hygromycin or methotrexate, on a host cell into which the vector has been introduced. For example, selectable marker genes include the dihydrofolate reductase (DHFR) gene (for use in dhfr-host cells with methotrexate selection/amplification), the neo gene (for G418 selection), and the glutamate synthetase gene.

Non-Hybridoma Host Cells and Methods of Recombinantly Producing Protein

Nucleic acid molecules encoding anti-ALK-1 antibodies and vectors comprising these nucleic acid molecules can be used for transfection of a suitable mammalian, plant, bacterial or yeast host cell. Transformation can be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, and direct microinjection of the DNA into nuclei. In addition, nucleic acid molecules may be introduced into mammalian cells by viral vectors. Methods of transforming cells are well known in the art. See, e.g., U.S. Pat. Nos. 4,399,216, 4,912,040, 4,740,461, and 4,959,455, incorporated herein by reference). Methods of transforming plant cells are well known in the art, including, e.g., *Agrobacterium*-mediated transformation, biolistic transformation, direct injection, electroporation and viral transformation. Methods of transforming bacterial and yeast cells are also well known in the art.

Mammalian cell lines available as hosts for expression are well known in the art and include many immortalized cell lines available from the American Type Culture Collection (ATCC). These include, inter alia, Chinese hamster ovary (CHO) cells, NS0 cells, SP2 cells, HEK-293T cells, 293 Freestyle cells (Invitrogen), NIH-3T3 cells, HeLa cells, baby hamster kidney (BHK) cells, African green monkey kidney cells (COS), human hepatocellular carcinoma cells (e.g., Hep G2), A549 cells, and a number of other cell lines. Cell lines of particular preference are selected through determining which cell lines have high expression levels. Other cell lines that may be used are insect cell lines, such as Sf9 or Sf21 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods. Plant host cells include, e.g., *Nicotiana, Arabidopsis*, duckweed, corn, wheat, potato, etc. Bacterial host cells include *E. coli* and *Streptomyces* species. Yeast host cells include *Schizosaccharomyces pombe, Saccharomyces cerevisiae* and *Pichia pastoris*.

Further, expression of antibodies of the invention from production cell lines can be enhanced using a number of known techniques. For example, the glutamine synthetase gene expression system (the GS system) is a common approach for enhancing expression under certain conditions. The GS system is discussed in whole or part in connection with European Patent Nos. 0 216 846, 0 256 055, 0 323 997 and 0 338 841.

It is likely that antibodies expressed by different cell lines or in transgenic animals will have different glycosylation from each other. However, all antibodies encoded by the nucleic acid molecules provided herein, or comprising the amino acid sequences provided herein are part of the instant invention, regardless of the glycosylation of the antibodies.

Transgenic Animals and Plants

Anti-ALK-1 antibodies of the invention also can be produced transgenically through the generation of a mammal or plant that is transgenic for the immunoglobulin heavy and light chain sequences of interest and production of the antibody in a recoverable form therefrom. In connection with the transgenic production in mammals, anti-ALK-1 antibodies can be produced in, and recovered from, the milk of goats, cows, or other mammals. See, e.g., U.S. Pat. Nos. 5,827,690, 5,756,687, 5,750,172, and 5,741,957, incorporated herein by reference. In some embodiments, non-human transgenic animals that comprise human immunoglobulin loci are immunized with ALK-1 or an immunogenic portion thereof, as described above. Methods for making antibodies in plants are described, e.g., in U.S. Pat. Nos. 6,046,037 and 5,959,177, incorporated herein by reference.

In some embodiments, non-human transgenic animals or plants are produced by introducing one or more nucleic acid molecules encoding an anti-ALK-1 antibody of the invention into the animal or plant by standard transgenic techniques. See Hogan and U.S. Pat. No. 6,417,429, supra. The transgenic cells used for making the transgenic animal can be embryonic stem cells or somatic cells or a fertilized egg. The transgenic non-human organisms can be chimeric, nonchimeric heterozygotes, and nonchimeric homozygotes. See, e.g., Hogan et al., *Manipulating the Mouse Embryo: A Laboratory Manual* $2^{nd}$ ed., Cold Spring Harbor Press (1999); Jackson et al., *Mouse Genetics and Transgenics: A Practical Approach*, Oxford University Press (2000); and Pinkert, *Transgenic Animal Technology: A Laboratory Handbook*, Academic Press (1999), all incorporated herein by reference. In some embodiments, the transgenic non-human animals have a targeted disruption and replacement by a targeting construct that encodes a heavy chain and/or a light chain of interest. In a preferred embodiment, the transgenic animals comprise and express nucleic acid molecules encoding heavy and light chains that specifically bind to ALK-1, preferably human ALK-1. In some embodiments, the transgenic animals comprise nucleic acid molecules encoding a modified antibody such as a single-chain antibody, a chimeric antibody or a humanized antibody. The anti-ALK-1 antibodies may be made in any transgenic animal. In a preferred embodiment, the non-human animals are mice, rats, sheep, pigs, goats, cattle or horses. The non-human transgenic animal expresses said encoded polypeptides in blood, milk, urine, saliva, tears, mucus and other bodily fluids.

Phage Display Libraries

The invention provides a method for producing an anti-ALK-1 antibody or antigen-binding portion thereof comprising the steps of synthesizing a library of human antibodies on phage, screening the library with ALK-1 or an antibody-binding portion thereof, isolating phage that bind ALK-1, and obtaining the antibody from the phage. By way of example, one method for preparing the library of antibodies for use in phage display techniques comprises the steps of immunizing a non-human animal comprising human immunoglobulin loci with ALK-1 or an antigenic portion thereof to create an immune response, extracting antibody-producing cells from the immunized animal; isolating RNA encoding heavy and light chains of antibodies of the invention from the extracted cells, reverse transcribing the RNA to produce cDNA, amplifying the cDNA using primers, and inserting the cDNA into a phage display vector such that antibodies are expressed on the phage. Recombinant anti-ALK-1 antibodies of the invention may be obtained in this way.

Recombinant human anti-ALK-1 antibodies of the invention can be isolated by screening a recombinant combinatorial antibody library. Preferably the library is a scFv phage display library, generated using human $V_L$ and $V_H$ cDNAs prepared from mRNA isolated from B cells. Methods for preparing and screening such libraries are known in the art. Kits for generating phage display libraries are commercially available (e.g., the Pharmacia Recombinant Phage Antibody System, catalog no. 27-9400-01; and the Stratagene SurfZAP phage display kit, catalog no. 240612). There also are other methods and reagents that can be used in generating and screening antibody display libraries (see, e.g., U.S. Pat. No. 5,223,409; PCT Publication Nos. WO 92/18619, WO 91/17271, WO 92/20791, WO 92/15679, WO 93/01288, WO 92/01047, WO 92/09690; Fuchs et al., *Bio/Technology* 9:1370-1372 (1991); Hay et al., *Hum. Antibod. Hybridomas* 3:81-85 (1992); Huse et al., *Science* 246:1275-1281 (1989); McCafferty et al., *Nature* 348:552-554 (1990); Griffiths et al., *EMBO J.* 12:725-734 (1993); Hawkins et al., *J. Mol. Biol.* 226:889-896 (1992); Clackson et al., *Nature* 352:624-628 (1991); Gram et al., *Proc. Natl. Acad. Sci. USA* 89:3576-3580 (1992); Garrad et al., *Bio/Technology* 9:1373-1377 (1991); Hoogenboom et al., *Nuc. Acid Res.* 19:4133-4137 (1991); and Barbas et al., *Proc. Natl. Acad. Sci. USA* 88:7978-7982 (1991), all incorporated herein by reference.

In one embodiment, to isolate and produce human anti-ALK-1 antibodies with the desired characteristics, a human anti-ALK-1 antibody as described herein is first used to select human heavy and light chain sequences having similar binding activity toward ALK-1, using the epitope imprinting methods described in PCT Publication No. WO 93/06213, incorporated herein by reference. The antibody libraries used in this method are preferably scFv libraries prepared and screened as described in PCT Publication No. WO 92/01047, McCafferty et al., *Nature* 348:552-554 (1990); and Griffiths et al., *EMBO J,* 12:725-734 (1993), all incorporated herein by reference. The scFv antibody libraries preferably are screened using human ALK-1 as the antigen.

Once initial human $V_L$ and $V_H$ domains are selected, "mix and match" experiments are performed, in which different pairs of the initially selected $V_L$ and $V_H$ segments are screened for ALK-1 binding to select preferred $V_L/V_H$ pair combinations. Additionally, to further improve the quality of the antibody, the $V_L$ and $V_H$ segments of the preferred $V_L/V_H$ pair(s) can be randomly mutated, preferably within the CDR3 region of $V_H$ and/or $V_L$, in a process analogous to the in vivo somatic mutation process responsible for affinity maturation of antibodies during a natural immune response. This in vitro affinity maturation can be accomplished by amplifying $V_H$ and $V_L$ domains using PCR primers complimentary to the $V_H$ CDR3 or $V_L$ CDR3, respectively, which primers have been "spiked" with a random mixture of the four nucleotide bases at certain positions such that the resultant PCR products encode $V_H$ and $V_L$ segments into which random mutations have been introduced into the $V_H$ and/or $V_L$ CDR3 regions. These randomly mutated $V_H$ and $V_L$ segments can be re-screened for binding to ALK-1.

Following screening and isolation of an anti-ALK-1 antibody of the invention from a recombinant immunoglobulin display library, nucleic acids encoding the selected antibody can be recovered from the display package (e.g., from the phage genome) and subcloned into other expression vectors by standard recombinant DNA techniques. If desired, the nucleic acid can further be manipulated to create other antibody forms of the invention, as described below. To express a recombinant human antibody isolated by screening of a combinatorial library, the DNA encoding the antibody is cloned into a recombinant expression vector and introduced into a mammalian host cells, as described above.

Deimmunized Antibodies

In another aspect of the invention, the antibody may be deimmunized to reduce its immunogenicity using the techniques described in, e.g., PCT Publication Nos. WO98/52976 and WO00/34317 (incorporated herein by reference).

Mutated Antibodies

In another embodiment, the nucleic acid molecules, vectors and host cells may be used to make mutated anti-ALK-1 antibodies. The antibodies may be mutated in the variable domains of the heavy and/or light chains, e.g., to alter a binding property of the antibody. For example, a mutation may be made in one or more of the CDR regions to increase or decrease the $K_D$ of the antibody for ALK-1, to increase or decrease $k_{off}$, or to alter the binding specificity of the antibody. Techniques in site-directed mutagenesis are well-known in the art. See, e.g., Sambrook et al. and Ausubel et al., supra. In another embodiment, one or more mutations are made at an amino acid residue that is known to be changed compared to the germline in monoclonal antibody 1.11.1; 1.12.1; 1.12.1 (rWT); 1.12.1(M29I/D19A); 1.12.1(M29I); 1.12.1(D19A); 1.13.1; 1.14.1; 1.151.1; 1.162.1; 1.183.1; 1.27.1; 1.29.1; 1.31.1; 1.8.1; 1.9.1; 4.10.1; 4.24.1; 4.38.1; 4.58.1; 4.62.1; 4.68.1; 4.72.1; 5.13.1; 5.34.1; 5.53.1; 5.56.1; 5.57.1; or 5.59.1. The mutations may be made in a CDR region or framework region of a variable domain, or in a constant domain. In a preferred embodiment, the mutations are made in a variable domain. In some embodiments, one or more mutations are made at an amino acid residue that is known to be changed compared to the germline in a CDR region or framework region of a variable domain of an amino acid sequence SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90 92 or 127, or whose nucleic acid sequence is presented in SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 95, 102 or 126.

In another embodiment, the framework region is mutated so that the resulting framework region(s) have the amino acid sequence of the corresponding germline gene. A mutation may be made in a framework region or constant domain to increase the half-life of the anti-ALK-1 antibody. See, e.g., PCT Publication No. WO 00/09560, incorporated herein by reference. A mutation in a framework region or constant domain also can be made to alter the immunogenicity of the antibody, to provide a site for covalent or non-covalent binding to another molecule, or to alter such properties as complement fixation, FcR binding and antibody-dependent cell-mediated cytotoxicity (ADCC). According to the invention, a single antibody may have mutations in any one or more of the CDRs or framework regions of the variable domain or in the constant domain.

In some embodiments, there are from 1 to 13, including any number in between, amino acid mutations in either the $V_H$ or $V_L$ domains of the mutated anti-ALK-1 antibody compared to the anti-ALK-1 antibody prior to mutation. In any of the above, the mutations may occur in one or more CDR regions. Further, any of the mutations can be conservative amino acid substitutions. In some embodiments, there are no more than 5, 4, 3, 2, or 1 amino acid changes in the constant domains.

Modified Antibodies

In another embodiment, a fusion antibody or immunoadhesin may be made that comprises all or a portion of an anti-ALK-1 antibody of the invention linked to another polypeptide. In a preferred embodiment, only the variable domains of the anti-ALK-1 antibody are linked to the polypeptide. In another preferred embodiment, the $V_H$ domain of an anti-ALK-1 antibody is linked to a first polypeptide, while the $V_L$ domain of an anti-ALK-1 antibody is linked to a second polypeptide that associates with the first polypeptide in a manner such that the $V_H$ and $V_L$ domains can interact with one another to form an antigen binding site. In another preferred embodiment, the $V_H$ domain is separated from the $V_L$ domain by a linker such that the $V_H$ and $V_L$ domains can interact with one another (see below under Single Chain Antibodies). The $V_H$-linker-$V_L$ antibody is then linked to the polypeptide of interest. In addition, fusion antibodies can be created in which two (or more) single-chain antibodies are linked to one another. This is useful if one wants to create a divalent or polyvalent antibody on a single polypeptide chain, or if one wants to create a bispecific antibody.

To create a single chain antibody, (scFv) the $V_H$- and $V_L$-encoding DNA fragments are operatively linked to another fragment encoding a flexible linker, e.g., encoding the amino acid sequence (Gly$_4$-Ser)$_3$, such that the $V_H$ and $V_L$ sequences can be expressed as a contiguous single-chain protein, with the $V_L$ and $V_H$ domains joined by the flexible linker. See, e.g., Bird et al., *Science* 242:423-426 (1988); Huston et al., *Proc. Natl. Acad. Sci. USA* 85:5879-5883 (1988); McCafferty et al., *Nature* 348:552-554 (1990). The single chain antibody may be monovalent, if only a single $V_H$ and $V_L$ are used, bivalent, if two $V_H$ and $V_L$ are used, or polyvalent, if more than two $V_H$ and $V_L$ are used. Bispecific or polyvalent antibodies may be generated that bind specifically to ALK-1 and to another molecule.

In other embodiments, other modified antibodies may be prepared using anti-ALK-1 antibody encoding nucleic acid molecules. For instance, "Kappa bodies" (Ill et al., *Protein Eng.* 10: 949-57 (1997)), "Minibodies" (Martin et al., *EMBO J.* 13: 5303-9 (1994)), "Diabodies" (Holliger et al., *Proc. Natl. Acad. Sci. USA* 90: 6444-6448 (1993)), or "Janusins" (Traunecker et al., *EMBO J.* 10:3655-3659 (1991) and Traunecker et al., *Int. J. Cancer* (Suppl.) 7:51-52 (1992)) may be prepared using standard molecular biological techniques following the teachings of the specification.

Bispecific antibodies or antigen-binding fragments can be produced by a variety of methods including fusion of hybridomas or linking of Fab' fragments. See, e.g., Songsivilai & Lachmann, *Clin. Exp. Immunol.* 79: 315-321 (1990), Kostelny et al., *J. Immunol*, 148; 1547-1553 (1992). In addition, bispecific antibodies may be formed as "diabodies" "Janusins." In some embodiments, the bispecific antibody binds to two different epitopes of ALK-1. In some embodiments, the bispecific antibody has a first heavy chain and a first light chain from monoclonal antibody 1.11.1; 1.12.1; 1.12.1(rWT); 1.12.1(M29I/D19A); 1.12.1(M29I); 1.12.1 (D19A); 1.13.1; 1.14.1; 1.151.1; 1.162.1; 1.183.1; 1.27.1; 1.29.1; 1.31.1; 1.8.1; 1.9.1; 4.10.1; 4.24.1; 4.38.1; 4.58.1; 4.62.1; 4.68.1; 4.72.1; 5.13.1; 5.34.1; 5.53.1; 5.56.1; 5.57.1; or 5.59.1 and an additional antibody heavy chain and light chain. In some embodiments, the additional light chain and heavy chain also are from one of the above-identified monoclonal antibodies, but are different from the first heavy and light chains.

In some embodiments, the modified antibodies described above are prepared using one or more of the variable domains or CDR regions from a human anti-ALK-1 monoclonal antibody provided herein.

Derivatized and Labeled Antibodies

An anti-ALK-1 antibody or antigen-binding portion of the invention can be derivatized or linked to another molecule (e.g., another peptide or protein). In general, the antibodies or portion thereof are derivatized such that the ALK-1 binding is not affected adversely by the derivatization or labeling. Accordingly, the antibodies and antibody portions of the invention are intended to include both intact and modified forms of the human anti-ALK-1 antibodies described herein.

For example, an antibody or antibody portion of the invention can be functionally linked (by chemical coupling, genetic fusion, noncovalent association or otherwise) to one or more other molecular entities, such as another antibody (e.g., a bispecific antibody or a diabody), a detection agent, a pharmaceutical agent, and/or a protein or peptide that can mediate association of the antibody or antibody portion with another molecule (such as a streptavidin core region or a polyhistidine tag).

One type of derivatized antibody is produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Il.

Another type of derivatized antibody is a labeled antibody. Useful detection agents with which an antibody or antigen-binding portion of the invention may be derivatized include fluorescent compounds, including fluorescein, fluorescein isothiocyanate, rhodamine, 5-dimethylamine-1-napthalene-sulfonyl chloride, phycoerythrin, lanthanide phosphors and the like. An antibody can also be labeled with enzymes that are useful for detection, such as horseradish peroxidase, $\beta$-galactosidase, luciferase, alkaline phosphatase, glucose oxidase and the like. When an antibody is labeled with a detectable enzyme, it is detected by adding additional reagents that the enzyme uses to produce a reaction product that can be discerned. For example, when the agent horseradish peroxidase is present, the addition of hydrogen peroxide and diaminobenzidine, leads to a colored reaction product, which is detectable. An antibody can also be labeled with biotin, and detected through indirect measurement of avidin or streptavidin binding. An antibody can also be labeled with a predetermined polypeptide epitope recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

An anti-ALK-1 antibody can also be derivatized with a chemical group such as polyethylene glycol (PEG), a methyl or ethyl group, or a carbohydrate group. These groups are useful to improve the biological characteristics of the antibody, e.g., to increase serum half-life.

Pharmaceutical Compositions and Administration

This invention also relates to a pharmaceutical composition for the treatment of conditions associated with undesirable increased angiogenesis in a mammal, including a human, comprising an amount of an anti-ALK-1 antibody or antigen binding portion thereof, as described herein, that is effective in treating such conditions, and a pharmaceutically acceptable carrier.

The antibodies and antigen-binding portions of the present invention can be incorporated into pharmaceutical compositions suitable for administration to a subject. Typically, the pharmaceutical composition comprises an antibody or antigen-binding portion of the invention and a pharmaceutically acceptable carrier. As used herein, "pharmaceutically acceptable carrier" means any and all solvents, dispersion media, coatings, antibacterial and antifungal agents, isotonic and absorption delaying agents, and the like that are physiologically compatible. Some examples of pharmaceutically acceptable carriers are water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Additional examples of pharmaceutically acceptable substances are wetting agents or minor amounts of auxiliary substances such as wetting or emulsifying agents, preservatives or buffers, which enhance the shelf life or effectiveness of the antibody.

The compositions of this invention may be in a variety of forms, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans. The preferred mode of administration is parenteral (e.g., intravenous, subcutaneous, intraperitoneal, intramuscular). In a preferred embodiment, the antibody is administered by intravenous infusion or injection. In another preferred embodiment, the antibody is administered by intramuscular or subcutaneous injection. Formulations for injection may be presented in unit dosage form, e.g., in ampoules or in multi-dose containers, with or without an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the anti-ALK-1 antibody in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable, solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The antibodies or antibody portions of the present invention can be administered by a variety of methods known in the art, although for many therapeutic applications, the preferred route/mode of administration is subcutaneous, intramuscular, or intravenous infusion. As will be appreciated by the skilled artisan, the route and/or mode of administration will vary depending upon the desired results.

In certain embodiments, the antibody compositions of the present invention may be prepared with a carrier that will protect the antibody against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are generally known to those skilled in the art. See, e.g., *Sustained and Controlled Release Drug Delivery Systems* J. R. Robinson, ed., Marcel Dekker, Inc., New York, 1978, which is incorporated herein by reference.

Additional active compounds also can be incorporated into the compositions. In certain embodiments, an inhibitory anti-ALK-1 antibody of the invention is co-formulated with and/or co-administered with one or more additional therapeutic agents. These agents include, without limitation, antibodies that bind other targets, anti-tumor agents, anti-angiogenesis agents, signal transduction inhibitors, anti-proliferative agents, chemotherapeutic agents, or peptide analogues that inhibit anti-ALK-1. Such combination therapies may require lower dosages of the inhibitory anti-ALK-1 antibody as well as the co-administered agents, thus avoiding possible toxicities or complications associated with the various monotherapies.

As noted above, the compositions of the present invention optionally may further comprise a pharmaceutically acceptable antioxidant in addition to a chelating agent. Suitable antioxidants include, but are not limited to, methionine, sodium thiosulfate, catalase, and platinum.

For example, the composition may contain methionine in a concentration that ranges from 1 mM to about 100 mM, and in particular, is about 27 mM. For example, an aqueous formulation may be: 10 mg/mL anti-ALK-1 antibody, 20 mM Histidine, pH 5.5, 84 mg/mL Trehalose dihydrate, 0.2 mg/mL Polysorbate 80, 0.05 mg/mL disodium EDTA, 0.1 mg/mL L-Methionine.

The compositions of the invention may include a "therapeutically effective amount" or a "prophylactically effective amount" of an antibody or antigen-binding portion of the invention. A "therapeutically effective amount" refers to an amount effective, at dosages and for periods of time necessary, to achieve the desired therapeutic result. A therapeutically effective amount of the antibody or antigen-binding portion may vary according to factors such as the disease state, age, sex, and weight of the individual, and the ability of the antibody or antibody portion to elicit a desired response in the individual. A therapeutically effective amount is also one in which any toxic or detrimental effects of the antibody or antigen-binding portion are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount may be less than the therapeutically effective amount.

Dosage regimens can be adjusted to provide the optimum desired response (e.g., a therapeutic or prophylactic response). For example, a single bolus can be administered, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the anti-ALK-1 antibody or portion thereof and the particular therapeutic or prophylactic effect to be achieved, and (b) the limitations inherent in the art of compounding such an antibody for the treatment of sensitivity in individuals.

An exemplary, non-limiting range for a therapeutically or prophylactically effective amount of an antibody or antibody portion of the invention is 0.025 to 50 mg/kg, more preferably 0.1 to 50 mg/kg, more preferably 0.1-25, 0.1 to 10 or 0.1 to 3 mg/kg. In some embodiments, a formulation contains 5 mg/mL of antibody in a buffer of 20 mM sodium citrate, pH 5.5, 140 mM NaCl, and 0.2 mg/mL polysorbate 80. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

Another aspect of the present invention provides kits comprising an anti-ALK-1 antibody or antigen-binding portion of the invention or a composition comprising such an antibody or portion. A kit may include, in addition to the antibody or composition, diagnostic or therapeutic agents. A kit can also include instructions for use in a diagnostic or therapeutic method. In a preferred embodiment, the kit includes the antibody or a composition comprising it and a diagnostic agent that can be used in a method described below. In another preferred embodiment, the kit includes the antibody or a composition comprising it and one or more therapeutic agents that can be used in a method described below.

Diagnostic Methods of Use

The anti-ALK-1 antibodies or antigen-binding portions thereof can be used in diagnostic methods to detect ALK-1 in a biological sample in vitro or in vivo. For example, the anti-ALK-1 antibodies can be used in a conventional immunoassay, including, without limitation, an ELISA, an RIA, flow cytometry, tissue immunohistochemistry. Western blot or immunoprecipitation. The anti-ALK-1 antibodies of the invention can be used to detect ALK-1 from humans. The anti-ALK-1 antibodies can also be used to detect ALK-1 from other primates, e.g. cynomolgus monkeys.

The invention provides a method for detecting ALK-1 in a biological sample comprising contacting the biological sample with an anti-ALK-1 antibody of the invention and detecting the bound antibody. In one embodiment, the anti-ALK-1 antibody is directly labeled with a detectable label. In another embodiment, the anti-ALK-1 antibody (the first antibody) is unlabeled and a second antibody or other molecule that can bind the anti-ALK-1 antibody is labeled. As is well known to one of skill in the art, a second antibody is chosen that is able to specifically bind the particular species and class of the first antibody. For example, if the anti-ALK-1 antibody is a human IgG, then the secondary antibody could be an anti-human-IgG. Other molecules that can bind to antibodies include, without limitation, Protein A and Protein G, both of which are available commercially, e.g., from Pierce Chemical Co.

Suitable labels for the antibody or secondary antibody have been discussed previously, and include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{125}I$, $^{131}I$, $^{35}S$ or $^{3}H$.

In other embodiments, ALK-1 can be assayed in a biological sample by a competition immunoassay utilizing ALK-1 standards labeled with a detectable substance and an unlabeled anti-ALK-1 antibody. In this assay, the biological sample, the labeled ALK-1 standards and the anti-ALK-1 antibody are combined and the amount of labeled ALK-1 standard bound to the unlabeled antibody is determined. The amount of ALK-1 in the biological sample is inversely proportional to the amount of labeled ALK-1 standard bound to the anti-ALK-1 antibody.

One can use the immunoassays disclosed above for a number of purposes. For example, the anti-ALK-1 antibodies can be used to detect ALK-1 in cultured cells. In a preferred embodiment, the anti-ALK-1 antibodies are used to determine the amount of ALK-1 produced by cells that have been treated with various compounds. This method can be used to identify compounds that modulate ALK-1 protein levels. According to this method, one sample of cells is treated with a test compound for a period of time while another sample is left untreated. If the total level of ALK-1 is to be measured, the cells are lysed and the total ALK-1 level is measured using one of the immunoassays described above. The total level of ALK-1 in the treated versus the untreated cells is compared to determine the effect of the test compound.

A preferred immunoassay for measuring total ALK-1 levels is flow cytometry or immunohistochemistry. Methods such as ELISA, RIA, flow cytometry. Western blot, immunohistochemistry, cell surface labeling of integral membrane proteins and immunoprecipitation are well known in the art. See, e.g., Harlow and Lane, supra. In addition, the immunoassays can be scaled up for high throughput screening in order to test a large number of compounds for either activation or inhibition of ALK-1 expression.

The anti-ALK-1 antibodies of the invention also can be used to determine the levels of ALK-1 in a tissue or in cells derived from the tissue. In some embodiments, the tissue is a diseased tissue. In some embodiments of the method, a tissue or a biopsy thereof is excised from a patient. The tissue or biopsy is then used in an immunoassay to determine, e.g., total ALK-1 levels or localization of ALK-1 by the methods discussed above.

The antibodies of the present invention also can be used in vivo to identify tissues and organs that express ALK-1. One advantage of using the human anti-ALK-1 antibodies of the present invention is that they may safely be used in vivo without eliciting a substantial immune response to the antibody upon administration, unlike antibodies of non-human origin or with humanized or chimeric antibodies.

The method comprises the steps of administering a detectably labeled anti-ALK-1 antibody or a composition comprising them to a patient in need of such a diagnostic test and subjecting the patient to imaging analysis to determine the location of the ALK-1-expressing tissues. Imaging analysis is well known in the medical art, and includes, without limitation, x-ray analysis, magnetic resonance imaging (MRI) or computed tomography (CT). The antibody can be labeled with any agent suitable for in vivo imaging, for example a contrast agent, such as barium, which can be used for x-ray analysis, or a magnetic contrast agent, such as a gadolinium chelate, which can be used for MRI or CT. Other labeling agents include, without limitation, radioisotopes, such as $^{99}Tc$. In another embodiment, the anti-ALK-1 antibody will be unlabeled and will be imaged by administering a second antibody or other molecule that is detectable and that can bind the anti-ALK-1 antibody. In one embodiment, a biopsy is obtained from the patient to determine whether the tissue of interest expresses ALK-1.

Therapeutic Methods of Use

In another embodiment, the invention provides a method for inhibiting ALK-1 activity by administering an anti-ALK-1 antibody to a patient in need thereof. Any of the antibodies or antigen-binding portions thereof described herein may be used therapeutically. In a preferred embodiment, the anti-ALK-1 antibody is a human, chimeric or humanized antibody. In another preferred embodiment, the anti-ALK-1 antibody is human antibody, and the patient is a human patient. Alternatively, the patient may be a mammal that expresses ALK-1 that the anti-ALK-1 antibody cross-reacts with. The antibody may be administered to a non-human mammal expressing ALK-1 with which the antibody cross-reacts (e.g. a cynomolgus monkey) for veterinary purposes or as an animal model of human disease. Such animal models may be useful for evaluating the therapeutic efficacy of antibodies of this invention.

In another embodiment, an anti-ALK-1 antibody or antibody portion thereof may be administered to a patient who expresses inappropriately high levels of ALK-1. The antibody may be administered once, but more preferably is administered multiple times. The antibody may be administered from three times daily to once every six months or longer. The administering may be on a schedule such as three times daily, twice daily, once daily, once every two days, once every three days, once weekly, once every two weeks, once every month, once every two months, once every three months and once every six months. The antibody may also be administered continuously via a minipump. The antibody may be administered via a mucosal, buccal, intranasal, inhalable, intravenous, subcutaneous, intramuscular, parenteral, or intratumor route. The antibody may be administered once, at least twice or for at least the period of time until the condition is treated, palliated or cured. The antibody generally will be administered for as long as the condition is present. The antibody will generally be administered as part of a pharmaceutical composition as described supra. The dosage of antibody will generally be in the range of 0.1 to 100 mg/kg, more preferably 0.5 to 50 mg/kg, more preferably 1 to 20 mg/kg, and even more preferably 1 to 10 mg/kg. The serum concentration of the antibody may be measured by any method known in the art.

In one embodiment, the antibody is administered in a formulation as a sterile aqueous solution having a pH that ranges from about 5.0 to about 6.5 and comprising from about 1 mg/ml about 200 mg/ml of antibody, from about 1 millimolar to about 100 millimolar histidine buffer, from about 0.01 mg/ml to about 10 mg/ml of polysorbate 80, from about 100 millimolar to about 400 millimolar of trehalose, and from about 0.01 millimolar to about 1.0 millimolar disodium EDTA dihydrate.

It is further contemplated by the present invention that any of the compositions herein may be administered to a patient susceptible to or suffering from a condition associated with increased angiogenesis ("an angiogenic condition").

Examples of angiogenic conditions that may be treated/prevented by the compositions/methods of the present invention include, but are not limited to, cancer (both solid and hematologic), age-related macular degeneration (AMD), developmental abnormalities (organogenesis), diabetic blindness, endometriosis, ocular neovascularization, psoriasis, rheumatoid arthritis (RA), and skin discolorations (e.g., hemangioma, nevus flammeus, or nevus simplex).

For example, the present invention relates to methods for treating or preventing conditions associated with ocular neovascularization using any of the compositions/methods herein. Conditions associated with ocular neovascularization include, but are not limited to, diabetic retinopathy, age related macular degeneration ("ARMD"), rubeotic glaucoma, interstitial keratitis, retinopathy, of prematurity, ischemic retinopathy (e.g., sickle cell), pathological myopic, ocular histoplasmosis, pterygia, punitiate inner choroidopathy, and the like.

Treatment of Abnormal Cell Growth

This invention also relates to a method for the treatment of abnormal cell growth in a mammal, including a human, comprising administering to said mammal a therapeutically effective amount of an anti-ALK-1 antibody or antigen binding portion thereof, as described herein, that is effective in treating abnormal cell growth.

In one embodiment of this method, the abnormal cell growth is cancer, including, but not limited to, mesothelioma, hepatobilliary (hepatic and billiary duct), a primary or secondary CNS tumor, a primary or secondary brain tumor, lung cancer (NSCLC and SCLC), bone cancer, pancreatic cancer, skin cancer, cancer of the head or neck, cutaneous or intraocular melanoma, ovarian cancer, colon cancer, rectal cancer, cancer of the anal region, stomach cancer, gastrointestinal (gastric, colorectal, and duodenal), breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, testicular cancer, chronic or acute leukemia, chronic myeloid leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, non hodgkins's lymphoma, spinal axis tumors, brain stem glioma, pituitary adenoma, adrenocortical cancer, gall bladder cancer, multiple myeloma, cholangiocarcinoma, fibrosarcoma, neuroblastoma, retinoblastoma, or a combination of one or more of the foregoing cancers.

In a preferred embodiment of the present invention the cancer is selected from lung cancer (NSCLC and SCLC), cancer of the head or neck, ovarian cancer, colon cancer, rectal cancer, cancer of the anal region, stomach cancer, breast cancer, cancer of the kidney or ureter, renal cell carcinoma, carcinoma of the renal pelvis, neoplasms of the central nervous system (CNS), primary CNS lymphoma, non hodgkins's lymphoma, spinal axis tumors, or a combination of one or more of the foregoing cancers.

In another preferred embodiment of the present invention the cancer is selected from lung cancer (NSCLC and SCLC), ovarian cancer, colon cancer, rectal cancer, cancer of the anal region, or a combination of one or more of the foregoing cancers.

In another embodiment of said method, said abnormal cell growth is a benign proliferative disease, including, but not limited to, psoriasis, benign prostatic hypertrophy or restinosis.

This invention also relates to a method for the treatment of abnormal cell growth in a mammal which comprises administering to said mammal an amount of an anti-ALK-1 antibody or antigen binding portion thereof, as described herein, that is effective in treating abnormal cell growth in combination with an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, and anti-androgens.

The invention also relates to a pharmaceutical composition for the treatment of abnormal cell growth in a mammal, including a human, which comprises an amount of an anti-ALK-1 antibody or antigen binding portion thereof, as described herein, that is effective in treating abnormal cell growth in combination with a pharmaceutically acceptable carrier and an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, and anti-androgens.

The invention also relates to a method for the treatment of a hyperproliferative disorder in a mammal which comprises administering to said mammal a therapeutically effective amount of an anti-ALK-1 antibody or antigen binding portion thereof, as described herein, in combination with an anti-tumor agent selected from the group consisting antiproliferative agents, kinase inhibitors, angiogenesis inhibitors, growth factor inhibitors, cox-I inhibitors, cox-II inhibitors, mitotic inhibitors, alkylating agents, anti-metabolites, intercalating antibiotics, growth factor inhibitors, radiation, cell cycle inhibitors, enzymes, topoisomerase inhibitors, biological response modifiers, antibodies, cytotoxics, anti-hormones, statins, and anti-androgens.

In one embodiment of the present invention the anti-tumor agent used in conjunction with an anti-ALK-1 antibody or antigen binding portion thereof, and pharmaceutical compositions described herein, is an anti-angiogenesis agent, kinase inhibitor, pan kinase inhibitor or growth factor inhibitor. Preferred pan kinase inhibitors include Sutent (Pfizer Inc., SU-11248), described in U.S. Pat. No. 6,573,293 (Pfizer, Inc, NY, USA).

Anti-angiogenesis agents, include but are not limited to the following agents, such as EGF inhibitor, EGFR inhibitors, VEGF inhibitors, VEGFR inhibitors, TIE2 inhibitors, IGF1R inhibitors, COX-II (cyclooxygenase II) inhibitors, MMP-2 (matrix-metalloprotienase 2) inhibitors, and MMP-9 (matrix-metalloprotienase 9) inhibitors. Preferred VEGF inhibitors, include for example, Avastin (bevacizumab), an anti-VEGF monoclonal antibody of Genentech, Inc, of South San Francisco, Calif.

Additional VEGF inhibitors include, CP-547,632 (Pfizer Inc., NY, USA), Axitinib (Pfizer Inc.; AG-013736), ZD-6474 (AstraZeneca), AEE788 (Novartis), AZD-2171), VEGF Trap (Regeneron/Aventis), Vatalanib (also known as PTK-787, ZK-222584: Novartis & Schering AG), MACUGEN® (pegaptanib sodium, NX-1838, EYE-001, Pfizer Inc./Gilead/Eyetech), IM862 (Cytran Inc. of Kirkland, Wash., USA); and angiozyme, a synthetic ribozyme, from Ribozyme (Boulder, Colo.) and Chiron (Emeryville, Calif.) and combinations thereof. VEGF inhibitors useful in the practice of the present invention are disclosed in U.S. Pat. Nos. 6,534,524 and 6,235,764, both of which are incorporated in their entirety for all purposed. Particularly preferred VEGF inhibitors include CP-547,632, AG13736, Vatalanib, MACUGEN® (pegaptanib sodium) and combinations thereof.

Additional VEGF inhibitors are described in, for example in WO 99/24440 (published May 20, 1999), PCT International Application PCT/IB99/00797 (filed May 3, 1999), in WO 95/21613 (published Aug. 17, 1995), WO 99/61422 (published Dec. 2, 1999), U.S. Pat. No. 6,534,524 (discloses AG13736), U.S. Pat. No. 5,834,504 (issued Nov. 10, 1998), WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), U.S. Pat. No. 6,653,308 (issued Nov. 25, 2003), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are herein incorporated by reference in their entirety.

Other antiproliferative agents that may be used with the antibodies, or antigen-binding portions thereof, of the present invention include inhibitors of the enzyme farnesyl protein transferase and inhibitors of the receptor tyrosine kinase PDGFr, including the compounds disclosed and claimed in the following U.S. patent application Ser. No. 09/221,946 (filed Dec. 28, 1998); Ser. No. 09/454,058 (filed Dec. 2, 1999); Ser. No. 09/501,163 (filed Feb. 9, 2000); Ser. No. 09/539,930 (filed Mar. 31, 2000); Ser. No. 09/202,796 (filed May 22, 1997); Ser. No. 09/384,339 (filed Aug. 26, 1999); and Ser. No. 09/383,755 (filed Aug. 26, 1999); and the compounds disclosed and claimed in the following U.S. provisional patent applications: 60/168,207 (filed Nov. 30, 1999); 60/170,119 (filed Dec. 10, 1999); 60/177,718 (filed Jan. 21, 2000); 60/168,217 (filed Nov. 30, 1999), and 60/200,834 (filed May 1, 2000). Each of the foregoing patent applications and provisional patent applications is herein incorporated by reference in their entirety.

For additional PDGRr inhibitors, see WO01/40217, published Jul. 7, 2001 and WO2004/020431, published Mar. 11, 2004, the contents of which are incorporated in their entirety for all purposes. Preferred PDGFr inhibitors include Pfizer's CP-868,596 and its pharmaceutically acceptable salts.

Preferred GARF inhibitors include Pfizer's AG-2037 (pelitrexol and its pharmaceutically acceptable salts). GARF inhibitors useful in the practice of the present invention are disclosed in U.S. Pat. No. 5,608,082 which is incorporated in its entirety for all purposes.

Examples of useful COX-II inhibitors which can be used in conjunction with a Anti-ALK-1 antibody or antigen binding portion thereof, as described herein, and pharmaceutical compositions described herein include CELEBREX® (celecoxib), parecoxib, deracoxib, ABT-963, MK-663 (etoricoxib), COX-189 (Lumiracoxib), BMS 347070, RS 57067, NS-398, BEXTRA® (valdecoxib), paracoxib, VIOXX® (rofecoxib), SD-8381, 4-Methyl-2-(3,4-dimethylphenyl)-1-(4-sulfamoyl-phenyl)-1H-pyrrole, 2-(4-Ethoxyphenyl)-4-methyl-1-(4-sulfamoylphenyl)-1H-pyrrole, 1-614, JTE-522, S-2474, SVT-2016, CT-3, SC-58125 and ARCOXIA® (etoricoxib). For additional COX-II inhibitors, see U.S. patent application Ser. Nos. 10/801,446 and 10/801,429, the contents of which are incorporated in their entirety for all purposes.

In one preferred embodiment the anti-tumor agent is celecoxib, see U.S. Pat. No. 5,466,823, the contents of which are incorporated by reference in its entirety for all purposes. The structure for Celecoxib is shown below:

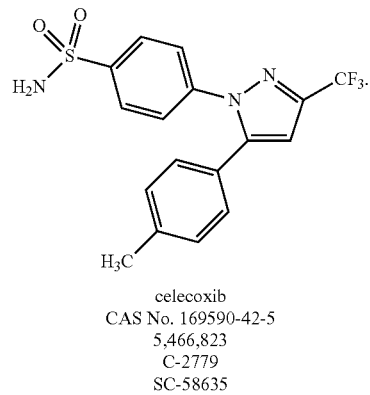 [SMILES: Cc1ccc(-c2cc(C(F)(F)F)nn2-c2ccc(S(N)(=O)=O)cc2)cc1]

celecoxib
CAS No. 169590-42-5
5,466,823
C-2779
SC-58635

In one preferred embodiment the anti-tumor agent is valecoxib, see U.S. Pat. No. 5,633,272, the contents of which are incorporated by reference in its entirety for ail purposes. The structure for valdecoxib is shown below:

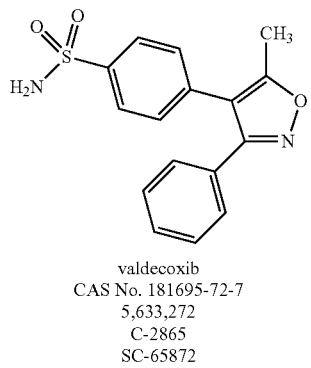 [SMILES: Cc1onc(-c2ccccc2)c1-c1ccc(S(N)(=O)=O)cc1]

valdecoxib
CAS No. 181695-72-7
5,633,272
C-2865
SC-65872

In one preferred embodiment the anti-tumor agent is parecoxib, see U.S. Pat. No. 5,932,598, the contents of which are incorporated by reference in its entirety for all purposes. The structure for paracoxib is shown below:

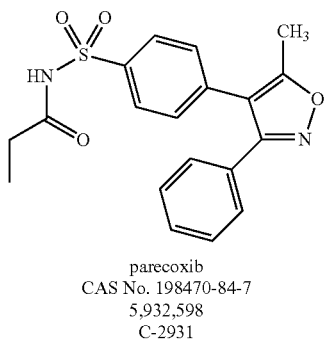 [SMILES: CCC(=O)NS(=O)(=O)c1ccc(-c2c(-c3ccccc3)noc2C)cc1]

parecoxib
CAS No. 198470-84-7
5,932,598
C-2931

In one preferred embodiment the anti-tumor agent is deracoxib, see U.S. Pat. No. 5,521,207, the contents of which are incorporated by reference in its entirety for all purposes. The structure for deracoxib is shown below:

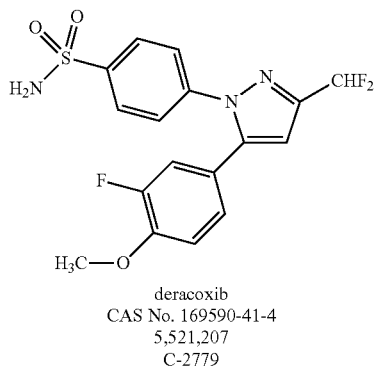 [SMILES: COc1ccc(-c2cc(C(F)F)nn2-c2ccc(S(N)(=O)=O)cc2)cc1F]

deracoxib
CAS No. 169590-41-4
5,521,207
C-2779

In one preferred embodiment the anti-tumor agent is SD-8381, see U.S. Pat. No. 6,034,256, the contents of which are incorporated by reference in its entirety for all purposes. The structure for SD-8381 is shown below:

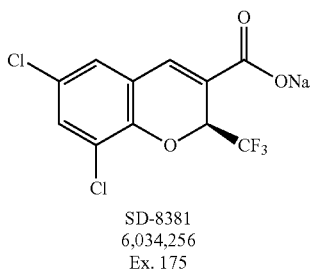

SD-8381
6,034,256
Ex. 175

In one preferred embodiment the anti-tumor agent is ABT-963, see International Publication Number WO 2002/24719, the contents of which are incorporated by reference in its entirety for all purposes. The structure for ABT-963 is shown below:

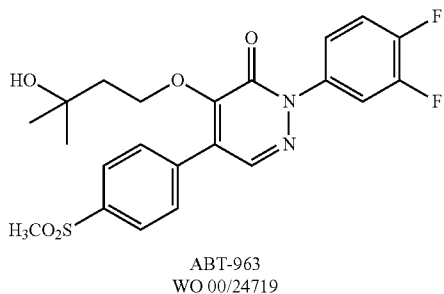

ABT-963
WO 00/24719

In one preferred embodiment the anti-tumor agent is rofecoxib as shown below:

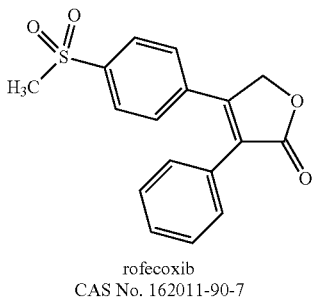 [SMILES: CS(=O)(=O)c1ccc(C2=C(c3ccccc3)C(=O)OC2)cc1]

rofecoxib
CAS No. 162011-90-7

In one preferred embodiment the anti-tumor agent is MK-663 (etoricoxib), see international Publication Number WO 1998/03484, the contents of which are incorporated by reference in its entirety for all purposes. The structure for etoricoxib is shown below:

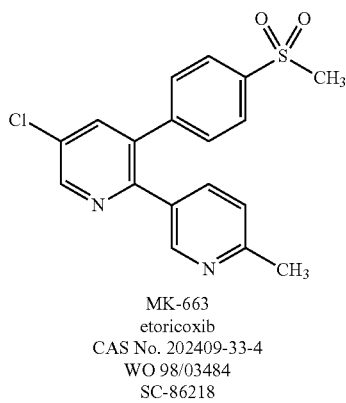 [SMILES: Cc1ccc(-c2ncc(Cl)cc2-c2ccc(S(C)(=O)=O)cc2)cn1]

MK-663
etoricoxib
CAS No. 202409-33-4
WO 98/03484
SC-86218

In one preferred embodiment the anti-tumor agent is COX-189 (Lumiracoxib), see International Publication Number WO 1999/11605, the contents of which are incorporated by reference in its entirety for all purposes. The structure for Lumiracoxib is shown below:

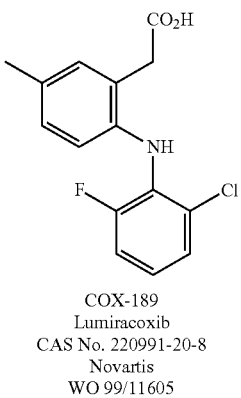 [SMILES: Cc1ccc(Nc2c(F)cccc2Cl)c(CC(=O)O)c1]

COX-189
Lumiracoxib
CAS No. 220991-20-8
Novartis
WO 99/11605

In one preferred embodiment the anti-tumor agent is BMS-347070, see U.S. Pat. No. 6,180,651, the contents of which are incorporated by reference in its entirety for all purposes. The structure for BMS-347070 is shown below:

BMS 347070
CAS No. 197438-48-5
6,180,651

In one preferred embodiment the anti-tumor agent is NS-398 (CAS 123653-11-2). The structure for NS-398 (CAS 123653-11-2) is shown below:

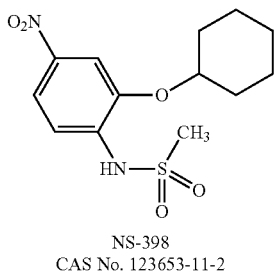 [SMILES: CS(=O)(=O)Nc1ccc([N+](=O)[O-])cc1OC1CCCCC1]

NS-398
CAS No. 123653-11-2

In one preferred embodiment the anti-tumor agent is RS 57067 (CAS 17932-91-3). The structure for RS-57067 (CAS 17932-91-3) is shown below:

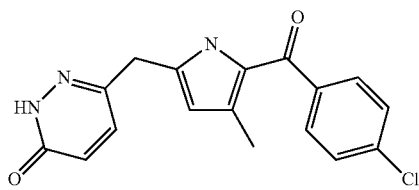

RS 57067
CAS No. 17932-91-3

In one preferred embodiment the anti-tumor agent is 4-Methyl-2-(3,4-dimethylphenyl)-1-(4-sulfamoyl-phenyl)-1H-pyrrole. The structure for 4-Methyl-2-(3,4-dimethylphenyl)-1-(4-sulfamoyl-phenyl)-1H-pyrrole is shown below:

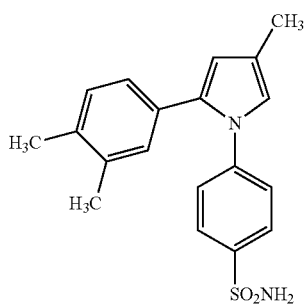

In one preferred embodiment the anti-tumor agent is 2-(4-Ethoxyphenyl)-4-methyl-1-(4-sulfamoylphenyl)-1H-pyrrole. The structure for 2-(4-Ethoxyphenyl)-4-methyl-1-(4-sulfamoylphenyl)-1H-pyrrole is shown below:

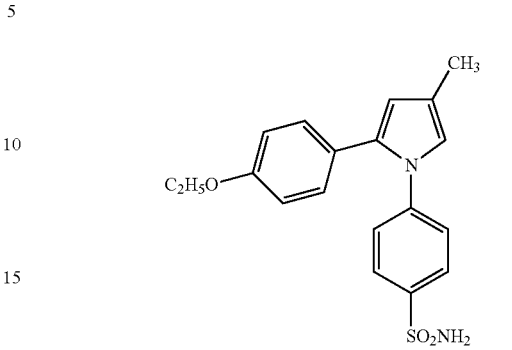

In one preferred embodiment the anti-tumor agent is meloxicam. The structure for meloxicam is shown below:

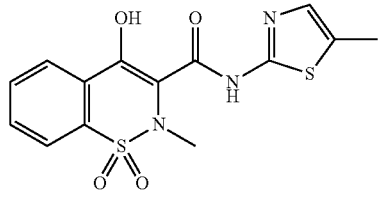

Meloxicam

Other useful inhibitors as anti-tumor agents used in conjunction with antibodies of the present invention and pharmaceutical compositions described herein include aspirin, and non-steroidal anti-inflammatory drugs (NSAIDs) which inhibit the enzyme that makes prostaglandins (cyclooxygenase I and II), resulting in lower levels of prostaglandins, include but are not limited to the following, Amigesic (salsalate), DOLOBID® (diflunisal), MOTRIN® (ibuprofen), ORUDIS® (ketoprofen), RELAFEN® (nabumetone), FELDENE® (piroxicam), ALEVE® (naproxen), NAPROSYN® (naproxen), VOLTAREN® (diclofenac), INDOCIN® (indomethacin), CLINORIL® (sulindac), TOLECTIN® (tolmetin), LOCINE® (etodolac), TORADOL® (ketorolac), DAYPRO® (oxaprozin) and combinations thereof. Preferred COX-I inhibitors include MOTRIN® (ibuprofen), NUPRIN® (ibuprofen), ALEVE® (naproxen), INDOCIN® (indomethacin), RELAFEN® (nabumetone) and combinations thereof.

Targeted agents used in conjunction with an anti-ALK-1 antibody or antigen binding portion thereof, as described herein, and pharmaceutical compositions thereof as described herein, include EGFr inhibitors such as IRESSA® (gefitinib, AstraZeneca), TARCEVA® (erlotinib or OSI-T74, OSI Pharmaceuticals Inc.), ERBITUX® (cetuximab, Imclone Pharmaceuticals, Inc.), EMD-7200 (Merck AG), ABX-EGF (Amgen Inc. and Abgenix Inc.), HR3 (Cuban Government), IgA antibodies (University of Erlangen-Nuremberg), TP-38 (IVAX), EGFR fusion protein, EGF-vaccine, anti-EGFr immunoliposomes (Hermes Biosciences Inc.) and combinations thereof.

Preferred EGFr inhibitors include IRESSA® (gefitinib), ERBITUX® (cetuximab), TARCEVA® (erlotinib) and combinations thereof.

The present invention also relates to anti-tumor agents selected from pan erb receptor inhibitors or ErbB2 receptor inhibitors, such as CP-724,714 (Pfizer, Inc.), CI-1033 (canertinib, Pfizer, Inc.), HERCEPTIN® (trastuzumab, Genentech Inc.), OMITARG® (2C4, pertuzumab, Genentech Inc.), TAK-165 (Takeda), GW-572016 (lonafamib, GlaxoSmithKline), GW-282974 (GlaxoSmithKline), EKB-569 (Wyeth), PKI-166 (Novartis), dHER2 (HER2 Vaccine, Corixa and GlaxoSmithKline), APC8024 (HER2 Vaccine, Dendreon), anti-HER2/neu bispecific antibody (Decof Cancer Center), B7.her2.IgG3 (Agensys), AS HER2 (Research Institute for Rad Biology & Medicine), trifuntional bispecific antibodies (University of Munich) and mAB AR-209 (Aronex Pharmaceuticals Inc) and mAB 2B-1 (Chiron) and combinations thereof. Preferred erb selective anti-tumor agents include HERCEPTIN® (trastuzumab), TAK-165, CP-724,714, ABX-EGF, HER3 and combinations thereof. Preferred pan erbb receptor inhibitors include GW572016, CI-1033, EKB-569, and OMITARG® (pertuzumab) and combinations thereof.

Additional erbB2 inhibitors include those in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), each of which is herein incorporated by reference in its entirety. For additional ErbB2 receptor inhibitors useful in the present invention, see U.S. Pat. Nos. 6,465,449, and 6,284,764, and international Application No. WO 2001/98277 each of which are herein incorporated by reference in their entirety.

Additionally, other anti-tumor agents may be selected from the following agents, Sorafenib (Onyx Pharmaceuticals Inc.; BAY-43-9006), GENASENSE® (augmerosen, Genta), Panitumumab (Abgenix/Amgen), ZEVALIN° (ibritumomab tiuxetan) (Schering), BEXXAR® (tositumomab) (Corixa/GlaxoSmithKline), Abarelix, ALIMTA® (pemetrexed), EPO 906 (Novartis), discodermolide (XAA-296), ABT-510 (Abbott), NEOVASTAT® (Aeterna), enzastaurin (Eli Lilly), Combrestatin A4P (Oxigene), ZD-6126 (AstraZeneca), flavopiridol (Aventis), CYC-202 (Cyclacel), AVE-8062 (Aventis), DMXAA (Roche/Antisoma), Thymitaq (nolatrexed dihydrochloride, Eximias), TEMODAR® (temozolomide, Schering Plough) and REVILIMD® (lenalidomide) (Celegene) and combinations thereof.

Other anti-tumor agents may be selected from the following agents, CYPAT® (cyproterone acetate), Histerelin (histrelin acetate), PLENAIXIS® (abarelix depot), Atrasentan (ABT-627), Satraplatin (JM-216), THALOMID® (thalidomide), THERATOPE®, Tesmilifene (DPPE), ABI-007 (paclitaxel), EVISTA® (raloxifene), Atamestane (Biomed-777), Xyotax (polyglutamate paclitaxel), TARGRETIN (bexarotine) and combinations thereof.

Additionally, other anti-tumor agents may be selected from the following agents, Trizaone (tirapazamine), APOSYN® (exisulind), NEOVASTAT® (AE-941), CEPLENE® (histamine dihydrochloride), ORATHECIN® (rubitecan), VIRULIZIN®, Gastrimmune (G17DT), DX-8951f (exatecan mesylate), ONCONASE® (ranpirnase), BEC2 (mitumoab), XCYTRIN® (motexatin gadolinium) and combinations thereof.

Further anti-tumor agents may be selected from the following agents, CeaVac (CEA), NEUTREXIN® (trimestrexate glucuronate) and combinations thereof. Additional anti-tumor agents may selected from the following agents, OVAREX® (oregovomab), OSIDEM® (IDM-1), and combinations thereof. Additional anti-tumor agents may be selected from the following agents, ADVEXIN® (ING 201), Tirazone (tirapazamine), and combinations thereof. Additional anti-tumor agents may selected from the following agents, RSR13 (efaproxiral), COTARA® (131 1chTNT 1/b), NBI-3001 (IL-4) and combinations thereof. Additional anti-tumor agents may be selected from the following agents, CANVAXIN®, GMK vaccine, PEG Intron A, TAXOPREXIN® (DHA/paclitaxel) and combinations thereof. Other preferred anti-tumor agents include Pfizer's MEK1/2 inhibitor PD325901, Array Biopharm's MEK inhibitor ARRY-142886, Bristol Myers' CDK2 inhibitor BMS-387,032, Pfizer's CDK inhibitor PD0332991 and AstraZeneca's AXD-5438 and combinations thereof. Additionally, mTOR inhibitors may also be utilized such as CCI-779 (Wyeth) and rapamycin derivatives RAD001 (Novartis) and AP-23573 (Ariad), HDAC inhibitors SAHA (Merck Inc./Aton Pharmaceuticals) and combinations thereof. Additional anti-tumor agents include aurora 2 inhibitor VX-680 (Vertex), Chk1/2 inhibitor XL844 (Exilixis).

The following cytotoxic agents, e.g., one or more selected from the group consisting of ELLENCE® (epirubicin), TAXOTERE® (docetaxel), paclitaxel, ZINECARD® (dexrazoxane), RITUXIN® (rituximab), GLEEVEC® (imatinib mesylate), and combinations thereof, may be used in conjunction with a Anti-ALK-1 antibody or antigen binding portion thereof, as described herein, and pharmaceutical compositions thereof, as described herein.

The invention also contemplates the use of the antibodies and antigen-binding portions thereof of the present invention together with hormonal therapy, including but not limited to, AROMASIN® (exemestane, Pfizer Inc.), LUPRON® or Leuplin (leuprorelin, TAP Pharmaceutical Products Inc./Abbott/Takeda), ARIMIDEX® (anastrozole, AstraZeneca), ZOLADEX® (goserelin, AstraZeneca), doxercalciferol, fadrozole, formestane, tamoxifen citrate, NOLVADEX® (tamoxifen, tamoxifen citrate, AstraZeneca), CASODEX® (bicalutamide, AstraZeneca), Abarelix (Praecis Pharmaceuticals), TRELSTAR® (triptorelin pamoate), and combinations thereof.

The invention also relates to hormonal therapy agents such as anti-estrogens including, but not limited to fulvestrant, toremifene, raloxifene, lasofoxifene, FEMARA® (letrozole, Novartis), anti-androgens such as bicalutamide, flutamide, mifepristone, nilutamide, CASODEX® (4'-cyano-3-(4-fluorophenylsulphonyl)-2-hydroxy-2-methyl-3'-(trifluoromethyl) propionanilide, bicalutamide) and combinations thereof.

Further, the invention provides antibodies of the present invention alone or in combination with one or more supportive care products, e.g., a product selected from the group consisting of Filgrastim (Neupogen), ZOFRAN® (ondansetron), FRAGMIN® (dalteparin), PROCRIT® (epoetin alfa), ALOXI® (palonosetron hydrochloride), EMEND® (aprepitant), or combinations thereof.

Particularly preferred cytotoxic agents include CAMPTOSAR® (irinotecan HCl), ERBITUX® (cetuximab), IRESSA® (gefitinib), GLEEVEC® (imatinib mexylate), TAXOTERE® (docetaxel), and combinations thereof.

The following topoisomerase I inhibitors may be utilized as anti-tumor agents camptothecin, CAMPTOSAR® (irinotecan HCl), edotecarin, ORATHECIN® (SuperGen), exatecan (Daiichi), BN-80915 (Roche) and combinations thereof. Particularly preferred toposimerase II inhibitors include ELLENCE® (epirubicin).

The antibodies of the invention may be used with antitumor agents, alkylating agents, antimetabolites, antibiotics, plant-derived antitumor agents, camptothecin derivatives, tyrosine kinase inhibitors, other antibodies, interferons, and/or biological response modifiers.

Alkylating agents include, but are not limited to, nitrogen mustard N-oxide, cyclophosphamide, ifosfamide, melphalan, busulfan, mitobronitol, carboquone, thiotepa, ranimustine, nimustine, temozolomide, AMD-473, altretamine, AP-5280, apaziquone, brostallicin, benclamustine, carmustine, estramustine, fotemustine, glufosfamide, ifosfamide, KW-2170, mafosfamide, and mitolactol; platinum-coordinated alkylating compounds include but are not limited to, cisplatin, PARAPLATIN® (carboplatin), eptaplatin, lobaplatin, neclaplatin, ELOXATIN® (oxaliplatin, Sanofi) satrplatin and combinations thereof. Particularly preferred alkylating agents include ELOXATIN® (oxaliplatin).

Antimetabolites include but are not limited to, methotrexate, 6-mercaptopurine riboside, mercaptopurine, 5-fluorouracil (5-FU) alone or in combination with leucovorin, tegafur, UFT, doxifluridine, carmofur, cytarabine, cytarabine ocfosfate, enocitabine, S-1, ALIMTA® (pemetrexed disodium, LY231514, MTA), GEMZAR® (gemcitabine, Eli Lilly), fludarabin, 5-azacitidine, capecitabine, cladribine, clofarabine, decitabine, eflornithine, ethynylcytidine, cytosine arabinoside, hydroxyurea. TS-1, melphalan, nelarabine, nolatrexed, ocfosfate, pemetrexed disodium, pentostatin, pelitrexol, raltitrexed, triapine, trimetrexate, vidarabine, vincristine, vinorelbine; or for example, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid and combinations thereof.

Antibiotics include intercalating antibiotics but are not limited to: aclarubicin, actinomycin D, amrubicin, annamycin, adriamycin, bleomycin, daunorubicin, doxorubicin, elsamitrucin, epirubicin, galarubicin, idarubicin, mitomycin C, nemorubicin, neocarzinostatin, peplomycin, pirarubicin, rebeccamycin, stimalamer, streptozocin, valrubicin, zinostatin and combinations thereof.

Plant derived anti-tumor substances include for example those selected from mitotic inhibitors, for example vinblastine, TAXOTERE® (docetaxel), paclitaxel and combinations thereof.

Cytotoxic topoisomerase inhibiting agents include one or more agents selected from the group consisting of aclarubicn, amonafide, belotecan, camptothecin, 10-hydroxycamptothecin, 9-aminocamptothecin, diflomotecan, CAMPTOSAR® (irinotecan HCl), edotecarin, ELLENCE® (epirubicin), etoposide, exatecan, gimatecan, lurtotecan, mitoxantrone, pirarubicin, pixantrone, rubitecan, sobuzoxane, SN-38, taflupoiside, topotecan, and combinations thereof.

Preferred cytotoxic topoisomerase inhibiting agents include one or more agents selected from the group consisting of camptothecin, 10-hydroxycamptothecin, 9-aminocamptothecin, CAMPTOSAR® (irinotecan HCl), edotecarin, ELLENCE® (epirubicin), etoposide, SN-38, topotecan, and combinations thereof.

Immunologicals include interferons and numerous other immune enhancing agents. Interferons include interferon alpha, interferon alpha-2a, interferon, alpha-2b, interferon beta, interferon gamma-1a, interferon gamma-1b (ACTIMMUNE®), or interferon gamma-n1 and combinations thereof. Other agents include filgrastim, lentinan, sizofilan, THERACYS®, ubenimex, WF-10, aldesleukin, alemtuzumab, BAM-002, dacarbazine, daclizumab, gemtuzumab ozogamicin, ibritumomab, imiquimod, lenograstim, lentinan, melanoma vaccine (Corixa), molgramostim, OncoVAX-CL, sargramostim, tasonermin, tecleukin, thymalasin, tositumomab, VIRULIZIN®, Z-100, epratuzumab, mitumomab, oregovomab, pemtumomab (Y-muHMFG1), PROVENGE® (Dendreon Corp.) and combinations thereof.

Biological response modifiers are agents that modify defense mechanisms of living organisms or biological responses, such as survival, growth, or differentiation of tissue cells to direct them to have anti-tumor activity. Such agents include krestin, lentinan, sizofiran, picibanil, ubenimex and combinations thereof.

Other anticancer agents include alitretinoin, ampligen, atrasentan bexarotene, bortezomib. Bosentan, calcitriol, exisulind, finasteride, fotemustine, ibandronic acid, miltefosine, mitoxantrone, I-asparaginase, procarbazine, dacarbazine, hydroxycarbamide, pegaspargase, pentostatin, tazarotne, TELCYTA® (TLK-286, Telik Inc.), VELCADE® (bortemazib, Millenium), tretinoin, and combinations thereof.

Other anti-angiogenic compounds include acitretin, fenretinide, thalidomide, zoledronic acid, angiostatin, cilengtide, combretastatin A-4, endostatin, halofuginone, rebimastat, removab, REVLIMID®, squalamine, ukrain, VITAXIN® and combinations thereof.

Platinum-coordinated compounds include but are not limited to, cisplatin, carboplatin, nedaplatin, oxaliplatin, and combinations thereof.

Camptothecin derivatives include but are not limited to camptothecin, 10-hydroxycamptothecin, 9-aminocamptothecin, irinotecan, SN-38, edotecarin, topotecan and combinations thereof.

Other antitumor agents include mitoxantrone, I-asparaginase, procarbazine, dacarbazine, hydroxycarbamide, pentostatin, tretinoin and combinations thereof.

Anti-tumor agents capable of enhancing antitumor immune responses, such as CTLA-4 (cytotoxic lymphocyte antigen 4) antibodies, and other agents capable of blocking CTLA-4 may also be utilized, such as MDX-010 (Medarex) and CTLA-4 compounds disclosed in U.S. Pat. No. 6,682,736; and anti-proliferative agents such as other farnesyl protein transferase inhibitors, for example the farnesyl protein transferase inhibitors. For additional, specific CTLA-4 antibodies that can be used in the present invention see U.S. Provisional Application 60/113,647 (filed Dec. 23, 1998), U.S. Pat. No. 6,682,736 both of which are herein incorporated by reference in their entirety. For example, another anti-CTLA-4 antibody that can be used in accordance with the present invention is ticilimumab, which has the sequence of monoclonal antibody 11.2.1 in U.S. Pat. No. 6,682,736.

For specific IGF1R antibodies that can be used in the present invention, see International Patent Application No. WO 2002/053596, which is herein incorporated by reference in its entirety.

For specific CD40 antibodies that can be used in the present invention, see International Patent Application No. WO 2003/040170, which is herein incorporated by reference in its entirety.

Gene therapy agents may also be employed as anti-tumor agents such as TNFerade (GeneVec), which express TNFalpha in response to radiotherapy.

In one embodiment of the present invention, statins may be used in conjunction with a Anti-ALK-1 antibody or antigen binding portion thereof, as described herein, and pharmaceutical compositions thereof. Statins (HMG-CoA reductase inhibitors) may be selected from the group consisting of LIPITOR® (atorvastatin, Pfizer Inc.), PRAVACHOL® (pravastatin, Bristol-Myers Squibb), MEVACOR® (lovastatin, Merck Inc.), ZOCOR® (simvastatin, Merck Inc.), LESCOL® (fluvastatin, Novartis), BAYCOL® (cerivastatin, Bayer), CRESTOR® (rosuvastatin, AstraZeneca), ADVICOR® (lovostatin and niacin, Kos Pharmaceuticals), derivatives and combinations thereof.

In a preferred embodiment the statin is selected from the group consisting of Atovorstatin and Lovastatin, derivatives and combinations thereof. Other agents useful as anti-tumor agents include CADUET® (amlodipine besylate and atorvastatin).

For any of the methods of treating a hyperproliferative disorder or abnormal cell growth as described herein using a combination of an anti-ALK-1 antibody or antigen binding portion with at least one additional therapeutic agent, the anti-ALK-1 antibody can be conjugated, or derivatized, with the additional therapeutic agent. The at least one additional therapeutic agent can also be administered separately, or in a non-derivatized or non-conjugated manner. When the at least one additional therapeutic agent is not derivatized or conjugated to the antibody, it can be administered within the same pharmaceutical formulation as the antibody, or it can be administered in a separate formulation.

Treatment of Vision Loss

The inventive compounds and pharmaceutical compositions containing them, are useful for treating severe vision loss from age-related macular degeneration and other diseases affecting the posterior segment of the eye, such as choroidal neovascularization, diabetic retinopathy, glaucoma, retinitis pigmentosa, and the like.

For example, the inventive compositions may be used to form a drug depot behind the eye and may include one or more pharmaceutically active agents, in addition to one or more non-active excipients as described herein. Examples of pharmaceutically active agents useful in the inventive compositions includes anti-infectives, including, without limitation, antibiotics, antivirals, and antifungals; antiallergenic agents and mast cell stabilizers; steroidal and nonsteroidal anti-inflammatory agents (such as nepafenac); cyclooxygenase inhibitors, including, without limitation, Cox I and Cox II inhibitors; combinations of anti-infective and anti-inflammatory agents; decongestants; anti-glaucoma agents, including, without limitation, adrenergics, beta-adrenergic blocking agents, alpha-adrenergic agonists, parasypathomimetic agents, cholinesterase inhibitors, carbonic anhydrase inhibitors, and prostaglandins; combinations of anti-glaucoma agents; antioxidants; nutritional supplements; drugs for the treatment of cystoid macular edema including, without limitation, non-steroidal anti-inflammatory agents; drugs for the treatment of age related macular degeneration (AMD) including nonexudative (dry) and exudative (wet) AMD, including, without limitation, angiogenesis inhibitors, including angiogenesis inhibitors that inhibit protein kinase receptors, including protein kinase receptors that are VEGF receptors; and nutritional supplements; drugs for the treatment of herpetic infections and CMV ocular infections; drugs for the treatment of proliferative vitreoretinopathy including, without limitation, antimetabolites and fibrinolytics; wound modulating agents, including, without limitation, growth factors; antimetabolites; neuroprotective drugs, including, without limitation, eliprodil; and angiostatic steroids for the treatment of diseases or conditions of posterior segment 26, including, without limitation, age related macular degeneration (AMD) including nonexudative (dry) and exudative (wet) AMD, choroidal neovascularization, retinopathies, retinitis, uveitis, macular edema, and glaucoma. For additional information about such angiostatic steroids see U.S. Pat. Nos. 5,679,666 and 5,770,592. A non-steroidal anti-inflammatory for the treatment of cystoid macular edema is nepafenac.

For administration to the eye, a compound of the present invention is delivered in a pharmaceutically acceptable ophthalmic vehicle such that the compound is maintained in contact with the ocular surface for a sufficient time period to allow the compound to penetrate the cornea and/or sclera and internal regions of the eye, including, for example, the anterior chamber, posterior chamber, vitreous body, aqueous humor, vitreous humor, cornea, iris/ciliary's, lens, choroid/retina and sclera. The pharmaceutically acceptable ophthalmic vehicle may be an ointment, vegetable oil, or an encapsulating material. A compound of the invention may also be injected directly into the vitreous humor or aqueous humor.

Further, a compound may be also be administered by well known, acceptable methods, such as sub-Tenon and/or sub-conjunctival injections. As is well known in the ophthalmic art, the macula is comprised primarily of retinal cones and is the region of maximum visual acuity in the retina. A Tenon's capsule or Tenon's membrane is disposed on the sclera. A conjunctiva covers a short area of the globe of the eyeposterior to the limbus (the bulbar conjunctiva) and folds up (the upper cul-de-sac) or down (the lower cul-de-sac) to cover the inner areas of the upper eyelid and lower eyelid, respectively. The conjunctiva is disposed on top of Tenon's capsule. The sclera and Tenon's capsule define the exterior surface of the globe of the eye. For treatment of ocular diseases such as age related macular degeneration (AMD) including nonexudative (dry) and exudative (wet) AMD, choroidal neovascularization, retinopathies (such as diabetic retinopathy, retinopathy of prematurity), diabetic macular edema, retinitis, uveitis, cystoid macular edema (CME), glaucoma, and other diseases or conditions of the posterior segment of the eye, it is preferable to dispose a depot of a specific quantity of an ophthalmically acceptable pharmaceutically active agent directly on the outer surface of the sclera and below Tenon's capsule. In addition, in cases of age related macular degeneration (AMD) including nonexudative (dry) and exudative (wet) AMD and CME it is most preferable to dispose the depot directly on the outer surface of the sclera, below Tenon's capsule, and generally above the macula.

The compounds may be formulated as a depot preparation. Such long-acting formulations may be administered by implantation (for example, subcutaneously or intramuscularly) intramuscular injection or by the above mentioned sub-Tenon or intravitreal injection. Alternatively, the active ingredient may be in powder form for constitution with a suitable vehicle, e.g., sterile pyrogen-free water, before use.

Within particularly preferred embodiments of the invention, the compounds may be prepared for topical administration in saline combined with any of the preservatives and antimicrobial agents commonly used in ocular preparations), and administered in eyedrop form. The solution or suspension may be prepared in its pure form and administered several times daily. Alternatively, the present compositions, prepared as described above, may also be administered directly to the cornea.

Within preferred embodiments, the composition is prepared with a mucoadhesive polymer that binds to cornea. Thus, for example, the compounds may be formulated with suitable polymeric or hydrophobic materials (for example, as an emulsion in an acceptable oil) or ion-exchange resins, or as sparingly soluble derivatives, for example, as a sparingly soluble salt.

A pharmaceutical carrier for hydrophobic compounds is a cosolvent system comprising benzyl alcohol, a nonpolar surfactant, a water-miscible organic polymer, and an aqueous phase. The cosolvent system may be a VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) contains VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid- or gel-phase carriers or excipients. Examples of such carriers or excipients include calcium carbonate, calcium phosphate, sugars, starches, cellulose derivatives, gelatin, and polymers such as polyethylene glycols.

Any of the compositions can be formulated for administration to an individual. An individual of the present invention is preferably a mammal, or more preferably a human.

The pharmaceutical formulations herein can further include a therapeutic agent selected from the group consisting of: an antineoplastic agent, an anti-inflammatory agent, an antibacterial agent, an antiviral agent, an angiogenic agent, and an anti-angiogenic agent. Examples of such agents are disclosed herein.

For example, an antineoplastic agent may be selected from the group consisting of Acodazole Hydrochloride; Acronine; Adozelesin; Aldesleukin; Altretamine; Ambomycin; Ametantrone, Acetate; Aminoglutethimide; Amsacrine; Anastrozole; Anthramycin; Asparaginase; Asperlin; Azacitidine; Azetepa; Azatomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; Fluorocitabine; Fosquidone; Fostriecin Sodium; Gemcitabine; Gemcitabine Hydrochloride; Gold Au 198; Hydroxyurea; Idarubicin Hydrochloride; Ifosfamide; Imofosine; Interferon Alfa-2a; Interferon Alfa-2b; Interferon Alfa-n1; Interferon Alfa-n3; Interferon Beta-Ia; Interferon Gamma-Ib; Iproplatin; Irinotecan Hydrochloride; Lanreotide Acetate; Letrozole; Leuprolide Acetate Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycinl, Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine. Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride.

An anti-angiogenic agents are any agents that inhibit angiogenesis, whether disclosed herein or known in the art. In preferred embodiments, an anti-angiogenic agent is an anti-VEGF agent, such as MACUGEN® (pegaptanib sodium) (Eyetech, New York, N.Y.); or anti-VEGF antibody.

Pharmaceutical compositions can be formulated by standard techniques using one or more suitable carriers; excipients, and dilutents. See, e.g., Remington's Pharmaceutical Sciences, (19$^{th}$ Ed. Williams & Wilkins, 1995) (incorporated herein by reference for all purposes).

Formulations suitable for parenteral administration include aqueous and non-aqueous formulations isotonic with the blood of the intended recipient; and aqueous and non-aqueous sterile suspensions which may include suspending systems designed to target the compound to blood components or one or more organs. The formulations may be presented in unit-dose or multi-dose sealed containers, for example, ampoules or vials. For intraocular formulations, unit dosages are preferred because no preservatives are in the formulation. For other parenteral formulations, preservative may be used, which would allow for multi dose containers Extemporaneous injections solutions and suspensions may be prepared, for example, from sterile powders. Parenteral and intravenous forms may also include minerals and other materials to make them compatible with the type of injection or delivery system chosen.

Particular parenteral administrations contemplated by the present invention include intraocular and intravitreous administrations to the eye. Pharmaceutical formulations for intraocular and intravitreous administrations include phosphate buffered saline (PBS) and balanced isotonic salt solution (BSS) with or without excipients such as mannitol or sorbitol as protein stabilizers.

In general, water, suitable oil, saline, aqueous dextrose (glucose), or related sugar solutions and glycols such as propylene glycol or polyethylene glycols are suitable carriers for parenteral solutions. Solutions for parenteral administration preferably contain a water soluble salt of the active ingredient, suitable stabilizing agents and, if necessary, buffer substances. Antioxidizing agents, such as sodium bisulfite, sodium sulfite, or ascorbic acid, either alone or combined, are suitable stabilizing agents. Also used are citric acid salts thereof, or sodium EDTA. In addition, parenteral solutions may contain preservatives, such as benzalkonium chloride, methyl- or propyl-paraben, or chlorobutanol. Suitable pharmaceutical carriers are described in Remington, cited supra.

In any of the embodiments herein, a composition or pharmaceutical formulation herein may by lypholized.

In any of the embodiments herein, the pharmaceutical formulations preferable have less than about 10, more preferably less than about 5, more preferably less than about 3, or more preferably less than about 1 endotoxin unit(s) per milligram of therapeutic agents.

In some embodiments, the methods of treatment disclosed herein further include administering to an individual suffering from an angiogenic condition one or more therapeutic agents selected from the group consisting of antineoplastic agents, antiviral agents, anti-inflammatory agents, antibacterial agents, anti-angiogenic agents, or anti-angiogenic agents.

Such combination treatments can be achieved by either administering to an individual a co-formulating of the compositions herein with the additional therapeutic agent(s) or by administering the compositions herein and the therapeutic agent(s) as two separate pharmaceutical formulations. In embodiments wherein more than one composition/therapeutic agent is administered to an individual, lower dosages of the compositions and/or therapeutic agent(s) may be utilized as a result of the synergistic effect of both active ingredients.

Antineoplastic agents that may be administered to an individual include, but are not limited to, Aclarubicin; Acodazole Hydrochloride; Acronine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; Fluorocitabine; Fosquidone; Fostriecin Sodium; Gemcitabine; Gemcitabine Hydrochloride; Gold Au 198; Hydroxyurea; Idarubicin Hydrochloride; Ifosfamide; Imofosine; Interferon Alfa-2a; Interferon Alfa-2b; Interferon Alfa-n1; Interferon Alfa-n3; Interferon Beta-Ia; Interferon Gamma-Ib; Iproplatin; Irinotecan Hydrochloride; Lanreotide Acetate; Letrazole; Leuprolide Acetate Liarozole Hydrochloride; Lometrexol Sodium; Lomustine; Losoxantrone. Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycinl, Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride.

Antibacterial agents that may be administered to an individual include, but are not limited to, penicillins, aminoglycosides, macrolides, monobactams, rifamycins, tetracyclines, chloramphenicol, clindamycin, lincomycin, imipenem, fusidic acid, noyobiocin, fosfomycin, fusidate sodium, neomycin, polymyxin, capreomycin, colistimethate, colistin, gramicidin, minocycline, doxycycline, vanomycin, bacitracin, kanamycin, gentamycin, erythromicin and cephalosporins.

Anti-inflammatory agents that may be administered to an individual include, but are not limited to, NSAIDS (e.g., aspirin (salicylamide), sodium salicylamide, indoprofen, indomethacin, sodium indomethacin trihydrate, BAYER®, BUFFERIN®, CELEBREX® (celecoxib), diclofenac, ECOTRIN®(aspirin), diflunisal, fenoprofen, naproxen, sulindac, VIOXX® (rofecoxib), corticosteroids or corticotropin (ACTH), colchicine, and anecortave acetate.

Antiviral agents that may be administered to an individual include, but are not limited to, α-methyl-P-adamantane methylamine, 1-D-ribofuranosyl-1,2,4-triazole-3 carboxamide, 9-[2-hydroxy-ethoxy]methylguanine, adamantanamine, 5-iodo-2'-deoxyuridine, trifluorothymidine, interferon, adenine arabinoside, CD4, 3'-azido-3'-deoxythymidine (AZT), 9-(2-hydroxyethoxymethyl)-guanine (acyclovir), phosphonoformic acid, 1-adamantanamine, peptide T, and 2',3'dideoxycytidine.

Administration of a composition of the present invention to a target cell in vivo can be accomplished using any of a variety of techniques well known to those skilled in the art.

For example, compositions of the present invention can be administered systemically or locally by any means known in the art (e.g., orally, intraocularly, intravascularly (i.v.), intradermally, intramuscularly, transdermally, transmucosally, enterically, parentally, by inhalation spray, rectally, or topically) in dosage unit formulations and containing conventional pharmaceutically acceptable carriers, adjuvants, and vehicles.

As used herein the term intraocularly includes intravitreal, sub-retinal, and the like.

As used herein the term parenteral as used herein includes, subcutaneous, intravenous, intramuscular, intrasternal, infusion techniques or intraperitoneally. Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

The dosage regimen for treating a disorder or a disease with the compositions of this invention is based on a variety of factors, including the type of disease, the age, weight, sex, medical condition of the patient, the severity of the condition, the route of administration, and the particular compound employed. Thus, the dosage regimen can vary widely, but can be determined routinely using standard methods.

For systemic administration, the anti-ALK-1 antibody or antigen-binding portion thereof of the present invention and/or one or more additional therapeutic agents are preferably administered at a dose of at least 0.05, 0.1, 0.2, 0.3, 0.4, 0.5, 0.6, 0.7, 0.8, 0.9, 1.0, 2.0, 3.0, 4.0, 5.0, 6.0, 7.0, 8.0, 9.0, 10, 20, 30, 40, 50, 75, 100, or 150 mg/kg body weight. In other embodiments, the poi/peptides (preferably dimers homodimers) and/or small molecules herein are administered systemically at a dose of 0.1-100 mg/kg, more preferably 0.5-50 mg/kg, more preferably 1-30 mg/kg body weight, or more preferably 5-20 mg/kg.

For localized administration, the anti-ALK-1 antibody or antigen-binding portion thereof of the present invention and/or one or more additional therapeutic agents are preferably administered at a dose of at least 50 μg, 100 μg, 150 μg, 200 μg, 250 μg, 300 μg, 350 μg, 400 μg, 450 μg, 500 μg, 550 μg, 600 μg, 650 μg, or 700 μg. In other embodiments, the polypeptides (preferably dimers homodimers) and/or small molecules herein are administered locally at a dose of 50-1000 μg, more preferably 100-800 μg, more preferably 200-500 μg, or more preferably 300-400 μg per site.

For example, for dermal administration the anti-ALK-1 antibody or antigen-binding portion thereof of the present invention and/or peptidomimetics and/or one or more additional therapeutic agents are administered at a dose of 50-1000 μg/cm$^2$, more preferably 100-800 μg/cm$^2$, or more preferably 200-500 μg/cm$^2$. In another example, for ocular administration, the polypeptides and/or peptidomimetics and/or small molecules of the present invention are administered at a dose of 50-1000 μg/eye, more preferably 100-800 μg/eye, or more preferably 200-500 μg/eye.

The pharmaceutical compositions preferably include the active ingredient (e.g., an anti-ALK-1 antibody) in an effective amount, i.e., in an amount effective to achieve therapeutic or prophylactic benefit. The actual amount effective for a particular application will depend on the condition being treated and the route of administration. Determination of an effective amount is well within the capabilities of those skilled in the art, especially in light of the disclosure herein.

Preferably, the effective amount of the active ingredient, e.g., an anti-ALK-1 antibody, is from about 0.0001 mg to about 500 mg active agent per kilogram body weight of a patient, more preferably from about 0.001 to about 250 mg active agent per kilogram body weight of the patient, still more preferably from about 0.01 mg to about 100 mg active agent per kilogram body weight of the patient, yet still more preferably from about 0.5 mg to about 50 mg active agent per kilogram body weight of the patient, and most preferably from about 1 mg to about 15 mg active agent per kilogram body weight of the patient.

In terms of weight percentage, the formulations of the present invention will preferably comprise the active agent, e.g., an anti-ALK-1 antibody, in an amount of from about 0.0001 to about 10 wt, %, more preferably from about 0.001 to about 1 wt. %, more preferably from about 0.05 to about 1 wt. %, or more preferably about 0.1 wt. to about 0.5 wt. %.

Gene Therapy

The nucleic acid molecules that encode the antibodies and antibody portions of the present invention can be administered to a patient in need thereof via gene therapy. The therapy may be either in vivo or ex vivo. In a preferred embodiment, nucleic acid molecules encoding both a heavy chain and a light chain are administered to a patient. In a more preferred embodiment, the nucleic acid molecules are administered such that they are stably integrated into chromosomes of B cells because these cells are specialized for producing antibodies. In a preferred embodiment, precursor B cells are transfected or infected ex vivo and re-transplanted into a patient in need thereof. In another embodiment, precursor B cells or other cells are infected in vivo using a virus known to infect the cell type of interest. Typical vectors used for gene therapy include liposomes, plasmids, and viral vectors. Exemplary viral vectors are retroviruses, adenoviruses and adeno-associated viruses. After infection either in vivo or ex vivo, levels of antibody expression can be monitored by taking a sample from the treated patient and using any immunoassay known in the art or discussed herein.

In a preferred embodiment, the gene therapy method comprises the steps of administering an isolated nucleic acid molecule encoding the heavy chain or an antigen-binding portion thereof of an anti-ALK-1 antibody and expressing the nucleic acid molecule. In another embodiment, the gene therapy method comprises the steps of administering an isolated nucleic acid molecule encoding the light chain or an antigen-binding portion thereof of an anti-ALK-1 antibody and expressing the nucleic acid molecule. In a more preferred method, the gene therapy method comprises the steps of administering an isolated nucleic acid molecule encoding the heavy chain or an antigen-binding portion thereof and an isolated nucleic acid molecule encoding the light chain or the antigen-binding portion thereof of an anti-ALK-1 antibody of the invention and expressing the nucleic acid molecules. The gene therapy method may also comprise the step of administering another therapeutic agent, such as any of the agents discussed previously in connection with combination therapy.

Method for Screening ALK-1 Antagonists or Agonists

In one embodiment, the present invention provides a method for determining if a substance inhibits up-regulation of a specific downstream target gene of ALK-1, Id1, such as, for example, the TAQMAN® Assay for Id1 described in Example 12. The method comprises contacting a sample of cells that express Id1 with the substance and determining if Id1 expression is inhibited, wherein a reduced level of Id1 expression in the sample of cells contacted with the substance as compared to a control sample of cells is indicative of said substance inhibiting Id1 expression. In one specific embodiment, the substance is an antibody that binds to the extracellular domain of ALK-1. In another embodiment, the substance is a small molecule. According to the invention, the cells can inherently express both ALK-1 and Id1, such as HUVECs described in Example 12, or which have been transformed or transfected with DNA encoding one or both of these. One can determine the expression of Id1 via, e.g., the use of TAQMAN® Assay for Id1 described in Example 12.

Conversely, activators or agonists can also be tested for, or utilized, following the same type of procedures.

In order that this invention may be better understood, the following examples are set forth. These examples are for purposes of illustration only and are not to be construed as limiting the scope of the invention in any manner.

EXAMPLES

In the following examples and preparations, "MW" means molecular weight; "His-Tag" means C-terminal polyhistidine (6×His) tag for rapid purification with nickel-chelating resin and detection with an anti-His (C-term) antibody; "BSA" means bovine serum albumin; "EDTA" means ethylenediaminetetraacetic acid; "DMSO" means dimethyl sulfoxide; "MOPS" means 3-(N-morpholino) propanesulfonic acid; "MES" means 2-(N-Morpholino)ethanesulfonic acid; "PBS" means phosphate buffered saline; "dPBS" means Dulbecco's phosphate buffered saline; "HEMA" means 2-hydroxy-ethyl methacrylate; "DMEM" means Dulbecco's modified eagle's medium; "FBS" means fetal bovine serum; "NEAA" means non-essential amino acids; "HEPES" means N-2-hydroxyethylpiperazine-N'-2-ethanesulfonic acid; and "DMF" means dimethyl formamide.

Example 1

ALK-1 Immunogen Preparation

The ECD of ALK-1 was cloned from full-length human ALK-1 ORF clone (Invitrogen, Clone ID IOH21048) by PCR using the forward 5'-ACGGCCCAGCCGGCCGACCCTGTGAAGCCGTCT (SEQ ID NO: 96) and reverse 5'-ACTAAGCTTTTAATGATGATGATGATGATGCTGGCCATCTGTTCCCG (SEQ ID NO: 97) primers. The PCR product was purified, treated with the SfiI and HindIII restriction enzymes, and cloned into the SfiI/HindIII site of a mammalian expression vector pSecTag2/Hygro (Invitrogen Inc., Catalog No. V910-20). The clone was used to transiently transfect 293T cells with Fugene 6 transfection reagent (Roche Applied Science, Catalog No. 1814443) following manufacture's instruction. Supernatant from the cell culture containing the secreted target protein was harvested 72 hours post-transfection and allowed to bind to Ni-NTA resin (Qiagen, Catalog No. 30430) at 4° C. overnight. The resin was then washed with buffer containing 20 mM Tris pH 8.0, 25 mM imidazole and 300 mM sodium chloride. The His-Tag protein was eluted off the resin using buffer containing 20 mM Tris pH 8.0, 300 mM imidazole and 300 mM sodium chloride. A CM Sepharose cation exchange resin was used to further purify the protein in 20 mM sodium phosphate (pH 7.0), and the unbound fraction containing the target protein was collected. The protein was buffer exchanged to PBS or 10 mM HEPES, pH 7.4, plus 150 mM sodium chloride by dialysis and concentrated to 0.2-1 mg/mL with a final purity of >90%, judged by SDS PAGE gel stained with Coomassie blue. The ALK-1 ECD His-Tag protein was heavily glycosylated with an apparent MW of 26 KDa, comparing to an 11 KDa theoretical MW for the protein. The ALK-1 ECD His-Tag protein (SEQ ID NO: 98) has been used for generation of hybridomas producing anti-ALK-1 antibody as described in Example 2.

Human ALK-1 ECD His-Tag protein:
gene sequence (lowercase part is the secretion signal):

(SEQ ID NO: 99)
atggagacagacacactcctgctatgggtactgctgctctgggttccagg ttccactggtgacgcggcccagccggccGACCCTGTGAAGCCGTCTCGGG

GCCCGCTGGTGACCTGCACGTGTGAGAGCCCACATTGCAAGGGGCCTACC

TGCCGGGGGCCTGGTGCACAGTAGTGCTGGTGCGGGAGGAGGGGAGGCA

CCCCCAGGAACATCGGGGCTGCGGGAACTTGCACAGGGAGCTCTGCAGGG

GGCGCCCCACCGAGTTCGTCAACCACTACTGCTGCGACAGCCACCTCTGC

AACCACAACGTGTCCCTGGTGCTGGAGGCCACCCAACCTCCTTCGGAGCA

GCCGGGAACAGATGGCCAGCATCATCATCATCATCAT protein sequence:

(SEQ ID NO: 98)
DPVKPSRGPLVTCTCTCESPHCKGPTCRGAWCTVVLVREEGRHPQEHRGCGN

LHRELCRGRPTEFVNHYCCDSHLCNHNVSLVEATQPPSEQPGTDGQHHHH

HH

Example 2

Generation of Hybridomas Producing Anti-ALK-1 Antibody

Eight to ten week old XENOMOUSE® mice were immunized in their hind footpads with 10 μg/mouse of either recombinant human ALK-1/Fc chimera (R&D Systems, Inc., Catalog Number 370-AL) or with the ALK-1 ECD His-Tag protein described in Example 1. This dose was repeated five to seven times over a three to five week period. Three or four days before fusion, the mice were given a final injection of the immunogen in PBS. The lymph node lymphocytes from immunized mice were fused with the non-secretory myeloma P3-X63-Ag8.653 cell line via electro cell fusion (ATCC Cat. No. CRL 1580), and these fused cells were subjected to HA-DMEM selection as previously described (DMEM/15% FBS/1% 200 mM L-glutamine/1% 100× Non-essential amino acid/1% 100× Pen/Strep/10 U/ml IL-6/1 vial/liter OPI media supplement plus 0.5×HA (Azaserine-Hypoxanthine, Sigma, Cat. #A9666)). A panel of hybridomas was recovered that all secrete ALK-1 specific human IgG2 antibodies.

ELISA assay was used to detect antibody binding. Immunogen was coated to the 96-well Immulon microtiter plate (NUNC-Immuno™ plate MaxiSorp™ surface, Nalge Nunc International, Cat. No. 439454) at 4 μg/mL in 50 mM sodium bicarbonate buffer for overnight at 4° C. Plates were washed, and then blocked with PBS with the addition of 0.1% Tween-20 and 0.5% bovine serum albumin. Antibodies were added to the blocked ELISA plates, incubated for 1 hour, and washed with PBS with Tween-20. The binding was detected by anti-human IgG-horseradish peroxidase (Pierce, Catalog No. 31420) followed by the addition of ABTS (Pierce, Catalog No. 37615). Calorimetric measurements were performed at 405 nm in a micro-plate reader (SpectraMax Plus 384, Molecular Devices).

Twenty five hybridomas were selected for further study. These were single-cell cloned by limiting dilution and were designated 1.11.1; 1.12.1; 1.12.1(rWT); 1.12.1(M29I/

D19A); 1.12.1(M29I); 1.12.1(D19A); 1.13.1; 1.14.1; 1.151.1; 1.162.1; 1.183.1; 1.27.1; 1.29.1; 1.31.1; 1.8.1; 1.9.1; 4.10.1; 4.24.1; 4.38.1; 4.58.1; 4.62.1; 4.68.1; 4.72.1; 5.13.1; 5.34.1; 5.53.1; 5.56.1; 5.57.1; and 5.59.1.

Mouse Hybridoma Cell line LN 15916 (the hybridoma 1.12.1) was deposited under terms in accordance with the Budapest Treaty with the American Type Culture Collection (ATCC), 10801 University Blvd., Manassas, Va. 20110-2209 on Jun. 21, 2005. The hybridoma 1.12.1 has been assigned the following accession number; PTA-6808.

Example 3

Sequences of Anti-ALK-1 Antibodies

To analyze the structure of antibodies produced in accordance with the invention, nucleic acids were cloned that encode heavy and light chain fragments from hybridomas producing anti-ALK-1 monoclonal antibodies. Cloning and sequencing was accomplished by standard means.

Poly(A)+ mRNA was isolated using a Fast-Track™ kit (Invitrogen) from approximately $2 \times 10^5$ hybridoma cells for each of the ALK-1 antibodies. cDNA was synthesized from the mRNA by using random primers. The random primed cDNA was amplified by PCR using human $V_H$ or human Vκ family specific variable domain primers in conjunction with primers specific for the human Cγ2 constant region, or a Cκ☐ constant region to amplify the antibody variable region including all the framework regions (FRs) and complementarity determining regions (CDRs). Nucleic acid sequences were obtained that encode human heavy and kappa light chain transcripts from the anti-ALK-1 producing hybridomas by direct sequencing of both strands of PCR products. Sequences were analyzed using Abgenix's proprietary software and publicly available sequence information for human VH and Vk genes, the "V BASE sequence directory", Tomlinson et al., MRC Centre for Protein Engineering, Cambridge, UK). Identical results could be obtained using publicly available sequence alignment software by someone of ordinary skill using MacVector and Geneworks software programs.

Specifically, full-length ALK-1 antibody 1.12.1 was cloned into expression vectors as follows: Poly(A)+ mRNA was isolated using an RNeasy Mini Kit (Qiagen) and cDNA synthesized from the mRNA with the Advantage RT-for-PCR kit (BD Biosciences) using oligo(dT) priming. The oligo(dT) primed cDNA for clone 1.12.1 was amplified using primers listed in Table 2. Amplification was achieved using the Pfu Ultra polymerase (Stratagene) and a PTC-200 DNA Engine (MJ Research) with cycling as follows: 3'@95☐ C; 25×(20"@95☐ C, 30"@52☐ C, 1'20"@72☐ C); 10'@72☐ C. Clones were sequence verified using Grills $16^{th}$ BDTv3.1/dGTP chemistry (Applied Biosystems Inc) and a 3730xl DNA Analyzer (Applied Biosystems Inc). In the process of cloning 1.12.1 $V_H$, a silent mutation was introduced in the $8^{th}$ codon, converting "GGC" to a "GGT," All sequences were analysed by alignments to the 'V BASE sequence directory' (Tomlinson, et al, *J. Mol. Biol.*, 227, 776-798 (1992); *Hum. Mol. Genet.*, 3, 853-850 (1994); *EMBO J.*, 14, 4628-4638 (1995).)

TABLE 2

Heavy and Light Chain Amplification Primers Used for Cloning full-length 1.12.1

| Primer Name | Primer Sequence | SEQ ID NO |
|---|---|---|
| 4-61 | 5' tcttcaagcttgatatctctagaagccgccaccATGAAACACCTGTGGTTCTTCCTCC 3' | 105 |
| G1/2_FL_R | 5' ttctctgatcagaattcctaCTATTTACCCGGAGACAGGGAGAGGC 3' | 106 |
| A11 | 5' tcttcaagcttcccgggagccgccaccaATGGAAACCCCAGCGCAGCTT 3' | 107 |
| K_FL_R | 5' ttctttgatcagaattctcaCTAACACTCTCCCCTGTTGAAGCTCTTTG 3' | 108 |

Non-hybridizing bases in lower case

Example 4

Gene Utilization Analysis and CDR Analysis

From the nucleic acid sequence and predicted amino acid sequence of the antibodies, the gene usage was identified for each antibody chain. Table 3 sets forth the gene utilization of selected hybridoma clones of antibodies in accordance with the invention.

TABLE 3

Heavy and Light Chain Gene Utilization

| | Heavy Chain Germline | | | | Kappa Light Chain Germline | | |
|---|---|---|---|---|---|---|---|
| Clone | SEQ ID NO: | $V_H$ | $D_H$ | $J_H$ | SEQ ID NO: | Vκ | Jκ |
| 1.11.1 | 9 | 3-33 | 6-19 | JH3B | 11 | L1 | JK4 |
| 1.12.1 | 103 | 4-31 | 6-19 | JH4B | 126 | A27 | JK5 |
| 1.13.1 | 13 | 4-61 | 6-19 | JH4B | 15 | A27 | JK5 |
| 1.14.1 | 17 | 4-61 | 6-19 | JH4B | 19 | A27 | JK5 |
| 1.151.1 | 21 | 4-31 | 3-3 | JH3B | 23 | B3 | JK1 |
| 1.162.1 | 25 | 4-31 | | JH3B | 27 | A27 | JK5 |
| 1.183.1 | 29 | 4-59 | 6-19 | JH4B | 31 | L2 | JK3 |
| 1.31.1 | | 4-31 | 6-19 | JH4B | | A27 | JK5 |
| 1.8.1 | 33 | 4-31 | 3-3 | JH3B | 35 | B3 | JK1 |
| 1.9.1 | 37 | 3-11 | 3-22 | JH6B | 39 | A2 | JK1 |
| 4.10.1 | 41 | 3-15 | 3-22 | JH4B | 43 | A3 | JK4 |
| 4.24.1 | 45 | 4-31 | 5-12 | JH6B | 47 | A27 | JK5 |
| 4.38.1 | 49 | 4-31 | 4-23 | JH4B | 51 | B3 | JK1 |
| 4.58.1 | 53 | 4-31 | 4-23 | JH4B | 55 | A27 | JK5 |
| 4.62.1 | 57 | 4-31 | 5-12 | JH6B | 59 | A27 | JK5 |
| 4.68.1 | 61 | 4-31 | 2-2 | JH5B | 63 | A27 | JK5 |

TABLE 3-continued

Heavy and Light Chain Gene Utilization

| | Heavy Chain Germline | | | | Kappa Light Chain Germline | | |
|---|---|---|---|---|---|---|---|
| Clone | SEQ ID NO: | $V_H$ | $D_H$ | $J_H$ | SEQ ID NO: | Vκ | Jκ |
| 4.72.1 | 65 | 4-31 | 5-12 | JH6B | 67 | A27 | JK5 |
| 5.13.1 | 69 | 4-31 | | JH3B | 71 | A27 | JK4 |
| 5.34.1 | 73 | 4-31 | | JH6B | 75 | A1 | JK1 |
| 5.53.1 | 77 | 3-15 | 1-1 | JH4B | 79 | B2 | JK4 |
| 5.56.1 | 81 | 3-11 | 6-19 | JH6B | 83 | A2 | JK1 |
| 5.57.1 | 85 | 3-11 | 3-10 | JH6B | 87 | A2 | JK1 |
| 5.59.1 | 89 | 3-11 | 6-6 | JH6B | 91 | A2 | JK1 |

Mutagenesis, in the $V_H$ (M29I) and $V_K$ (D19A) regions of clone 1.12.1, was conducted with the primers listed in Table 4 and the QuickChange kit (Stratagene) according to the manufacturer's instructions. The mutated variants were sequence verified and cloned into expression vectors by standard procedures.

TABLE 4

Mutagenic Oligonucleotides (sequences 5' to 3):

| Primer | Sense | Antisense |
|---|---|---|
| 1.12.1(D19A) | CTCCAGGGGAAAGAGCCACCCTCTCCTGTAGG (SEQ ID NO: 109) | CCTACAGGAGAGGGTGGCTCTTTCCCCTGGAG (SEQ ID NO: 110) |
| 1.12.1(M29I) | GGTGGCTCCATCAGCAGTGGTGAATACTAC (SEQ ID NO: 111) | GTAGTATTCACCACTGCTGATGGAGCCACC (SEQ ID NO: 112) |

Mutations are indicated in bold and underlined.

Nucleic acid molecules encoding the variable domain of heavy chain (SEQ ID NO: 5) and the variable domain light chain (SEQ ID: 7) chain of the 1.12.1(M29I/D19A) antibody were deposited under terms in accordance with the Budapest Treaty with the American Type Culture Collection (ATCC), 10801 University Blvd., Manassas, Va. 20110-2209 on Jul. 14, 2005. The deposits have been assigned the following accession numbers: ATCC No. PTA-6864 for *E. coli* DH5α containing plasmid pCR2.1 TOPO 1.12.1 $V_H$ (M29I):UC 25502; and ATCC No. PTA-6865 for *E. coli* DH5α containing plasmid pCR2.1 TOPO 1.12.1 $V_K$ (D19A): UC 25503.

A number of anti-ALK-1 specific human antibodies exhibited a common pattern in CDR1 of the heavy chain variable domain. These lead molecules utilize the 4-31 or 4-61 heavy chain V-gene segments. The FR1 and CDR1 sequences corresponding to these antibody heavy chains are shown in Table 4A, aligned against the germline sequences. A dash (-) in the alignment indicates a residue identical to germline. In all cases, the GYYWS (SEQ ID NO: 136) pattern at the end of CDR1 has undergone somatic mutations to yield a new sequence pattern, whereby the G residue is changed to an acidic residue (D or E), and the final S residue is changed to an N in 9 out of the 12 examples. Sequence diversity in other regions of VH indicates that these are likely to be independent somatic mutation events leading to the same sequence pattern at the end of CDR1 of VH.

TABLE 4A

ALK-1 Antibody Heavy Chain Sequence Patterns

| Clone | V-gene | D-gene | J-gene | FR1 | CDR1 |
|---|---|---|---|---|---|
| Germline | | | | QVQLQESGPGLVKPSQTLSLTCTVS (SEQ ID NO: 122) | GGSISSGGYYWS (SEQ ID NO: 123) |
| 5.34.1 | VH4-31 | -NA- | JH6B | ------------------------ | -------D---N |
| 4.58.1 | VH4-31 | D4-23 | JH4B | ------------------------ | -------D---N |
| 4.38.1 | VH4-31 | D4-23 | JH4B | ------------------------ | -------D---- |
| 5.13.1 | VH4-31 | -NA- | JH3B | ------------------------ | -------D---N |
| 1.162.1 | VH4-31 | -NA- | JH3B | --------------------I---- | -------E---- |
| 4.72.1 | VH4-31 | D5-12 | JH6B | ------------------------ | -------E---- |
| 4.24.1 | VH4-31 | D5-12 | JH6B | ------------------------ | -------ND---N |
| 4.62.1 | VH4-31 | D5-12 | JH6B | ------------------------ | -------D---N |
| 1.31.1 | VH4-31 | D6-19 | JH4B | ------------------------ | -------D---N |
| 1.12.1 | VH4-31 | D6-19 | JH4B | ------------------------ | ---M---E---N |
| Germline | | | | QVQLQESGPGLVKPSETLSLTCTVS (SEQ ID NO: 124) | GGSVSSGGYYWS (SEQ ID NO: 125) |
| 1.13.1 | VH4-61 | D6-19 | JH4B | --H--------------------- | -------D---N |
| 1.14.1 | VH4-61 | D6-19 | JH4B | ------------------------ | -------D---N |

Example 5

Preparation of 1.12.1 Fab Molecules

Fab fragment of 1.12.1(M29I/D19A) was prepared by digesting 1.12.1(M29I/D19A) IgG1 using papain. Protein A purified full length 1.12.1(M29I/D19A) IgG1 was incubated with papain (VWR) at 1:50 ratio (papain:protein) in buffer containing 30 mM sodium phosphate (pH 7.0), 2 mM EDTA and 2 mM cysteine at 37° C. for 2-3 hours. The digestion mixture was then applied to a protein A mini-column to remove undigested full length protein and Fc fragment. Unbound Fab was collected in the flow-through. A size exclusion column (Superdex 200, Amersham Pharmacia Biotech) was then used to further purify the Fab protein and to exchange the buffer into PBS. Endotoxin was removed by applying the protein solution through Detoxi gel (PIERCE) and VIVAPURE® Mini Q ion exchange column (VivaScience) subsequently. The protein was filtered with 0.2 μm syringe filter and endotoxin level was tested with a LAL pyrogent kit (Cambrex). The final purified protein was at concentration of 2-3 mg/mL, with endotoxin level of <0.1 EU/mg and purity of >95%, 1.12.1(M29I/D19A) Fab fragment has a molecular weight of 47,347 under non-reduced condition as shown by electron-spray mass spectrometry. Edman N-terminal sequencing analysis confirmed the light chain N-termini sequence of EIVLTQSPG (SEQ ID NO: 113) and heavy chain sequence of QVQLQESG (SEQ ID NO: 114), respectively.

Example 6

Determination of Avidity Values of Fully Human Anti-ALK-1 Monoclonal Antibodies by Surface Plasmon Resonance (SPR) Using BIACORE®

Avidity measures of purified anti-ALK-1 antibodies by surface plasmon resonance using the BIACORE® 3000 instrument were performed as follows using the manufacturer's protocols.

To perform kinetic analyses, recombinant human ALK-1/Fc fusion protein (hALK-1/Fc) and cynomologus ALK-1/Fc fusion protein (cALK-1/Fc) were immobilized on separate flow cells of a CM5 BIAcore sensor chip using routine amine coupling. Surfaces were prepared using 10 mM acetate buffer, pH 5.0 as the immobilization buffer and protein densities of 300 and 150 RU were achieved for the hALK-1/Fc and cALK-1/Fc fusion proteins, respectively. Deactivation of unreacted N-hydroxysuccinimide esters was performed using 1 M ethanolamine hydrochloride, pH 8.5. Antibody samples in running buffer were prepared at concentrations ranging from 0.125 to 2 nM (a 0 nM solution comprising running buffer alone was included as a zero reference). Samples were randomized and injected in duplicate for 10 minutes each across all 4 flow cells using HBS-EP (10 mM HEPES pH 7.4, 150 mM NaCl, 3 mM EDTA, 0.005% Surfactant P20) as running buffer. On-rates were observed to be independent of flow rates from 1 to 100 μL/min indicating no mass transport limitation. A flow rate of 25 μL/min was used to determine avidity values. The dissociation of the antibody was monitored for 10 minutes, the surface regenerated by a 12 second injection of 100 mM $H_3PO_4$ (25 μL/min). The raw data were processed using the Scrubber (©BioLogic Software) software package and analyzed using the CLAMP (©BioLogic Software) software package. Multiple data sets from a single surface, six data sets at a time, were simultaneously fit globally to a simple 1:1 Langmuir binding model utilizing a common variable Rmax value. Table 5 lists avidity values for representative anti-ALK-1 antibodies of the present invention. The represented data indicate that the antibodies prepared in accordance with the invention possess high affinities and strong binding constants for human ALK-1.

TABLE 5

Determination of Avidity Value by Surface Plasmon Resonance (BIACORE ®)

| Clone | hALK-1/Fc Avidity(pM) | hALK-1/Fc $k_{off}$(1/s) | cALK-1/Fc Avidity (pM) |
|---|---|---|---|
| 1.12.1(M29I/D19A) | <6.8 | <5.0 × 10$^{-6}$ | 27 |
| 1.14.2 | 76 | 5.6 × 10$^{-5}$ | 280 |
| 1.27.3 | 2.9 | 1.9 × 10$^{-5}$ | 60 |
| 1.31.1 | <13 | <5.0 × 10$^{-6}$ | 150 |
| 1.162.1 | 18 | 1.1 × 10$^{-5}$ | 62 |
| 1.183.2 | 220 | 3.1 × 10$^{-5}$ | 1800 |
| 4.24.2 | 70 | 4.4 × 10$^{-5}$ | 430 |
| 4.38.1 | 100 | 4.0 × 10$^{-5}$ | 150 |
| 4.58.2 | 40 | 1.6 × 10$^{-5}$ | 130 |
| 4.62.1 | 9.6 | 7.6 × 10$^{-6}$ | 19 |
| 4.68.2 | 86 | 3.8 × 10$^{-5}$ | 320 |
| 4.72.2 | 73 | 3.4 × 10$^{-5}$ | 280 |
| 5.13.3 | 91 | 6.3 × 10$^{-5}$ | 190 |

1.12.1(M29I/D19A) refers to the mAb 1.12.1 variant that was expressed recombinant mAb containing two specific amino acid mutations (methionine at position 29 in the heavy chain replaced with isoleucine and aspartic acid at position 19 in the light chain replaced with alanine).

Example 7

Determination of Affinity Constants ($K_D$) of Variants of Fully Human Anti-ALK-1 Monoclonal Antibody 1.12.1 by Surface Plasmon Resonance (SPR) Using BIACORE®

Affinity measures of purified anti-ALK-1 antibodies by surface plasmon resonance using the BIACORE® 3000 instrument were performed as follows using the manufacturer's protocols.

To perform kinetic analyses, variants of fully human anti-ALK-1 monoclonal antibody 1.12.1 were immobilized onto the dextran layer of a CM5 biosensor chip using amine coupling. Surfaces were prepared using 10 mM acetate buffer pH 5.0 as the immobilization buffer and protein densities of 3500-4800 RU were achieved. Deactivation of unreacted N-hydroxysuccinimide esters was performed using 1 M ethanolamine hydrochloride, pH 8.5. Samples of monomeric ALK-ECD in running buffer were prepared at concentrations ranging from 2.63 to 640 nM (a 0 nM solution comprising running buffer alone was included as a zero reference). Samples were randomized and injected for 2 minutes each across all 4 flow cells using HBS-EP (10 mM HEPES pH 7.4, 150 NaCl, 3 mM EDTA, 0.005% Surfactant P20) as running buffer. A flow rate of 25 μL/min was used to determine affinity constants. Dissociation of monomeric ALK-ECD was monitored for 10 minutes, the surface regenerated by a 12 second injection of 100 mM $H_3PO_4$ (25 μL/min). The raw data were processed using the Scrubber (©BioLogic Software) software package and analyzed using the CLAMP (©BioLogic Software) software package. The data were fit globally to a simple 1:1 Langmuir binding model. Table 6 lists affinity measurements for variants of human anti-ALK-1 monoclonal antibody 1.12.1 of the present invention.

TABLE 6

Determination of mAb 1.12.1 variant affinity constant, $K_D$, by surface plasmon resonance (BIACORE ®)

| Antibody | on-rate ($M^{-1} s^{-1}$) | Off-rate ($s^{-1}$) | $K_D$ (nM) |
|---|---|---|---|
| 1.12.1 | $1.9 \times 10^3$ | $7.4 \times 10^{-5}$ | 39 |
| 1.12.1(rWT) | $2.2 \times 10^3$ | $5.8 \times 10^{-5}$ | 26 |
| 1.12.1(D19A) | $2.6 \times 10^3$ | $4.4 \times 10^{-5}$ | 17 |
| 1.12.1(M29I) | $2.4 \times 10^3$ | $9.1 \times 10^{-5}$ | 38 |
| 1.12.1(M29I/D19A) (1)* | $2.2 \times 10^3$ | $9.5 \times 10^{-5}$ | 43 |
| 1.12.1(M29I/D19A) (2)* | $2.3 \times 10^3$ | $8.4 \times 10^{-5}$ | 37 |

*The two affinity constants for 1.12.1(M29I/D19A) (1) and (2) were obtained using two separate surfaces.

1.12.1 refers to the mAb 1.12.1 variant that was isolated from the hybridoma.

1.12.1(rWT) refers to the mAb 1.12.1 variant that was expressed recombinant mAb.

1.12.1(M29I) refers to the mAb 1.12.1 variant that was expressed recombinant mAb containing a specific single amino acid mutation where the methionine at position 29 in the heavy chain was replaced with isoleucine.

1.12.1(D19A) refers to the mAb 1.12.1 variant that was expressed recombinant mAb containing a specific single amino acid mutation where the aspartic acid at position 19 in the light chain was replaced with alanine.

1.12.1(M29I/D19A) refers to the mAb 1.12.1 variant that was expressed recombinant mAb containing two specific amino acid mutations (methionine at position 29 in the heavy chain replaced with isoleucine and aspartic acid at position 19 in the light chain replaced with alanine).

Example 8

Determination of Affinity Constants ($K_D$) of Representative Fully Human Anti-ALK-1 Monoclonal Antibodies by Surface Plasmon Resonance (SPR) Using BIACORE®

Affinity measures ($K_D$ and $k_{off}$) of purified anti-ALK-1 antibodies by surface plasmon resonance using the BIACORE® 3000 instrument were performed as follows using the manufacturer's protocols.

To perform kinetic analyses, affinity-purified mAbs were immobilized onto the dextran layer of a CM5 biosensor chip using amine coupling. Surfaces were prepared using 10 mM acetate buffer pH 5.0 as the immobilization buffer and protein densities of 200-400 RU were achieved. Deactivation of unreacted N-hydroxysuccinimide esters was performed using 1 M ethanolamine hydrochloride, pH 8.5. Samples of monomeric ALK-ECD in running buffer were prepared at concentrations ranging from 3.125-400 nM (a 0 nM solution comprising running buffer alone was included as a zero reference). Samples were randomized and injected in duplicate for 2 minutes each across all 4 flow cells using HBS-EP (10 mM HEPES pH 7.4, 150 mM NaCl, 3 mM EDTA, 0.005% Surfactant P20) as running buffer. On-rates were observed to be independent of flow rates from 1 to 100 µL/min indicating no mass transport limitation. A flow rate of 25 µL/min was used to determine affinity constants. Dissociation of monomeric ALK-ECD was monitored for 10 minutes, the surface regenerated by a 12 second injection of 100 mM $H_3PO_4$ (25 µL/min). The raw data were processed using the Scrubber (©BioLogic Software) software package and analyzed using the CLAMP (©BioLogic Software) software package. The data were fit globally to a simple 1:1 Langmuir binding model. Table 7 lists affinity measurements for representative anti-ALK-1 antibodies of the present invention:

TABLE 7

Determination of Affinity Constant, $K_D$, for Representative Monoclonal Antibodies by Surface Plasmon Resonance (BIACORE ®)

| mAb | on-rate ($M^{-1} s^{-1}$) | off-rate ($s^{-1}$) | $K_D$ (nM) |
|---|---|---|---|
| 1.12.1(M29I/D19A) | $3.3 \times 10^4$ | $8.2 \times 10^{-4}$ | 25 |
| 1.31.1 | $3.2 \times 10^4$ | $1.9 \times 10^{-4}$ | 6.0 |
| 4.72.1 | $3.2 \times 10^4$ | $2.5 \times 10^{-5}$ | 0.8 |
| Fab 1.12.1(M29I/D19A) | $3.8 \times 10^4$ | $8.2 \times 10^{-4}$ | 22 |

The monomeric ALK-ECD used to generate the data in Example 8 was a different preparation than that used to generate the data in Example 7.

1.12.1(M29I/D19A) refers to the mAb 1.12.1 variant that was expressed recombinant mAb containing two specific amino acid mutations mentioned above (aspartic acid at position 19 in the light chain replaced with alanine and methionine at position 29 in the heavy chain replaced with isoleucine).

Fab 1.12.1(M29I/D19A) refers to the Fab fragment of mAb 1.12.1(M29I/D19A) prepared by digesting 1.12.1(M29I/D19A) IgG1 using papain.

Example 9

Identification of Epitope Selectivity of Anti-ALK-1 Antibodies

Cross-competition experiments were performed using the BIACORE® 3000 instrument (Biacore international AB, Uppsala, Sweden and Piscataway, N.J), following the manufacturer's protocols.

Recombinant human ALK-1/FC chimera was immobilized onto the dextran layer of a CM5 biosensor chip using amine coupling. Chips were prepared using 10 mM acetate buffer pH 5.0 as the immobilization buffer and a protein density of 940 RU was achieved. Deactivation of unreacted N-hydroxysuccinimide esters was performed using 1 M ethanolamine hydrochloride, pH 8.5.

Purified mAbs were diluted to a concentration of 50 nM in FIBS-EP running buffer (0.01 M HEPES pH 7.4, 0.15 M NaCl, 3 mM EDTA, 0.005% Polysorbate 20). A primary antibody was chosen and then injected across the flow cell for 600 seconds at a rate of 10 µL/min. After the injection was complete, a secondary antibody was chosen and injected across the same flow cell for 600 seconds at a rate of 10 µL/min. The sensor surface was regenerated by a 12 second injection of 100 mM $H_3PO_4$ (25 µL/min).

After regeneration, the primary antibody was again injected across the flow cell for 600 seconds at a rate of 10 µL/min. After the injection was complete, a different secondary antibody was chosen and injected across the same flow cell for 600 seconds at a rate of 10 µL/min. Once the entire panel of 14 antibodies had been used as the secondary antibody a new primary antibody was chosen and the procedure repeated with the new primary antibody. These procedures were carried out until all possible combinations of primary and secondary antibodies had been injected across the flow cell. Binding of the secondary antibody was considered to have occurred if the total response observed after injecting both antibodies exceeded that observed for both possible threshold values. Threshold values were determined by using the same antibody as both the primary antibody and secondary antibody. Shown in Table 8, a response matrix was created based on whether binding was observed: - indicates no binding of the secondary antibody, x indicates binding was observed (response was greater than the threshold values for the individual antibodies). Grouping the clones that show the same reactivity pattern gives rise to two different epitope bins with 1.11.1 in one bin and all the other antibodies in the other bin.

A pair of primers (forward: 5'-GATTATGGCCTTGGGCTCCCCCAGGAAA (Seq ID NO: 117) and reverse: 5'-GGGCTATTGAATCACTTTAGGCTTCTCTGGACTGTTG) (Seq ID NO: 118) were used to PCR amplify the full-length Cynomolgus ALK-1 gene.

TABLE 8

BIACORE ® epitope binning response matrix

| Primary mAb | Secondary mAb | | | | | | | | | | | | | |
|---|---|---|---|---|---|---|---|---|---|---|---|---|---|---|
|  | 1.9.1 | 1.11.1 | 1.12.1(M29I/D19A) | 1.27.3 | 1.31.1 | 1.162.1 | 1.183.2 | 4.24.2 | 4.38.1 | 4.58.2 | 4.62.1 | 4.68.2 | 4.72 | 5.13 |
| 1.9.1 | ▨ | x | - | - | - | - | - | - | - | - | - | - | - | - |
| 1.11.1 | - | ▨ | x | x | x | x | x | x | x | x | x | x | x | x |
| 1.21.1(M29I/D19A) | - | x | ▨ | - | - | - | - | - | - | - | - | - | - | - |
| 1.27.3 | - | x | - | ▨ | - | - | - | - | - | - | - | - | - | - |
| 1.31.1 | - | x | - | - | ▨ | - | - | - | - | - | - | - | - | - |
| 1.62.1 | - | x | - | - | - | ▨ | - | - | - | - | - | - | - | - |
| 1.93.2 | - | x | - | - | - | - | ▨ | - | - | - | - | - | - | - |
| 4.24.2 | - | x | - | - | - | - | - | ▨ | - | - | - | - | - | - |
| 4.38.1 | - | x | - | - | - | - | - | - | ▨ | - | - | - | - | - |
| 4.58.2 | - | x | - | - | - | - | - | - | - | ▨ | - | - | - | - |
| 4.62.1 | - | x | - | - | - | - | - | - | - | - | ▨ | - | - | - |
| 4.68.2 | - | x | - | - | - | - | - | - | - | - | - | ▨ | - | - |
| 4.72 | - | x | - | - | - | - | - | - | - | - | - | - | ▨ | - |
| 5.13 | - | x | - | - | - | - | - | - | - | - | - | - | - | ▨ |

Example 10

Isolation of Cynomolgus Monkey ALK-1 Gene

Cynomolgus monkey ("Cyno") ALK-1 gene was extracted from Cyno lung tissue. Based on the published gene sequence for human ALK-1 (Genebank record L17075), primers were designed to FOR amplify the full-length Cynomolgus ALK-1. mRNA was prepared from frozen excised cynomolgus lung tissue (ca. 1 g) using the mRNA purification kit (Ambion, Catalog No. 1915) according to the manufacturer's instructions. 200 ng of the mRNA was reverse transcribed and FOR amplified using the OneStep RT-PCR kit (Qiagen, Catalog No. 210210) utilizing gene-specific oligos: 5'-AGOGGGC-CCAGAGGGACC*ATG* (Seq ID NO: 115) (forward) and 5'-CAGAAAGGAATCAGGTGCTCCTGGG*CTA* (Seq ID NO: 116) (reverse) at an annealing temperature of 61'C. An RT-PCR product of the appropriate size (~1.5 Kb) was excised and purified from a 0.9% agarose gel after electrophoresis, then TOPO-TA cloned into the pCR4-TOPO vector (Invitrogen, Catalog No. K4575-01). The insert was sequenced to obtain the ORF nucleotide sequence of Cynomolgus ALK-1. The nucleotide and predicted translated amino acid sequences are shown in SEQ ID NOs: 93 and 94, respectively. While the cytoplasmic portion of the gene encodes identical protein sequences between Cyno and human, there are 5 amino acid differences in the extracellular domain (ECD, which includes positions 22-118) and 1 amino acid difference in the transmembrane domain of the protein ECD sequence identity between human and Cyno is 94.8%. An alignment of the human and primate ECD is shown in FIG. 2.

Example 11

Determination of Cell Surface Binding Characteristics and Primate Crosshybridisation by Flow Cytometry (FACS)

To generate ALK-1-overexpressing cell lines, which can be used to test anti-ALK-1 binding affinity using flow cytometry (FACS), full-length human, Cyno, and rat ALK-1 genes were cloned into Invitrogen's (Catalog No. K6510-20) pcDNA5/FRT/To TOPO vector and transfected into 293 Flp-In T-Rex host cell (Invitrogen, Catalog No. R780-07), respectively. Selections were carried out using hygromycin to obtain the final stable cell lines. Overexpressing of the respective full-length ALK-1 proteins were achieved by tetracycline (2 µg/mL) induction at 37° C./5% $CO_2$ for 24 hours.

Anti-ALK-1 mAbs were tested for their binding affinities to cell surface ALK-1 using FACS assay, employing 293 stable cells overexpressing ALK-1 proteins. The cells were detached using trypsin-EDTA and washed with cold PBS-SA. After being aliquoted into 96-well plates, the cells were blocked by serum and incubated with different concentrations of specific mAb for 1 hour at 4° C. Subsequently, the cells were washed and incubated with an anti-human κ secondary antibody conjugated with the R-PE fluorophore before analyzed using a FACSCalibur flow cytometer (BD Biosciences). 10,000 events were collected for each sample without applying any gating. Shown in Table 9, the geometric mean of each sample histogram was plotted as a function of the mAb concentration and $K_D$ was calculated for each mAb after fitting to a two-state equilibrium model. Examples of equivalent human and primate FACS experiments are shown in FIG. 3.

TABLE 9

Mean Binding Affinity ($K_D$) Results of Anti-ALK-1 Monoclonal Antibodies to Cell Surface Human or Cyno ALK-1 Measured by FACS

| Antibody | $K_D$ (nM) Human | $K_D$ (nM) Cyno |
|---|---|---|
| 1.12.1 | 6.7 | 2.0 |
| 1.27.1 | 3.7 | 2.2 |
| 1.162.1 | 5.6 | 3.0 |
| 4.38.1 | 9.3 | 3.4 |
| 4.58.1 | 14.0 | 6.7 |
| 4.72.1 | 6.4 | 3.8 |
| 5.13.1 | 3.2 | 1.6 |
| 1.31.1 | 3.2 | 1.7 |
| 4.24.1 | 7.6 | 3.1 |
| 4.62.1 | 2.3 | 0.78 |
| 4.68.1 | 8.4 | 9.0 |

In addition, 1.12.1 was shown by the FACS assay to have very limited cross-over to rat ($K_D$>100 nM) and is predicted to have very low cross-over to mouse in view of 74% and 68% ECD sequence identity between rat/human and mouse/human ALK-1, respectively).

FACS assay was also used to determine $K_D$ of the recombinant 1.12.1 mAb variants. Shown in Table 10, the results indicate similar binding affinity from the recombinant antibody,

TABLE 10

Mean Binding Affinity ($K_D$) Results of 1.12.1(M29I/D19A) Variants to Cell Surface Human or Cyno ALK-1 Measured by FACS

| Antibody | $K_D$ (nM) Human | $K_D$ (nM) Cyno |
|---|---|---|
| 1.12.1 | 6.7 | 2.0 |
| 1.12.1(rWT) | 5.9 | 6.0 |
| 1.12.1(M29I) | 6.0 | 3.3 |
| 1.12.1(D19A) | 5.7 | 3.8 |
| 1.12.1(M29I/D19A) | 7.2 | 3.4 |
| Fab 1.12.1(M29I/D19A) | 0.77 | ND |

1.12.1 refers to the mAb 1.12.1 variant that was isolated from the hybridoma.

1.12.1(rWT) refers to the mAb 1.12.1 variant that was expressed recombinant mAb.

1.12.1(M29I) refers to the mAb 1.12.1 variant that was expressed recombinant mAb containing a specific single amino acid mutation where the methionine at position 29 in the heavy chain was replaced with isoleucine.

1.12.1(D19A) refers to the mAb 1.12.1 variant that was expressed recombinant mAb containing a specific single amino acid mutation where the aspartic acid at position 19 in the light chain was replaced with alanine.

1.12.1(M29I/D19A) refers to the mAb 1.12.1 variant that was expressed recombinant mAb containing two specific amino acid mutations (methionine at position 29 in the heavy chain replaced with isoleucine and aspartic acid at position 19 in the light chain replaced with alanine).

Fab 1.12.1(M29I/D19A) refers to the Fab fragment of in Ab 1.12.1(M29I/D19A) prepared by digesting 1.12.1(M29I/D19A) IgG1 using papain.

Example 12

TAQMAN® Assay for Id1

HUVECs (Biowhittaker, Cat, # CC-2519) were seeded on 24-well plates, 12000 cells/well in 600 μL of complete HUVEC medium (EGM-2 Bullet kit, Biowhittaker, Cat. # CC-3162), and allowed to grow overnight. The following day the cells were typically 50% confluent. Complete Medium was removed and 200 μL of Starvation Medium (EBM-2 with 0.2% FBS only) was added. Cells were incubated for 2 hrs. Then the cells were treated with 40 μL of antibody solution in PBS. Lyophilized Ab was reconstituted with sterile PBS. Finally, the cells were treated with 1% FBS/Basal medium (final concentrations) for 30 minutes, the medium was removed and the cells were lysed in 400 μL of RTL Buffer (Rneasy 96 kit, Qiagen, Cat, #74182), according to the manufacturer's protocols. Subsequently, RNA was prepared using RNeasy kit (according to manufacturer's instructions). The RNA was eluted and quantitated with RIBOGREEN® RNA Quantitation Kit (Molecular probes, Cat. # R-11490). Equal amount of total RNA was used for real time PCR analysis to detect Id1 RNA expression (ABI 7900 instrument). PCR was conducted using the Taqman One Step PCR Master Mix Kit (RBI, Cat, #4309169) and the ID1 primer/Probe sequences listed below, PCR was conducted using 40 cycles of the following annealing and amplification conditions: 95° C. 15 seconds; 60° C., 1 min.

TAQMAN® probe: CPG-conjugated 5'-6-FAM, and 3-TAMRA.

```
Name:
ID1-Probe

Sequence:
5' CCAGCACGTCATCGACTACATCAGGGA 3'   (Seq ID NO: 119)
```

TAQMAN® PCR Primers:

```
Name:
ID1-F

Sequence:
5' AAGGTGAGCAAGGTGGAGATTC 3'   (Seq ID NO: 120)

Name:
ID1-R

Sequence:
5' TTCCGAGTTCAGCTCCAACTG 3'   (Seq ID NO: 121)
```

Examples of Id1 titrations for the 1.12.1(M29I/D19A) lead molecule (including 1.12.1 sequence variants) and the Fab derivative are shown in FIGS. 4 and 5.

A summary of mean $IC_{50}$ values for this assay is shown in Table 11. All $IC_{50}$ determinations were run in triplicate.

Example 13

Smad1 Phosphorylation Detected by ODYSSEY® Infrared Imaging System from LI-COR Biosciences (24-Well Plate)

HUVECs (Biowhittaker, Cat, # CC-2519) were seeded on 24-well plates, 18000 cells/well in 600 μL of complete HUVEC medium (EGM-2 Bullet kit, Biowhittaker, Cat. # CC-3162), and allowed to grow overnight. The following day the cells were typically 50% confluent. Complete Medium was removed and 200 μL of Starvation Medium was added (Starvation Medium: EBM-2 with 0.2% FBS only). Cells were Incubated for 2 hrs. Then the cells were treated with 40 μL of antibody solution in PBS for 3 hour. Finally, the cells were treated with 0.3× Complete Medium (final concentration) for 35 minutes. The medium was removed, and the cells were lysed in 80 μL of 1.1× Sample Buffer (Invitrogen, Cat.

No. NP0007). Phosphorylated Smad1 was determined by Western Blotting using XCELL SURELOCK® Mini-Cell & Blot Module (invitrogen, Cat. # EI0002). Phosphorylated Smad1 was detected using rabbit anti-phosphor-Smad1 antibody (Cell Signaling, Cat. No. 9511), which is then detected by IRDye™ 800 Conjugated Anti-RABBIT IgG (Rockland Immunochemicals, Cat. No. 611-732-127). Amount of phosphorylated Smad1 was quantified using Odyssey Infrared Imager (Li-Cor). Actin (Santa Cruz, # sc-8432) was used for normalization (anti-mouse Alex 680, Molecular Probe, Cat. No. A-21058). A summary of mean $IC_{50}$, values for this assay is shown in Table 11. All $IC_{50}$ determinations were run in triplicate.

TABLE 11

| Clone | ID1 TAQMAN® $IC_{50}$ nM | pSmad1 Western $IC_{50}$ nM |
| --- | --- | --- |
| 1.11.1 | nd | nd |
| 1.12.1(M29I/D19A) | 16 | 18 |
| 1.13.1 | 100 | 87 |
| 1.27.1 | 82 | 70 |
| 1.29.1 | 94 | 82 |
| 1.31.1 | 24 | 21 |
| 1.162.1 | 75 | 15 |
| 1.183.1 | 58 | 17 |
| 4.24.1 | 100 | 82 |
| 4.38.1 | 87 | 52 |
| 4.58.1 | 14 | 15 |
| 4.62.1 | 24 | 34 |
| 4.68.1 | 141 | 110 |
| 4.72.1 | 21 | 35 |
| 5.13.1 | 30 | 68 |

Example 14

Internalization Characteristics of Anti-ALK-1 Monoclonal Antibodies

FACS was used to monitor the time course of the remaining cell-surface receptor ALK-1 as well as the neutralizing antibody. Remaining cell-surface ALK-1 is monitored by a marker antibody which is capable of binding cell surface, ALK-1 yet recognizing a different epitope from the neutralizing antibody. A mouse anti-human ALK-1 ECD mAb (R&D systems, Cat. No # AF310) was identified and used in the study as the marker antibody.

Time course of internalization was studied using endothelial cell lines HUVEC and HUAEC. The cells were grown at 37° C. with 5% $CO_2$ in 24-well plates containing 200 µL of complete culture medium per well. At each of 11 time points over the course of 48 hours, 2 µL of 1 mg/mL antibody solution was added to one well and mixed (final concentration of the neutralizing antibody is 10 µg/mL). The plate was then put back into the 37° C. incubator until the 0 hour time point, when the plate was placed on ice to stop the internalization process. Marker antibody was added to the wells at this point (10 µg/mL final concentration) and incubated on ice for 1 hr. The cells were then washed with PBS detached by trypsination and transferred into a 96-well plate. Cells were then washed, blocked, and treated with secondary antibodies bearing different fluorophores in order to monitor both neutralizing antibody and receptor ALK-1 remaining on the cell surface. The samples were assayed on a FACSCalibur flow cytometry instrument, counting 3,000-5,000 events/sample. The Geometric Mean of each sample in the specific fluorescence channel was calculated and plotted as a function of time. The data were fitted to a modified radio-decay equation to obtain the half-time ($t_{1/2}$) of internalization as well as the percentage of neutralizing antibody or receptor ALK-1 remaining on the cell surface when the internalization reached steady-state. As shown in FIG. 6, mAb 1.12.1(M29I/D19A) internalizes at the same rate and to the same extend as the cell surface receptor ALK-1. Half-life of the 1.12.1(M29I/D19A) internalization is ~2 hr. An equilibrium was reached when 50% of the antibody was internalized. A polyclonal antibody purchased from R&D systems (Cat. No # AF370) internalizes at a $t_{1/2}$ of 1 hr and reaches the steady-state with ~70% of the receptor being internalized (FIG. 6). Similar internalization characteristics were observed with other human anti-ALK-1 mAbs of the invention (not shown).

Example 15

Establishment of Human Foreskin—SCID Chimera Mice

Significant modification of the surgery procedure was made to a procedure published previously by H-C Yan, et al "Human/Severe Combined Immunodeficient Mouse Chimeras, An Experimental In Vivo Model System to Study the Regulation of Human Endothelial Cell-Leukocyte Adhesion Molecules", *J. Clin. Invest.* 91:986, 1993; J. Varner "Regulation of Angiogenesis in Vivo by Ligation of Integrin a5b1 with the Central Cell-Binding Domain of Fibronectin" *Amer. J. Path.* 156 (4):1345, 2000; K. Tahtis, et al "Expression and Targeting of Human Fibroblast Activation Protein in a Human Skin/Severe Combined Immunodeficient Mouse Breast Cancer Xenograft Model" *Mol. Cancer. Ther.* 2(8):729, 2003. Upon arrival from National Disease Research Institute and Cooperative Human Tissue Network, human foreskin pieces were trimmed of unhealthy regions and transferred to RPMI media (CELLGRO®/Mediatech, Cat# MT-15-040-CV supplemented with Penicillin and Streptomycin (GIBCO®/Life Tech, Cat#15070-063) (add 5 mLs of the pen/strep stock solution into 500 mLs of RPMI). Using a scalpel and cutting in sterile petri dish, the skins were trimmed to an oval shape of approximately 8×13 mm cleaning any ragged ends and connective tissues, and stored on wet ice prior to surgery. The appropriate volume (4 µL/gram of animal) of 100 mg/ml. KETASET® (ketamine), Fort Dodge Animal Health)/1 medetomidine (Pfizer Animal Health—DORMITOR® (medetomidine)) solution was intraperitoneally injected into scid mouse abdomen (i.e., at a 45° angle, under skin but not too deep internally). Once anesthetized, the mice were applied with eye lubricant, a subcutaneuosly injection of Ketoprofen (10 mg/kg, Fort Dodge Animal Health) and hair was shaved over the site of the surgery. The surgical region was surgically scrubbed three times using the Chlorhexiderm (Butler, Chclo-Scrub 40, cat #WAB20109) and then the alcohol in a circular motion that started from the center of the surgical site outward and avoided going from a dirty area back into a clean area. The mice were transferred to the prepared surgical hood and placed on the heated water pad (Gaymar industries, cat# TP500 T/Pump) that was maintained at 37° C. The mice were then placed under isofluorin anesthesia for the duration of the surgery. The dorsal side of a mouse was covered with a surgical drape cut to expose the surgery site. The mouse skin was picked up with forceps and an oval shaped skin tissue was cut with curved scissors with one motion. An appropriate sized human foreskin was placed on the mouse. The human and mouse skin were sutured together using the ETHILON® suture (Ethicon cat#697H.), starting at top of oval, then the bottom, then the farthest right and then farthest left side. More stitches were made in between to further secure the tissues together. Approximately 8 stitches were made equal-distantly around the skin. During the surgery, used a syringe with sterile saline to irrigate the skin/mouse surgical wound when it became dry. A BANDAID® was placed over the wound. A transparent dressing (3M TEGADERM®) was then used to loosely wrap around the bandage. The dressing was cut to size to cover an area slightly wider than the BANDAID®. The mouse was then given Atipamezole (50-100 µL, Pfizer Animal Health—ANTISEDAN® (atipamezole)) and the mouse recovered in a heated cage in 5-10 min. The dressing and the bandages were removed in 7-10 days and by 15' day most of the skins appeared as scabs. Complete healing occurred between 21-28 days after which time skins were ready to be inoculated with tumor cells. Shown in FIG. 8 is an example of the histological (H & E Staining) analysis of a section of the engrafted skin post surgery. The histology of the engrafted skin closely mimics the characteristics of human skin implanted in mice described by Tahtis, et al "Expression and Targeting of Human Fibroblast Activation Protein in a Human Skin/Severe Combined Immunodeficient Mouse Breast Cancer Xenograft Model" *Mol. Cancer. Ther.* 2(8):729, 2003. h.e.: human epidermal layer; h.d.: human dermal layer.

Example 16

Collagen Model in Human Foreskin—SCID Chimera Mice

Collagen I stock solution (cat#354236, Becten-Dickinson) was diluted to 4 mg/mL with 0.02 N acetic acid and was kept on ice before implantation. The acidic collagen solution (8 parts) was mixed with 10×M199 (Sigma, Cat# M9163) (1 part) and human plasma fibronectin (Fn) (cat#354008, Becten-Dickinson) to reach a final Fn concentration of 90 µL/mL; NaOH (1.0 N) was added to adjust pH to ~7.2. The Collagen/Fn mixture was kept on ice until use. The implant mix was prepared using the above Collagen/Fn mixture plus angiogenic inhibitor of interest with or without human macrovascular endothelial cells (HMVEC), (Cascade Biologics, Cat# C-010-5C). The HMVECs were prepared as $6 \times 10^6$ cells/mL in PBS. 50-100 µL of the implant mixture was injected intradermally into the foreskin in the scid chimera mouse. 7-14 days later, the collagen plugs were harvested, embedded in the OCT compound (cat#4583, Sajura Finetek, CA) and snap frozen for immunohistochemistry analysis. The collagen plug in the foreskin was identified with the Trichrome Kit (cat# KC1641, Mater Tech, CA) as blue staining as shown in FIG. 9 (A). Human vessels were identified by staining for human P-CAM using the anti-human CD-31 antibody (Clone 13.3, Vector Laboratories) (FIG. 9 (B)). Table 12 summarizes the human vessel staining and quantification in the collagen model in the foreskin—SCID chimera mice.

TABLE 12

Summary of the Collagen model results

| Matrix | HMVEC in Matrix | Treatment (Rx) | Days of Rx | Study End Point | Human vessel scoring ($1 \times 10^3$) | % of Control (human vessels) |
|---|---|---|---|---|---|---|
| 1.6 mg/ml Collagen | None | no treatment | 4 | human CD-31 Staining | 0.036 ± 0.001 | 40 |
| 1.6 mg/ml Collagen | $7 \times 10^3$ | no treatment | 4 | | 0.071 ± 0.022 | 78 |
| 1.6 mg/ml Collagen | $1.4 \times 10^4$ | no treatment | 4 | | 0.063 ± 0.016 | 69 |
| 2.4 mg/ml Collagen | None | no treatment | 4 | | 0.091 ± 0.056 | 100 |
| 2.4 mg/ml Collagen | $7 \times 10^3$ | no treatment | 4 | | 0.067 ± 0.049 | 74 |
| 2.4 mg/ml Collagen | $1.4 \times 10^4$ | no treatment | 4 | | 0.062 ± 0.047 | 68 |
| 3.0 mg/ml Collagen | $8.8 \times 10^3$ | Non-treatment | 4 | human CD-31 Staining | 54 ± 9 | 100 |
| 3.0 mg/ml Collagen | $8.8 \times 10^3$ | Isotype control antibody 100 µg/ml mixed in gel | 4 | | 52 ± 13 | 96 |
| 3.0 mg/ml Collagen | $8.8 \times 10^3$ | 1.12.1(M29I/D19A) antibody 100 µg/ml mixed in gel | 4 | | 15 ± 3 | 28 |
| 3.0 mg/ml Collagen | none | no treatment | 4 | human CD-31 Staining | 0.112 + 0.026 | 100 |
| 5.0 mg/ml Collagen | none | no treatment | 4 | | 0.031 + 0.012 | 28 |
| 3.0 mg/ml Collagen | none | Isotype control antibody 100 µg/ml, id. Injection | 4 | human CD-31 Staining | 75 ± 15 | 100 |

TABLE 12-continued

Summary of the Collagen model results

| Matrix | HMVEC in Matrix | Treatment (Rx) | Days of Rx | Study End Point | Human vessel scoring ($1 \times 10^3$) | % of Control (human vessels) |
|---|---|---|---|---|---|---|
| 3.0 mg/ml Collagen | none | 1.12.1(M29I/ D19A) antibody 100 µg/ml, id. injection | 4 | | 39 ± 11 | 52 |
| 3.0 mg/ml Collagen | none | 1.14.1 antibody 100 µg/ml, id. injection | 4 | | 44 ± 28 | 59 |

Example 17

M24met Tumor Model in Human Foreskin—SCID Chimera Mice

Typically graft age of between 5-10 weeks post surgery were used in these studies. The M24met cell line was described by Mueller and coworkers in "Tissue factor-initiated thrombin generation activates the signaling thrombin receptor on malignant melanoma cells", *Cancer Research*, 55(8):1629-32, 1995. M24met cell suspension was prepared as following: 80% confluent M24met cells were washed, typsonized using Trpsin/EDTA (Gibco, Cat#25200-056) and collected in the PRMI (CELLGRO®/Mediatech, cat# MT-15-040-CV) media supplemented with 10% FBS (CELLGRO®/Mediatech, Cat# AKD-11775) and 2 mM L-glutamine (CELLGRO®/Mediatech, Cat#25-005-CI). The cells were centrifuged at 600 rpm for 5 min, resuspended in sterile PBS. Cell counts were estimated using Coulter Counter (Beckman Coulter, Model Z2). The Cells were centrifuged at 600 rpm for 5 min and were re-suspended in Collagen/and Fri (3 mg/ml) mixture to obtain a $4 \times 10^7$ cells/ml cell suspension for implantation.

To inoculate, $2 \times 10^6$ above cells were injected (50 µl of $4 \times 10^7$ cells/ml) intradermally into the engrafted human skin in the mouse. At day 5-7 post implant, the tumors would be palpable and the mice were randomized into the Control and the Treatment groups before the dosing would start. The Control group is defined as such that the animals would receive either no dose, dose of the Vehicle in which the anti-ALK-1 antibody was constituted, or dose of the isotype matched IgG$_2$ human monoclonal antibody anti-KW (Pfizer Inc). The Treatment group is defined as such that the animals would receive a dose of the anti-ALK-1 antibody 1.12.1 (M29I/D19A).

Example 18

Human and Mouse CD-31 Immunofluorescence (IF) Dual Staining

The frozen tissue sections were air-dried and fix at −20° C. in acetone (Fisher, Cat#A16S-4), or 10 min. The samples were air dried again and washed in PBS three times at 5 min each. The samples were blocked in 5% rabbit serum (Vector Laboratories, Cat# S-5000) in PBS for 30 min at room temperature. Primary antibody mixture was prepared in 5% rabbit serum with the anti-human CD-31 antibody (Santa Cruz, Cat# SC1505) and the anti-mouse CD-31 (Pharmingen, Clone Mec1 3.3, Cat#01951A) at 1:100 and 1:150 dilutions, respectively. The above antibody mixture was added to the tissue samples for 1 hour at RT. The blocks were washed in PBS for three times at 5 min each before incubated with the secondary antibody mixture for 1 hour at RT. The secondary antibody mixture was prepared in PBS/0.05% Tween-20 (Sigma, Cat# P1379), Texas Red rabbit anti-goat antibody (Jackson Labs, Cat#305-075-003) and FITC rabbit anti-Rat antibody (Jackson Labs, Cat#312-095-003). The antibodies were diluted at 1:50 if frozen antibodies were used or at 1:100 if fresh antibodies were used. The slides were washed again in PBS for three times at 5 min each before mounted in VECTASHIELD® (Hard Set, Mounting medium with DAPI, Vector Lab, CA, Cat# H-1500). The slides were kept in dark and 4° C. until image analysis. The image analysis was performed using an Olympus BX60 fluorescent microscope and photographs were taken using an Olympus microfire digital color camera. Pictures from 3-5 hot spots/slide, one slide/animal, 4-7 animals/group were taken and the vessel areas as indicated by positive staining of anti-human CD-31 were quantified by three individuals using Image Pro Plus v4.5 (MediaCybernetics). The pharmacodynamic end point (group mean) was expressed as either the percent of human CD-31 inhibition compared to the Control group or as total human vessel area. Statistical significance was determined by ANOVA. Shown in FIG. 10 is an immunofluorescent image of human (red) and mouse (green) vessels of the M24met tumor in the human foreskin SCID chimera mouse.

Example 19

Human CD-31

Immunohistochemistry (IHC) Staining

The frozen tissue sections were air-dried and fix at −20° C. in acetone for 10 min. The samples were air dried again and washed in PBS twice at 5 min each. The samples were incubated in 0.075% $H_2O_2$/methanol (Fisher Cat# A433-4) for 15 min and wash in PBS three times at 5 min each. The samples were blocked in 5% rabbit serum/PBS for 30 min and applied with anti-human CD-31 antibody 1:100 (Santa Cruz, Cat# SC1505) in 5% rabbit serum for 1 hour at RT. The samples were washed in PBS twice at 5 min each and applied with rabbit anti-goat at 1:200 (Vector Labs, Cat# BA-5000) in 5% rabbit serum for 35 min at RT. The slides were then washed in PBS twice at 5 min each and freshly made streptavidin (Vector Labs, ABC Elite kit, Cat# PK-6100) was added. The slides were washed again in PBS twice at 5 min each and then developed in diaminobenzidine (DAB) (Vector Labs, Cat#SK-4100). The slides were wash in PBS twice at 5 min each followed by Mayers haematoxylin (Sigma, Cat# HHS-32) for 5 seconds. The samples were rinsed well in diH$_2$O and dipped twice briefly in the diluted (5 ml stock in 1 L of diH$_2$O)

ammonium hydroxide solution (Sigma, Cat# A-6899) and rinsed in diH$_2$O again. The samples were then dehydrated in the 70%, 90% and then 100% alcohol (Harlem Cat#65347/85) 1 minute each and finally in xylene (JT Baker, Cat#516, 09). The slides were mounted with Cytoseal 60 (Stephens Scientific, Cat #8310-4,) and covered with cover slips for image analysis. Shown in FIG. 11 is the IHC image of human vessels (brown) of the M24met tumor in the human foreskin-SCID chimera mouse.

Example 20

Therapeutic Treatment with the Anti-ALK-1 Antibody 1.12.1(M29I/D19A)

For treatment, the dosing was performed either subcutaneously (sc) or intravenously (iv). Typically one dose of the 1.12.1(M29I/D19A) antibody was given for each study. The second dose of the ALK-1 antibody, if necessary, was administered on day 9 or 10. Some times multiple dose levels, i.e., 1, 5, 10, 50 mg/kg, were administered to investigate dose-dependent inhibition of human vessel growth. Animals were monitored daily and tumors were measured three times/week by calipers. By day 14-17 the tumors were between 250-350 mm$^3$ and were removed from the mice, embedded in OCT and frozen down for IF or IHC analysis. Shown in FIG. 12 are representative immunofluorescent images of human (red) and mouse (green) vessels of the Control and 1.12.1(M29I/D19A) Treated (10 mg/kg) M24met tumors in the human foreskin scid chimera mouse. Dose-dependent inhibition of human tumor vessels by 1.12.1(M29I/D19A) in the human foreskin SCID chimera mouse model is shown in FIG. 13 and a summary of related studies is presented in Table 13.

TABLE 13

Summary of in vivo model characterization and the inhibition of human vessel growth of the M24met tumors in the SCID-chimera model

| | Protocol Parameters | | | | Endpoints CD31 (% inhibition Compared to Control) | Day of Study | General notes |
|---|---|---|---|---|---|---|---|
| Tumor | Drug | Dose | Route | Schedule | | | |
| MCF-7 | none | na | na | na | not quantified | 19 | Tumors implanted intradermally. Tested with and with out estradiol and collagen implant. Tumors grew slowly and expressed little human CD31 |
| M24met | none | na | na | na | not quantified | 19 | Tumors implanted intradermally. Tested with and with out collagen/FN matrix. With matrix found superior tumor growth, all future studies will contain matrix supliments. Tumors showed good human CD31 staining |
| M24met (small) | none | na | na | na | not quantified | 9 | Tumor size <100 mm$^3$. Little human CD31 |
| M24met (medium) | none | na | na | na | not quantified | 12 | Tumor size <100-200 mm$^3$. Some human CD31 |
| M24met (large) | none | na | na | na | not quantified | 12 | Tumor size <200 mm$^3$. Large M24met tumors have superior numbers of human vessel staining, future studies will be conducted with larger tumors |
| M24met | Non-Specific human IgG | 10 mg/kg | IV | 2 doses (day 5 & 9) | 0 | 15 | First screening study. 1.12.1(M29I/D19A) showed significant reduction of human CD31 staining. No tumor growth inhibition observed |
| | 1.12.1(M29I/D19A) | 10 mg/kg | IV | | 42 | | |
| M24met | Non-Specific human IgG | 10 mg/kg | IV | 2 doses (day 5 & 10) | 0 | 14 | Second screening study. Confirmed results of GW-366. No tumor growth inhibition observed |
| | 1.12.1(M29I/D19A) | 10 mg/kg | IV | | 40 | | |
| M24met | Non-Specific human IgG | 10 mg/kg | SC | 2 doses (day 5 & 10) | 0 | 14 | First test of dose dependent activity of 1.12.1(M29I/D19A) against human CD31. Some dose dependent effect observed. PK results that single dose will be sufficient for significant reduction in CD31. No tumor growth inhibiton observed |
| | 1.12.1(M29I/D19A) | 10 mg/kg | SC | | 43 | | |
| | 1.12.1(M29I/D19A) | 1 mg/kg | SC | | 50 | | |
| | 1.12.1(M29I/D19A) | 0.1 mg/kg | SC | | 20 | | |

TABLE 13-continued

Summary of in vivo model characterization
and the inhibition of human vessel growth of
the M24met tumors in the SCID-chimera model

| | Protocol Parameters | | | | Endpoints CD31 (% inhibition Compared to Control) | Day of Study | General notes |
|---|---|---|---|---|---|---|---|
| Tumor | Drug | Dose | Route | Schedule | | | |
| M24met | No Dose | 0 mg/kg | na | na | ND | 16 | Second test of dose dependent activity of 1.12.1(M29I/D19A) against human CD31. Clear dose dependent anti-CD31 effect observed. No tumor growth inhibition observed |
| | Isotype matched IgG | 10 mg/kg | SC | one dose (day 5) | 0 | | |
| | Non-Specific human IgG | 10 mg/kg | SC | | ND | | |
| | 1.12.1(M29I/D19A) | 1 mg/kg | SC | | 24 | | |
| | 1.12.1(M29I/D19A) | 5 mg/kg | SC | | 59 | | |
| | 1.12.1(M29I/D19A) | 10 mg/kg | SC | | 72 | | |
| M24met | Isotype matched IgG | 10 mg/kg | SC | one dose (day 5) | 0 | 14 | Final broad dose range test for 1.12.1(M29I/D19A). Study showed good dose dependent effects. Fitting data to a sigmoidal dose response curve yields an $IC_{50}$ of 93 nM. No tumor growth inhibiton observed. |
| | 1.12.1(M29I/D19A) | 1 mg/kg | SC | | 33 | | |
| | 1.12.1(M29I/D19A) | 3 mg/kg | SC | | 41 | | |
| | 1.12.1(M29I/D19A) | 5 mg/kg | SC | | 60 | | |
| | 1.12.1(M29I/D19A) | 7.5 mg/kg | SC | | 60 | | |
| | 1.12.1(M29I/D19A) | 10 mg/kg | SC | | 73 | | |
| | 1.12.1(M29I/D19A) | 50 mg/kg | SC | | 70 | | |

Example 21

In Vivo EC50 Determination

Human foreskin SCID chimera mice were intradermally implanted with M24met cells and were treated (sc) with anti-ALK-1 antibody 1.12.1(M29I/D19A) at 1, 3, 5, 7.5, 10 and 50 mg/kg or with isotype match anti-human KLH antibody (10 mg/kg). Upon the conclusion of the experiment, human vessel area in each tumor were quantified as described above. Mouse plasma concentrations of anti-ALK-1 antibody 1.12.1 (M29I/D19A) were measured using the method described as following: serum samples from mice were analyzed for anti-ALK-1 antibody 1.12.1(M29I/D19A) concentration by an ELISA (enzyme-linked immunosorbent Assay). ELISA plates were coated with 10 ug/ml goat anti-human IgG Fc specific antibody (Pierce, cat#31123) in PBS, incubated overnight at 4° C., and then blocked with StartBlock blocking buffer (Pierce, cat#37542) at room temperature for 1 hr. Serum samples were diluted prior to the analysis 100 and 1000-fold in StartBlock blocking buffer. Two sets of standards were prepared in the blank serum diluted 100 and 100-fold. Standards and diluted serum samples were incubated on the plate for 1 hr. Bound anti-ALK-1 antibody 1.12.1 (M29I/D19A) was detected using horseradish peroxidase (HRP)-labeled goat anti-human IgG (Fab-specific) antibody (Sigma, cat# A0293). The substrate used was 3,3',5,5"-tetramethyl benzidine (Sigma, cat# T8665). Absorbance was read at 450 nm on a Vmax plate reader (Molecular Devices, Menlo Park, Calif.). A standard curve was fit using nonlinear regression. The detection limit of this assay was 10 ng/ml of anti-ALK-1 antibody 1.12.1(M29I/D19A).

SCID mouse plasma concentration of anti-ALK-1 antibody 1.12.1(M29I/D19A) is shown in FIG. 15.

FIG. 15 represents the estimated $EC_{50}$ for 1.12.1(M29I/D19A) in the M24met Foreskin SCID-chimera Model. Human vessel area was plotted against the average plasma PK across the study period (14 days) for each treatment group. A fitted curve was produced by the Sigmoidal Dose Dependent program in the GRAPHPAD® (Prizm), $EC_{50}$ of 93 ng/ml ($EC_{50}$ is defined as the plasma concentration required for a 50% reduction of human vessel area in the Control group) was derived from the curve fit.

All publications, patents, and patent applications cited in this specification are incorporated herein by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

Applicants incorporate herein by reference in its entirety the document "sequencelisting.TXT," which is electronically submitted concurrently with this application. This document was created on Oct. 26, 2011 and has a size of 114,229 bytes.

We claim:

1. A method for treating cancer in a human in need thereof, comprising the step of administering to said human an anti-activin receptor-like kinase-1 (ALK-1) antibody or an antigen-binding portion thereof, wherein said antibody comprises the heavy chain CDR1-3 and the light chain CDR1-3 found in the following amino acid sequences, respectively:
   a) SEQ ID NO: 6 and SEQ ID NO: 8;
   b) SEQ ID NO: 14 and SEQ ID NO: 16;
   c) SEQ ID NO: 18 and SEQ ID NO: 20;
   d) SEQ ID NO: 26 and SEQ ID NO: 28;
   e) SEQ ID NO: 30 and SEQ ID NO: 32;
   f) SEQ ID NO: 38 and SEQ ID NO: 40;
   g) SEQ ID NO: 46 and SEQ ID NO: 48;
   h) SEQ ID NO: 50 and SEQ ID NO: 52;
   i) SEQ ID NO: 54 and SEQ ID NO: 56;
   j) SEQ ID NO: 58 and SEQ ID NO: 60;
   k) SEQ ID NO: 62 and SEQ ID NO: 64;
   l) SEQ ID NO: 66 and SEQ ID NO: 68; or
   m) SEQ ID NO: 70 and SEQ ID NO: 72.

2. The method according to claim 1, wherein said cancer is selected from melanoma; mesothelioma; renal cell carcinoma; breast cancer; head and neck cancer; brain cancer; cervical cancer; prostate cancer; pancreatic cancer; testicular cancer; hepatobiliary cancer; hepatic duct cancer; biliary duct cancer; bladder cancer; urethral cancer; lung cancer; non-small cell lung cancer; small cell lung cancer; ovarian cancer; colon cancer; rectal cancer; and cancer of the anal region.

3. The method according to claim 1 or 2, wherein said method inhibits angiogenesis.

4. The method according to claim 1, wherein said antibody is a human antibody.

5. The method according to claim 1, wherein the heavy chain and the light chain of said antibody comprise the following amino acid sequences, respectively:
   a) SEQ ID NO: 6 and SEQ ID NO: 8;
   b) SEQ ID NO: 14 and SEQ ID NO: 16;
   c) SEQ ID NO: 18 and SEQ ID NO: 20;
   d) SEQ ID NO: 26 and SEQ ID NO: 28;
   e) SEQ ID NO: 30 and SEQ ID NO: 32;
   f) SEQ ID NO: 38 and SEQ ID NO: 40;
   g) SEQ ID NO: 46 and SEQ ID NO: 48;
   h) SEQ ID NO: 50 and SEQ ID NO: 52;
   i) SEQ ID NO: 54 and SEQ ID NO: 56;
   j) SEQ ID NO: 58 and SEQ ID NO: 60;
   k) SEQ ID NO: 62 and SEQ ID NO: 64;
   l) SEQ ID NO: 66 and SEQ ID NO: 68;
   m) SEQ ID NO: 70 and SEQ ID NO: 72;
   n) SEQ ID NO: 104 and SEQ ID NO: 127;
   o) SEQ ID NO: 6 and SEQ ID NO: 127; or
   p) SEQ ID NO: 104 and SEQ ID NO: 8.

6. The method according to claim 1, wherein the heavy chain and the light chain of said antibody comprise the following amino acid sequences, respectively:
   a) SEQ ID NO: 2 and SEQ ID NO: 4;
   b) SEQ ID NO: 2 and SEQ ID NO: 102;
   c) SEQ ID NO: 100 and SEQ ID NO: 4; or
   d) SEQ ID NO: 100 and SEQ ID NO: 102.

7. The method according to claim 1, wherein said antibody or antigen-binding portion is derivatized or linked to another molecule.

8. The method according to claim 7, wherein said molecule is a detection agent, a cytotoxic agent, a pharmaceutical agent, a peptide or a protein.

9. The method according to claim 1, wherein the cancer is a solid tumor.

10. The method according to claim 2, wherein the cancer is hepatobiliary cancer.

11. The method according to claim 2, wherein the cancer is renal cell carcinoma.

12. A method of inhibiting angiogenesis in a human suffering from cancer, the method comprising the step of administering to said human a therapeutically effective amount of an anti-ALK-1 antibody or an antigen-binding portion thereof, wherein said antibody comprises the heavy chain CDR1, CDR2, and CDR3 amino acid sequences in SEQ ID NO: 6 and the light chain CDR1, CDR2, and CDR3 amino acid sequences in SEQ ID NO: 8.

13. The method according to claim 12, wherein said antibody is a human antibody.

14. The method according to claim 12, wherein said antibody comprises a heavy chain comprising the amino acid sequence of SEQ ID NO: 6 and a light chain comprising the amino acid sequence of SEQ ID NO: 8.

15. The method according to claim 12, wherein said antibody comprises a heavy chain comprising the amino acid sequence of SEQ ID NO: 2 and a light chain comprising the amino acid sequence of SEQ ID NO: 4.

16. A method of inhibiting angiogenesis in a human suffering from cancer, the method comprising the step of administering to said human a therapeutically effective amount of an antibody or an antigen-binding portion thereof, wherein said antibody comprises a $V_H$ amino acid sequence encoded by the nucleotide sequence of the plasmid insert found in the E. coli clone deposited under ATCC accession number PTA-6864, and wherein said antibody further comprises a $V_L$ amino acid sequence encoded by the nucleotide sequence of the plasmid insert found in the E. coli clone deposited under ATCC accession number PTA-6865.

17. The method according to claim 16, wherein said antibody is a human antibody.

18. The method according to claim 16, wherein said antibody or antigen-binding portion is derivatized or linked to another molecule.

19. The method according to claim 18, wherein said molecule is a detection agent, a cytotoxic agent, a pharmaceutical agent, a peptide or a protein.

20. The method according to claim 16, wherein the human suffers from a cancer selected from melanoma; mesothelioma; renal cell carcinoma; breast cancer; head and neck cancer; brain cancer; cervical cancer; prostate cancer; pancreatic cancer; testicular cancer; hepatobiliary cancer; hepatic duct cancer; biliary duct cancer; bladder cancer; urethral cancer; lung cancer; non-small cell lung cancer; small cell lung cancer; ovarian cancer; colon cancer; rectal cancer; and cancer of the anal region.

21. The method according to claim 12 or 16, wherein human suffers from hepatobiliary cancer.

22. The method according to claim 12 or 16, wherein the human suffers from renal cell carcinoma.

23. A method for treating hepatobiliary cancer in a human in need thereof, comprising the step of administering to said human a monoclonal antibody comprising a heavy chain amino acid sequence of SEQ ID NO: 2 and a light chain amino acid sequence of SEQ ID NO: 4.

24. A method for treating renal cell carcinoma in a human in need thereof, comprising the step of administering to said human a monoclonal antibody comprising a heavy chain amino acid sequence of SEQ ID NO: 2 and a light chain amino acid sequence of SEQ ID NO: 4.

25. The method according to claim 23 or 24, wherein said antibody is derivatized or linked to another molecule.

26. The method according to claim 25, wherein said molecule is a detection agent, a cytotoxic agent, a pharmaceutical agent, a peptide or a protein.

* * * * *

SEQUENCE LISTING

<160> NUMBER OF SEQ ID NOS: 136

<210> SEQ ID NO 1
<211> LENGTH: 1332
<212> TYPE: DNA
<213> ORGANISM: Human

<400> SEQUENCE: 1

| | | |
|---|---|---|
| caggtgcagc tgcaggagtc gggtccagga ctggtgaagc cttcacagac cctgtccctc | 60 |
| acctgcactg tctctggtgg ctccatcagc agtggtgaat actactggaa ctggatccgc | 120 |
| cagcacccag ggaagggcct ggagtggatt gggtacatct attacagtgg gagtacctac | 180 |
| tacaacccgt ccctcaagag tcgagttacc atatcagtag acacgtctaa gaaccagttc | 240 |
| tccctgaagc tgagctctgt gactgccgcg gacacggccg tgtattactg tgcgagagag | 300 |
| tcagtggctg ggtttgacta ctggggccag ggaaccctgg tcaccgtctc ctcagcctcc | 360 |
| accaagggcc catcggtctt ccccctggcg ccctgctcca ggagcacctc cgagagcaca | 420 |
| gcggccctgg gctgcctggt caaggactac ttccccgaac cggtgacggt gtcgtggaac | 480 |
| tcaggcgctc tgaccagcgg cgtgcacacc ttcccggctg tcctacagtc ctcaggactc | 540 |
| tactccctca gcagcgtagt gaccgtgccc tccagcaact tcggcaccca gacctacacc | 600 |
| tgcaacgtag atcacaagcc cagcaacacc aaggtggaca gacagttga gcgcaaatgt | 660 |
| tgtgtcgagt gcccaccgtg cccagcacca cctgtggcag gaccgtcagt cttcctcttc | 720 |
| cccccaaaac ccaaggacac cctcatgatc tcccggaccc ctgaggtcac gtgcgtggtg | 780 |
| gtggacgtga gccacgaaga ccccgaggtc cagttcaact ggtacgtgga cggcgtggag | 840 |
| gtgcataatg ccaagacaaa gccacgggag gagcagttca acagcacgtt ccgtgtggtc | 900 |
| agcgtcctca ccgtcgtgca ccaggactgg ctgaacggca aggagtacaa gtgcaaggtc | 960 |
| tccaacaaag gcctcccagc ccccatcgag aaaaccatct ccaaaaccaa agggcagccc | 1020 |
| cgagaaccac aggtgtacac cctgccccca tcccgggagg agatgaccaa gaaccaggtc | 1080 |
| agcctgacct gcctggtcaa aggcttctac cccagcgaca tcgccgtgga gtgggagagc | 1140 |
| aatgggcagc cggagaacaa ctacaagacc acacctccca tgctggactc cgacggctcc | 1200 |
| ttcttcctct acagcaagct caccgtggac aagagcaggt ggcagcaggg gaacgtcttc | 1260 |
| tcatgctccg tgatgcatga ggctctgcac aaccactaca cacagaagag cctctccctg | 1320 |
| tctccgggta aa | 1332 |

<210> SEQ ID NO 2
<211> LENGTH: 444
<212> TYPE: PRT
<213> ORGANISM: Human

<400> SEQUENCE: 2

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Glu Tyr Tyr Trp Asn Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

```
Ser Leu Lys Leu Ser Ser Val Thr Ala Ala Asp Thr Ala Val Tyr Tyr
                85                  90                  95

Cys Ala Arg Glu Ser Val Ala Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Cys Val Glu Cys
210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
290                 295                 300

Val Val His Gln Asp Trp Leu Asn Gly Lys Glu Tyr Lys Cys Lys Val
305                 310                 315                 320

Ser Asn Lys Gly Leu Pro Ala Pro Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440

<210> SEQ ID NO 3
<211> LENGTH: 645
<212> TYPE: DNA
<213> ORGANISM: Human

<400> SEQUENCE: 3
gaaattgtgt tgacgcagtc tccaggcacc ctgtctttgt ctccagggga aagagccacc      60
```

```
ctctcctgta gggccagtca gagtgtcagc agcagctact tagcctggta ccagcagaaa    120
cctggccagg ctcccaggct cctcatctat ggtacatcca gcagggccac tggcatccca    180
gacaggttca gtggcagtgg gtctgggaca gacttcaccc tcaccatcag cagactggag    240
cctgaagatt ttgcagtgta ttactgtcag cagtatggta gctcgccgat caccttcggc    300
caagggacac gactggagat taaacgaact gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca aagcagacta cgagaaacac aaagtctacg cctgcgaagt cacccatcag    600
ggcctgagct cgcccgtcac aaagagcttc aacaggggag agtgt                    645
```

<210> SEQ ID NO 4
<211> LENGTH: 215
<212> TYPE: PRT
<213> ORGANISM: Human

<400> SEQUENCE: 4

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
        35                  40                  45

Ile Tyr Gly Thr Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Ile Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 5
<211> LENGTH: 355
<212> TYPE: DNA
<213> ORGANISM: Human

<400> SEQUENCE: 5

```
caggtgcagc tgcaggagtc gggtccagga ctggtgaagc cttcacagac cctgtccctc    60
```

```
acctgcactg tctctggtgg ctccatcagc agtggtgaat actactggaa ctggatccgc    120
cagcacccag ggaagggcct ggagtggatt gggtacatct attacagtgg gagtacctac    180
tacaacccgt ccctcaagag tcgagttacc atatcagtag acacgtctaa gaaccagttc    240
tccctgaagc tgagctctgt gactgccgcg gacacggccg tgtattactg tgcgagagag    300
tcagtggctg gtttgactac tggggccag ggaaccctgg tcaccgtctc ctcag           355
```

<210> SEQ ID NO 6
<211> LENGTH: 118
<212> TYPE: PRT
<213> ORGANISM: Human

<400> SEQUENCE: 6

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Glu Tyr Tyr Trp Asn Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Ser Val Ala Gly Phe Asp Tyr Trp Gly Gln Gly Thr
            100                 105                 110

Leu Val Thr Val Ser Ser
        115
```

<210> SEQ ID NO 7
<211> LENGTH: 325
<212> TYPE: DNA
<213> ORGANISM: Human

<400> SEQUENCE: 7

```
gaaattgtgt tgacgcagtc tccaggcacc ctgtctttgt ctccagggga aagagccacc     60
ctctcctgta gggccagtca gagtgtcagc agcagctact tagcctggta ccagcagaaa    120
cctggccagg ctcccaggct cctcatctat ggtacatcca gcagggccac tggcatccca    180
gacaggttca gtggcagtgg gtctgggaca gacttcaccc tcaccatcag cagactggag    240
cctgaagatt ttgcagtgta ttactgtcag cagtatggta gctcgccgat caccttcggc    300
caagggacac gactggagat taaac                                          325
```

<210> SEQ ID NO 8
<211> LENGTH: 108
<212> TYPE: PRT
<213> ORGANISM: Human

<400> SEQUENCE: 8

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
        35                  40                  45
```

```
Ile Tyr Gly Thr Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Ile Thr Phe Gly Gln Gly Thr Arg Leu Glu Ile Lys
                100                 105
```

```
<210> SEQ ID NO 9
<211> LENGTH: 361
<212> TYPE: DNA
<213> ORGANISM: Human

<400> SEQUENCE: 9
caggtgcagc tggtggagtc tgggggaggc gtggtccagc ctggggaggtc cctgagactc    60 tcctgtgcag cgtctggatt caccttcagt agtcatggca tgtactgggt ccgccaggct   120
ccaggcaagg ggctggagtg ggtggcagct atatggtatg atggaagtaa taaatactat   180
gcagactccg tgaagggccg attcaccatc tccagagaca attccaagaa cacgctgtat   240
ctgcaaatga atagcctgag agccgaggac acggctgtgt attactgtgc gagagatcag   300
gagcagtggc ccgatgtttt tgatatctgg ggccaaggga caatggtcac cgtctcttca   360
g                                                                  361
```

```
<210> SEQ ID NO 10
<211> LENGTH: 120
<212> TYPE: PRT
<213> ORGANISM: Human

<400> SEQUENCE: 10

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser His
                20                  25                  30

Gly Met Tyr Trp Val Arg Gln Ala Pro Gly Lys Gly Leu Glu Trp Val
            35                  40                  45

Ala Ala Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gln Glu Gln Trp Pro Asp Val Phe Asp Ile Trp Gly Gln
            100                 105                 110

Gly Thr Met Val Thr Val Ser Ser
        115                 120
```

```
<210> SEQ ID NO 11
<211> LENGTH: 322
<212> TYPE: DNA
<213> ORGANISM: Human

<400> SEQUENCE: 11
gacatccaga tgacccagtc tccatcctca ctgtctgcat ctgtaggaga cagagtcacc    60
atcacttgtc gggcgagtca gggcattaga aattatttag cctggtttca gcagaaacca   120
```

```
gggaaagccc ctaagtccct gatctatggt gcatccagtt tgcaaagtgg ggtcccatca      180
aagttcagcg gcagtggatc tgggacagat ttcactctca ccatcagcag cctgcagcct      240
gaagattttg caacttatta ctgccaacag tataatagtt acccgctcac tttcggcgga      300
gggaccaagg tggagatcaa ac                                              322
```

<210> SEQ ID NO 12
<211> LENGTH: 107
<212> TYPE: PRT
<213> ORGANISM: Human

<400> SEQUENCE: 12

```
Asp Ile Gln Met Thr Gln Ser Pro Ser Ser Leu Ser Ala Ser Val Gly
1               5                  10                  15

Asp Arg Val Thr Ile Thr Cys Arg Ala Ser Gln Gly Ile Arg Asn Tyr
            20                  25                  30

Leu Ala Trp Phe Gln Gln Lys Pro Gly Lys Ala Pro Lys Ser Leu Ile
        35                  40                  45

Tyr Gly Ala Ser Ser Leu Gln Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105
```

<210> SEQ ID NO 13
<211> LENGTH: 355
<212> TYPE: DNA
<213> ORGANISM: Human

<400> SEQUENCE: 13

```
caggtgcacc tgcaggagtc gggcccagga ctggtgaagc cttcggagac cctgtccctc       60
acctgcactg tctctggtgg ctccgtcagc agtggtgatt actactggaa ctggatccgg      120 cagcccccg ggaagggact ggagtggatt gggtatatct attacagtgg gagcaccaac      180
tacaacccct ccctcaagag tcgaatcacc atatcaatag acacgtccaa gaaccagttc      240
tccctgaagc tgaactctgt gaccgctgcg gacacggccg tgtattactg tgcgagagaa      300
tcagtggccg cctttgacta ctggggccag ggaaccctgg tcaccgtctc ctcag           355
```

<210> SEQ ID NO 14
<211> LENGTH: 118
<212> TYPE: PRT
<213> ORGANISM: Human

<400> SEQUENCE: 14

```
Gln Val His Leu Gln Glu Ser Gly Pro Gly Leu Val Lys Pro Ser Glu
1               5                  10                  15

Thr Leu Ser Leu Thr Cys Thr Val Ser Gly Gly Ser Val Ser Ser Gly
            20                  25                  30

Asp Tyr Tyr Trp Asn Trp Ile Arg Gln Pro Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Ile Thr Ile Ser Ile Asp Thr Ser Lys Asn Gln Phe
65                  70                  75                  80
```

```
Ser Leu Lys Leu Asn Ser Val Thr Ala Ala Asp Thr Ala Leu Tyr Tyr
            85                  90                  95

Cys Ala Arg Glu Ser Val Ala Ala Phe Asp Tyr Trp Gly Gln Gly Thr
        100                 105                 110

Leu Val Thr Val Ser Ser
        115
```

<210> SEQ ID NO 15
<211> LENGTH: 325
<212> TYPE: DNA
<213> ORGANISM: Human

<400> SEQUENCE: 15

```
gaaattgtgt tgacgcagtc tccaggcacc ctgtctttgt ctccagggga aagagccacc      60
ctctcctgca gggccagtca gagtattagc agtaggtact tagcctggta ccagcaggaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcaa cactatggta gctcaccgat caccttcggc     300
caagggacac gactggagat taaac                                           325
```

<210> SEQ ID NO 16
<211> LENGTH: 108
<212> TYPE: PRT
<213> ORGANISM: Human

<400> SEQUENCE: 16

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Ser Ser Arg
            20                  25                  30

Tyr Leu Ala Trp Tyr Gln Gln Glu Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Gly Ser Ser Pro
                85                  90                  95

Ile Thr Phe Gly Gln Gly Thr Arg Leu Glu Ile Lys
            100                 105
```

<210> SEQ ID NO 17
<211> LENGTH: 355
<212> TYPE: DNA
<213> ORGANISM: Human

<400> SEQUENCE: 17

```
caggtgcagc tgcaggagtc gggcccagga ctggtgaagc cttcggagac cctgtccctc      60
acctgcactg tctctggtgg ctccgtcagc agtggtgatt actactggaa ctggatccgg     120
cagcccccag ggaagggact ggagtggatt gggtatatct attacagtgg gagcaccaac     180
tacaacccct ccctcaagag tcgagtcacc atatcagtag acacgtccaa gaaccagttc     240
tccctgaagc tgagctctgt gaccgctgcg gacacggccg tgtattactg tgcgagagaa     300
gcagtgtccg cctttgacta ctggggccag ggaaccctgg tcaccgtctc ctcag          355
```

<210> SEQ ID NO 18
<211> LENGTH: 118
<212> TYPE: PRT
<213> ORGANISM: Human

<400> SEQUENCE: 18

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Asp Tyr Tyr Trp Asn Trp Ile Arg Gln Pro Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Ala Val Ser Ala Phe Asp Tyr Trp Gly Gln Gly Thr
            100                 105                 110

Leu Val Thr Val Ser Ser
        115
```

<210> SEQ ID NO 19
<211> LENGTH: 325
<212> TYPE: DNA
<213> ORGANISM: Human

<400> SEQUENCE: 19

```
gaaattgtgt tgacgcagtc tccaggcacc ctgtctttgt ctccagggga aagagccacc      60
ctctcctgca gggccagtca gagtgttagc agtaccacct agcctggca ccagcagaaa     120 cctggccagg ctcccaggct cctcatctat ggtgtatcca gcagggccag tggcgtccca    180
gacaggttca gtggcagtgg gtctgggaca gacttcactc tcaccatcag cagactggag    240
cctgaagatt ttgcagtgta ttactgtcag cagtatggta gttcaccgat caccttcggc    300
caagggacac gactggagat taaac                                          325
```

<210> SEQ ID NO 20
<211> LENGTH: 108
<212> TYPE: PRT
<213> ORGANISM: Human

<400> SEQUENCE: 20

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Thr
            20                  25                  30

Tyr Leu Ala Trp His Gln Gln Lys Pro Gly Gln Ala Pro Arg Leu Leu
        35                  40                  45

Ile Tyr Gly Val Ser Ser Arg Ala Ser Gly Val Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Ile Thr Phe Gly Gln Gly Thr Arg Leu Glu Ile Lys
```

<210> SEQ ID NO 21
<211> LENGTH: 370
<212> TYPE: DNA
<213> ORGANISM: Human

<400> SEQUENCE: 21
caggtgcagc tgcaggagtc gggcccagga ctggtgaagc cttcacagac cctgtccctc      60
acctgcactg tctctggtgg ctccatcagc agtggtggtc actactggag ctggatccgc     120
cagcacccag ggaagggcct ggagtggatt gggtacatct attacagtgg gagcacctac     180
tacaacccgt ccctcaagag tcgagttacc atatcagtag acacgtctaa gaaccagttc     240
tccctgaagc tgagttctgt gactgccgcg gacacggccg tatattactg tgcgagagcg     300
gggcgatttt tggagtggtc tgatgttttt gatatctggg gccaagggac aatggtcacc     360
gtctcctcag                                                            370

<210> SEQ ID NO 22
<211> LENGTH: 123
<212> TYPE: PRT
<213> ORGANISM: Human

<400> SEQUENCE: 22

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly His Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Gly Arg Phe Leu Glu Trp Ser Asp Val Phe Asp Ile
            100                 105                 110

Trp Gly Gln Gly Thr Met Val Thr Val Ser Ser
        115                 120

<210> SEQ ID NO 23
<211> LENGTH: 340
<212> TYPE: DNA
<213> ORGANISM: Human

<400> SEQUENCE: 23
gacatcgtga tgacccagtc tccagactcc ctggctgtgt ctctgggcga gagggccacc      60
atcaactgca gtccagcca gagtgtttta tacagctcca acaataagaa ctacttagct     120
tggtaccagc agaaaccagg gcagcctcct aagctgctca tttactgggc atctacccgg     180
gaatccgggg tccctgaccg attcagtggc agcgggtctg ggacagattt cactctcacc     240
atcagcagcc tgcaggctga agatgtggca gtttattact gtcagcaata ttatgatact     300
cctccgacgt tcggccaagg gaccaaggtg gaaatcaaac                           340

<210> SEQ ID NO 24
<211> LENGTH: 113

```
<212> TYPE: PRT
<213> ORGANISM: Human

<400> SEQUENCE: 24

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Asp Thr Pro Pro Thr Phe Gly Gln Gly Thr Lys Val Glu Ile
            100                 105                 110

Lys

<210> SEQ ID NO 25
<211> LENGTH: 355
<212> TYPE: DNA
<213> ORGANISM: Human

<400> SEQUENCE: 25
caggtgcagc tgcaggagtc gggcccagga ctggtgaagc cctcacagac cctgtccctc      60
atctgtactg tttctggtgg ctccatcagc agtggtgaat actactggag ctggatccgc     120
cagcacccag ggaagggcct ggagtggatt gggtacatct attacagtgg gagcacctac     180
tacaacccgt ccctcaagag tcgacttacc atatcagtag acacgtctaa gaaccagttc     240
tccctgaagc tgagctctgt gactgccgcg gacacggccg tgtattactg tgcgagagag     300
gggatcggtg cttttgatat ctggggccaa gggacaatgg tcaccgtctc ttcag          355

<210> SEQ ID NO 26
<211> LENGTH: 118
<212> TYPE: PRT
<213> ORGANISM: Human

<400> SEQUENCE: 26

Gln Val Gln Leu Gln Glu Ser Gly Pro Gly Leu Val Lys Pro Ser Gln
1               5                   10                  15

Thr Leu Ser Leu Ile Cys Thr Val Ser Gly Gly Ser Ile Ser Ser Gly
            20                  25                  30

Glu Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
50                  55                  60

Leu Lys Ser Arg Leu Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Gly Ile Gly Ala Phe Asp Ile Trp Gly Gln Gly Thr
            100                 105                 110

Met Val Thr Val Ser Ser
            115
```

<210> SEQ ID NO 27
<211> LENGTH: 325
<212> TYPE: DNA
<213> ORGANISM: Human

<400> SEQUENCE: 27

```
gaaattgtgt tgacgcagtc gccaggcacc ctgtctttgt ctccagggga aagagccacc      60
ctctcctgca gggccagtca gagtgttagc agcagctact tagcctggta ccagcagaaa     120
cctggccagg ctcctaggct cctcatctat ggagcatcca gcagggccac tggcatccca     180
gacaggttca gtggcagtgg gtctgggaca gacttcactc tcaccatcat cagactggac     240
cctgaagatt ttgcagtgta ttactgtcag cggtatggta gctcaccgat caccttcggc     300
caagggacac gactggagat taaac                                           325
```

<210> SEQ ID NO 28
<211> LENGTH: 108
<212> TYPE: PRT
<213> ORGANISM: Human

<400> SEQUENCE: 28

```
Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Ser
             20                  25                  30

Tyr Leu Ala Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
     50                  55                  60

Gly Ser Gly Ser Gly Thr Asp Phe Thr Leu Thr Ile Ile Arg Leu Asp
 65                  70                  75                  80

Pro Glu Asp Phe Ala Val Tyr Tyr Cys Gln Arg Tyr Gly Ser Ser Pro
                 85                  90                  95

Ile Thr Phe Gly Gln Gly Thr Arg Leu Glu Ile Lys
            100                 105
```

<210> SEQ ID NO 29
<211> LENGTH: 361
<212> TYPE: DNA
<213> ORGANISM: Human

<400> SEQUENCE: 29

```
caggtgcagc tgcaggagtc gggcccagga ctggtgaagc cttcggagac cctgtccctc      60
acctgcactg tctctggtgg ctccatcagt agttactact ggagctggat ccggcagccc     120
ccagggaagg gactggagtg gattgggtat atctattaca gtgggagcac caactacaac     180
ccctccctca agagtcgagt caccatatca gtagacacgt ccaagaacca gttctccctg     240
aagctgagct ctgtgaccgc tgcggacacg gccgtgtatt actgtgcgag agaggacgat     300
agcagtggct gcccctactt tgactactgg ggccagggaa ccctggtcac cgcttcctca     360
g                                                                    361
```

<210> SEQ ID NO 30
<211> LENGTH: 120
<212> TYPE: PRT
<213> ORGANISM: Human

<400> SEQUENCE: 30

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Asp Asp Ser Ser Gly Cys Pro Tyr Phe Asp Tyr Trp Gly Gln
                100                 105                 110

Gly Thr Leu Val Thr Ala Ser Ser
        115                 120

<210> SEQ ID NO 31
<211> LENGTH: 322
<212> TYPE: DNA
<213> ORGANISM: Human

<400> SEQUENCE: 31
gaaatagtga tgacgcagtc tccagccacc ctgtctgtgt ctccagggga aagagccacc      60
ctctcctgca gggccagtca gagtgttagc agcaacttag cctggtacca gcagaaacct     120
ggccaggctc ccagggtcct catctatggt gcatccacca gggccactgg tatcccagtc     180
aggttcagtg gcagtgggtc tgggacagag ttcactctca ccatcagcag cctgcagtct     240
gaagattttg cagtttatta ctgtcagcag tataataact ggccattcac tttcggccct     300
gggaccaaag tggatatcaa ac                                              322

<210> SEQ ID NO 32
<211> LENGTH: 107
<212> TYPE: PRT
<213> ORGANISM: Human

<400> SEQUENCE: 32

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Val Leu Ile
        35                  40                  45

Tyr Gly Ala Ser Thr Arg Ala Thr Gly Ile Pro Val Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Phe
                85                  90                  95

Thr Phe Gly Pro Gly Thr Lys Val Asp Ile Lys
                100                 105

<210> SEQ ID NO 33
<211> LENGTH: 370
<212> TYPE: DNA
<213> ORGANISM: Human

```
<400> SEQUENCE: 33
cagatgcagc tgcaggagtc gggcccagga ctggtgaagc cttcgcagac cctgtccctc    60
acctgcactg tctctggtgg ctccatcagc agtggtggtc actactggag ctggatccgc   120
cagcaccccg ggaagggcct ggagtggatt gggtacatct attacagtgg gagcgcctac   180
tacaacccgt ccctcaagag tcgagttacc atatcagtag acacgtctaa gaaccagttc   240
tccctgaagc tgagctctgt gactgccgcg gacacggccg tgtattactg tgcgagagcg   300
gggcgatttt tggagtggtc tgatgttttt gatatctggg gccaaggac aatggtcacc    360 gtctctttag                                                          370

<210> SEQ ID NO 34
<211> LENGTH: 123
<212> TYPE: PRT
<213> ORGANISM: Human

<400> SEQUENCE: 34

Gln Met Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly His Tyr Trp Ser Trp Ile Arg Gln His Pro Gly Lys Gly Leu Glu
        35                  40                  45

Trp Ile Gly Tyr Ile Tyr Tyr Ser Gly Ser Ala Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Gly Arg Phe Leu Glu Trp Ser Asp Val Phe Asp Ile
            100                 105                 110

Trp Gly Gln Gly Thr Met Val Thr Val Ser Leu
        115                 120

<210> SEQ ID NO 35
<211> LENGTH: 340
<212> TYPE: DNA
<213> ORGANISM: Human

<400> SEQUENCE: 35
gacatcgtga tgacccagtc tccagactcc ctggctgtgt ctctgggcga gagggccacc    60
atcaactgca gtccagcca gagtgtttta tacagctcca acaataagaa ctacttaact   120
tggtaccagc agaaaccagg acggcctcct aagctgctca tttactgggc atctacccgg   180
gaatccgggg tccctgaccg attcagtggc agcgggtctg ggacagattt cactctcacc   240
atcagcagcc tgcaggctga agatgtggca gtttattact gtcaacaata ttataatact   300
cctccgacgt tcggccaagg gaccaaggtg gaaatcaagc                         340

<210> SEQ ID NO 36
<211> LENGTH: 113
<212> TYPE: PRT
<213> ORGANISM: Human

<400> SEQUENCE: 36

Asp Ile Val Met Thr Gln Ser Pro Asp Ser Leu Ala Val Ser Leu Gly
1               5                   10                  15
```

Glu Arg Ala Thr Ile Asn Cys Lys Ser Ser Gln Ser Val Leu Tyr Ser
                    20                  25                  30

Ser Asn Asn Lys Asn Tyr Leu Thr Trp Tyr Gln Gln Lys Pro Gly Arg
                35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
65                   70                  75                  80

Ile Ser Ser Leu Gln Ala Glu Asp Val Ala Val Tyr Cys Gln Gln
                    85                  90                  95

Tyr Tyr Asn Thr Pro Pro Thr Phe Gly Gln Gly Thr Lys Val Glu Ile
                100                 105                 110

Lys

<210> SEQ ID NO 37
<211> LENGTH: 379
<212> TYPE: DNA
<213> ORGANISM: Human

<400> SEQUENCE: 37
caggtgcagc tggtggagtc tgggggaggc ttggtcaagc ctggagggtc cctgagactc      60
tcctgtgcag cctctggatt caccttcagt gactactaca tgagctggat ccgccaggct     120
ccagggaagg ggctggagtg ggtttcatac attagtagta gtggtaatac catatactac     180
gcagactctg tgaagggccg attcaccatc tccagggaca acgccaggaa ctcactgtat     240
ctgcaaatga acagcctgag agccgaggac acggccgtgt attactgtgc gagggaagcc     300
tatgatagta gtggttacta ctactactac tacggtatgg acgtctgggg ccaagggacc     360
acggtcaccg tctcctcag                                                  379

<210> SEQ ID NO 38
<211> LENGTH: 126
<212> TYPE: PRT
<213> ORGANISM: Human

<400> SEQUENCE: 38

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
                20                  25                  30

Tyr Met Ser Trp Ile Arg Gln Ala Pro Gly Lys Gly Leu Glu Trp Val
            35                  40                  45

Ser Tyr Ile Ser Ser Ser Gly Asn Thr Ile Tyr Tyr Ala Asp Ser Val
     50                  55                  60

Lys Gly Arg Phe Thr Ile Ser Arg Asp Asn Ala Arg Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Tyr Asp Ser Ser Gly Tyr Tyr Tyr Tyr Tyr Tyr Gly
                100                 105                 110

Met Asp Val Trp Gly Gln Gly Thr Thr Val Thr Val Ser Ser
            115                 120                 125

<210> SEQ ID NO 39
<211> LENGTH: 337
<212> TYPE: DNA

<213> ORGANISM: Human

<400> SEQUENCE: 39

```
gatattgtga tgacccagac tccactctct ctgtccgtca cccctggaca gccggcctcc      60
atctcctgca agtctagtca gagcctcctg catagtgatg gaaagaccta cttgtattgg    120
tacctgcaga agccaggcca gcctccacag ctcctgatct atgaagtttc aaccggttc     180
tctggagtgc cagataggtt cagtggcagc gggtcaggga cagatttcac actgacaatc    240
agccgggtgg aggctgacga tgttggggtt tattactgca tgcaaagtac acaccttcct    300
tggacgttcg gccaagggac caaggtggaa atcaaac                             337
```

<210> SEQ ID NO 40
<211> LENGTH: 112
<212> TYPE: PRT
<213> ORGANISM: Human

<400> SEQUENCE: 40

```
Asp Ile Val Met Thr Gln Thr Pro Leu Ser Leu Ser Val Thr Pro Gly
1               5                   10                  15
Gln Pro Ala Ser Ile Ser Cys Lys Ser Ser Gln Ser Leu Leu His Ser
            20                  25                  30
Asp Gly Lys Thr Tyr Leu Tyr Trp Tyr Leu Gln Lys Pro Gly Gln Pro
        35                  40                  45
Pro Gln Leu Leu Ile Tyr Glu Val Ser Asn Arg Phe Ser Gly Val Pro
    50                  55                  60
Asp Arg Phe Ser Gly Ser Gly Ser Gly Thr Asp Phe Thr Leu Thr Ile
65                  70                  75                  80
Ser Arg Val Glu Ala Asp Asp Val Gly Val Tyr Tyr Cys Met Gln Ser
                85                  90                  95
Thr His Leu Pro Trp Thr Phe Gly Gln Gly Thr Lys Val Glu Ile Lys
                100                 105                 110
```

<210> SEQ ID NO 41
<211> LENGTH: 376
<212> TYPE: DNA
<213> ORGANISM: Human

<400> SEQUENCE: 41

```
gaggtgcagc tggtggagtc tgggggaggc ttggtaaagc ctggggggtc ccttagactc      60
tcctgtgcag cctctggatt cactttcagt aacgcctgga tgagctgggt ccgccaggct    120
ccagggaagg␣ggctggagtg␣ggttggccgt␣attaaaagca␣aaagtgatgg␣tgggacaaca    180
gactacgctg cacccgtgaa aggcagattc accatctcaa gagatgattc aaaaaacacg    240
ctgtatctgc aaatgaacag cctgaaaacc gaggacacag ccgtgtatta ctgtaccaca    300
gggaattact atgatggtag tggttattac tcttttgact actggggcca gggaaccctg    360
gtcaccgtct cctcag                                                    376
```

<210> SEQ ID NO 42
<211> LENGTH: 125
<212> TYPE: PRT
<213> ORGANISM: Human

<400> SEQUENCE: 42

```
Glu Val Gln Leu Val Glu Ser Gly Gly Gly Leu Val Lys Pro Gly Gly
1               5                   10                  15
Ser Leu Arg Leu Ser Cys Ala Ala Ser Gly Phe Thr Phe Ser Asn Ala
```

```
                        20                  25                  30
Trp Met Ser Trp Val Arg Gln Ala Pro Gly Lys Gly Leu Glu Trp Val
                35                  40                  45

Gly Arg Ile Lys Ser Lys Ser Asp Gly Gly Thr Thr Asp Tyr Ala Ala
         50                  55                  60

Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Thr Thr Gly Asn Tyr Tyr Asp Gly Ser Gly Tyr Tyr Ser Phe
            100                 105                 110

Asp Tyr Trp Gly Gln Gly Thr Leu Val Thr Val Ser Ser
            115                 120                 125

<210> SEQ ID NO 43
<211> LENGTH: 337
<212> TYPE: DNA
<213> ORGANISM: Human

<400> SEQUENCE: 43
gatattgtga tgactcagtc tccactctcc ctgcccgtca cccctggaga gccggcctcc     60
atctcctgca ggtctagtca gagcctcctg catagtaatg gatacaacta tttggattgg    120
tacctgcaga agccagggca gtctccacag ctcctgatct atttgggttc aatcgggcc     180 tccggggtcc ctgacaggtt cagtggcagt ggatcaggca cagatttac actgaaaatc     240 agcagagtgg aggctgagga tgttggggtt tattactgca tgcaagctct acaaactcct    300
cccactttcg gcggagggac caaggtggag atcaaac                            337

<210> SEQ ID NO 44
<211> LENGTH: 112
<212> TYPE: PRT
<213> ORGANISM: Human

<400> SEQUENCE: 44

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
             20                  25                  30

Asn Gly Tyr Asn Tyr Leu Asp Trp Tyr Leu Gln Lys Pro Gly Gln Ser
         35                  40                  45

Pro Gln Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro Pro Thr Phe Gly Gly Gly Thr Lys Val Glu Ile Lys
            100                 105                 110

<210> SEQ ID NO 45
<211> LENGTH: 355
<212> TYPE: DNA
<213> ORGANISM: Human

<400> SEQUENCE: 45
caggtgcagc tgcaggagtc gggcccagga ctggtgaagc cttcacagac cctgtccctc     60
```

```
acctgcactg tctctggtgg ctccatcagc agtaatgatt actactggaa ctggatccgc    120
cagcacccag ggaagggcct ggagtggatt gggtacatct attacagtgg gagcacctac    180
tacaacccgt ccctcaagag tcgagttacc atatcagtag acacgtctaa gaaccagttc    240
tccctgaagc tgagctctgt gactgccgcg gacacggccg tgtattactg tgcgagagaa    300
tccacggacg gtatggacgt ctggggccaa gggaccacgg tcaccgtctc ctcag         355
```

<210> SEQ ID NO 46
<211> LENGTH: 118
<212> TYPE: PRT
<213> ORGANISM: Human

<400> SEQUENCE: 46

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Asn
            20                  25                  30

Asp Tyr Tyr Trp Asn Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Ser Thr Asp Gly Met Asp Val Trp Gly Gln Gly Thr
            100                 105                 110

Thr Val Thr Val Ser Ser
        115
```

<210> SEQ ID NO 47
<211> LENGTH: 325
<212> TYPE: DNA
<213> ORGANISM: Human

<400> SEQUENCE: 47

```
gaaaatgtgt tgacgcagtc tccaggcacc ctgtctttgt ctccagggga aagagccacc     60
ctctcctgca gggccagtca gagtgttagc agcaactact tagcctggta ccagcagaaa    120
cctggccagg ctcccaggct cctcatctat ggtgcttcca gcggggccac tggcatccca    180
gacaggttca gtggcagtgg gtctgggaca gacttcactc tcaccatcag cagactggag    240
cctgaagatt ttgcagtgta ttactgtcag cattatggta gctcaccgat caccttcggc    300
caagggacac gactggagat taaac                                          325
```

<210> SEQ ID NO 48
<211> LENGTH: 108
<212> TYPE: PRT
<213> ORGANISM: Human

<400> SEQUENCE: 48

```
Glu Asn Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
        35                  40                  45
```

```
Ile Tyr Gly Ala Ser Ser Gly Ala Thr Gly Ile Pro Asp Arg Phe Ser
            50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln His Tyr Gly Ser Ser Pro
                85                  90                  95

Ile Thr Phe Gly Gln Gly Thr Arg Leu Glu Ile Lys
            100                 105
```

```
<210> SEQ ID NO 49
<211> LENGTH: 361
<212> TYPE: DNA
<213> ORGANISM: Human

<400> SEQUENCE: 49
caggtgcagc tgcaggagtc gggcccagga ctggtgaagc cttcacagac cctgtccctc      60
acctgcactg tctctggtgg ctccatcagc agtggtgatt actactggag ctggatccgc     120
cagcacccag ggaagggcct ggagtggatt gggtacatct attacagtgg gagcacctac     180
tacaacccgt ccctcaagag tcgagttacc atatcaatag acacgtctaa gaaccagttc     240
tccctgaagc tgagctctgt gactgccgcg gacacggccg tgtattactg tgcgagagaa     300
cgtgactacg gtggtggctt tgactactgg ggccagggaa ccctggtcac cgtctcctca     360
g                                                                     361

<210> SEQ ID NO 50
<211> LENGTH: 120
<212> TYPE: PRT
<213> ORGANISM: Human

<400> SEQUENCE: 50

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
                20                  25                  30

Asp Tyr Tyr Trp Ser Trp Ile Arg Gln His Pro Gly Lys Gly Leu Glu
            35                  40                  45

Trp Ile Gly Tyr Ile Tyr Tyr Ser Gly Ser Thr Tyr Tyr Asn Pro Ser
 50                  55                  60

Leu Lys Ser Arg Val Thr Ile Ser Ile Asp Thr Ser Lys Asn Gln Phe
 65                  70                  75                  80

Ser Leu Lys Leu Ser Ser Val Thr Ala Ala Asp Thr Ala Val Tyr Tyr
                85                  90                  95

Cys Ala Arg Glu Arg Asp Tyr Gly Gly Gly Phe Asp Tyr Trp Gly Gln
            100                 105                 110

Gly Thr Leu Val Thr Val Ser Ser
            115                 120

<210> SEQ ID NO 51
<211> LENGTH: 340
<212> TYPE: DNA
<213> ORGANISM: Human

<400> SEQUENCE: 51
gacatcgtga tgacccagtc tccagactcc ctggctgtgt ctctgggcga gagggccacc      60
atcaactgca gtccagcca gagtgtttta tacagctcca tcaataagat ctacttagct     120
tggtaccagc agaaaccagg acagcctcct aagctgctca tttactgggc atctacccgg     180
```

```
gaatccgggg tccctgaccg attcagtggc agcgggtctg ggacagattt cactctcacc    240
atcagcagcc tgcaggctga agatgtggca gtttattact gtcaccaata ttatagtact    300
ccgtggacgt tcggccaagg gaccaaggtg gaaatcaaac                          340
```

<210> SEQ ID NO 52
<211> LENGTH: 113
<212> TYPE: PRT
<213> ORGANISM: Human

<400> SEQUENCE: 52

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Ile Asn Lys Ile Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys His Gln
                85                  90                  95

Tyr Tyr Ser Thr Pro Trp Thr Phe Gly Gln Gly Thr Lys Val Glu Ile
            100                 105                 110

Lys

<210> SEQ ID NO 53
<211> LENGTH: 355
<212> TYPE: DNA
<213> ORGANISM: Human

<400> SEQUENCE: 53

```
caggtgcagc tgcaggagtc gggcccagga ctggtgaagc cttcacagac cctgtccctc     60
acctgcactg tctctggtgg ctccatcagc agtggtgatt actactggaa ctggatccgc    120
cagcacccag ggaagggcct ggagtggatt gggtacatct attacagtgg gagcacctac    180
tacaacccgt ccctcaagag tcgagttacc atttcagtag ccacgtctaa gaaccagttc    240
tccctgaagc tgagctctgt gactgccgcg gacacggccg tgtattactg tgcgagagag    300
gctacggagg ggtttgacta ctggggccag ggaaccctgg tcaccgtctc ctcag        355
```

<210> SEQ ID NO 54
<211> LENGTH: 118
<212> TYPE: PRT
<213> ORGANISM: Human

<400> SEQUENCE: 54

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Asn Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Ala Thr Ser Lys Asn Gln Phe

```
                65                  70                  75                  80
Ser Leu Lys Leu Ser Ser Val Thr Ala Ala Asp Thr Ala Val Tyr Tyr
                    85                  90                  95

Cys Ala Arg Glu Ala Thr Glu Gly Phe Asp Tyr Trp Gly Gln Gly Thr
                100                 105                 110

Leu Val Thr Val Ser Ser
            115

<210> SEQ ID NO 55
<211> LENGTH: 325
<212> TYPE: DNA
<213> ORGANISM: Human

<400> SEQUENCE: 55
gaaattgtgt tgacgcagtc tccaggcacc ctgtctttgt ctccagggga aagggccacc      60
ctctcctgca gggccagtca gagtgttagc accacctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcactgta ttactgtcag cactatggta cctcatcgat caccttcggc     300
caagggacac gactggagat taaac                                           325

<210> SEQ ID NO 56
<211> LENGTH: 108
<212> TYPE: PRT
<213> ORGANISM: Human

<400> SEQUENCE: 56

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Thr Thr
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Leu Tyr Tyr Cys Gln His Tyr Gly Thr Ser Ser
                85                  90                  95

Ile Thr Phe Gly Gln Gly Thr Arg Leu Glu Ile Lys
            100                 105

<210> SEQ ID NO 57
<211> LENGTH: 355
<212> TYPE: DNA
<213> ORGANISM: Human

<400> SEQUENCE: 57
caggtgcagc tgcaggagtc gggcccagga ctggtgaagc cttcacagac cctgtccctc      60
acctgcactg tctctggtgg ctccatcagc agtggtgatt actactggaa ctggatccgc     120
cagcacccag ggaagggcct ggagtggatt gggtacatct attacagtgg gagcacctac     180
tacaacccgt ccctcaagag tcgagttacc atatcagtag acacgtctaa gaaccagttc     240
tccctgaagc tgagctctgt gactgccgcg gacacggccg tgtattactg tgcgagagaa     300
tccacggacg gtatggacgt ctggggccaa gggaccacgg tcaccgtctc ctcag          355
```

<210> SEQ ID NO 58
<211> LENGTH: 118
<212> TYPE: PRT
<213> ORGANISM: Human

<400> SEQUENCE: 58

Gln Val Gln Leu Gln Glu Ser Gly Pro Gly Leu Val Lys Pro Ser Gln
1               5                   10                  15

Thr Leu Ser Leu Thr Cys Thr Val Ser Gly Ser Ile Ser Ser Gly
            20                  25                  30

Asp Tyr Tyr Trp Asn Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Ser Thr Asp Gly Met Asp Val Trp Gly Gln Gly Thr
            100                 105                 110

Thr Val Thr Val Ser Ser
        115

<210> SEQ ID NO 59
<211> LENGTH: 325
<212> TYPE: DNA
<213> ORGANISM: Human

<400> SEQUENCE: 59
gaaagtgtgt tgacgcagtc tcctggcacc ctgtctttgt ctccagggga aagagccacc      60
ctctcctgca gggccagtca gagtgttagc agcagctact tagcctggta ccagcagaaa     120
cctggccagg ctcccaggct cctcatatat ggtgtttcca gcagggccac tggcatccca     180
gacaggttca gtggcagtgg gtctgggaca gacttcactc tcaccatcag cagactggag     240
cctgaagatt ttgcagtgta ttactgtcag cagtatggta gctcaccgat caccttcggc     300
caagggacac gactggagat taaac                                          325

<210> SEQ ID NO 60
<211> LENGTH: 108
<212> TYPE: PRT
<213> ORGANISM: Human

<400> SEQUENCE: 60

Glu Ser Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Val Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Ile Thr Phe Gly Gln Gly Thr Arg Leu Glu Ile Lys
            100                 105

<210> SEQ ID NO 61
<211> LENGTH: 355
<212> TYPE: DNA
<213> ORGANISM: Human

<400> SEQUENCE: 61

```
caggtgcagc tgcaggagtc gggcccagga ctggtgaagc cttcacagac cctgtccctc    60
acctgcactg tctctggtgg ctccatcagc agtggtgatt actactggaa ctggatccgc   120
cagcacccag ggaagggcct ggagtggatt gggtacatct attacagtgg gagcacctac   180
tacaacccgt ccctcaagag tcgagttacc atatcagtag acacgtctaa gaaccagttc   240
tccctgaagc tgagctctgt gactgccgcg gacacggccg tgtattactg tgcgagagag   300
gatattgcag gattcgaccc ctggggccag ggaaccctgg tcaccgtctc ctcag        355
```

<210> SEQ ID NO 62
<211> LENGTH: 118
<212> TYPE: PRT
<213> ORGANISM: Human

<400> SEQUENCE: 62

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Asn Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Asp Ile Ala Gly Phe Asp Pro Trp Gly Gln Gly Thr
            100                 105                 110

Leu Val Thr Val Ser Ser
        115

<210> SEQ ID NO 63
<211> LENGTH: 325
<212> TYPE: DNA
<213> ORGANISM: Human

<400> SEQUENCE: 63

```
gaaattgtgt tgacgcagtc tccaggcacc ctgtctttgt ctccagggga aagagccacc    60
ctctcctgca gggccagtca gagtgttagc agcagctact tagcctggta ccagcagaaa   120
cctggccagg ctcccaggct cctcatctac ggtgcatcca gcagggccac tggcatccca   180
gacaggttca gtggcagtgg gtctgggaca gactccactc tcaccatcag cagactggag   240
cctgaagatt ttgcagtata ttactgtcag cagtatggta gctcacctat caccttcggc   300
caagggacac gactggagat taaac                                          325
```

<210> SEQ ID NO 64
<211> LENGTH: 108
<212> TYPE: PRT

<213> ORGANISM: Human

<400> SEQUENCE: 64

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Ile Thr Phe Gly Gln Gly Thr Arg Leu Glu Ile Lys
            100                 105

<210> SEQ ID NO 65
<211> LENGTH: 355
<212> TYPE: DNA
<213> ORGANISM: Human

<400> SEQUENCE: 65
caggtgcagc tgcaggagtc gggcccagga ctggtgaagc cttcacagac cctgtccctc     60
acctgcactg tctctggtgg ctccatcagc agtggtgaat actactggag ctggatccgc    120
cagcacccag ggaagggcct ggagtggatt gggtatatct tttacagtgg gagcacctac    180
tacaacccgt ccctcaagag tcgagttacc atatcactag acacgtctaa gaaccagttc    240
tccctgaagc tgagctctgt gactgccgcg gacacggccg tgtattactg tgcgagagaa    300
tccacggacg gtatggacgt ctggggccaa gggaccacgg tcaccgtctc ctcag         355

<210> SEQ ID NO 66
<211> LENGTH: 118
<212> TYPE: PRT
<213> ORGANISM: Human

<400> SEQUENCE: 66

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Glu Tyr Tyr Trp Ser Trp Ile Arg Gln His Pro Gly Lys Gly Leu Glu
        35                  40                  45

Trp Ile Gly Tyr Ile Phe Tyr Ser Gly Ser Thr Tyr Tyr Asn Pro Ser
    50                  55                  60

Leu Lys Ser Arg Val Thr Ile Ser Leu Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Ser Thr Asp Gly Met Asp Val Trp Gly Gln Gly Thr
            100                 105                 110

Thr Val Thr Val Ser Ser
        115

<210> SEQ ID NO 67

```
<211> LENGTH: 325
<212> TYPE: DNA
<213> ORGANISM: Human

<400> SEQUENCE: 67
gaaattgtgt tgacgcagtc tccaggcacc ctgtctttgt ctccagggga aagagccacc        60
ctctcctgca gggccagtca gagtgttagc agcagctact tagcctggta ccagcggaaa       120
cctggccagg ctcccaggct cctcatatat ggtgtatcca gtagggccac tggcatccca       180
gacaggttca gtggcagtgg gtctgggaca gacttcactc tcaccatcag cagactggag       240
cctgaagatt ttgcagtgta ttactgtcag caatatggta gctcaatgat caccttcggc       300
caagggacac gactggagat taaac                                              325

<210> SEQ ID NO 68
<211> LENGTH: 108
<212> TYPE: PRT
<213> ORGANISM: Human

<400> SEQUENCE: 68

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Arg Lys Pro Gly Gln Ala Pro Arg Leu Leu
        35                  40                  45

Ile Tyr Gly Val Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Met
                85                  90                  95

Ile Thr Phe Gly Gln Gly Thr Arg Leu Glu Ile Lys
            100                 105

<210> SEQ ID NO 69
<211> LENGTH: 355
<212> TYPE: DNA
<213> ORGANISM: Human

<400> SEQUENCE: 69
caggtgcagc tgcaggagtc gggcccagga ctggtgaagc cttcacagac cctgtccctc        60
acctgcactg tctctggtgg ctccatcagc agtggtgatt actactggaa ctggatccgc       120
cagcacccag ggaagggcct ggagtggatt gggtacatct attacagtgg gagcacctac       180
tacaacccgt ccctcaagag tcgagttacc atatcagtag acacgtctaa gaaccagttc       240
tccctgaagc tgagctctgt gactgccgcg gacacggccg tgtattactg cgagagag        300 ggcctcgagg cttttgatat ctggggtcaa gggacaatgg tcaccgactc ttcag             355

<210> SEQ ID NO 70
<211> LENGTH: 118
<212> TYPE: PRT
<213> ORGANISM: Human

<400> SEQUENCE: 70

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
```

```
                    20                  25                  30

Asp Tyr Tyr Trp Asn Trp Ile Arg Gln His Pro Gly Lys Gly Leu Glu
            35                  40                  45

Trp Ile Gly Tyr Ile Tyr Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                85                  90                  95

Cys Ala Arg Glu Gly Leu Glu Ala Phe Asp Ile Trp Gly Gln Gly Thr
                100                 105                 110

Met Val Thr Asp Ser Ser
        115

<210> SEQ ID NO 71
<211> LENGTH: 325
<212> TYPE: DNA
<213> ORGANISM: Human

<400> SEQUENCE: 71
gaaattgtgt tgacgcagtc tccaggcacc ctgtctttgt ctccagggga aagagccacc     60
ctctcctgca gggccagtca gagtgttagc agcagctact tagcctggta ccagcagaaa   120
cctggccagg ctcccaggct cctcatctat gatgcatcca gcagggccac tggcatccca   180
gacaggttca gtggcagtgg gtctgggaca gacttcactc tcaccatcag cagactggag   240
cctgaagatt ttgcagtgta ctactgtcag cattatggta gctcacttct cactttcggc   300
ggagggacca aggtggagat caaac                                         325

<210> SEQ ID NO 72
<211> LENGTH: 108
<212> TYPE: PRT
<213> ORGANISM: Human

<400> SEQUENCE: 72

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Asp Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln His Tyr Gly Ser Ser Leu
                85                  90                  95

Leu Thr Phe Gly Gly Gly Thr Lys Val Glu Ile Lys
                100                 105

<210> SEQ ID NO 73
<211> LENGTH: 355
<212> TYPE: DNA
<213> ORGANISM: Human

<400> SEQUENCE: 73
caggtgcagc tgcaggagtc gggcccagga ctggtgaagc cttcacagac cctgtccctc     60
```

```
acctgcactg tctctggtgg ctccatcagc agtggtgatt actactggaa ctggatccgc    120
cagcacccag ggaagggcct ggagtggatt gggtacatct attacagtgg gagcacctac    180
tacaactcgt ccctcaagag tcgagttacc atatcagtag acacgtctaa gaaccagttc    240
tccctgaagc tgagctctgt gactgccgcg gacacggccg tgtattactg tgcgagagag    300
ggccagaacg gtatggacgt ctggggccaa gggaccacgg tcaccgtctc ctcag         355

<210> SEQ ID NO 74
<211> LENGTH: 118
<212> TYPE: PRT
<213> ORGANISM: Human

<400> SEQUENCE: 74

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Asn Trp Ile Arg Gln His Pro Gly Lys Gly Leu Glu
        35                  40                  45

Trp Ile Gly Tyr Ile Tyr Tyr Ser Gly Ser Thr Tyr Tyr Asn Ser Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Gly Gln Asn Gly Met Asp Val Trp Gly Gln Gly Thr
            100                 105                 110

Thr Val Thr Val Ser Ser
        115

<210> SEQ ID NO 75
<211> LENGTH: 340
<212> TYPE: DNA
<213> ORGANISM: Human

<400> SEQUENCE: 75
gatgttgtga tgactcagtc tccactctcc ctgcccgtca cccttggaca gccggcctcc     60
atctcctgca ggtctagtca aagcctcgta tacagtgatg gaaacaccta cttgaattgg    120
tttcagcaga ggccaggcca atctccaagg cgcctaattt ataaggtttc taactgggac    180
tctggggtcc cagacagatt cagcggcagt gggtcaggca ctgatttcac actgaaaatc    240
agcagggtgg aggctgagga tgttggggtt tattactgca tgcaaggtac acactggcct    300
ccgtggacgt tcggccaagg gaccaaggtg gaaatcaaac                          340

<210> SEQ ID NO 76
<211> LENGTH: 113
<212> TYPE: PRT
<213> ORGANISM: Human

<400> SEQUENCE: 76

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45
```

```
Pro Arg Arg Leu Ile Tyr Lys Val Ser Asn Trp Asp Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Met Gln Gly
                85                  90                  95
Thr His Trp Pro Pro Trp Thr Phe Gly Gln Gly Thr Lys Val Glu Ile
            100                 105                 110
Lys
```

<210> SEQ ID NO 77
<211> LENGTH: 358
<212> TYPE: DNA
<213> ORGANISM: Human

<400> SEQUENCE: 77

```
gaggtgcagc tggtggagtc tgggggaggc ttggtaaagc ctgggggtc ccttagactc       60
tcctgtgcag cctctggatt cactttcagt aacgcctgga tgagctgggt ccgccaggct     120
ccagggaagg gctggagtg gttggccgt attaaaagca aaactgatgg tgggacaaca       180
gactacgctg cacccgtgaa aggcagattc accatctcaa gagatgattc aaaaaacacg    240
ctgtatctgc aaatgaacag cctgaaaacc gaggacacag ccgtgtatta ctgtaccaca    300
ggggatggaa cgcactttga ctactggggc cagggaaccc tggtcaccgt ctcctcag     358
```

<210> SEQ ID NO 78
<211> LENGTH: 119
<212> TYPE: PRT
<213> ORGANISM: Human

<400> SEQUENCE: 78

```
Glu Val Gln Leu Val Glu Ser Gly Gly Gly Leu Val Lys Pro Gly Gly
1               5                   10                  15
Ser Leu Arg Leu Ser Cys Ala Ala Ser Gly Phe Thr Phe Ser Asn Ala
                20                  25                  30
Trp Met Ser Trp Val Arg Gln Ala Pro Gly Lys Gly Leu Glu Trp Val
            35                  40                  45
Gly Arg Ile Lys Ser Lys Thr Asp Gly Gly Thr Thr Asp Tyr Ala Ala
    50                  55                  60
Pro Val Lys Gly Arg Phe Thr Ile Ser Arg Asp Asp Ser Lys Asn Thr
65                  70                  75                  80
Leu Tyr Leu Gln Met Asn Ser Leu Lys Thr Glu Asp Thr Ala Val Tyr
                85                  90                  95
Tyr Cys Thr Thr Gly Asp Gly Thr His Phe Asp Tyr Trp Gly Gln Gly
            100                 105                 110
Thr Leu Val Thr Val Ser Ser
        115
```

<210> SEQ ID NO 79
<211> LENGTH: 322
<212> TYPE: DNA
<213> ORGANISM: Human

<400> SEQUENCE: 79

```
gaaacgacac tcacgcagtc tccagcattc atgtcagcga ctccaggaga caaagtcaac     60
atctcctgca agccagcca agacattgat gatgatatga actggtacca acagaaacca    120
ggagaagctg ctattttcat tattcaagaa gctactactc tcgttcctgg aatcccacct    180
```
cgattcagtg gcagcgggta tggaacagat tttaccctca caattaataa catagaatct     240
gaggatgctg catattactt ctgtctacaa catgataatt ccccgctcac tttcggcgga     300
gggaccaagg tggagatcaa ac                                              322

<210> SEQ ID NO 80
<211> LENGTH: 107
<212> TYPE: PRT
<213> ORGANISM: Human

<400> SEQUENCE: 80

Glu Thr Thr Leu Thr Gln Ser Pro Ala Phe Met Ser Ala Thr Pro Gly
1               5                   10                  15

Asp Lys Val Asn Ile Ser Cys Lys Ala Ser Gln Asp Ile Asp Asp Asp
                20                  25                  30

Met Asn Trp Tyr Gln Gln Lys Pro Gly Glu Ala Ala Ile Phe Ile Ile
            35                  40                  45

Gln Glu Ala Thr Thr Leu Val Pro Gly Ile Pro Pro Arg Phe Ser Gly
        50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro Leu
                85                  90                  95

Thr Phe Gly Gly Gly Thr Lys Val Glu Ile Lys
            100                 105

<210> SEQ ID NO 81
<211> LENGTH: 379
<212> TYPE: DNA
<213> ORGANISM: Human

<400> SEQUENCE: 81
caggtgcagc tggtggagtc tgggggaggc ttggtcaagc ctggagggtc cctgagactc      60
tcctgtgcag cctctggatt caccttcagt gactactaca tgagctggat ccgccaggct     120
ccagggaagg gctggagtg gtttcatac attagtagta gtggtagtac cacatactac      180
gcagactctg tgaagggccg attcaccatc tccagggaca acgccaagaa gtcactgtat     240
ctgcaaatga acagcctgag agccgaggac acggccgtgt attactgtgc gagagaggg      300 tatagcagtg gctggtacga ggactactac tacggtatgg acgtctgggg ccaagggacc     360
acggtcaccg tctcctcag                                                  379

<210> SEQ ID NO 82
<211> LENGTH: 126
<212> TYPE: PRT
<213> ORGANISM: Human

<400> SEQUENCE: 82

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
                20                  25                  30

Tyr Met Ser Trp Ile Arg Gln Ala Pro Gly Lys Gly Leu Glu Trp Val
            35                  40                  45

Ser Tyr Ile Ser Ser Ser Gly Ser Thr Thr Tyr Tyr Ala Asp Ser Val
        50                  55                  60

Lys Gly Arg Phe Thr Ile Ser Arg Asp Asn Ala Lys Lys Ser Leu Tyr

```
            65                  70                  75                  80
Leu Gln Met Asn Ser Leu Arg Ala Glu Asp Thr Ala Val Tyr Tyr Cys
                    85                  90                  95

Ala Arg Glu Gly Tyr Ser Ser Gly Trp Tyr Glu Asp Tyr Tyr Tyr Gly
                100                 105                 110

Met Asp Val Trp Gly Gln Gly Thr Thr Val Thr Val Ser Ser
                115                 120                 125

<210> SEQ ID NO 83
<211> LENGTH: 337
<212> TYPE: DNA
<213> ORGANISM: Human

<400> SEQUENCE: 83
gatattgtga tgacccagac tccactctct ctgtccgtca cccctggaca gccggcctcc      60
atctcctgca gtttagtca gagcctcctg catagtgatg gaaagaccta tttgtattgg     120
tacctgcaga agccaggcca gcctccacag ctcctgatct atgaagtttc caaccggttt     180
tctggagtgc cagataggtt cagtggcagc gggtcaggga cagatttcac actgaaaatc     240
agccgggtgg aggctgagga tgttggggtt tattactgca tgcaaagtat acagcttcct     300
cggacgttcg gccaagggac caaggtggaa atcaaac                              337

<210> SEQ ID NO 84
<211> LENGTH: 112
<212> TYPE: PRT
<213> ORGANISM: Human

<400> SEQUENCE: 84

Asp Ile Val Met Thr Gln Thr Pro Leu Ser Leu Ser Val Thr Pro Gly
 1               5                  10                  15

Gln Pro Ala Ser Ile Ser Cys Lys Phe Ser Gln Ser Leu Leu His Ser
                20                  25                  30

Asp Gly Lys Thr Tyr Leu Tyr Trp Tyr Leu Gln Lys Pro Gly Gln Pro
            35                  40                  45

Pro Gln Leu Leu Ile Tyr Glu Val Ser Asn Arg Phe Ser Gly Val Pro
        50                  55                  60

Asp Arg Phe Ser Gly Ser Gly Ser Gly Thr Asp Phe Thr Leu Lys Ile
 65                 70                  75                  80

Ser Arg Val Glu Ala Glu Asp Val Gly Val Tyr Tyr Cys Met Gln Ser
                85                  90                  95

Ile Gln Leu Pro Arg Thr Phe Gly Gln Gly Thr Lys Val Glu Ile Lys
                100                 105                 110

<210> SEQ ID NO 85
<211> LENGTH: 388
<212> TYPE: DNA
<213> ORGANISM: Human

<400> SEQUENCE: 85
caggtgcagc tggtggagtc tgggggaggc ttggtcaagc ctggagggtc cctgagactc      60
tcctgtgcag cctctggatt caccttcagt gacttctaca tgagctggat ccgccaggct     120
ccagggaagg ggctggaatg gatttcatac attagtagta gtggtagtac catttactac     180
gcagactctg tgaagggccg attcaccatg tccagggaca acgccaagaa ctcactgtat     240
ctgcaaatga acagcctgag agccgaggac acggccgtgt attattgtgc gagagaagga     300
tactatgatt cggggagtta ttataaggac tacgactact acggtatgga cgtctgggc      360
```

```
caagggacca cggtcaccgt ctcctcag                                          388
```

<210> SEQ ID NO 86
<211> LENGTH: 129
<212> TYPE: PRT
<213> ORGANISM: Human

<400> SEQUENCE: 86

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Phe
            20                  25                  30

Tyr Met Ser Trp Ile Arg Gln Ala Pro Gly Lys Gly Leu Glu Trp Ile
        35                  40                  45

Ser Tyr Ile Ser Ser Ser Gly Ser Thr Ile Tyr Tyr Ala Asp Ser Val
    50                  55                  60

Lys Gly Arg Phe Thr Met Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Tyr Tyr Asp Ser Gly Ser Tyr Tyr Lys Asp Tyr Asp
            100                 105                 110

Tyr Tyr Gly Met Asp Val Trp Gly Gln Gly Thr Thr Val Thr Val Ser
        115                 120                 125

Ser
```

<210> SEQ ID NO 87
<211> LENGTH: 337
<212> TYPE: DNA
<213> ORGANISM: Human

<400> SEQUENCE: 87

```
gatattgtga tgacccagac tccactctct ctgtccgtca cccctggaca gccggcctcc    60
atctcctgca gtctagtca gagcctcctg catagtgatg gaaagaccta tttgtattgg   120
tacctgcaga agccaggcca gcctccacag ctcctgatct atgaagtttc caaccggttc   180
tctggagtgc cagataggtt cagtggcagc gggtcaggga cagatttcac actgaaaatc   240
agccgggtgg aggctgagga tgttggggtt tattactgca tgcaaagtat acagcttcct   300
cggacgttcg gccaagggac caaggtggaa atcaaac                            337
```

<210> SEQ ID NO 88
<211> LENGTH: 112
<212> TYPE: PRT
<213> ORGANISM: Human

<400> SEQUENCE: 88

```
Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Pro
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80
```

Ser Arg Val Glu Ala Glu Asp Val Gly Val Tyr Tyr Cys Met Gln Ser
                85                  90                  95

Ile Gln Leu Pro Arg Thr Phe Gly Gln Gly Thr Lys Val Glu Ile Lys
            100                 105                 110

<210> SEQ ID NO 89
<211> LENGTH: 379
<212> TYPE: DNA
<213> ORGANISM: Human

<400> SEQUENCE: 89
caggtgcggc tggtggagtc tgggggaggc ttggtcaagc ctggagggtc cctgagactc    60
tcctgtgcag cctctggatt caccttcagt gactactaca tgagctggat ccgccaggct   120
ccagggaagg ggctggagtg ggtttcatac attagtagta gtggtatttc catatactac   180
gcagactctg tgaagggccg attcaccatc tccagggaca acgccaagaa ctcactgtat   240
ctgcaaatga acagcctgag agccgaggac acggccgtgt attactgtgc gagagaagga   300
tatagcagct cgtcacatta ctacgactac tacggtatgg acgtctgggg ccaagggacc   360
acggtcaccg tctcctcag                                                 379

<210> SEQ ID NO 90
<211> LENGTH: 126
<212> TYPE: PRT
<213> ORGANISM: Human

<400> SEQUENCE: 90

Gln Val Arg Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ile Ser Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Tyr Ser Ser Ser His Tyr Tyr Asp Tyr Tyr Gly
            100                 105                 110

Met Asp Val Trp Gly Gln Gly Thr Thr Val Thr Val Ser Ser
        115                 120                 125

<210> SEQ ID NO 91
<211> LENGTH: 337
<212> TYPE: DNA
<213> ORGANISM: Human

<400> SEQUENCE: 91
gatattgtga tgacccagac tccactctct ctgtccgtca cccctggaca gccggcctcc    60
atctcctgca agtctagtca gagcctcctg catagtgatg gaaagaccta tttgtattgg   120
tacctgcaga agccaggcca gcctccacag gtccttatct atgaagtttc caaccggttc   180
tctggagtgc cagataggtt cagtggcagc gggtcaggga cagatttcac actgaaaatc   240
agccgggtgg aggctgagga tgttgggggtt tattactgca tgcaaagtac acagcttcct   300
cggacgttcg gccaagggac caaggtggaa atcaaac 337

<210> SEQ ID NO 92
<211> LENGTH: 112
<212> TYPE: PRT
<213> ORGANISM: Human

<400> SEQUENCE: 92

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Pro
        35                  40                  45

Pro Gln Val Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Thr Gln Leu Pro Arg Thr Phe Gly Gln Gly Thr Lys Val Glu Ile Lys
            100                 105                 110

<210> SEQ ID NO 93
<211> LENGTH: 503
<212> TYPE: PRT
<213> ORGANISM: Cynomolgus Monkey

<400> SEQUENCE: 93

Met Thr Leu Gly Ser Pro Arg Arg Gly Leu Leu Met Leu Leu Met Ala
1               5                   10                  15

Leu Val Thr Gln Gly Asp Pro Val Lys Pro Ser Arg Gly Pro Leu Val
            20                  25                  30

Thr Cys Thr Cys Glu Ser Pro His Cys Arg Gly Pro Thr Cys Gln Gly
        35                  40                  45

Ala Trp Cys Thr Val Val Leu Val Arg Glu Glu Gly Arg His Pro Gln
    50                  55                  60

Glu His Arg Gly Cys Gly Asn Leu His Arg Glu Leu Cys Arg Gly Arg
65                  70                  75                  80

Pro Thr Glu Phe Val Asn His Tyr Cys Cys Asp Ser His Leu Cys Asn
                85                  90                  95

Arg Asn Val Ser Leu Val Leu Glu Ala Thr Gln Thr Pro Ser Glu Gln
            100                 105                 110

Pro Gly Thr Asp Ser Gln Leu Ala Leu Ile Leu Gly Pro Val Leu Ala
        115                 120                 125

Leu Leu Ala Leu Val Ala Leu Gly Val Val Gly Leu Trp His Val Arg
    130                 135                 140

Arg Arg Gln Glu Lys Gln Arg Gly Leu His Ser Glu Leu Gly Glu Ser
145                 150                 155                 160

Ser Leu Ile Leu Lys Ala Ser Glu Gln Gly Asp Ser Met Leu Gly Asp
                165                 170                 175

Leu Leu Asp Ser Asp Cys Thr Thr Gly Ser Gly Ser Gly Leu Pro Phe
            180                 185                 190

Leu Val Gln Arg Thr Val Ala Arg Gln Val Ala Leu Val Glu Cys Val
        195                 200                 205

Gly Lys Gly Arg Tyr Gly Glu Val Trp Arg Gly Leu Trp His Gly Glu

```
Ser Val Ala Val Lys Ile Phe Ser Ser Arg Asp Glu Gln Ser Trp Phe
225                 230                 235                 240

Arg Glu Thr Glu Ile Tyr Asn Thr Val Leu Leu Arg His Asp Asn Ile
                245                 250                 255

Leu Gly Phe Ile Ala Ser Asp Met Thr Ser Arg Asn Ser Ser Thr Gln
            260                 265                 270

Leu Trp Leu Ile Thr His Tyr His Glu His Gly Ser Leu Tyr Asp Phe
        275                 280                 285

Leu Gln Arg Gln Thr Leu Glu Pro His Leu Ala Leu Arg Leu Ala Val
    290                 295                 300

Ser Ala Ala Cys Gly Leu Ala His Leu His Val Glu Ile Phe Gly Thr
305                 310                 315                 320

Gln Gly Lys Pro Ala Ile Ala His Arg Asp Phe Lys Ser Arg Asn Val
                325                 330                 335

Leu Val Lys Ser Asn Leu Gln Cys Cys Ile Ala Asp Leu Gly Leu Ala
            340                 345                 350

Val Met His Ser Gln Gly Ser Asp Tyr Leu Asp Ile Gly Asn Asn Pro
        355                 360                 365

Arg Val Gly Thr Lys Arg Tyr Met Ala Pro Glu Val Leu Asp Glu Gln
    370                 375                 380

Ile Arg Thr Asp Cys Phe Glu Ser Tyr Lys Trp Thr Asp Ile Trp Ala
385                 390                 395                 400

Phe Gly Leu Val Leu Trp Glu Ile Ala Arg Arg Thr Ile Val Asn Gly
                405                 410                 415

Ile Val Glu Asp Tyr Arg Pro Pro Phe Tyr Asp Val Val Pro Asn Asp
            420                 425                 430

Pro Ser Phe Glu Asp Met Lys Lys Val Val Cys Val Asp Gln Gln Thr
        435                 440                 445

Pro Thr Ile Pro Asn Arg Leu Ala Ala Asp Pro Val Leu Ser Gly Leu
    450                 455                 460

Ala Gln Met Met Arg Glu Cys Trp Tyr Pro Asn Pro Ser Ala Arg Leu
465                 470                 475                 480

Thr Ala Leu Arg Ile Lys Lys Thr Leu Gln Lys Ile Ser Asn Ser Pro
                485                 490                 495

Glu Lys Pro Lys Val Ile Gln
            500

<210> SEQ ID NO 94
<211> LENGTH: 1512
<212> TYPE: DNA
<213> ORGANISM: Cynomolgus Monkey

<400> SEQUENCE: 94
atgaccttgg gctccccgag gagaggcctt ctgatgctgc tgatggcctt ggtgacccag      60
ggtgaccccg tgaagccctc tcggggcccg ctggtgacct gcacatgtga gagcccacat     120 tgcaggggc ctacctgcca gggggcctgg tgcacagtag tgctggtgcg ggaggagggg     180
aggcaccccc aggaacatcg gggctgcggg aacttgcaca gggagctctg caggggcgc     240 cccaccgagt tcgtcaacca ctactgctgt gacagccacc tctgcaaccg caacgtgtcc     300
ctggtgctgg aggccaccca aactccttcg gagcagccgg aacagacag ccagctggcc     360 ctgatcctgg gccccgtgct ggccttgctg gccctggtgg ccctgggtgt cgtgggcctg     420
tggcatgtcc gacggaggca ggagaagcag cggggcctgc acagcgagct gggagagtcc     480
```

```
agtctcatcc tgaaagcatc tgagcagggc gacagcatgt tgggggacct cctggacagt      540
gactgcacca cagggagtgg ctcggggctc cccttcctgg tgcagaggac agtggcacgg      600
caggttgcct tggtggagtg tgtgggaaaa ggccgctatg cgaagtgtg gcggggcttg       660 tggcacggtg agagtgtggc cgtcaagatc ttctcctcga gggacgaaca gtcctggttc      720
cgggagactg agatctacaa cacagtgttg ctcagacacg acaacatcct aggcttcatc      780
gcctcagaca tgacctcccg caactcgagc acgcagctgt ggctcatcac gcattaccac      840
gagcacggct ccctctacga ctttctgcag agacagacgc tggagccgca tttggctctg      900
aggctagctg tgtccgcagc ctgtggcctg cacacctgc acgtggagat cttcggtaca       960
cagggcaaac cggccattgc ccaccgtgac ttcaagagcc gcaacgtgct ggtcaagagc     1020
aacctgcagt gttgcattgc tgacctgggc ctggctgtga tgcactcaca gggcagcgat     1080
tacctggaca tcggcaacaa cccgagagta ggcaccaaga ggtacatggc acccgaggtg     1140
ctggatgagc agatccgcac ggactgcttt gagtcctata agtggactga catctgggcc     1200
tttggcctgg tgctgtggga gatcgcccgc cggaccatcg tgaacggcat cgtggaggac     1260
tatagaccac ccttctatga tgtggtgccc aatgacccca gctttgagga catgaagaag     1320
gtggtgtgtg tggatcagca gaccccccacc atccctaacc ggctggctgc agacccggtc    1380
ctctcaggcc tagctcagat gatgcgggag tgctggtacc aaacccctc tgcccgactc      1440 actgcgctgc ggatcaagaa gacactacag aaaattagca acagtccaga gaagcccaaa     1500
gtgattcagt ag                                                         1512
```

<210> SEQ ID NO 95
<211> LENGTH: 1332
<212> TYPE: DNA
<213> ORGANISM: Human

<400> SEQUENCE: 95

```
caggtgcagc tgcaggagtc gggcccagga ctggtgaagc cttcacagac cctgtccctc       60
acctgcactg tctctggtgg ctccatgagc agtggtgaat actactgaa ctggatccgc       120 cagcacccag ggaagggcct ggagtggatt gggtacatct attacagtgg gagtacctac      180
tacaacccgt ccctcaagag tcgagttacc atatcagtag acacgtctaa gaaccagttc      240
tccctgaagc tgagctctgt gactgccgcg gacacggccg tgtattactg tgcgagagag      300
tcagtggctg ggtttgacta ctggggccag ggaaccctgg tcaccgtctc ctcagcctcc      360
accaagggcc catcggtctt ccccctggcg ccctgctcca ggagcacctc cgagagcaca     420
gcggccctgg gctgcctggt caaggactac ttccccgaac cggtgacggt gtcgtggaac     480
tcaggcgctc tgaccagcgg cgtgcacacc ttcccagctg tcctacagtc ctcaggactc     540
tactccctca gcagcgtggt gaccgtgccc tccagcaact tcggcaccca gacctacacc     600
tgcaacgtag atcacaagcc cagcaacacc aaggtggaca agacagttga gcgcaaatgt    660
tgtgtcgagt gcccaccgtg cccagcacca cctgtggcag gaccgtcagt cttcctcttc    720 ccccaaaac ccaaggacac cctcatgatc tcccggaccc ctgaggtcac gtgcgtggtg     780
gtggacgtga gccacgaaga ccccgaggtc cagttcaact ggtacgtgga cggcgtggag    840
gtgcataatg ccaagacaaa gccacgggag gagcagttca acagcacgtt ccgtgtggtc     900
agcgtcctca ccgttgtgca ccaggactgg ctgaacggca aggagtacaa gtgcaaggtc     960
tccaacaaag gcctcccagc ccccatcgag aaaaccatct ccaaaaccaa agggcagccc    1020
```

```
cgagaaccac aggtgtacac cctgccccca tcccgggagg agatgaccaa gaaccaggtc    1080
agcctgacct gcctggtcaa aggcttctac cccagcgaca tcgccgtgga gtgggagagc    1140
aatgggcagc cggagaacaa ctacaagacc acacctccca tgctggactc cgacggctcc    1200
ttcttcctct acagcaagct caccgtggac aagagcaggt ggcagcaggg gaacgtcttc    1260
tcatgctccg tgatgcatga ggctctgcac aaccactaca cgcagaagag cctctccctg    1320
tctccgggta aa                                                        1332

<210> SEQ ID NO 96
<211> LENGTH: 33
<212> TYPE: DNA
<213> ORGANISM: Artificial
<220> FEATURE:
<223> OTHER INFORMATION: The forward primer used for cloning ECD of
      ALK-1

<400> SEQUENCE: 96
acggcccagc cggccgaccc tgtgaagccg tct                                 33

<210> SEQ ID NO 97
<211> LENGTH: 47
<212> TYPE: DNA
<213> ORGANISM: Artificial
<220> FEATURE:
<223> OTHER INFORMATION: The reverse primer used for cloning ECD of
      ALK-1

<400> SEQUENCE: 97
actaagcttt taatgatgat gatgatgatg ctggccatct gttcccg                  47

<210> SEQ ID NO 98
<211> LENGTH: 103
<212> TYPE: PRT
<213> ORGANISM: Human

<400> SEQUENCE: 98

Asp Pro Val Lys Pro Ser Arg Gly Pro Leu Val Thr Cys Thr Cys Glu
1               5                   10                  15

Ser Pro His Cys Lys Gly Pro Thr Cys Arg Gly Ala Trp Cys Thr Val
            20                  25                  30

Val Leu Val Arg Glu Glu Gly Arg His Pro Gln Glu His Arg Gly Cys
        35                  40                  45

Gly Asn Leu His Arg Glu Leu Cys Arg Gly Arg Pro Thr Glu Phe Val
    50                  55                  60

Asn His Tyr Cys Cys Asp Ser His Leu Cys Asn His Asn Val Ser Leu
65                  70                  75                  80

Val Leu Glu Ala Thr Gln Pro Pro Ser Glu Gln Pro Gly Thr Asp Gly
                85                  90                  95

Gln His His His His His His
            100

<210> SEQ ID NO 99
<211> LENGTH: 387
<212> TYPE: DNA
<213> ORGANISM: Human

<400> SEQUENCE: 99
atggagacag acacactcct gctatgggta ctgctgctct ggttccaggt tccactggt     60 gacgcggccc agccggccga ccctgtgaag ccgtctcggg gccgctggt gacctgcacg    120
```

-continued

```
tgtgagagcc cacattgcaa ggggcctacc tgccgggggg cctggtgcac agtagtgctg    180 gtgcggagg agggaggca ccccaggaa catcggggct gcggaactt gcacagggag        240 ctctgcaggg ggcgcccac cgagttcgtc aaccactact gctgcgacag ccacctctgc    300
aaccacaacg tgtccctggt gctggaggcc acccaacctc cttcggagca gccgggaaca    360
gatggccagc atcatcatca tcatcat                                        387
```

<210> SEQ ID NO 100
<211> LENGTH: 444
<212> TYPE: PRT
<213> ORGANISM: Human

<400> SEQUENCE: 100

| | | | | | | | | | | | | | | |
|---|---|---|---|---|---|---|---|---|---|---|---|---|---|---|
| Gln | Val | Gln | Leu | Gln | Glu | Ser | Gly | Pro | Gly | Leu | Val | Lys | Pro | Ser | Gln |
| 1 | | | | 5 | | | | | 10 | | | | | 15 | |
| Thr | Leu | Ser | Leu | Thr | Cys | Thr | Val | Ser | Gly | Gly | Ser | Met | Ser | Ser | Gly |
| | | | 20 | | | | | 25 | | | | | 30 | | |
| Glu | Tyr | Tyr | Trp | Asn | Trp | Ile | Arg | Gln | His | Pro | Gly | Lys | Gly | Leu | Glu |
| | | 35 | | | | | 40 | | | | | 45 | | | |
| Trp | Ile | Gly | Tyr | Ile | Tyr | Tyr | Ser | Gly | Ser | Thr | Tyr | Tyr | Asn | Pro | Ser |
| 50 | | | | | 55 | | | | | 60 | | | | | |
| Leu | Lys | Ser | Arg | Val | Thr | Ile | Ser | Val | Asp | Thr | Ser | Lys | Asn | Gln | Phe |
| 65 | | | | 70 | | | | | 75 | | | | | 80 | |
| Ser | Leu | Lys | Leu | Ser | Ser | Val | Thr | Ala | Ala | Asp | Thr | Ala | Val | Tyr | Tyr |
| | | | 85 | | | | | 90 | | | | | 95 | | |
| Cys | Ala | Arg | Glu | Ser | Val | Ala | Gly | Phe | Asp | Tyr | Trp | Gly | Gln | Gly | Thr |
| | | 100 | | | | | 105 | | | | | 110 | | | |
| Leu | Val | Thr | Val | Ser | Ser | Ala | Ser | Thr | Lys | Gly | Pro | Ser | Val | Phe | Pro |
| | | 115 | | | | | 120 | | | | | 125 | | | |
| Leu | Ala | Pro | Cys | Ser | Arg | Ser | Thr | Ser | Glu | Ser | Thr | Ala | Ala | Leu | Gly |
| 130 | | | | | 135 | | | | | 140 | | | | | |
| Cys | Leu | Val | Lys | Asp | Tyr | Phe | Pro | Glu | Pro | Val | Thr | Val | Ser | Trp | Asn |
| 145 | | | | | 150 | | | | | 155 | | | | | 160 |
| Ser | Gly | Ala | Leu | Thr | Ser | Gly | Val | His | Thr | Phe | Pro | Ala | Val | Leu | Gln |
| | | | | 165 | | | | | 170 | | | | | 175 | |
| Ser | Ser | Gly | Leu | Tyr | Ser | Leu | Ser | Ser | Val | Val | Thr | Val | Pro | Ser | Ser |
| | | | 180 | | | | | 185 | | | | | 190 | | |
| Asn | Phe | Gly | Thr | Gln | Thr | Tyr | Thr | Cys | Asn | Val | Asp | His | Lys | Pro | Ser |
| | | 195 | | | | | 200 | | | | | 205 | | | |
| Asn | Thr | Lys | Val | Asp | Lys | Thr | Val | Glu | Arg | Lys | Cys | Cys | Val | Glu | Cys |
| | 210 | | | | | 215 | | | | | 220 | | | | |
| Pro | Pro | Cys | Pro | Ala | Pro | Pro | Val | Ala | Gly | Pro | Ser | Val | Phe | Leu | Phe |
| 225 | | | | | 230 | | | | | 235 | | | | | 240 |
| Pro | Pro | Lys | Pro | Lys | Asp | Thr | Leu | Met | Ile | Ser | Arg | Thr | Pro | Glu | Val |
| | | | | 245 | | | | | 250 | | | | | 255 | |
| Thr | Cys | Val | Val | Val | Asp | Val | Ser | His | Glu | Asp | Pro | Glu | Val | Gln | Phe |
| | | | 260 | | | | | 265 | | | | | 270 | | |
| Asn | Trp | Tyr | Val | Asp | Gly | Val | Glu | Val | His | Asn | Ala | Lys | Thr | Lys | Pro |
| | | 275 | | | | | 280 | | | | | 285 | | | |
| Arg | Glu | Glu | Gln | Phe | Asn | Ser | Thr | Phe | Arg | Val | Val | Ser | Val | Leu | Thr |
| | 290 | | | | | 295 | | | | | 300 | | | | |
| Val | Val | His | Gln | Asp | Trp | Leu | Asn | Gly | Lys | Glu | Tyr | Lys | Cys | Lys | Val |
| 305 | | | | | 310 | | | | | 315 | | | | | 320 |
| Ser | Asn | Lys | Gly | Leu | Pro | Ala | Pro | Ile | Glu | Lys | Thr | Ile | Ser | Lys | Thr |

```
                    325                 330                 335
Lys Gly Gln Pro Arg Glu Pro Gln Val Tyr Thr Leu Pro Pro Ser Arg
                340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
        370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440

<210> SEQ ID NO 101
<211> LENGTH: 645
<212> TYPE: DNA
<213> ORGANISM: Human

<400> SEQUENCE: 101
gaaattgtgt tgacgcagtc tccaggcacc ctgtctttgt ctccagggga aagagacacc        60
ctctcctgta gggccagtca gagtgtcagc agcagctact tagcctggta ccagcagaaa       120
cctggccagg ctcccaggct cctcatctat ggtacatcca gcagggccac tggcatccca       180
gacaggttca gtggcagtgg gtctgggaca gacttcaccc tcaccatcag cagactggag       240
cctgaagatt ttgcagtgta ttactgtcag cagtatggta gctcgccgat caccttcggc       300
caagggacac gactggagat taaacgaact gtggctgcac catctgtctt catcttcccg       360
ccatctgatg agcagttgaa atctggaact gcctctgttg tgtgcctgct gaataacttc       420
tatcccagag aggccaaagt acagtggaag gtggataacg ccctccaatc gggtaactcc       480
caggagagtg tcacagagca ggacagcaag gacagcacct acagcctcag cagcaccctg       540
acgctgagca agcagactac gagaaacac aaagtctacg cctgcgaagt cacccatcag       600
ggcctgagct cgcccgtcac aaagagcttc aacaggggag agtgt                      645

<210> SEQ ID NO 102
<211> LENGTH: 215
<212> TYPE: PRT
<213> ORGANISM: Human

<400> SEQUENCE: 102

Glu Ile Val Leu Thr Gln Ser Pro Gly Thr Leu Ser Leu Ser Pro Gly
1               5                   10                  15

Glu Arg Asp Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Thr Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95
```

```
Ile Thr Phe Gly Gln Gly Thr Arg Leu Glu Ile Lys Arg Thr Val Ala
                100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 103
<211> LENGTH: 355
<212> TYPE: DNA
<213> ORGANISM: Human

<400> SEQUENCE: 103
caggtgcagc tgcaggagtc gggcccagga ctggtgaagc cttcacagac cctgtccctc    60
acctgcactg tctctggtgg ctccatgagc agtggtgaat actactggaa ctggatccgc   120
cagcacccag ggaagggcct ggagtggatt gggtacatct attacagtgg gagtacctac   180
tacaacccgt ccctcaagag tcgagttacc atatcagtag acacgtctaa gaaccagttc   240
tccctgaagc tgagctctgt gactgccgcg gacacggccg tgtattactg tgcgagagag   300
tcagtggctg gtttgacta ctggggccag ggaaccctgg tcaccgtctc ctcag        355

<210> SEQ ID NO 104
<211> LENGTH: 118
<212> TYPE: PRT
<213> ORGANISM: Human

<400> SEQUENCE: 104

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Met Ser Ser Gly
            20                  25                  30

Glu Tyr Tyr Trp Asn Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Ser Val Ala Gly Phe Asp Tyr Trp Gly Gln Gly Thr
            100                 105                 110

Leu Val Thr Val Ser Ser
        115

<210> SEQ ID NO 105
<211> LENGTH: 58
```

```
<212> TYPE: DNA
<213> ORGANISM: Artificial
<220> FEATURE:
<223> OTHER INFORMATION: Amplification Primer Used for Cloning Full-
      Length 1.12.1

<400> SEQUENCE: 105
tcttcaagct tgatatctct agaagccgcc accatgaaac acctgtggtt cttcctcc        58

<210> SEQ ID NO 106
<211> LENGTH: 46
<212> TYPE: DNA
<213> ORGANISM: Artificial
<220> FEATURE:
<223> OTHER INFORMATION: Amplification Primer Used for Cloning Full-
      Length 1.12.1

<400> SEQUENCE: 106
ttctctgatc agaattccta ctatttaccc ggagacaggg agaggc                     46

<210> SEQ ID NO 107
<211> LENGTH: 48
<212> TYPE: DNA
<213> ORGANISM: Artificial
<220> FEATURE:
<223> OTHER INFORMATION: Amplification Primer Used for Cloning Full-
      Length 1.12.1

<400> SEQUENCE: 107
tcttcaagct tcccgggagc cgccaccatg gaaaccccag cgcagctt                   48

<210> SEQ ID NO 108
<211> LENGTH: 49
<212> TYPE: DNA
<213> ORGANISM: Artificial
<220> FEATURE:
<223> OTHER INFORMATION: Amplification Primer Used for Cloning Full-
      Length 1.12.1

<400> SEQUENCE: 108
ttctttgatc agaattctca ctaacactct cccctgttga agctctttg                  49

<210> SEQ ID NO 109
<211> LENGTH: 32
<212> TYPE: DNA
<213> ORGANISM: Artificial
<220> FEATURE:
<223> OTHER INFORMATION: Mutagenic Oligonucleotide

<400> SEQUENCE: 109
ctccagggga aagagccacc ctctcctgta gg                                    32

<210> SEQ ID NO 110
<211> LENGTH: 32
<212> TYPE: DNA
<213> ORGANISM: Artificial
<220> FEATURE:
<223> OTHER INFORMATION: Mutagenic Oligonucleotide

<400> SEQUENCE: 110
cctacaggag agggtggctc tttcccctgg ag                                    32

<210> SEQ ID NO 111
<211> LENGTH: 30
<212> TYPE: DNA
<213> ORGANISM: Artificial
<220> FEATURE:
```

<223> OTHER INFORMATION: Mutagenic Oligonucleotide

<400> SEQUENCE: 111
ggtggctcca tcagcagtgg tgaatactac                                30

<210> SEQ ID NO 112
<211> LENGTH: 30
<212> TYPE: DNA
<213> ORGANISM: Artificial
<220> FEATURE:
<223> OTHER INFORMATION: Mutagenic Oligonucleotide

<400> SEQUENCE: 112
gtagtattca ccactgctga tggagccacc                                30

<210> SEQ ID NO 113
<211> LENGTH: 9
<212> TYPE: PRT
<213> ORGANISM: Human

<400> SEQUENCE: 113

Glu Ile Val Leu Thr Gln Ser Pro Gly
1               5

<210> SEQ ID NO 114
<211> LENGTH: 8
<212> TYPE: PRT
<213> ORGANISM: Human

<400> SEQUENCE: 114

Gln Val Gln Leu Gln Glu Ser Gly
1               5

<210> SEQ ID NO 115
<211> LENGTH: 21
<212> TYPE: DNA
<213> ORGANISM: Artificial
<220> FEATURE:
<223> OTHER INFORMATION: Forward Primer

<400> SEQUENCE: 115
agcgggccca gagggaccat g                                         21

<210> SEQ ID NO 116
<211> LENGTH: 28
<212> TYPE: DNA
<213> ORGANISM: Artificial
<220> FEATURE:
<223> OTHER INFORMATION: Reverse Primer

<400> SEQUENCE: 116
cagaaaggaa tcaggtgctc ctgggcta                                  28

<210> SEQ ID NO 117
<211> LENGTH: 28
<212> TYPE: DNA
<213> ORGANISM: Artificial
<220> FEATURE:
<223> OTHER INFORMATION: Forward Primer

<400> SEQUENCE: 117
gattatggcc ttgggctccc ccaggaaa                                  28

<210> SEQ ID NO 118
<211> LENGTH: 37

-continued

```
<212> TYPE: DNA
<213> ORGANISM: Artificial
<220> FEATURE:
<223> OTHER INFORMATION: Reverse Primer

<400> SEQUENCE: 118
gggctattga atcactttag gcttctctgg actgttg                              37

<210> SEQ ID NO 119
<211> LENGTH: 27
<212> TYPE: DNA
<213> ORGANISM: Artificial
<220> FEATURE:
<223> OTHER INFORMATION: TaqMan Probe (ID1-Probe)

<400> SEQUENCE: 119
ccagcacgtc atcgactaca tcaggga                                         27

<210> SEQ ID NO 120
<211> LENGTH: 22
<212> TYPE: DNA
<213> ORGANISM: Artificial
<220> FEATURE:
<223> OTHER INFORMATION: Taqman PCR Primer (ID1-F)

<400> SEQUENCE: 120
aaggtgagca aggtggagat tc                                              22

<210> SEQ ID NO 121
<211> LENGTH: 21
<212> TYPE: DNA
<213> ORGANISM: Artificial
<220> FEATURE:
<223> OTHER INFORMATION: Taqman PCR Primer (ID1-R)

<400> SEQUENCE: 121
ttccgagttc agctccaact g                                               21

<210> SEQ ID NO 122
<211> LENGTH: 25
<212> TYPE: PRT
<213> ORGANISM: Human

<400> SEQUENCE: 122

Gln Val Gln Leu Gln Glu Ser Gly Pro Gly Leu Val Lys Pro Ser Gln
 1               5                  10                  15

Thr Leu Ser Leu Thr Cys Thr Val Ser
             20                  25

<210> SEQ ID NO 123
<211> LENGTH: 12
<212> TYPE: PRT
<213> ORGANISM: Human

<400> SEQUENCE: 123

Gly Gly Ser Ile Ser Ser Gly Gly Tyr Tyr Trp Ser
 1               5                  10

<210> SEQ ID NO 124
<211> LENGTH: 25
<212> TYPE: PRT
<213> ORGANISM: Human

<400> SEQUENCE: 124

Gln Val Gln Leu Gln Glu Ser Gly Pro Gly Leu Val Lys Pro Ser Glu
```

```
                1               5                   10                  15
Thr Leu Ser Leu Thr Cys Thr Val Ser
                20                  25

<210> SEQ ID NO 125
<211> LENGTH: 12
<212> TYPE: PRT
<213> ORGANISM: Human

<400> SEQUENCE: 125

Gly Gly Ser Val Ser Ser Gly Gly Tyr Tyr Trp Ser
1               5                   10

<210> SEQ ID NO 126
<211> LENGTH: 325
<212> TYPE: DNA
<213> ORGANISM: Human

<400> SEQUENCE: 126
gaaattgtgt tgacgcagtc tccaggcacc ctgtctttgt ctccagggga aagagacacc      60
ctctcctgta gggccagtca gagtgtcagc agcagctact tagcctggta ccagcagaaa     120
cctggccagg ctcccaggct cctcatctat ggtacatcca gcagggccac tggcatccca     180
gacaggttca gtggcagtgg gtctgggaca gacttcaccc tcaccatcag cagactggag     240
cctgaagatt ttgcagtgta ttactgtcag cagtatggta gctcgccgat caccttcggc     300
caagggacac gactggagat taaac                                           325

<210> SEQ ID NO 127
<211> LENGTH: 108
<212> TYPE: PRT
<213> ORGANISM: Human

<400> SEQUENCE: 127

Glu Ile Val Leu Thr Gln Ser Pro Gly Thr Leu Ser Leu Ser Pro Gly
1               5                   10                  15

Glu Arg Asp Thr Leu Ser Cys Arg Ala Ser Gln Ser Val Ser Ser
                20                  25                  30

Tyr Leu Ala Trp Tyr Gln Gln Lys Pro Gly Gln Ala Pro Arg Leu Leu
            35                  40                  45

Ile Tyr Gly Thr Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Ile Thr Phe Gly Gln Gly Thr Arg Leu Glu Ile Lys
            100                 105

<210> SEQ ID NO 128
<211> LENGTH: 1332
<212> TYPE: DNA
<213> ORGANISM: Human

<400> SEQUENCE: 128
caggtgcagc tgcaggagtc gggtccagga ctggtgaagc cttcacagac cctgtccctc      60
acctgcactg tctctggtgg ctccatgagc agtggtgaat actactggaa ctggatccgc     120
cagcacccag ggaagggcct ggagtggatt gggtacatct attacagtgg gagtacctac     180
```

```
tacaacccgt ccctcaagag tcgagttacc atatcagtag acacgtctaa gaaccagttc      240
tccctgaagc tgagctctgt gactgccgcg gacacggccg tgtattactg tgcgagagag      300
tcagtggctg ggtttgacta ctggggccag ggaaccctgg tcaccgtctc ctcagcctcc      360
accaagggcc catcggtctt ccccctggcg ccctgctcca ggagcacctc cgagagcaca      420
gcggccctgg gctgcctggt caaggactac ttccccgaac cggtgacggt gtcgtggaac      480
tcaggcgctc tgaccagcgg cgtgcacacc ttcccagctg tcctacagtc ctcaggactc      540
tactccctca gcagcgtggt gaccgtgccc tccagcaact tcggcaccca gacctacacc      600
tgcaacgtag atcacaagcc cagcaacacc aaggtggaca agacagttga gcgcaaatgt      660
tgtgtcgagt gcccaccgtg cccagcacca cctgtggcag gaccgtcagt cttcctcttc      720
cccccaaaac ccaaggacac cctcatgatc tcccggaccc ctgaggtcac gtgcgtggtg      780
gtggacgtga gccacgaaga ccccgaggtc cagttcaact ggtacgtgga cggcgtggag      840
gtgcataatg ccaagacaaa gccacgggag gagcagttca acagcacgtt ccgtgtggtc      900
agcgtcctca ccgttgtgca ccaggactgg ctgaacggca aggagtacaa gtgcaaggtc      960
tccaacaaag gcctcccagc ccccatcgag aaaaccatct ccaaaaccaa agggcagccc     1020
cgagaaccac aggtgtacac cctgccccca tcccgggagg agatgaccaa gaaccaggtc     1080
agcctgacct gcctggtcaa aggcttctac cccagcgaca tcgccgtgga gtgggagagc     1140
aatgggcagc cggagaacaa ctacaagacc acacctcccg tgctggactc cgacggctcc     1200
ttcttcctct acagcaagct caccgtggac aagagcaggt ggcagcaggg gaacgtcttc     1260
tcatgctccg tgatgcatga ggctctgcac aaccactaca cgcagaagag cctctccctg     1320
tctccgggta aa                                                         1332
```

<210> SEQ ID NO 129
<211> LENGTH: 355
<212> TYPE: DNA
<213> ORGANISM: Human

<400> SEQUENCE: 129

```
caggtgcagc tgcaggagtc gggtccagga ctggtgaagc cttcacagac cctgtccctc       60
acctgcactg tctctggtgg ctccatgagc agtggtgaat actactggaa ctggatccgc      120
cagcacccag gaagggcct ggagtggatt gggtacatct attacagtgg gagtacctac       180
tacaacccgt ccctcaagag tcgagttacc atatcagtag acacgtctaa gaaccagttc      240
tccctgaagc tgagctctgt gactgccgcg gacacggccg tgtattactg tgcgagagag      300
tcagtggctg ggtttgacta ctggggccag ggaaccctgg tcaccgtctc ctcag          355
```

<210> SEQ ID NO 130
<211> LENGTH: 503
<212> TYPE: PRT
<213> ORGANISM: Human

<400> SEQUENCE: 130

```
Met Thr Leu Gly Ser Pro Arg Lys Gly Leu Leu Met Leu Leu Met Ala
1               5                   10                  15

Leu Val Thr Gln Gly Asp Pro Val Lys Pro Ser Arg Gly Pro Leu Val
            20                  25                  30

Thr Cys Thr Cys Glu Ser Pro His Cys Lys Gly Pro Thr Cys Arg Gly
        35                  40                  45

Ala Trp Cys Thr Val Val Leu Val Arg Glu Glu Gly Arg His Pro Gln
    50                  55                  60
```

```
Glu His Arg Gly Cys Gly Asn Leu His Arg Glu Leu Cys Arg Gly Arg
 65                  70                  75                  80

Pro Thr Glu Phe Val Asn His Tyr Cys Cys Asp Ser His Leu Cys Asn
                 85                  90                  95

His Asn Val Ser Leu Val Leu Glu Ala Thr Gln Pro Pro Ser Glu Gln
            100                 105                 110

Pro Gly Thr Asp Gly Gln Leu Ala Leu Ile Leu Gly Pro Val Leu Ala
        115                 120                 125

Leu Leu Ala Leu Val Ala Leu Gly Val Leu Gly Leu Trp His Val Arg
130                 135                 140

Arg Arg Gln Glu Lys Gln Arg Gly Leu His Ser Glu Leu Gly Glu Ser
145                 150                 155                 160

Ser Leu Ile Leu Lys Ala Ser Glu Gln Gly Asp Thr Met Leu Gly Asp
                165                 170                 175

Leu Leu Asp Ser Asp Cys Thr Thr Gly Ser Gly Ser Gly Leu Pro Phe
            180                 185                 190

Leu Val Gln Arg Thr Val Ala Arg Gln Val Ala Leu Val Glu Cys Val
        195                 200                 205

Gly Lys Gly Arg Tyr Gly Glu Val Trp Arg Gly Leu Trp His Gly Glu
210                 215                 220

Ser Val Ala Val Lys Ile Phe Ser Ser Arg Asp Glu Gln Ser Trp Phe
225                 230                 235                 240

Arg Glu Thr Glu Ile Tyr Asn Thr Val Leu Leu Arg His Asp Asn Ile
                245                 250                 255

Leu Gly Phe Ile Ala Ser Asp Met Thr Ser Arg Asn Ser Ser Thr Gln
            260                 265                 270

Leu Trp Leu Ile Thr His Tyr His Glu His Gly Ser Leu Tyr Asp Phe
        275                 280                 285

Leu Gln Arg Gln Thr Leu Glu Pro His Leu Ala Leu Arg Leu Ala Val
290                 295                 300

Ser Ala Ala Cys Gly Leu Ala His Leu His Val Glu Ile Phe Gly Thr
305                 310                 315                 320

Gln Gly Lys Pro Ala Ile Ala His Arg Asp Phe Lys Ser Arg Asn Val
                325                 330                 335

Leu Val Lys Ser Asn Leu Gln Cys Cys Ile Ala Asp Leu Gly Leu Ala
            340                 345                 350

Val Met His Ser Gln Gly Ser Asp Tyr Leu Asp Ile Gly Asn Asn Pro
        355                 360                 365

Arg Val Gly Thr Lys Arg Tyr Met Ala Pro Glu Val Leu Asp Glu Gln
370                 375                 380

Ile Arg Thr Asp Cys Phe Glu Ser Tyr Lys Trp Thr Asp Ile Trp Ala
385                 390                 395                 400

Phe Gly Leu Val Leu Trp Glu Ile Ala Arg Arg Thr Ile Val Asn Gly
                405                 410                 415

Ile Val Glu Asp Tyr Arg Pro Pro Phe Tyr Asp Val Val Pro Asn Asp
            420                 425                 430

Pro Ser Phe Glu Asp Met Lys Lys Val Val Cys Val Asp Gln Gln Thr
        435                 440                 445

Pro Thr Ile Pro Asn Arg Leu Ala Ala Asp Pro Val Leu Ser Gly Leu
450                 455                 460

Ala Gln Met Met Arg Glu Cys Trp Tyr Pro Asn Pro Ser Ala Arg Leu
465                 470                 475                 480
```

```
Thr Ala Leu Arg Ile Lys Lys Thr Leu Gln Lys Ile Ser Asn Ser Pro
                485                 490                 495

Glu Lys Pro Lys Val Ile Gln
            500
```

<210> SEQ ID NO 131
<211> LENGTH: 120
<212> TYPE: PRT
<213> ORGANISM: Human

<400> SEQUENCE: 131

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Ile Ala Val Ala Gly Tyr Phe Asp Tyr Trp Gly Gln
            100                 105                 110

Gly Thr Leu Val Thr Val Ser Ser
        115                 120
```

<210> SEQ ID NO 132
<211> LENGTH: 108
<212> TYPE: PRT
<213> ORGANISM: Human

<400> SEQUENCE: 132

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Ile Thr Phe Gly Gln Gly Thr Arg Leu Glu Ile Lys
            100                 105
```

<210> SEQ ID NO 133
<211> LENGTH: 96
<212> TYPE: PRT
<213> ORGANISM: Human

<400> SEQUENCE: 133

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
```

```
                  20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

<210> SEQ ID NO 134
<211> LENGTH: 99
<212> TYPE: PRT
<213> ORGANISM: Human

<400> SEQUENCE: 134

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
                 20                  25                  30

Gly Tyr Tyr Trp Ser Trp Ile Arg Gln His Pro Gly Lys Gly Leu Glu
            35                  40                  45

Trp Ile Gly Tyr Ile Tyr Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg

<210> SEQ ID NO 135
<211> LENGTH: 108
<212> TYPE: PRT
<213> ORGANISM: Human

<400> SEQUENCE: 135

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
                 20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln His Phe Gly Ser Ser Pro
                 85                  90                  95

Ile Thr Phe Gly Gln Gly Thr Arg Leu Glu Ile Lys
                100                 105
```

```
<210> SEQ ID NO 136
<211> LENGTH: 5
<212> TYPE: PRT
<213> ORGANISM: Human

<400> SEQUENCE: 136

Gly Tyr Tyr Trp Ser
1               5
```